(12) United States Patent
Bushell et al.

(10) Patent No.: US 7,851,439 B2
(45) Date of Patent: Dec. 14, 2010

(54) EFTU INHIBITORS OR AMINOTHIAZOLES AND THEIR USES

(75) Inventors: Simon Bushell, Boston, MA (US); Matthew LaMarche, Reading, MA (US); Michael J. Patane, Reading, MA (US); Lewis Whitehead, Swampscott, MA (US)

(73) Assignee: Novartis AG, Basel (CH)

( * ) Notice: Subject to any disclaimer, the term of this patent is extended or adjusted under 35 U.S.C. 154(b) by 459 days.

(21) Appl. No.: 11/755,481

(22) Filed: May 30, 2007

(65) Prior Publication Data

US 2008/0221142 A1 Sep. 11, 2008

Related U.S. Application Data

(60) Provisional application No. 60/809,693, filed on May 31, 2006.

(51) Int. Cl.
*A61K 38/00* (2006.01)
*A61K 38/12* (2006.01)
*A61K 31/4436* (2006.01)
*A61P 31/00* (2006.01)
*C07D 267/00* (2006.01)

(52) U.S. Cl. .............................. 514/11; 514/9; 514/279; 424/116; 424/117; 540/455

(58) Field of Classification Search .................. None
See application file for complete search history.

(56) References Cited

U.S. PATENT DOCUMENTS

| | | | |
|---|---|---|---|
| 5,139,778 A | 8/1992 | Selva et al. |
| 5,202,241 A | 4/1993 | Selva et al. |
| 5,322,777 A | 6/1994 | Selva et al. |
| 5,514,649 A | 5/1996 | Selva et al. |
| 5,547,666 A | 8/1996 | Selva et al. |
| 5,599,791 A | 2/1997 | Tavecchia et al. |
| 5,747,295 A | 5/1998 | Selva et al. |
| 5,843,890 A | 12/1998 | Selva et al. |
| 5,882,900 A | 3/1999 | Rizzo et al. |
| 5,891,869 A | 4/1999 | Lociura et al. |
| 6,008,225 A | 12/1999 | Lociura et al. |
| 6,143,739 A | 11/2000 | Lociura et al. |

FOREIGN PATENT DOCUMENTS

| | | | |
|---|---|---|---|
| EP | 0494078 A | | 7/1992 |
| EP | 0675900 B1 | | 2/1998 |
| WO | 9614427 A1 | | 5/1996 |
| WO | 03105881 A1 | | 12/2003 |
| WO | 2006086012 A | | 8/2006 |
| WO | 2007142986 A | | 12/2007 |

OTHER PUBLICATIONS

Wolf H, Chinali G, Parmeggiani A, "Kirromycin, an Inhibitor of Protein Biosynthesis that Acts on Elongation Factor Tu," Proceedings of National Academy of Sciences, USA, Dec. 1974, 71(12): 4910-4914.*
Structure of Kirromycin (K1507) from SIGMA, pp. 1. Accessed Apr. 16, 2009.*
Types of bacterial infection from Merck manual, http://www.merck.com/mmhe/sec17/ch190/ch190a.html, pp. 1-6. Accessed Apr. 16, 2009.*
Definition of residue from http://dictionary.reference.com/browse/residue, pp. 1-4. Accessed Jul. 13, 2009.*
Cislak Fe, "Pyridine-N-Oxide," Industrial and Engineering Chemistry, 1955, 47(4): 800-802.*
Atropisomer from http://www.allwords.com/word-atropisomer.html, pp. 1-2. Accessed Jul. 23, 2009.*
Stereoisomer from http://www.chemicool.com/definition/stereoisomers.html, pp. 1-3. Accessed Jul. 23, 2009.*
Rotamer from http://www.chemicool.com/definition/rotamer.html, pp. 1-2. Accessed Jul. 23, 2009.*
Racemate from http://www.chemicool.com/definition/racemate.html, pp. 1-2. Accessed Jul. 23, 2009.*
Enantiomer from http://www.chemicool.com/definition/enantiomer.html, pp. 1-2. Accessed Jul. 23, 2009.*
Tautomer from http://medical-dictionary.thefreedictionary.com/tautomer, pp. 1-2. Accessed Jul. 23, 2009.*
Pyridine N-Oxide from SIGMA.com, pp. 1-6. Accessed Jul. 23, 2009.*
Diastereomer from http://www.allwords.com/word-diastereoisomer.html, pp. 1-2. Accessed Jul. 23, 2009.*
Enrico, Selva et al. "Components of the GE2270 Complex Produced by Planobispora Rosea ATCC 53773" Journal of Antibiotics, Japan Antibiotics Research Association, Tokyo, JP vol. 48, No. 9, 1995, pp. 1039-1042.
International Search Report for related application PCT/US2007/012768 mailed Sep. 11, 2007.
Tavecchia, P. et al. "Degradation Studies of Antibiotic MDL 62,879 (GE2270A) and Revision of the Structure", Tetrahedron vol. 51, No. 16. Great Britain, 1995, pp. 4867-4890.
Selva, E. et al "Antibiotic GE2270 A: A Novel Inhibitor of bacterial Protein Synthesis, I. Isolation and Characterization", Journal of Antibiotics, vol. 44, No. 7, 1991, pp. 693-701.

* cited by examiner

*Primary Examiner*—Julie Ha
(74) *Attorney, Agent, or Firm*—John Alexander

(57) ABSTRACT

Organic compounds that are useful for the treatment, prevention and/or amelioration of diseases are described.

10 Claims, No Drawings

EFTU INHIBITORS OR AMINOTHIAZOLES AND THEIR USES

BACKGROUND

Since the discovery of penicillin, pharmaceutical companies have produced a number of antibacterial agents to combat a wide variety of bacterial infections. In the past several years, there has been rapid emergence of bacterial resistance to several of these antibiotics. The multidrug resistance among these bacterial pathogens may also be due to mutation leading to more virulent clinical isolation. Perhaps the most disturbing occurrence has been the acquisition of resistance to vancomycin, an antibiotic generally regarded as the agent of last resort for serious Gram-positive infections.

This is true especially of some Gram-positive pathogen groups, such as staphylococci, pneumococci and enterococci (S. Ewig et al.; Antibiotika-Resistenz bei Erregem ambulant erworbener Atemwegsinfektionen (Antibiotic resistance in pathogens of outpatient-acquired respiratory tract infections); Chemother. J. 2002, 11, 12-26; F. Tenover; Development and spread of bacterial resistance to antimicrobial agents: an overview; Clin. Infect. Dis. 2001 Sep. 15, 33 Suppl. 3, 108-115) as well as *Staphylococcus, Streptococcus, Mycobacterium, Enterococcus, Corynebacterium, Borrelia, Bacillus, Chlamydia, Mycoplasma*, and the like.

A problem of equally large dimension is the increasing incidence of the more virulent, methicillin-resistant *Staphylococcus aureas* (MRSA) among clinical isolates found worldwide. As with vancomycin resistant organisms, many MRSA strains are resistant to most of the known antibiotics, but MRSA strains have remained sensitive to vancomycin. However, in view of the increasing reports of vancomycin resistant clinical isolates and growing problem of bacterial resistance, there is an urgent need for new molecular entities effective against the emerging and currently problematic Gram-positive organisms.

This growing multidrug resistance has recently rekindled interest in the search for new structural classes of antibiotics that inhibit or kill these bacteria.

SUMMARY OF THE INVENTION

There remains a need for new treatments and therapies for bacterial infections. There is also a need for compounds useful in the treatment or prevention or amelioration of one or more symptoms of bacterial infections. Furthermore, there is a need for methods for modulating the activity of the elongation factor EF-Tu, using the compounds provided herein.

In one aspect, the invention provides a compound of formula I:

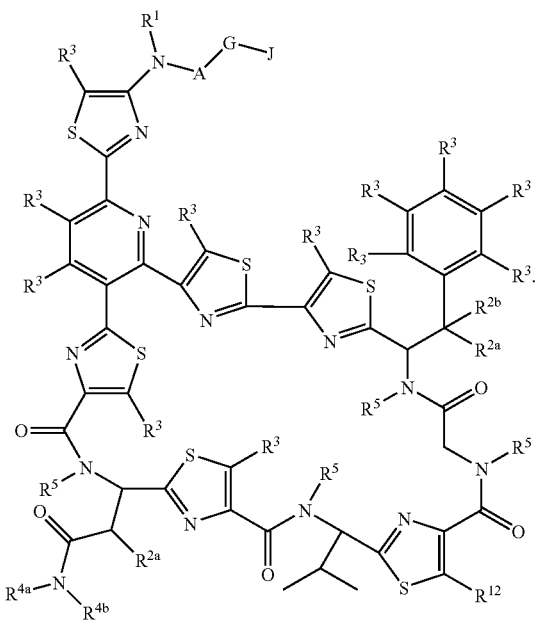

In yet another aspect, the invention provides a compound of formula II:

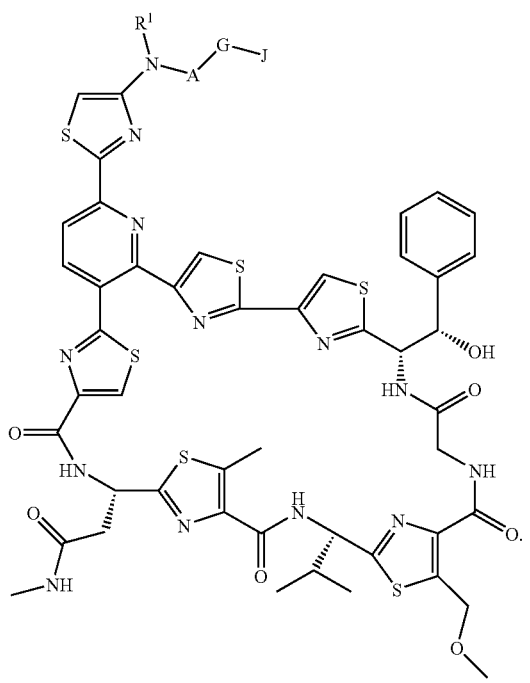

In still another aspect, the invention provides a compound of formula III:
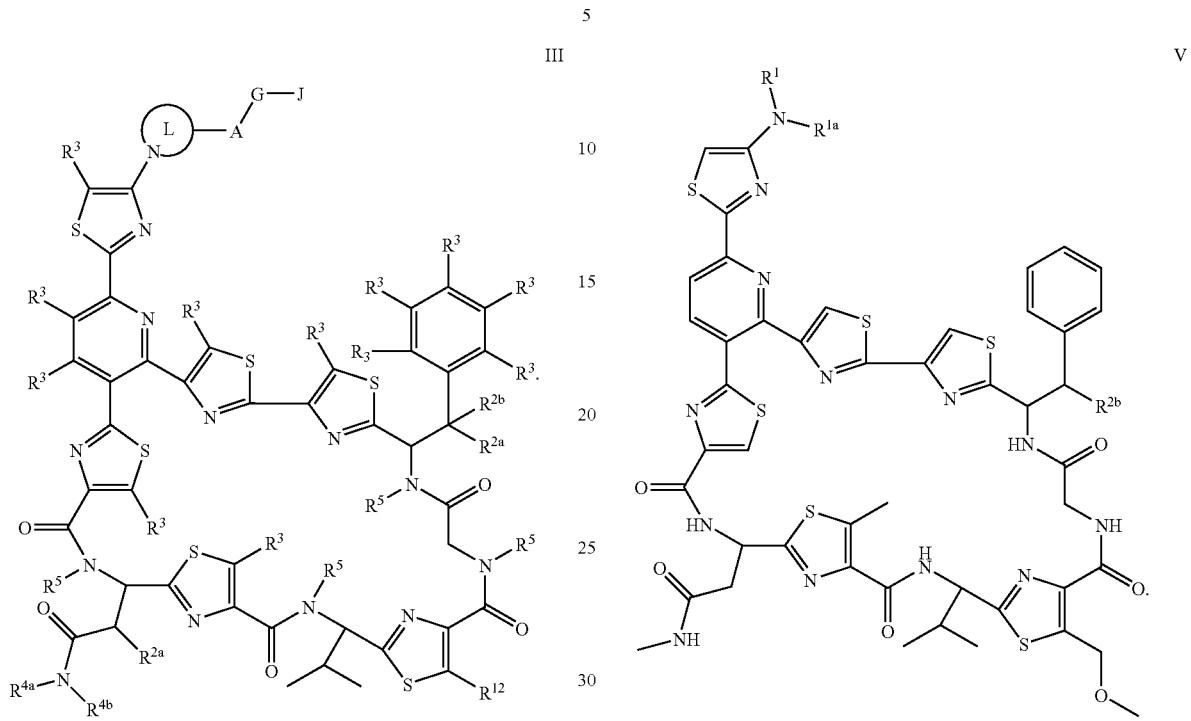
In another aspect, the invention provides a compound of formula IV:
In another aspect, the invention provides a compound of formula V:
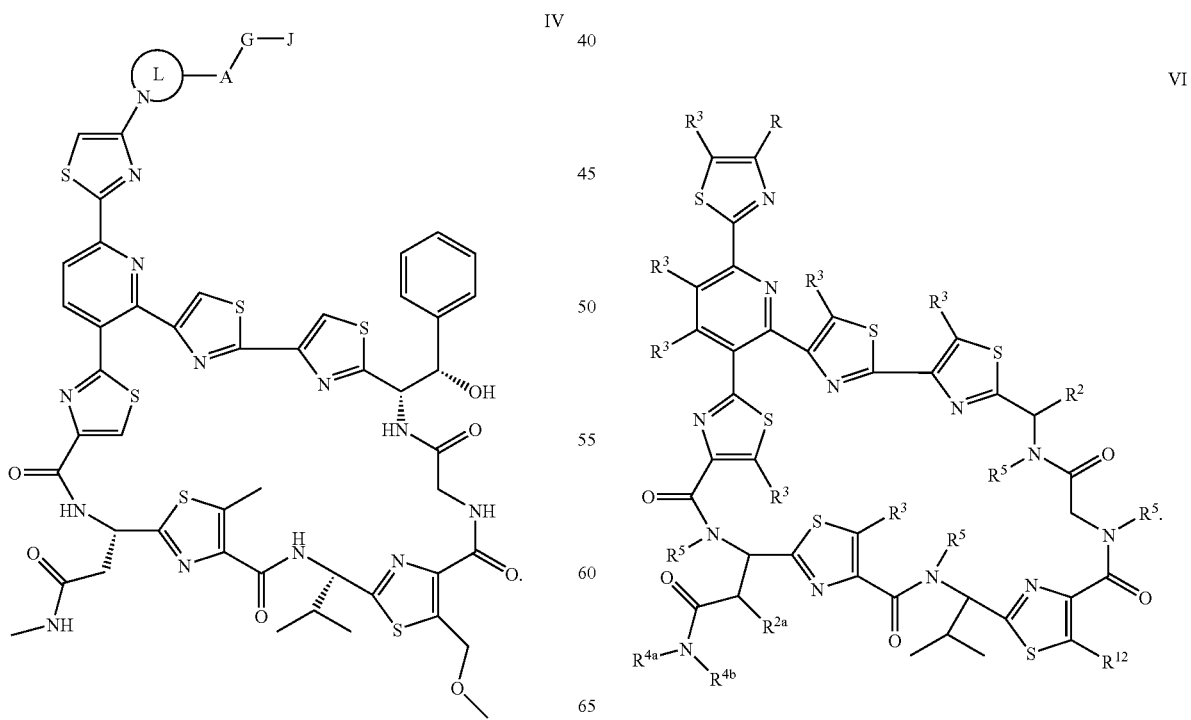
In another aspect, the invention provides a compound of formula VI:

In yet another aspect, the invention provides a compound of formula VII:

VII

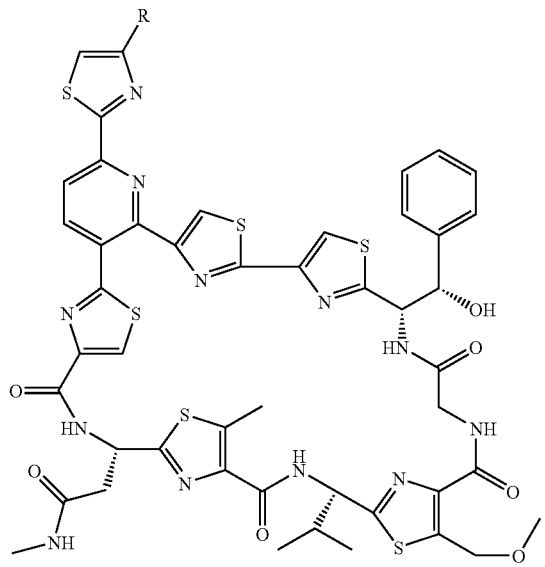

In another aspect, the invention provides a compound of formula VIII:

VIII

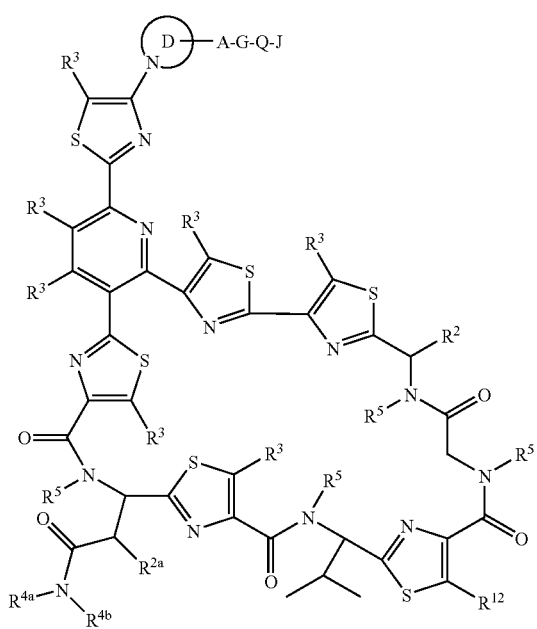

In another aspect, the invention provides a method of treating a bacterial infection wherein the treatment includes administering to a subject in need thereof a pharmaceutically acceptable amount of a compound of formula I, II, III, IV, V, VI, VII or VIII, such that the bacterial infection is treated.

In another aspect, the invention provides a method of treating an EF-Tu associated-state wherein the treatment includes administering to a subject in need thereof a pharmaceutically acceptable amount of a compound of formula I, II, III, IV, V, VI, VII or VIII, such that the EF-Tu associated state is treated.

In still another aspect, the invention provides a method of treating, inhibiting or preventing the activity of EF-Tu in a subject in need thereof, which includes administering to the subject a pharmaceutically acceptable amount of a compound of formula I, II, III, IV, V, VI, VII or VIII. In one embodiment, a bacterial infection is treated in a subject in need thereof.

In another aspect, the invention provides a method of treating, inhibiting or preventing the activity of bacteria in a subject in need thereof, which includes administering to the subject a pharmaceutically acceptable amount of a compound of formula I, II, III, IV, V, VI, VII or VIII, wherein the compound interacts with any target in the life cycle of the bacteria. In one embodiment, the target is EF-Tu.

In another aspect, the invention provides a method of treating a bacterial infection in a subject, wherein the treatment includes administering to a subject in need thereof a pharmaceutically acceptable amount of a compound of the formula I, II, III, IV, V, VI, VII or VIII, and a pharmaceutically acceptable carrier, such that the bacterial infection is treated.

In still another aspect, the invention provides a method of treating a bacterial infection wherein the treatment includes administering to a subject in need thereof a pharmaceutically effective amount of a compound of the formula I, II, III, IV, V, VI, VII or VIII, in combination with a pharmaceutically effective amount of an additional therapeutic agent, such that the bacterial infection is treated. In one embodiment, the compound of the formula I, II, III, IV, V, VI, VII or VIII and the other pharmaceutical agent are administered as part of the same pharmaceutical composition. In another embodiment, the compound of the formula I, II, III, IV, V, VI, VII or VIII and the other therapeutic agent are administered as separate pharmaceutical compositions, and the compound is administered prior to, at the same time as, or following administration of the other agent.

In another aspect, the invention provides a packaged bacterial infection treatment, comprised of formula I, II, III, IV, V, VI, VII or VIII, packaged with instructions for using an effective amount of the compound to treat a bacterial infection.

In another aspect, the invention provides a method of treating acne in subject in need thereof, wherein the treatment includes administering to the subject a pharmaceutically acceptable amount of a compound of formula I, II, III, IV, V, VI, VII or VIII.

In yet another aspect, the invention provides a pharmaceutical composition which includes a compound of formula I, II, III, IV, V, VI, VII or VIII, and at least one pharmaceutically acceptable carrier or diluent.

DETAILED DESCRIPTION OF THE INVENTION

This invention is directed to compounds, e.g., thiopeptide compounds, and intermediates thereto, as well as pharmaceutical compositions containing the compounds for use in treatment of bacterial infection. This invention is also directed to the compounds of the invention or compositions thereof as modulators of the elongation factor EF-Tu. The compounds are particularly useful in interfering with the life cycle of bacteria and in treating or preventing a bacterial infection or physiological conditions associated therewith. The present invention is also directed to methods of combination therapy for inhibiting EF-Tu activity in cells, or for treating or preventing a bacterial infection in patients using the compounds of the invention or pharmaceutical compositions, or kits thereof.

In one aspect, the invention provides compounds of the formula I:

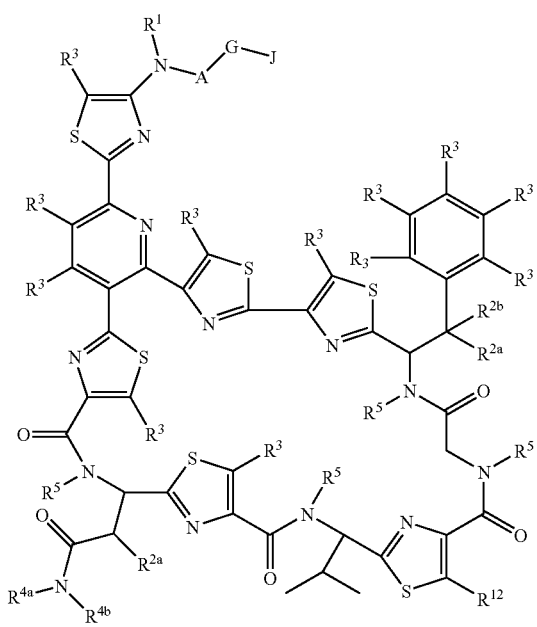

I and pharmaceutically acceptable salts, enantiomers, stereoisomers, rotamers, tautomers, diastereomers, atropisomers or racemates thereof, including the pyridine N-oxide thereof;

wherein

A is selected from the group consisting of a bond, H, —($CH_2$)—, —C(alkyl)$_2$—, —($CH_2$)$_{1-8}$—, —[C(alkyl)$_2$]$_{1-8}$—, -(cycloalkyl)-, -(aryl)-, -(heteroaryl)-, —C(O)—, —C(O)C(O)—, —C(O)O—, —C(O)N($R^{8a}$)—, —S(O)$_2$—, —S(O)—, —S(O)$_2$N($R^{8a}$)—, —S(O)N($R^{8a}$)—, —C(=$NR^8$)N($R^{8a}$)—, —C(=$NR^8$)N($R^{8a}$)C(O)—, —C(=$NR^8$)—, —C=C—C(O)—, —C=C—C(O)O—, —C=C—C(O)N($R^{8a}$)—;

G is absent, or selected from the group consisting of H, —[C($R^a$)($R^b$)]$_x$—, —[C($R^a$)($R^b$)]$_x$—O—[C($R^a$)($R^b$)]$_y$—, —[C($R^a$)($R^b$)]$_x$—N($R^{8a}$)—[C($R^a$)($R^b$)]$_y$—, -(cycloalkyl)-, -(heterocycle)-, -(aryl)-, -(heteroaryl)-;

J is selected from the group consisting of H, F, O-alkyl, N($R^{8a}$)$_2$, N$^+$($R^{8a}$)$_3$, N($R^{8a}$)C(O)alkyl, $CO_2$H, C(=O)N($R^{8a}$)$_2$, $CO_2$-alkyl, P(O)(OH)$_2$, P(O)(O-alkyl)$_2$, and a substituted nitrogen-containing heterocycle;

$R^a$ is selected from the group consisting of H, alkyl, F, $CO_2$H, $CO_2$-alkyl, —N($R^1$)$_2$, —O$R^1$, —($CH_2$)$_{0-4}$-J and —$R^{4b}$;

$R^b$ is selected from the group consisting of H, alkyl, and F;

x and y are each, independently, integers from 0-10;

$R^1$ is selected from —H, —C(alkyl)$_2$-J, —$R^{4b}$.

$R^{2a}$ is selected from the group consisting of H, substituted or unsubstituted alkyl, OH, O$R^{4a}$, OC(O)$R^{4a}$, OC(O)N($R^{8a}$)$_2$ and N($R^{8a}$)$_2$;

$R^{2b}$ is selected from the group consisting of absent, H and alkyl, or $R^{2a}$ and $R^{2b}$ may together form =O or =NH;

$R^3$ an $R^{12}$ are each, independently, selected from the group consisting of H, halogen, O$R^{4b}$, -G-J, and N($R^{8a}$)$_2$;

$R^{4a}$ is selected from the group consisting of H, and alkyl;

$R^{4b}$ is selected from the group consisting of alkyl and —($CH_2$—$CH_2$—O—)$_n$—$R^9$, wherein n is an integer equal to or averaging 1-60,000, e.g., 1-500, 1,000, 2,000, 3,000, 4,000, 5,000, 10,000, 20,000, 30,000, 40,000, 50,000, 60,000;

$R^5$ is selected from the group consisting of H, alkyl, and $R^{4b}$;

$R^8$ is selected from the group consisting of H, CN, $NO_2$, alkyl, cycloalkyl, and $SO_2$-alkyl;

$R^{8a}$ is absent, or selected from the group consisting of H, -(alkyl)-, -(cycloalkyl)-, C(alkyl)$_2$-J, —$R^{4b}$, wherein $R^{8a}$ can also cyclize with the atom to which $R^{8a}$ is bonded to form a 3, 4, 5, 6 or 7-membered ring that is aromatic or non-aromatic and may contain one or more heteroatoms, wherein the ring may be further substituted one or more times with substitutents that are the same or different; and $R^9$ is selected from the group consisting of H, alkyl and $CH_2CO_2$H.

In one embodiment of formula I, $R^{2b}$, $R^{4b}$ and $R^5$ are H, and $R^{4a}$ is $CH_3$. In another embodiment of formula I, $R^{2b}$, $R^{4b}$ and $R^5$ are H, $R^{4a}$ is $CH_3$, and $R^{12}$ is $CH_2$—O—$CH_3$.

In another embodiment, formula I is represented by a compound of formula II:

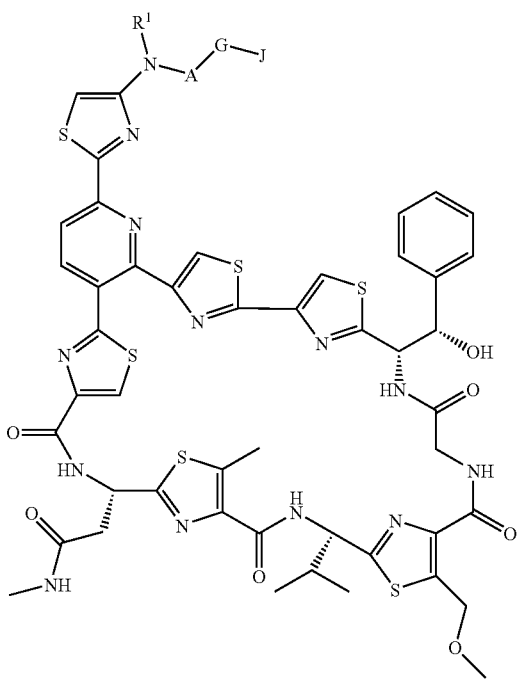

II and pharmaceutically acceptable salts thereof.

In another aspect, the invention provides a compound of the formula III:

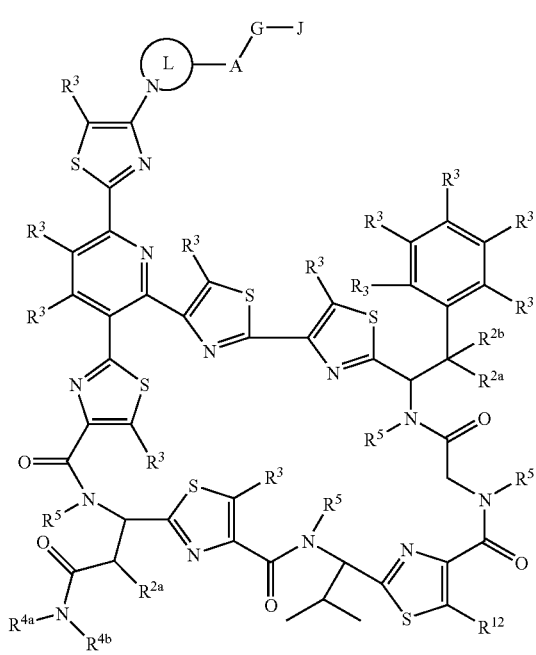

III and pharmaceutically acceptable salts, enantiomers, stereoisomers, rotamers, tautomers, diastereomers, atropisomers or racemates thereof, including the pyridine N-oxide thereof; wherein $R^{2a}$, $R^{2b}$, $R^3$, $R^{4a}$, $R^{4b}$, $R^5$, $R^{12}$, A, G and J have the meanings set forth for formula I;

and ring L is selected form the group consisting of cycloalkyl, heterocycle, aryl and heteroaryl, all of which may be further optionally substituted with -A-G-J.

In one embodiment of formula III, $R^{2b}$, $R^{4b}$ and $R^5$ are H, and $R^{4a}$ is $CH_3$. In another embodiment of formula III, $R^{2b}$, $R^{4b}$ and $R^5$ are H, $R^{4a}$ is $CH_3$, and $R^{12}$ is $CH_2$—O—$CH_3$.

In another embodiment, formula III is represented by a compound of formula IV:

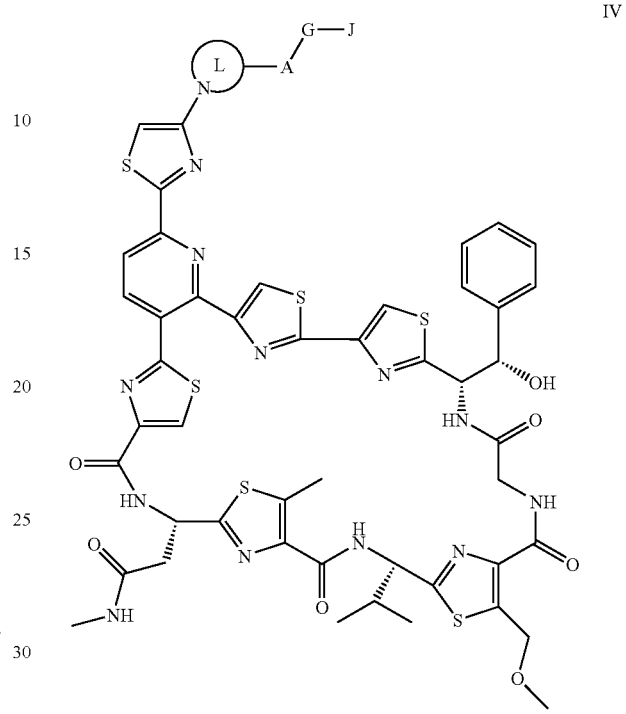

IV and pharmaceutically acceptable salts thereof
wherein ring L, A, G and J have the meanings set forth for formula III.

In another aspect, the invention provides a compound of the formula V:

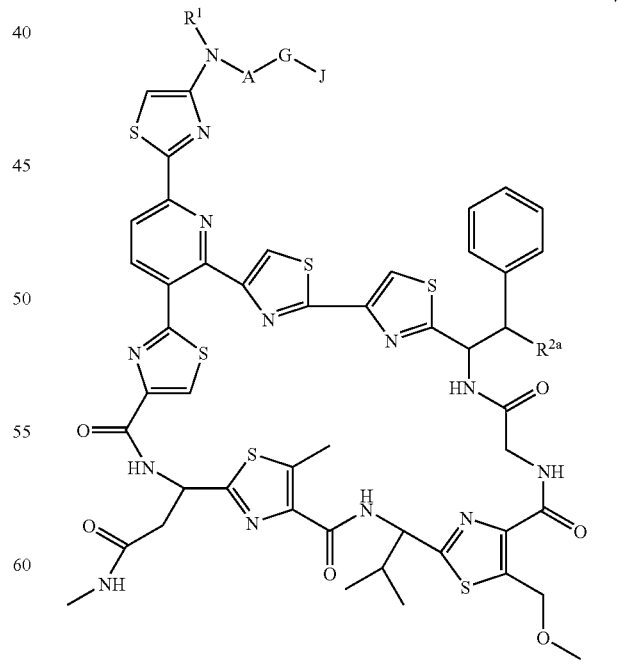

V wherein A-G-J is $R^{1a}$;
wherein $R^1$, $R^{1a}$ and $R^{2a}$ are each, independently, selected from the group consisting of H, substituted or unsubstituted alkyl, alkyl-aryl, heteroalkyl, heterocyclyl, heteroaryl, aryl-heteroaryl, alkyl-heteroaryl, cycloalkyl, alkyloxy, alkyl-aryloxy, aryloxy, heteroaryloxy, heterocyclyloxy, cycloalkyloxy, amino, alkylamino, arylamino, alkyl-arylamino, arylamino, heteroarylamino, cycloalkylamino, carboxyalkylamino, arlylalkyloxy and heterocyclylamino; all of which may be further independently substituted one or more times with $Z^1$ and $Z^2$; wherein $Z^1$ is alkyl, alkenyl, alkynyl, cycloalkyl, cycloalkyl-alkyl, heterocyclyl, heterocyclylalkyl, aryl, alkylaryl, arylalkyl, arylheteroaryl, heteroaryl, heterocyclylamino, alkylheteroaryl, or heteroarylalkyl; wherein $Z^1$ can be independently substituted with one or more of $Z^2$ moieties which can be the same or different and are independently selected; wherein $Z^2$ is hydroxy, alkyl, aryl, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, keto, ester or nitro; wherein each of said alkyl, alkoxy, and aryl can be unsubstituted or optionally independently substituted with one or more moieties which can be the same or different and are independently selected from alkyl, alkenyl, alkynyl, cycloalkyl, cycloalkyl-alkyl, heterocyclyl, heterocyclylalkyl, aryl, alkylaryl, arylalkyl, arylheteroaryl, heteroaryl, heterocyclylamino, alkylheteroaryl and heteroarylalkyl;

or $R^1$ and $R^{1a}$ may together form a 3, 4, 5, 6 or 7-membered ring that is aromatic or non-aromatic and may contain one or more heteroatoms, wherein the ring may be further substituted one or more times with substitutents that are the same or different.

In one embodiment of formula V, $R^{2a}$ is OH.

In another embodiment of the compounds of the invention, $R^1$ is H or $CH_3$, and A-G-J together form H, or together form a functional group selected from the group consisting of

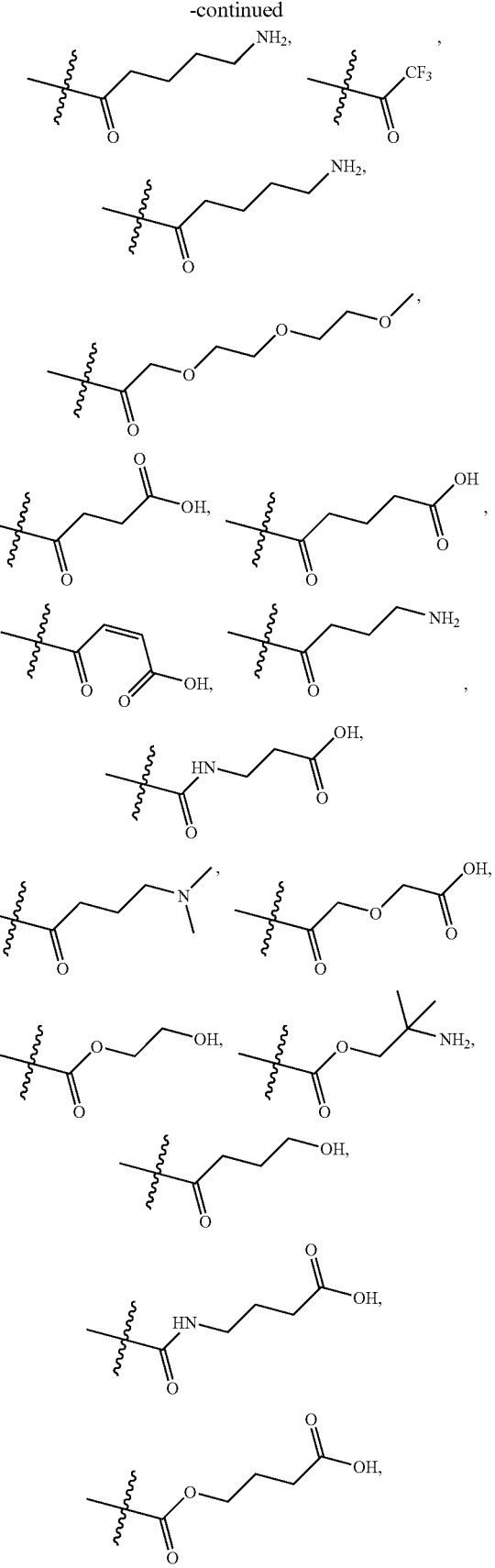

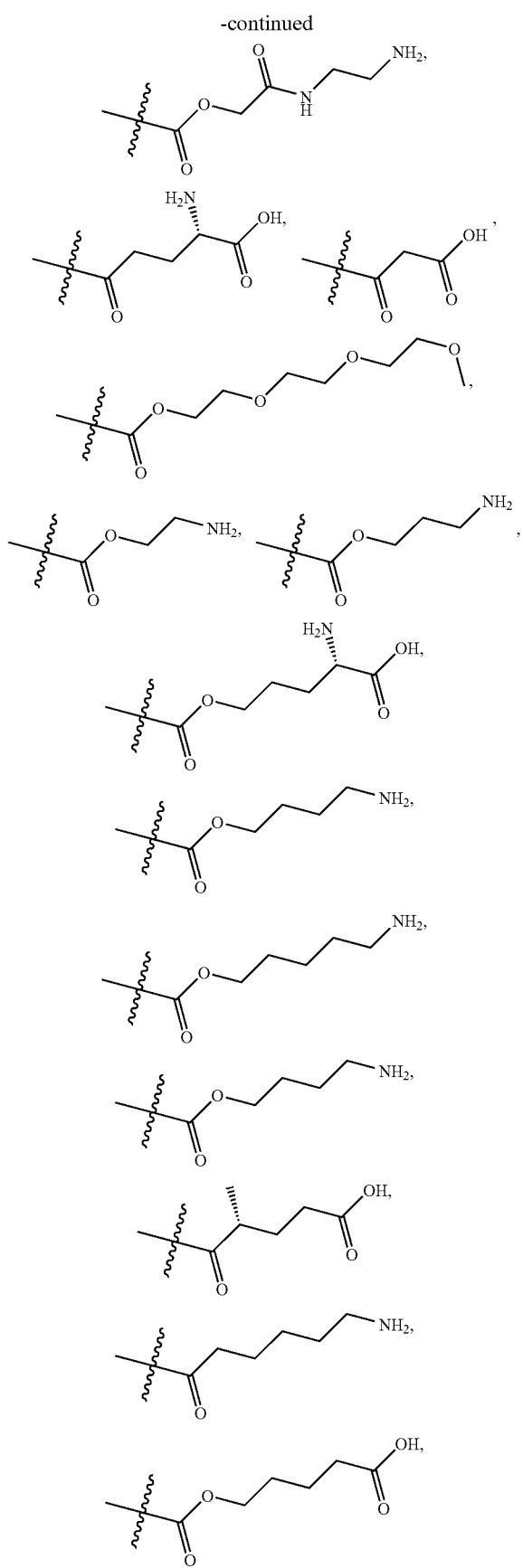
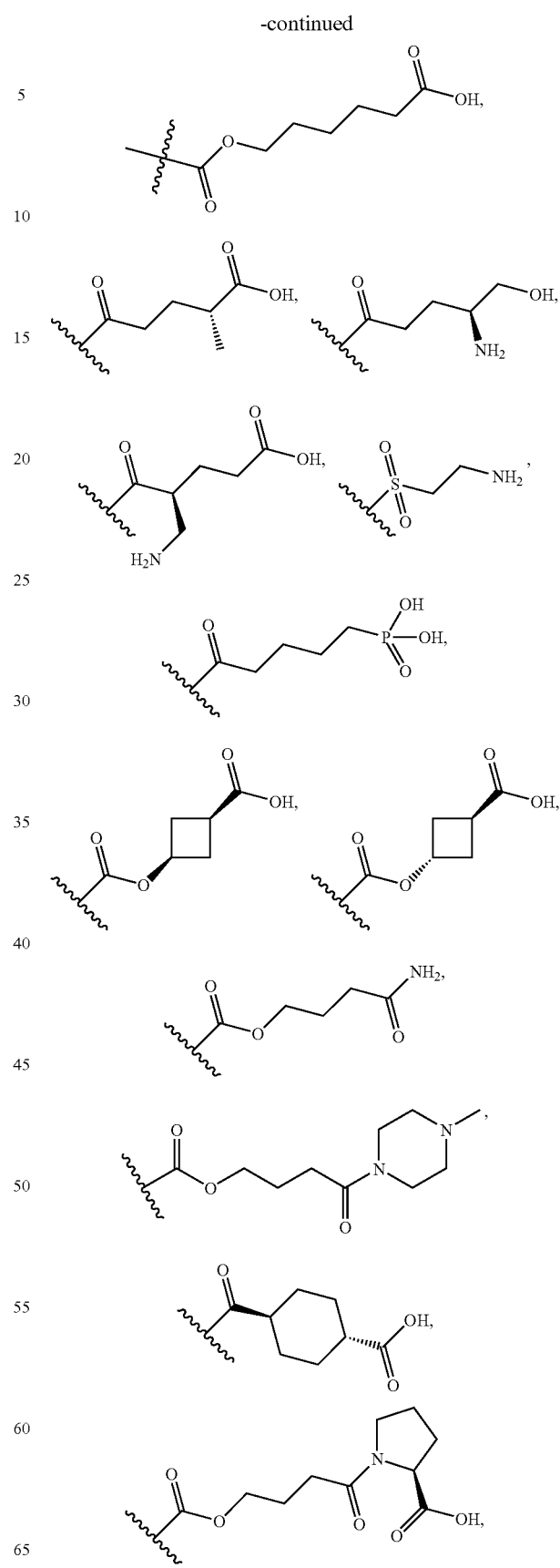

-continued
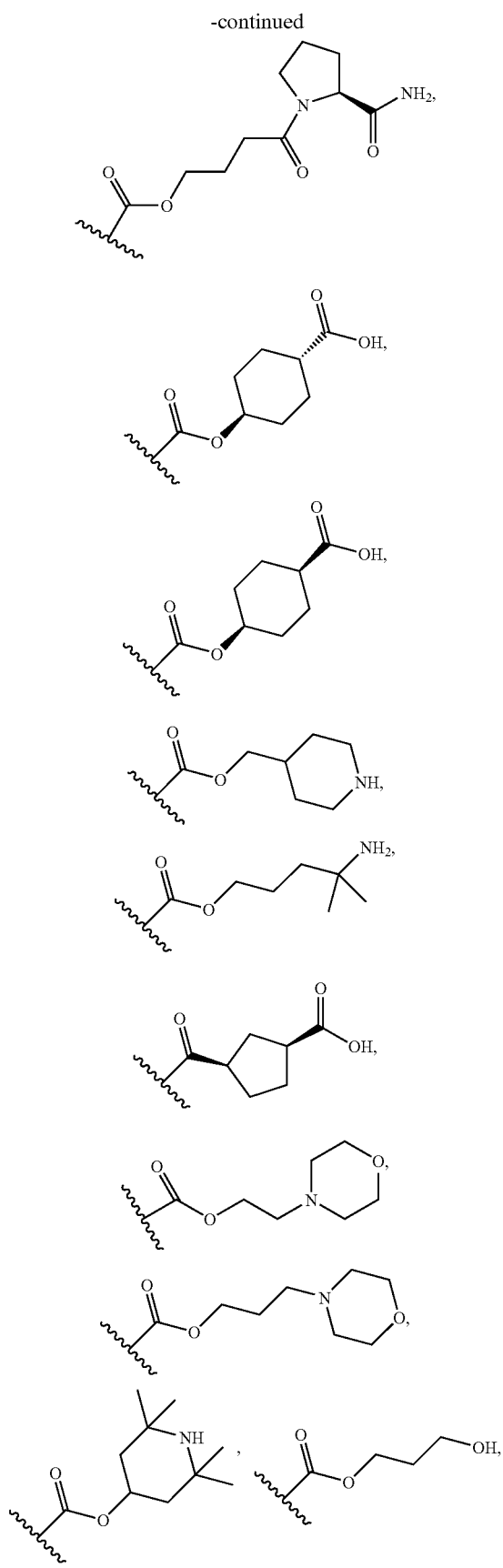
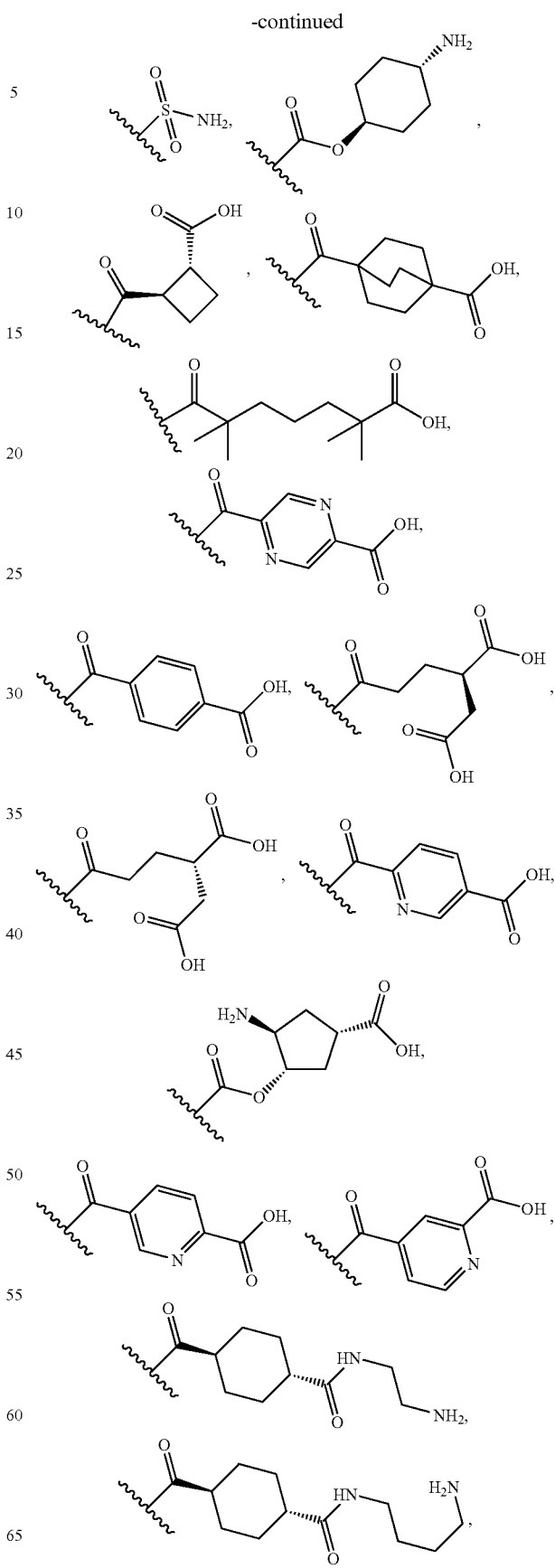

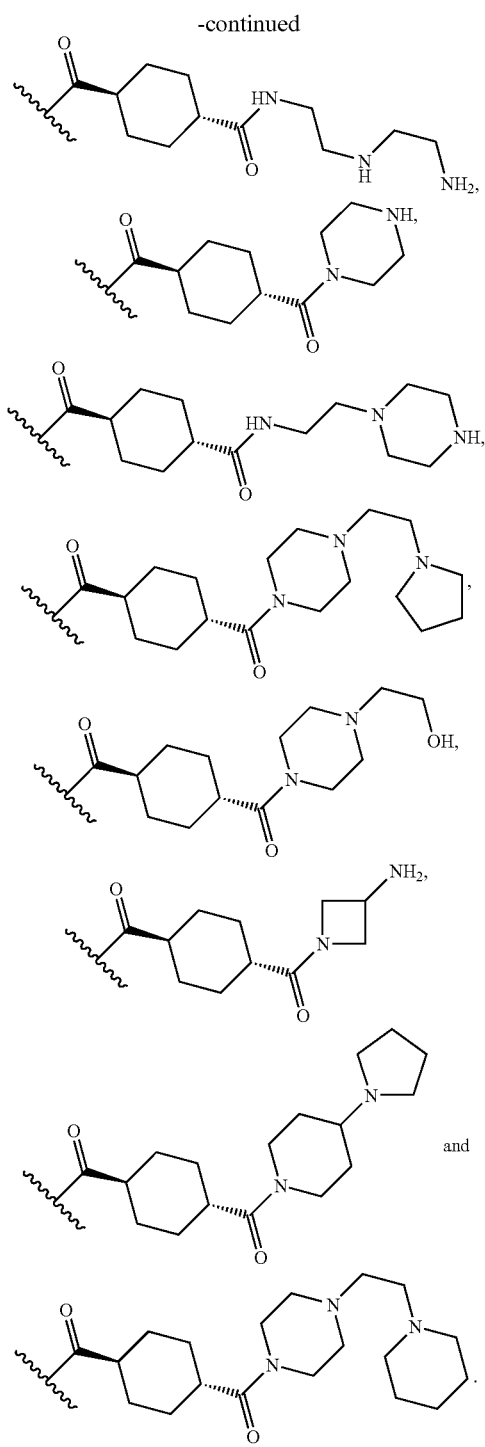
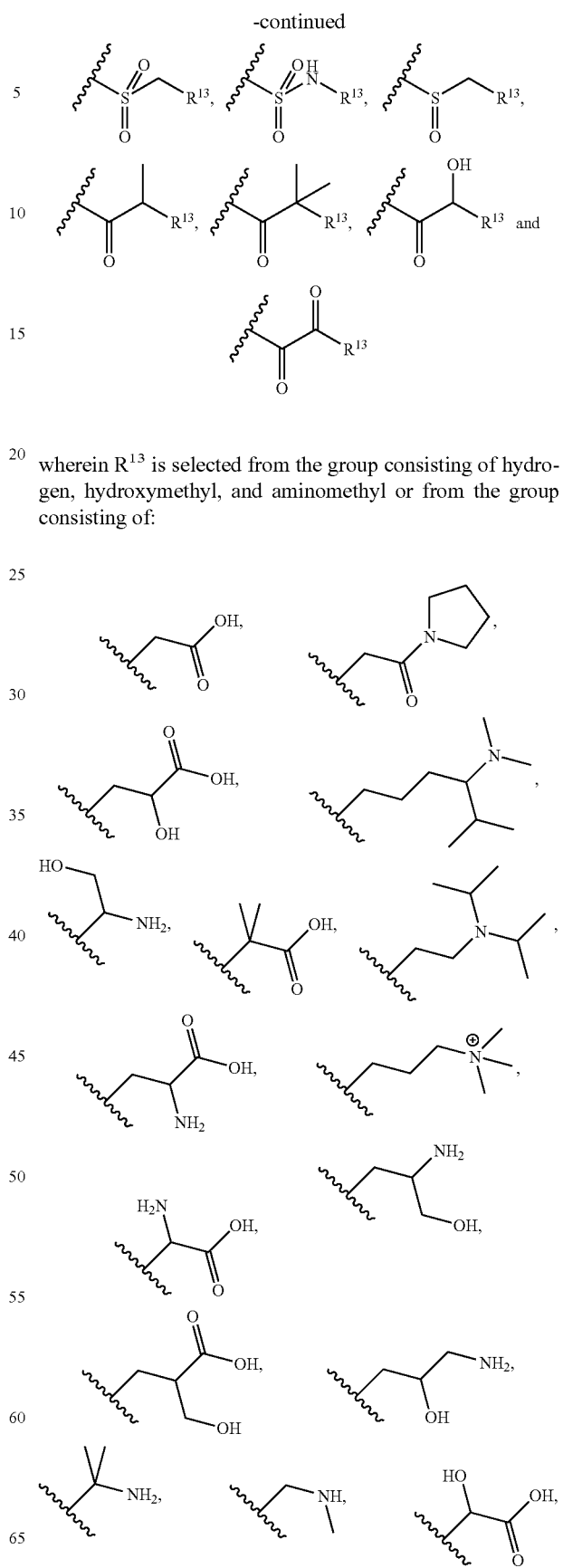
wherein $R^{13}$ is selected from the group consisting of hydrogen, hydroxymethyl, and aminomethyl or from the group consisting of:
In another embodiment of the compounds of the invention, $R^1$ is H, and A-G-J together form a functional group selected from the group consisting of
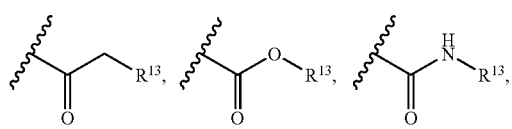

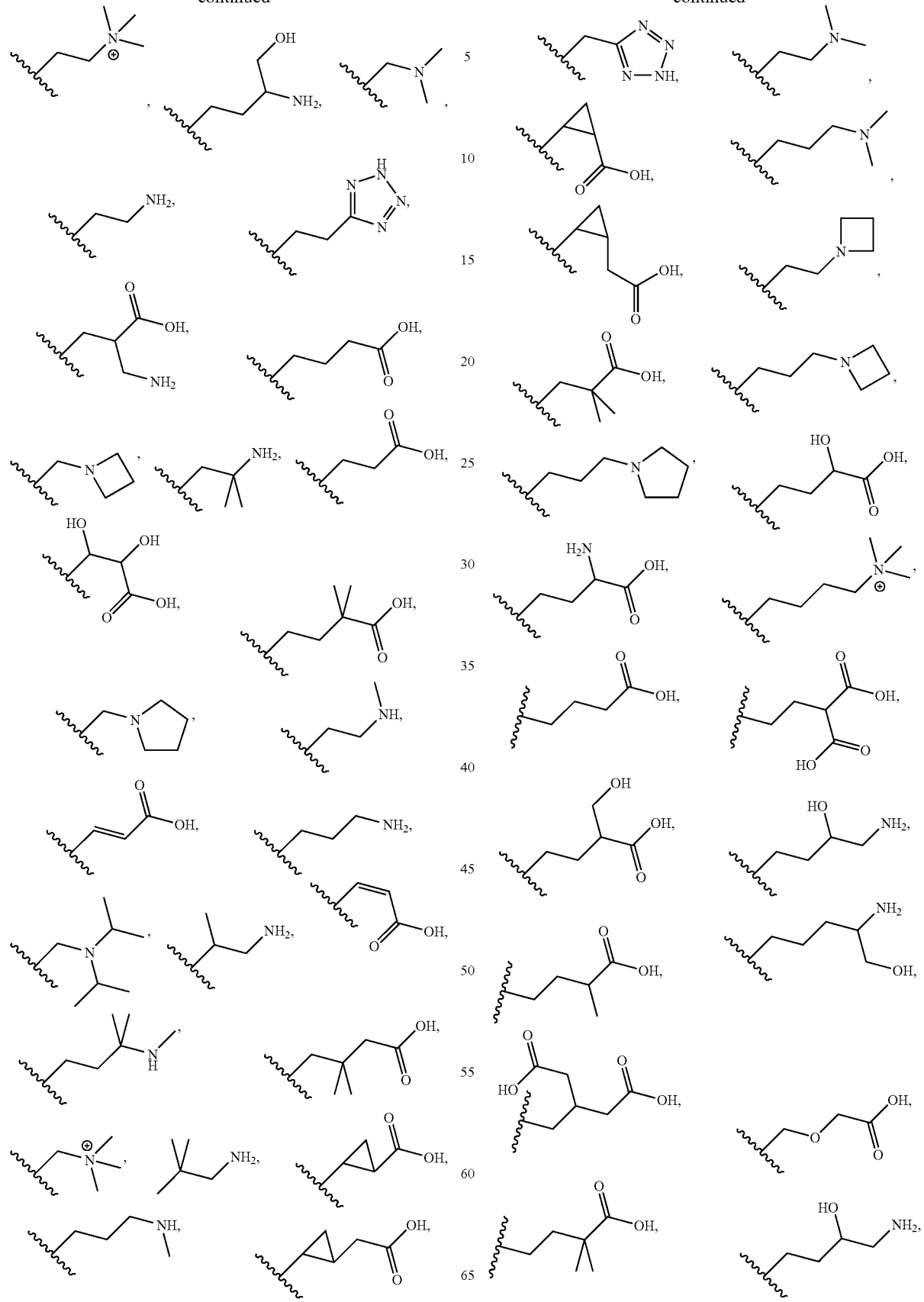

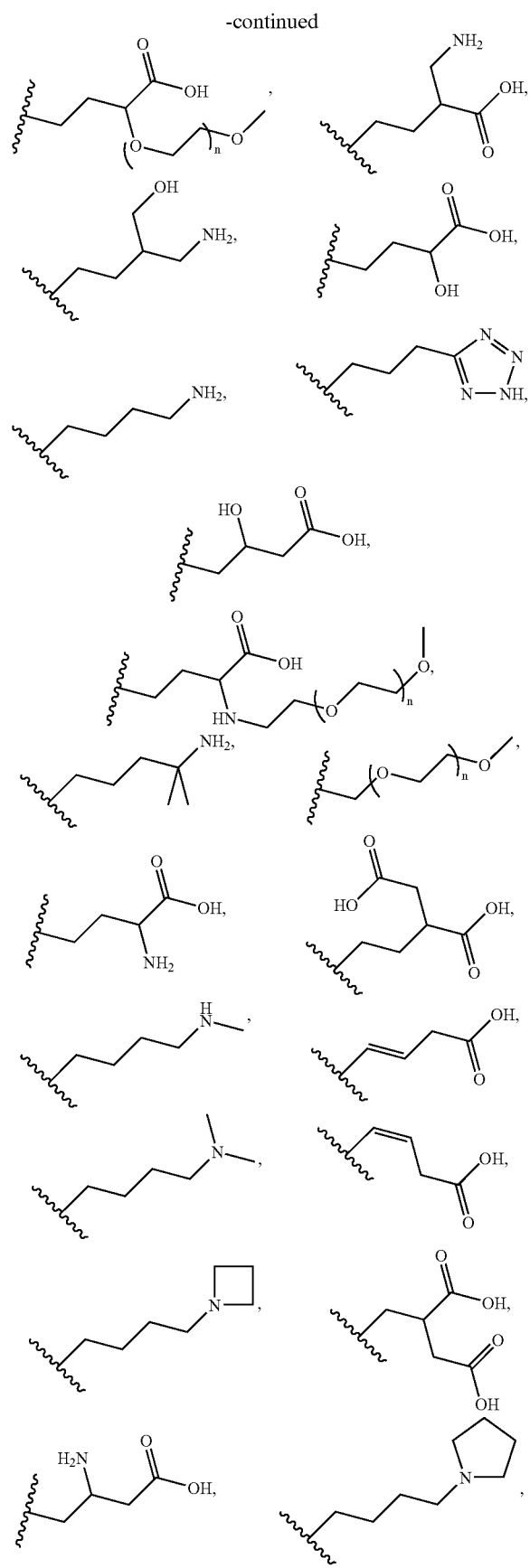
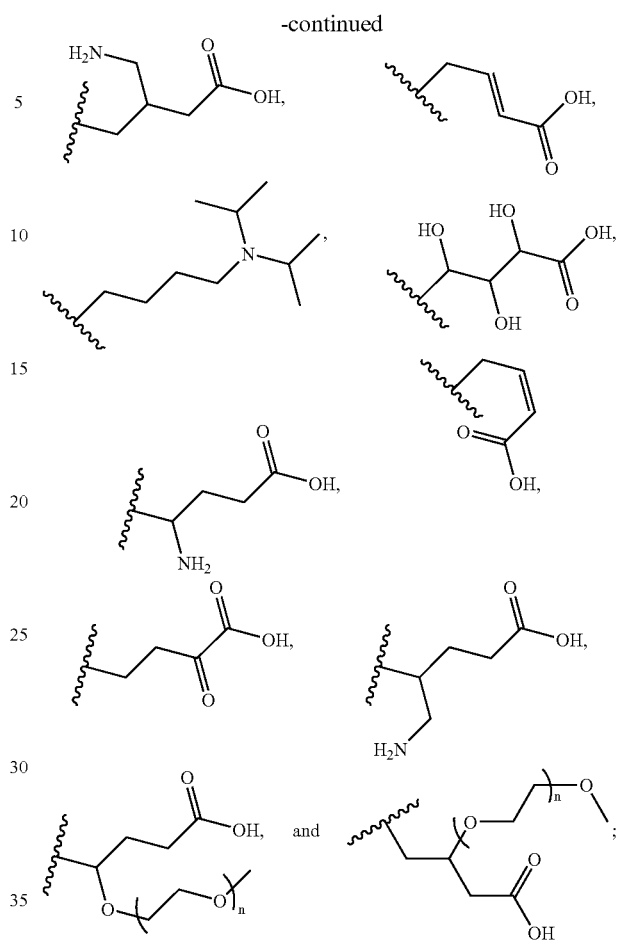

wherein n is an integer equal to or averaging 1-500, 1,000, 2,000, 3,000, 4,000, 5,000, 10,000, 20,000, 30,000, 40,000, 50,000, 60,000.

In another embodiment of formulas I or III, the core pyridine functionality is of the following N-oxide formula:

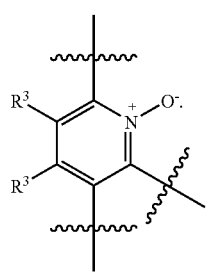

In one embodiment of the compounds of the invention, when J is not F, J is bonded to or N. In another embodiment, when $R^b$ is not F, $R^a$ is —$(R^1)_2$.

Preferred embodiments of formulas I, II, III, IV and V (including pharmaceutically acceptable salts thereof, as well as enantiomers, stereoisomers, rotamers, tautomers, diastereomers, atropisomers or racemates thereof, including N-pyridine-oxides thereof) are shown below in Table A and Table B, and are also considered to be "compounds of the invention."

The compounds of the invention are also referred to herein as "antibiotics" and "EF-Tu inhibitors."

In yet another aspect, the invention provides a compound of the formula VI:

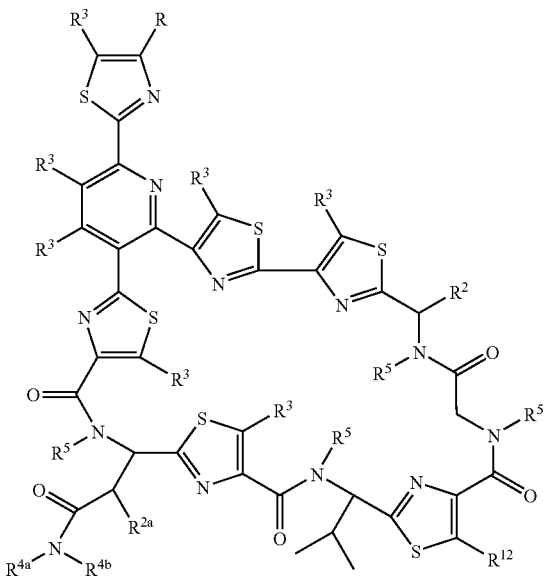

VI and pharmaceutically acceptable salts, enantiomers, stereoisomers, rotamers, tautomers, diastereomers, atropisomers or racemates thereof, including the pyridine N-oxide thereof; wherein R is selected from the group consisting of $N(R^1)_2$, $N(R^1)$-A-G-Q-J, and -(heteroaryl)-A-G-Q-J;

A is a bond or is selected from the group consisting of —C(O)—, —C(O)C(O)—, —C(O)O—, —C(O)N($R^{8a}$)—, —S(O)$_2$—, —S(O)—, —S(O)$_2$N($R^{8a}$)—, —S(O)N($R^{8a}$)—, —C(=N$R^8$)N($R^{8a}$)—, —C(=N$R^8$)N($R^{8a}$)C(O)—, —C(=N$R^8$)—, —C=C—C(O)—, —C=C—C(O)O—, —C=C—C(O)N($R^{8a}$)—;

G is absent, selected from the group consisting of $[C(R^a)(R^b)]_x$—, $[C(R^a)(R^b)]_x$—C($R^a$)=C($R^a$)—$[C(R^a)(R^b)]_y$—, —$[C(R^a)(R^b)]_x$—O—$[C(R^a)(R^b)]_y$—, and —$[C(R^a)(R^b)]_x$—N($R^a$)—$[C(R^a)(R^b)]_y$—, or is selected from the group consisting of -(cycloalkyl)-, -(heterocycle)-, -(aryl)-, and -(heteroaryl)- each of which has 0-4 substituents;

Q is absent, selected from the group consisting of —C(O)—$[C(R^a)(R^b)]_x$—, —C(O)—$[C(R^a)(R^b)]_x$—C($R^a$)=C($R^a$)—$[C(R^a)(R^b)]_y$—, —C(O)—$[C(R^a)(R^b)]_y$—O—$[C(R^a)(R^b)]_y$—, and —C(O)—{N($R^{8a}$)—$[C(R^a)(R^b)]_y\}_p$—, or is selected from the group consisting of -(cycloalkyl)-, -(heterocycle)-, -(aryl)-, -(heteroaryl)-, —C(O)-(cycloalkyl)-, —C(O)-(heterocycle)-, —C(O)-(aryl)-, and —C(O)-(heteroaryl)-, each of which has 0-4 substituents;

J is selected from the group consisting of H, $C_{1-4}$alkyl, halogen, $C_{1-4}$alkoxy, hydroxy, amino, mono- and di-$C_{1-4}$alkylamino, tri$C_{1-4}$alkylammonium, N($R^{3a}$)C(O)$C_{1-4}$alkyl, $CO_2H$, C(=O)N($R^{8a}$)$_2$, $CH_2CO_2H$, $CH_2C$(=O)N($R^{8a}$)$_2$, $CO_2$—$C_{1-4}$alkyl, C(O)$C_{1-4}$alkyl, P(O)(OH)$_2$, P(O)(O—$C_{1-4}$alkyl)$_2$, $C_{0-4}$alkylene-(cycloalkyl) and $C_{0-4}$alkylene-(heterocycle), which heterocycle may be substituted 0-4 times;

$R^a$ is selected from the group consisting of H, alkyl, F, $CO_2H$, $CO_2$-alkyl, —N($R^1$)$_2$, —$OR^1$, —$(CH_2)_{0-4}$-J and —$R^{4b}$;

$R^b$ is selected from the group consisting of H, alkyl, and F; p is 0, 1, 2, or 3;

x and y are each, independently selected at each occurrence from integers from 0-10;

$R^1$ is independently selected at each occurrence from —H, alkyl substituted with J, and —$R^{4b}$.

$R^2$ is hydrogen, $C_{1-6}$alkyl, hydroxy$C_{1-6}$alkyl, $C_{1-6}$alkoxy$C_{0-6}$alkyl, $C_{3-7}$cycloalkyl$C_{0-4}$-alkyl, aryl$C_{0-4}$alkyl, or a residue of the formula:

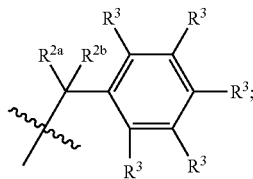

$R^{2a}$ is selected from the group consisting of H, $C_{1-6}$alkyl, OH, $OR^{4a}$, OC(O)$R^{4a}$, OC(O)N($R^{8a}$)$_2$ and N($R^{8a}$)$_2$;

$R^{2b}$ is H or $C_{1-6}$alkyl, or $R^{2a}$ and $R^{2b}$ taken in combination form an oxo or imino group;

$R^3$ and $R^{12}$ are each, independently, selected from the group consisting of H, halogen, $OR^{4b}$-G-J, and N($R^{8a}$)$_2$;

$R^{4a}$ is selected from the group consisting of H and alkyl;

$R^{4b}$ is selected from the group consisting of alkyl and —(CH$_2$—CH$_2$—O—)$_n$—$R^9$, wherein n is an integer of 1-500, 1,000, 2,000, 3,000, 4,000, 5,000, 10,000, 20,000, 30,000, 40,000, 50,000, or 60,000 or is a mean of a plurality of integers having a value of 1-500, 1,000, 2,000, 3,000, 4,000, 5,000, 10,000, 20,000, 30,000, 40,000, 50,000, or 60,000;

$R^5$ is selected from the group consisting of H, alkyl, and $R^{4b}$;

$R^8$ is selected from the group consisting of H, CN, NO$_2$, $C_{1-6}$alkyl, $C_{3-7}$cycloalkyl, and SO$_2$—$C_{1-6}$alkyl;

$R^{8a}$ is absent, or selected from the group consisting of H, $C_{1-6}$alkyl, $C_{3-7}$cycloalkyl, $C^{1-6}$alkyl substituted with J, and $R^{4b}$, or two $R^{8a}$ residues, taken in combination may form a saturated, unsaturated or aromatic ring having 3 to 7 ring atoms, which ring may be substituted 0-4 times; and $R^9$ is selected from the group consisting of H, alkyl and $CH_2CO_2H$.

Certain compounds of Formula VI include those compounds in which $R^2$ is a residue of the formula:

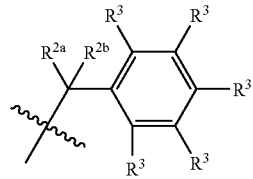

$R^{2a}$ is selected from the group consisting of H, $C_{1-6}$alkyl, OH, $OR^{4a}$, OC(O)$R^{4a}$, OC(O)N($R^{8a}$)$_2$ and N($R^{8a}$)$_2$; and $R^{2b}$ is H or $C_{1-6}$alkyl, or $R^{2a}$ and $R^{2b}$ taken in combination form an oxo or imino group.

Still other compounds of Formula VI include those compounds in which $R^{2b}$, $R^{4b}$ and $R^5$ are H, and $R^{4a}$ is $CH_3$. Certain other compounds of Formula VI include those compounds in which $R^{2b}$, $R^{4b}$ and $R^5$ are H, $R^{4a}$ is $CH_3$, and $R^{12}$ is $CH_2$—O—$CH_3$. Other compounds of Formula VI include compounds in which $R^{2a}$ is OH or OAc and $R^{2b}$ is H. Still other compounds of Formula VI include those compounds in which A is C(O), C(O)O, or C(O)NH; G is $C_{4-7}$cycloalkyl; Q is absent; and J is $CO_2H$ or $CO_2C_{1-4}$alkyl.
Other compounds of Formula VI include those compounds in which R is $N(R^1)$-A-G-Q-J, $R^1$ is H and A-G-Q-J together form H, or together form a functional group selected from the group consisting of
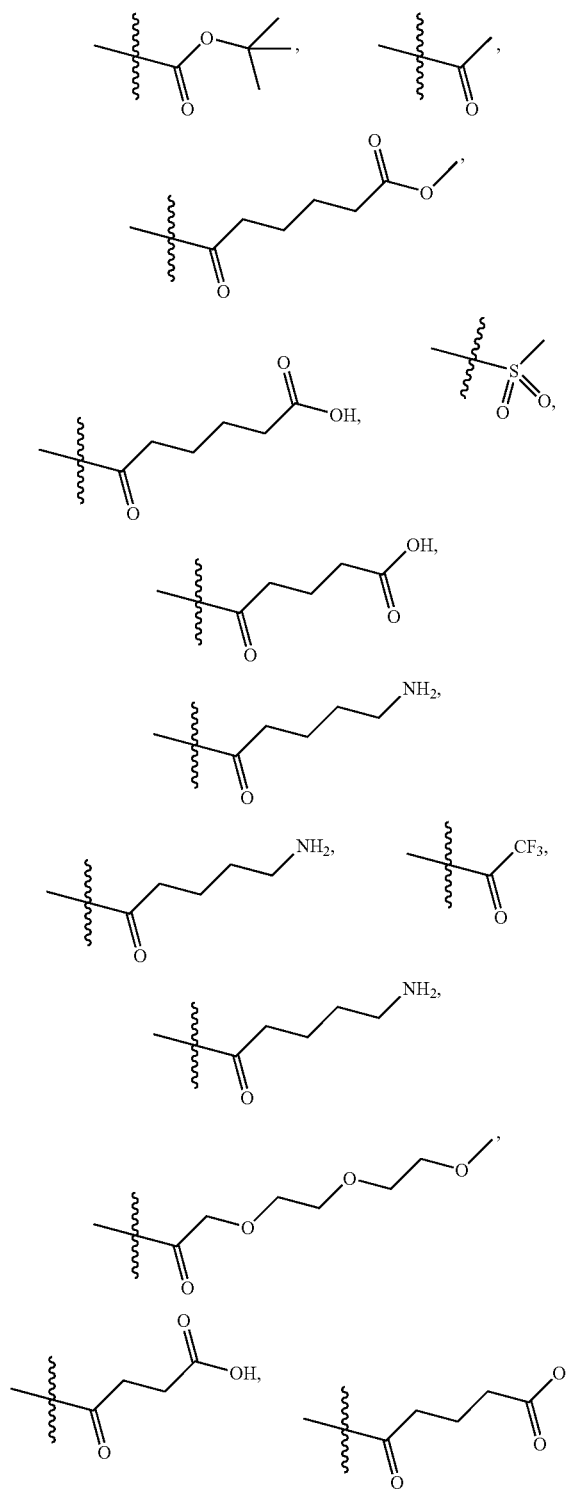
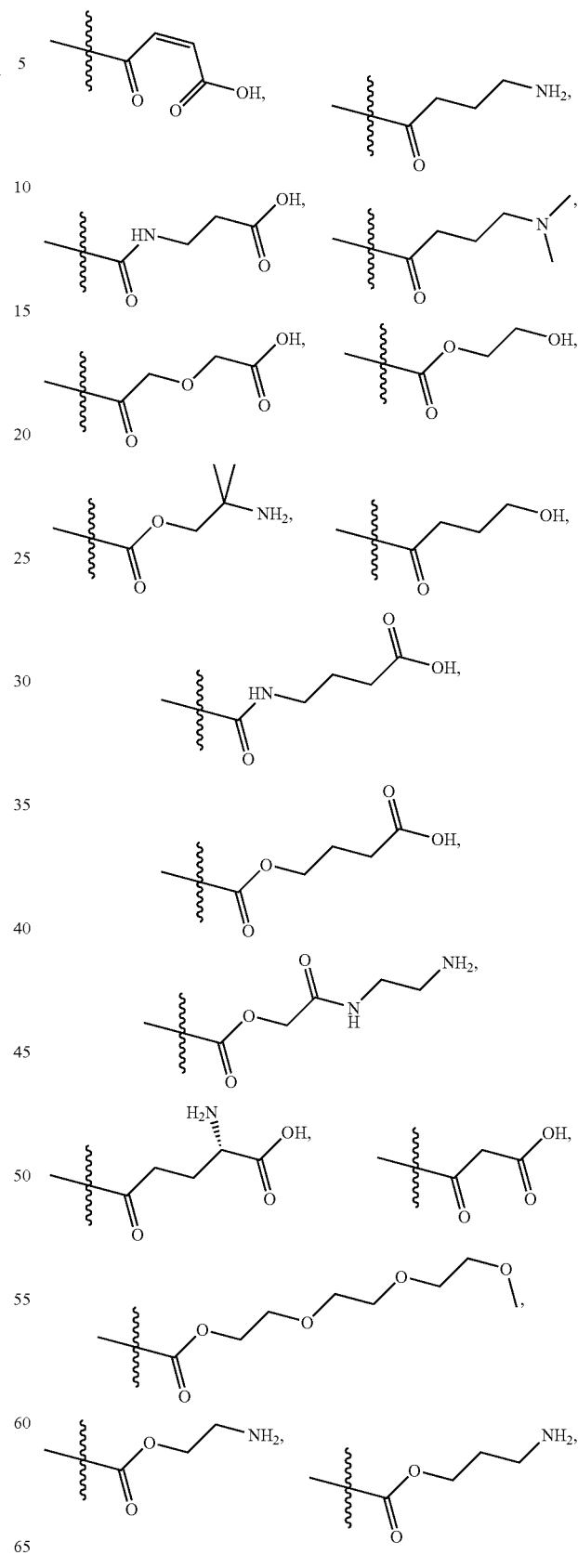

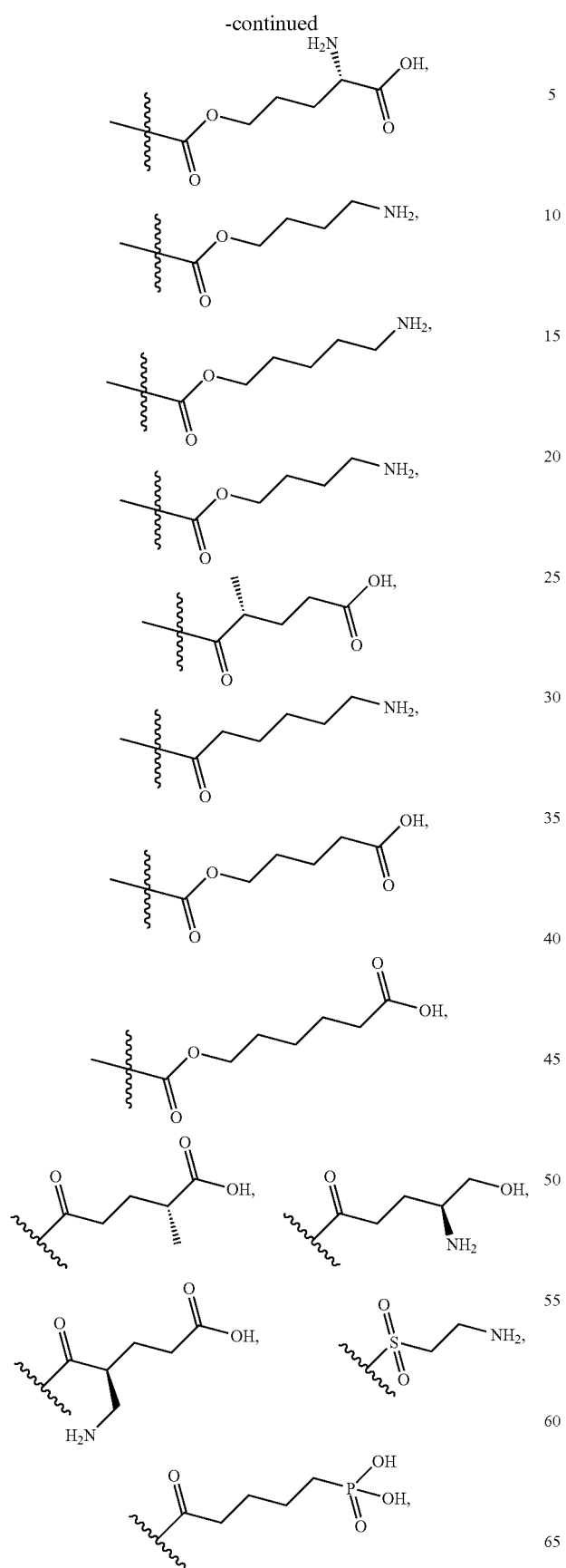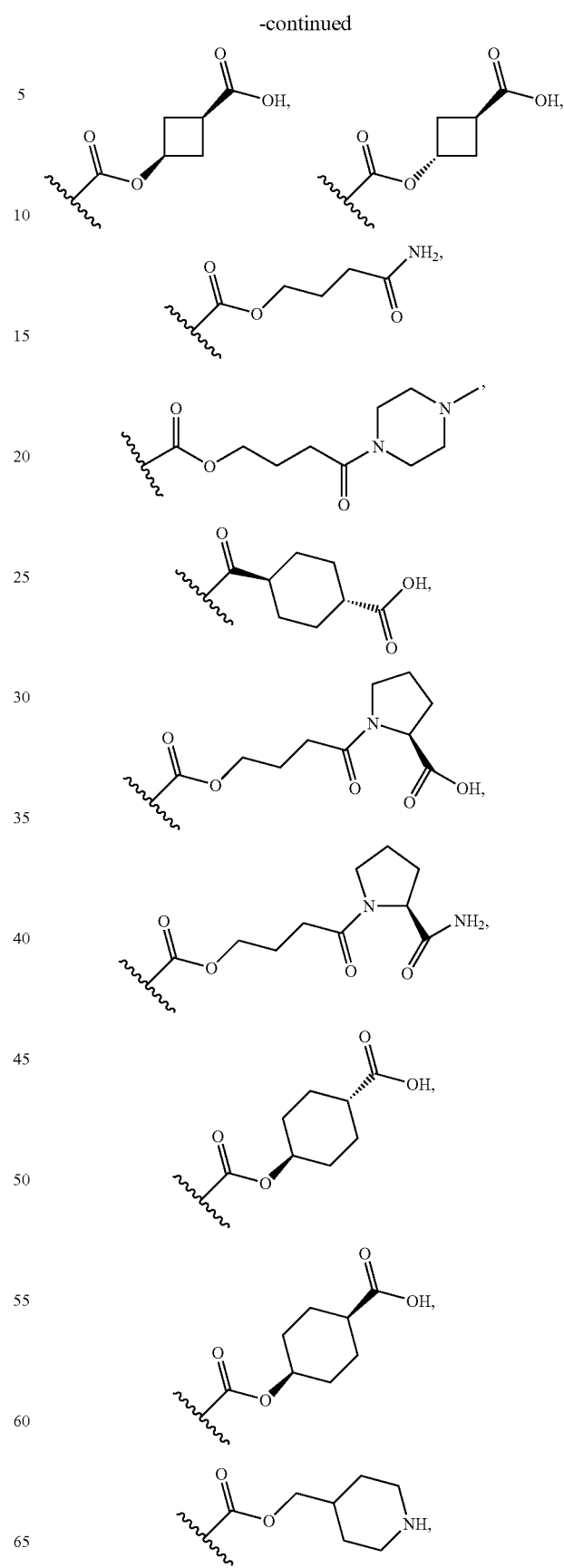

-continued
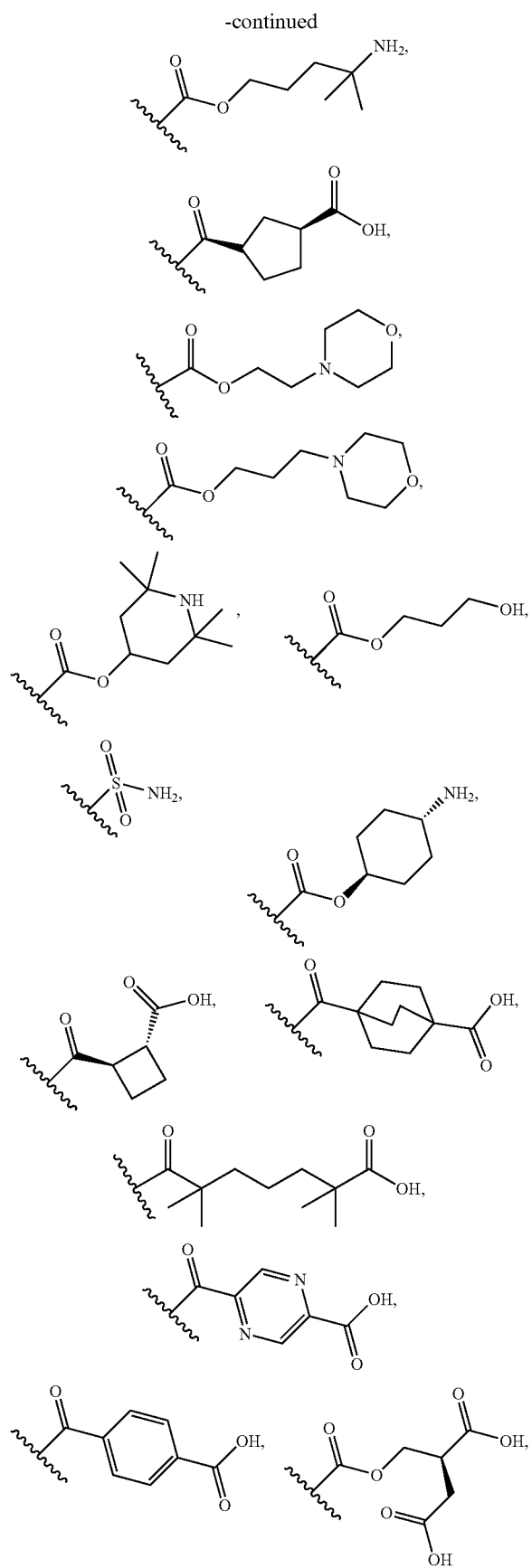
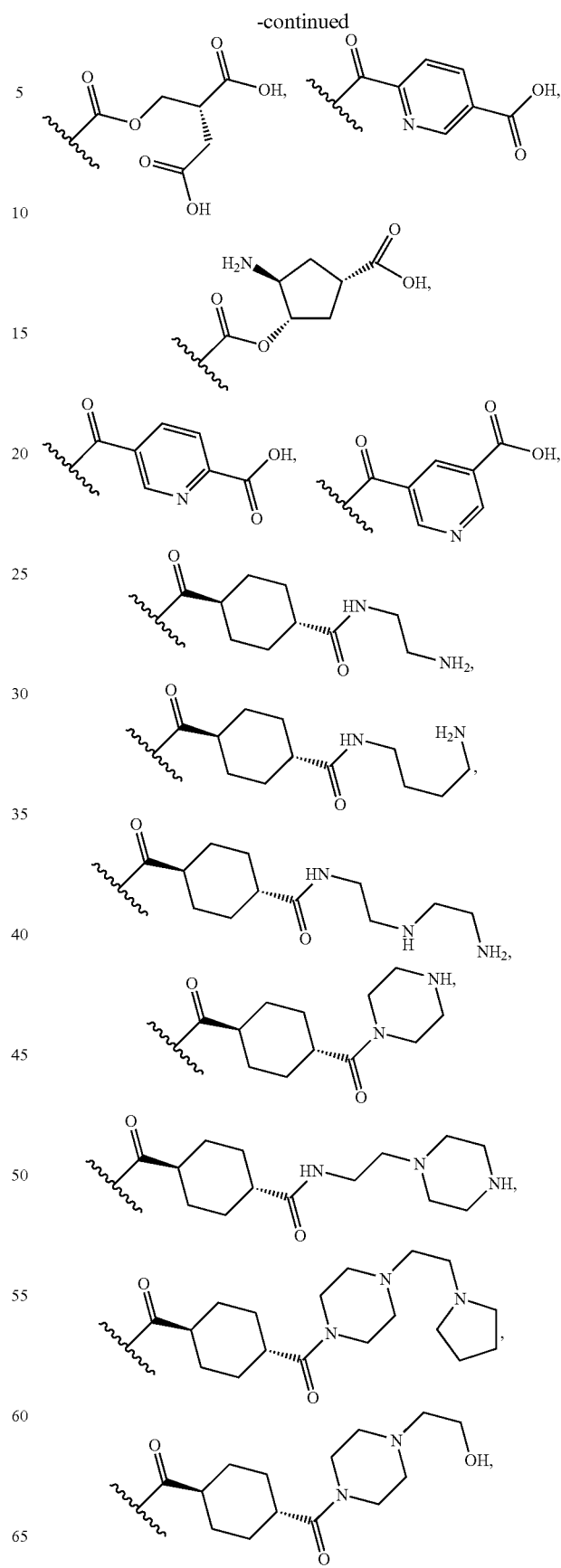

-continued
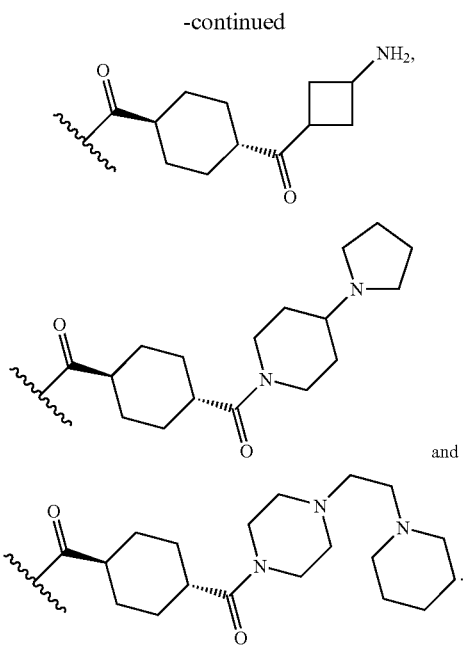
Yet other compounds of Formula VI include those compounds in which R is N(R¹)-A-G-Q-J, R¹ is H and A-G-Q-J together form a functional group selected from the group consisting of
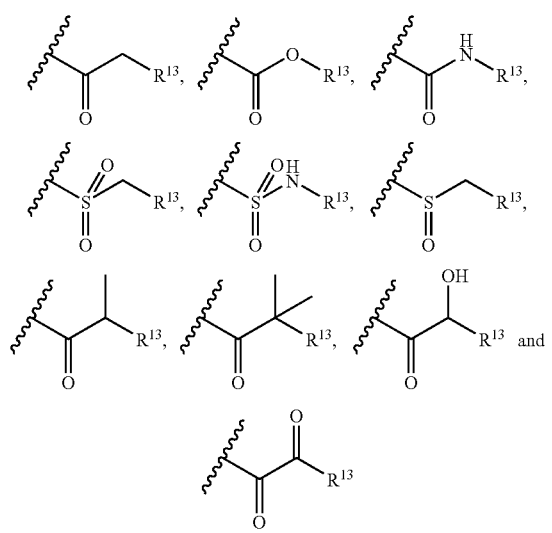
wherein $R^{13}$ is selected from the group consisting of hydrogen, hydroxymethyl, and aminomethyl or from the group consisting of:
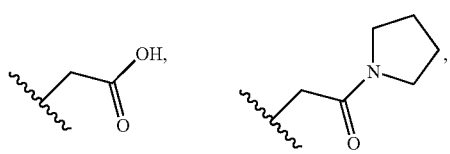
-continued
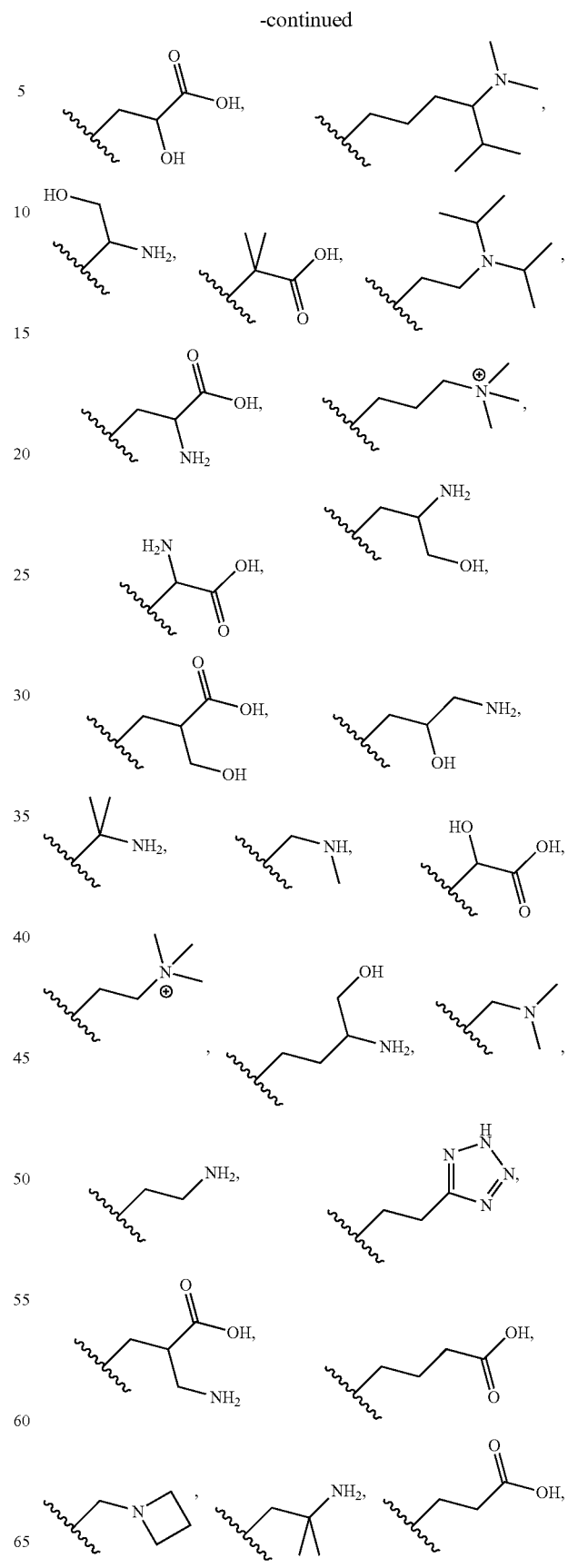

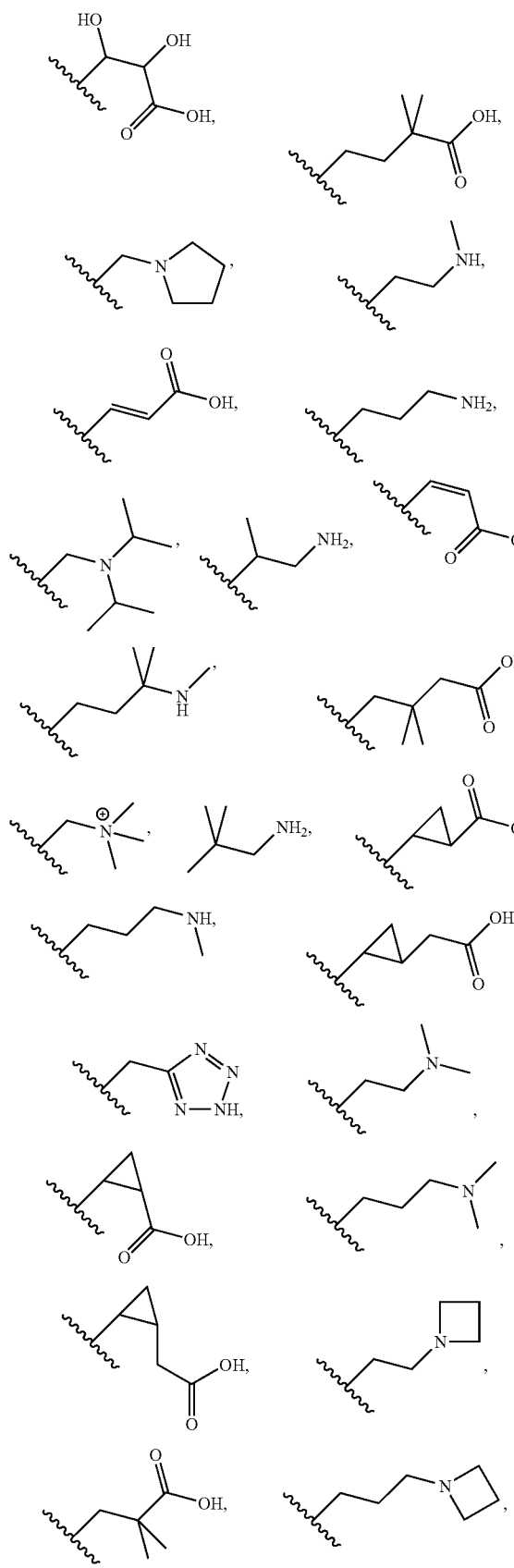
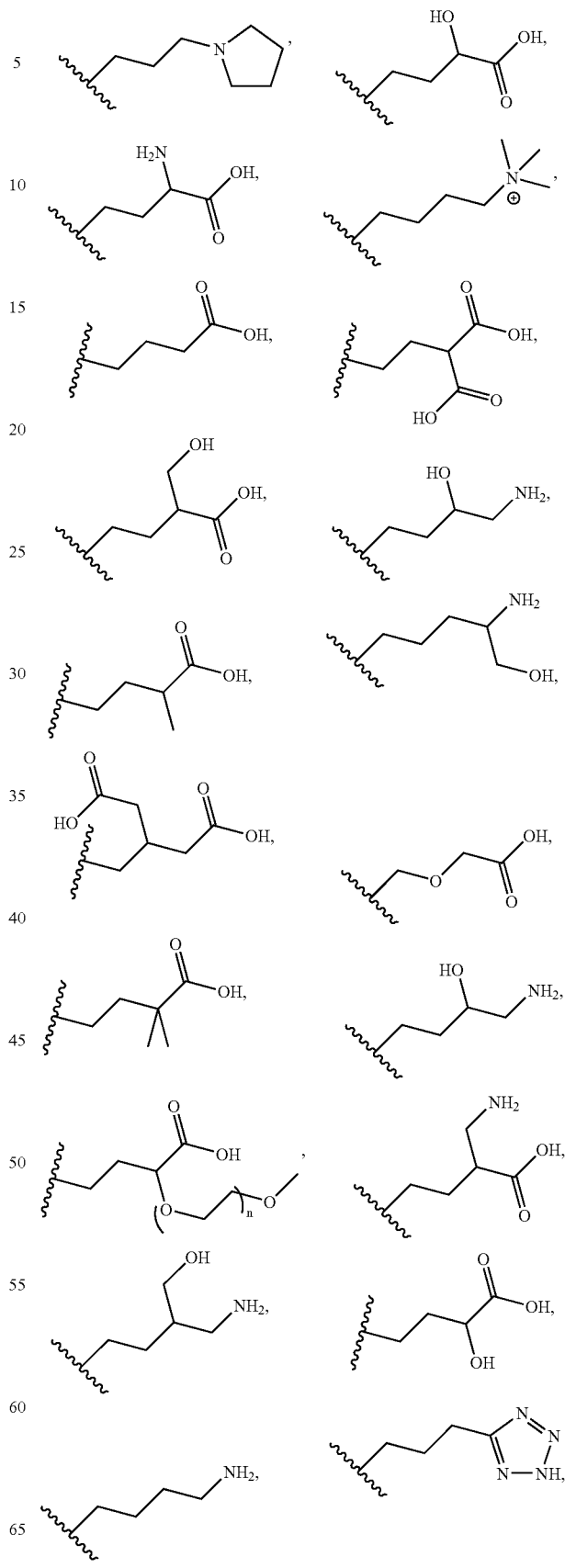

-continued
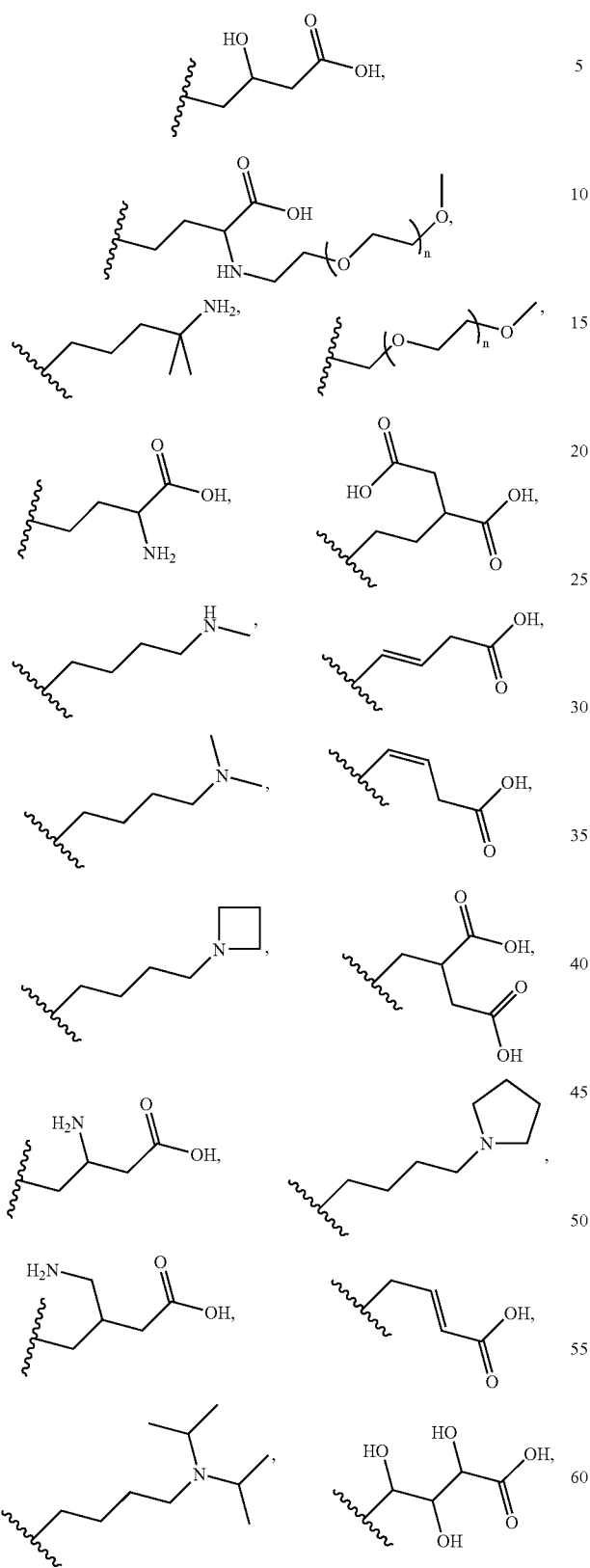
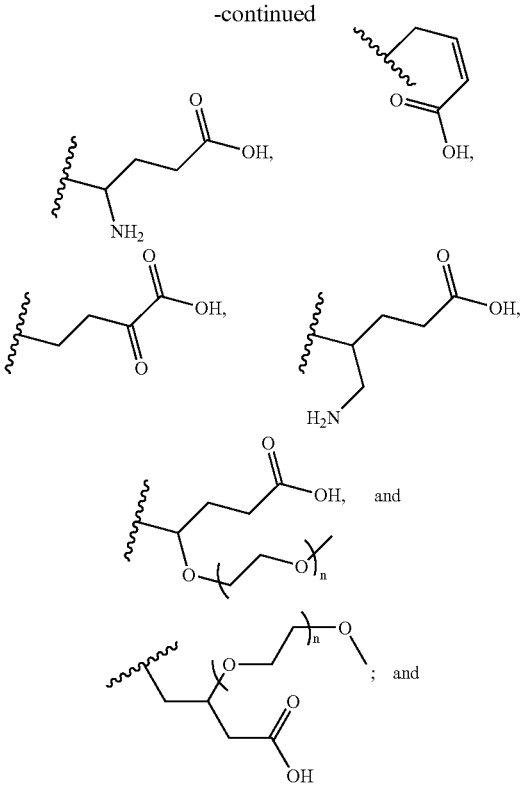
n is an integer of 1-500, 1,000, 2,000, 3,000, 4,000, 5,000, 10,000, 20,000, 30,000, 40,000, 50,000, or 60,000 or is a mean of a plurality of integers having a value of 1-500, 1,000, 2,000, 3,000, 4,000, 5,000, 10,000, 20,000, 30,000, 40,000, 50,000, or 60,000.
Certain preferred compounds of Formula VI include, but are not limited to, compounds of Formula VII:
VII
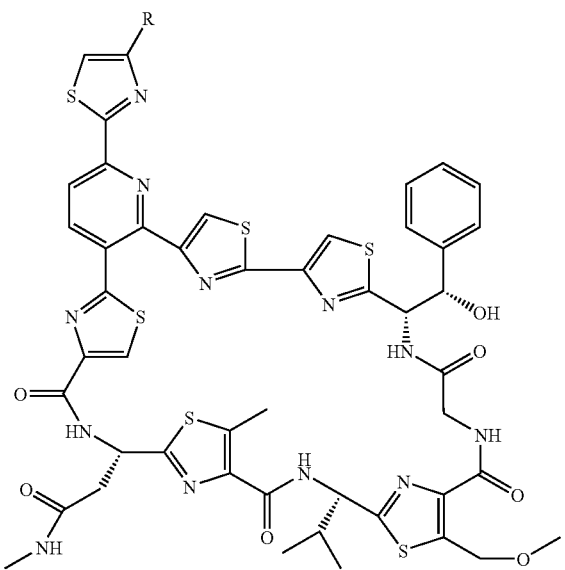
and pharmaceutically acceptable salts thereof.

In yet another aspect, compounds are provided according to Formula VIII:

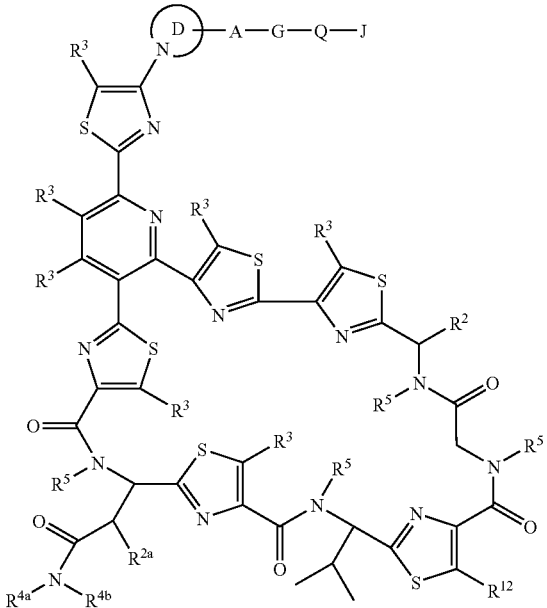

VIII and pharmaceutically acceptable salts, enantiomers, stereoisomers, rotamers, tautomers, diastereomers, atropisomers or racemates thereof, including the pyridine N-oxide thereof; wherein

is a 4-7 membered heteroaryl ring having 0-2 additional ring heteroatoms which is substituted with a -A-G-Q-J residue and 0-4 additional substituents;

A is a bond or is selected from the group consisting of —C(O)—, —C(O)C(O)—, —C(O)O—, —C(O)N($R^{8a}$)—, —S(O)$_2$—, —S(O)—, —S(O)$_2$N($R^{8a}$)—, —S(O)N($R^{8a}$)—, —C(=N$R^8$)N($R^{8a}$)—, —C(=N$R^8$)N($R^{8a}$)C(O)—, —C(=N$R^8$)—, —C=C—C(O)—, —C=C—C(O)O—, —C=C—C(O)N($R^{8a}$)—;

G is absent, selected from the group consisting of [C($R^a$)($R^b$)]$_x$—, [C($R^a$)($R^b$)]$_x$—C($R^a$)=C($R^a$)—[C($R^a$)($R^b$)]$_y$, —[C($R^a$)($R^b$)]$_x$—O—[C($R^a$)($R^b$)]$_y$—, and —[C($R^a$)($R^b$)]$_x$—N($R^{8a}$)—[C($R^a$)($R^b$)]$_y$—, or is selected from the group consisting of -(cycloalkyl)-, -(heterocycle)-, -(aryl)-, and -(heteroaryl)- each of which has 0-4 substituents;

Q is absent, selected from the group consisting of —C(O)—[C($R^a$)($R^b$)]$_x$—, —C(O)-[C($R^a$)($R^b$)]$_x$—C(R)=C($R^a$)—[C($R^a$)($R^b$)]$_y$—, —C(O)—[C($R^a$)($R^b$)]$_x$—O—[C($R^a$)($R^b$)]$_y$—, and —C(O)—{N($R^{8a}$)—[C($R^a$)($R^b$)]$_y$}$_p$—, or is selected from the group consisting of -(cycloalkyl)-, -(heterocycle)-, -(aryl)-, -(heteroaryl)-, —C(O)-(cycloalkyl)-, —C(O)-(heterocycle)-, —C(O)-(aryl)-, and —C(O)-(heteroaryl)-, each of which has 0-4 substituents;

J is selected from the group consisting of H, $C_{1-4}$alkyl, halogen, $C_{1-4}$alkoxy, hydroxy, amino, mono- and di-$C_{1-4}$alkylamino, tri$C_{1-4}$alkylammonium, N($R^{3a}$)C(O)$C_{1-4}$alkyl, CO$_2$H, C(=O)N($R^{8a}$)$_2$, CH$_2$CO$_2$H, CH$_2$C(=O)N($R^{8a}$)$_2$, CO$_2$—$C_{1-4}$alkyl, C(O)$C_{1-4}$alkyl, P(O)(OH)$_2$, P(O)(O—$C_{1-4}$alkyl)$_2$, $C_{0-4}$alkylene-(cycloalkyl) and $C_{0-4}$alkylene-(heterocycle), which heterocycle may be substituted 0-4 times;

$R^a$ is selected from the group consisting of H, alkyl, F, CO$_2$H, CO$_2$-alkyl, —N($R^1$)$_2$, —OR$^1$, —(CH$_2$)$_{0-4}$-J and —$R^{4b}$;

$R^b$ is selected from the group consisting of H, alkyl, and F;

p is 0, 1, 2, or 3;

x and y are each, independently selected at each occurrence from integers from 0-10;

$R^1$ is independently selected at each occurrence from —H, alkyl substituted with J, and $R^{4b}$.

$R^2$ is hydrogen, $C_{1-6}$alkyl, hydroxy$C_{1-6}$alkyl, $C_{1-6}$alkoxy$C_{0-6}$alkyl, $C_{3-7}$cycloalkyl$C_{0-4}$-alkyl, aryl$C_{0-4}$-alkyl, or a residue of the formula:

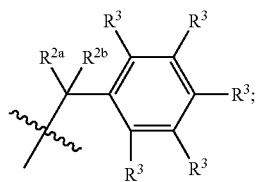

$R^{2a}$ is selected from the group consisting of H, $C_{1-6}$alkyl, OH, OR$^{4a}$, OC(O)R$^{8a}$, OC(O)N($R^{8a}$)$_2$ and N($R^{8a}$)$_2$;

$R^{2b}$ is H or $C_{1-6}$alkyl, or $R^{2a}$ and $R^{2b}$ taken in combination form an oxo or imino group;

$R^3$ and $R^{12}$ are each, independently, selected from the group consisting of H, halogen, OR$^{4b}$, -G-J, and N($R^{8a}$)$_2$;

$R^{4a}$ is selected from the group consisting of H and alkyl;

$R^{4b}$ is selected from the group consisting of alkyl and —(CH$_2$—CH$_2$—O—)$_n$—$R^9$, wherein n is an integer of 1-500, 1,000, 2,000, 3,000, 4,000, 5,000, 10,000, 20,000, 30,000, 40,000, 50,000, or 60,000 or is a mean of a plurality of integers having a value of 1-500, 1,000, 2,000, 3,000, 4,000, 5,000, 10,000, 20,000, 30,000, 40,000, 50,000, or 60,000;

$R^5$ is selected from the group consisting of H, alkyl, and $R^{4b}$;

$R^8$ is selected from the group consisting of H, CN, NO$_2$, $C_{1-6}$alkyl, $C_{3-7}$cycloalkyl, and SO$_2$—$C_{1-6}$alkyl;

$R^{8a}$ is absent, or selected from the group consisting of H, $C_{1-6}$alkyl, $C_{3-7}$cycloalkyl, $C_{1-6}$alkyl substituted with J, and $R^{4b}$, or two $R^{8a}$ residues, taken in combination may form a saturated, unsaturated or aromatic ring having 3 to 7 ring atoms, which ring may be substituted 0-4 times; and $R^9$ is selected from the group consisting of H, alkyl and CH$_2$CO$_2$H.

Certain compounds of Formula VI include those compounds in which $R^2$ is a residue of the formula:

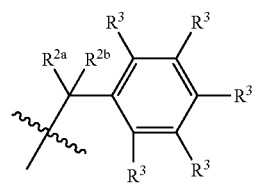

$R^{2a}$ is selected from the group consisting of H, $C_{1-6}$alkyl, OH, OR$^{4a}$, OC(O)R$^{4a}$, OC(O)N($R^{8a}$)$_2$ and N($R^{8a}$)$_2$; and $R^{2b}$ is H or $C_{1-6}$alkyl, or $R^{2a}$ and $R^{2b}$ taken in combination form an oxo or imino group.

Still other compounds of Formula VIII include those compounds in which $R^{2b}$, $R^{4b}$ and $R^5$ are H, and $R^{4a}$ is $CH_3$. Certain other compounds of Formula VIII include those compounds in which $R^{2b}$, $R^{4b}$ and $R^5$ are H, $R^{4a}$ is $CH_3$, and $R^{12}$ is $CH_2$—O—$CH_3$. Other compounds of Formula VIII include compounds in which $R^{2a}$ is OH or OAc and $R^{2b}$ is H. Still other compounds of Formula VIII include those compounds in which A is C(O), C(O)O, or C(O)NH; G is $C_{4-7}$cycloalkyl; Q is absent; and J is $CO_2H$ or $CO_2C_{1-4}$alkyl.

Still other compounds of Formula VIII include those compounds in which the

residue is an imidazolyl ring substituted with A-G-Q-J; and A-G-Q-J together form H, or together form a functional group selected from the group consisting of

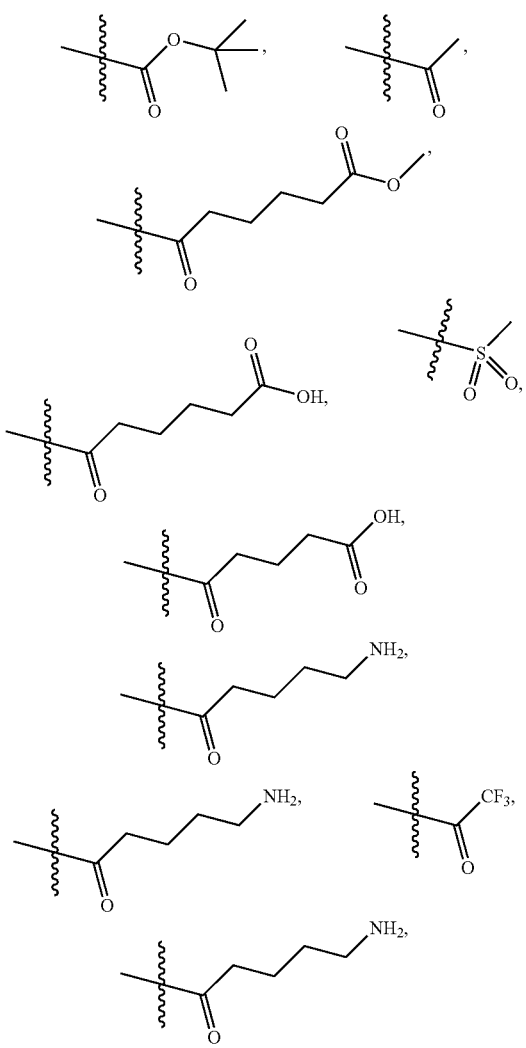

-continued

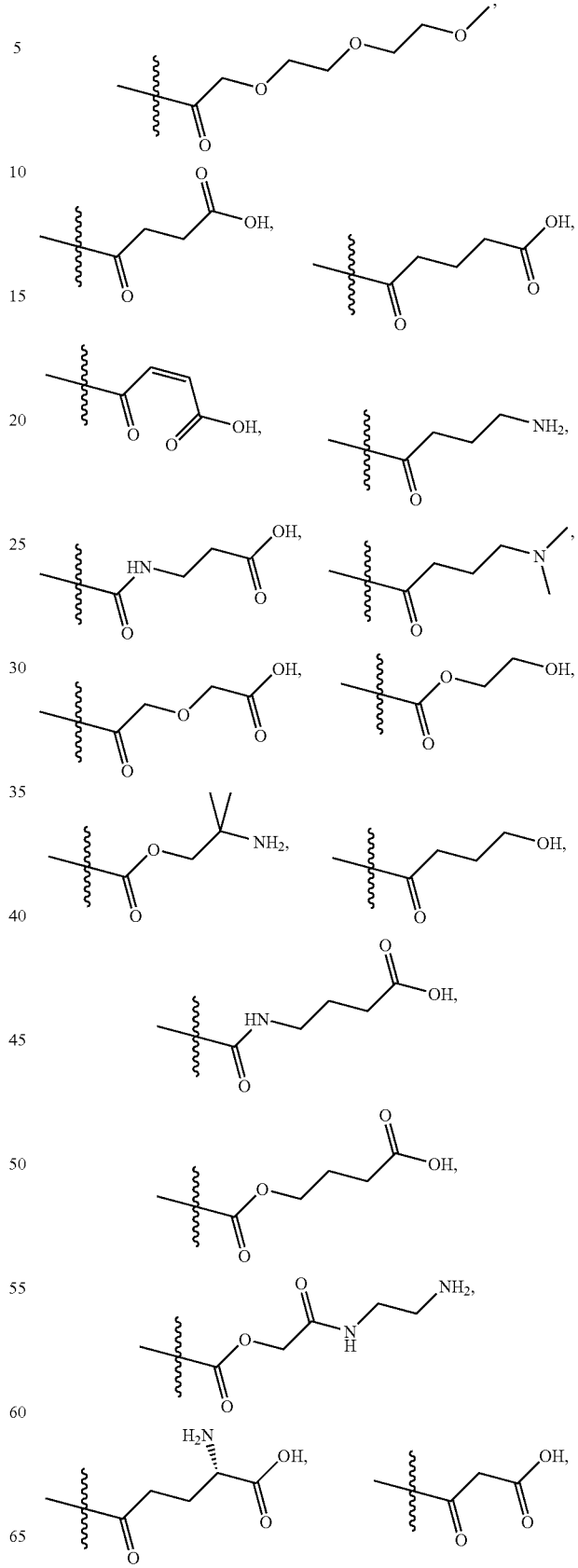

-continued
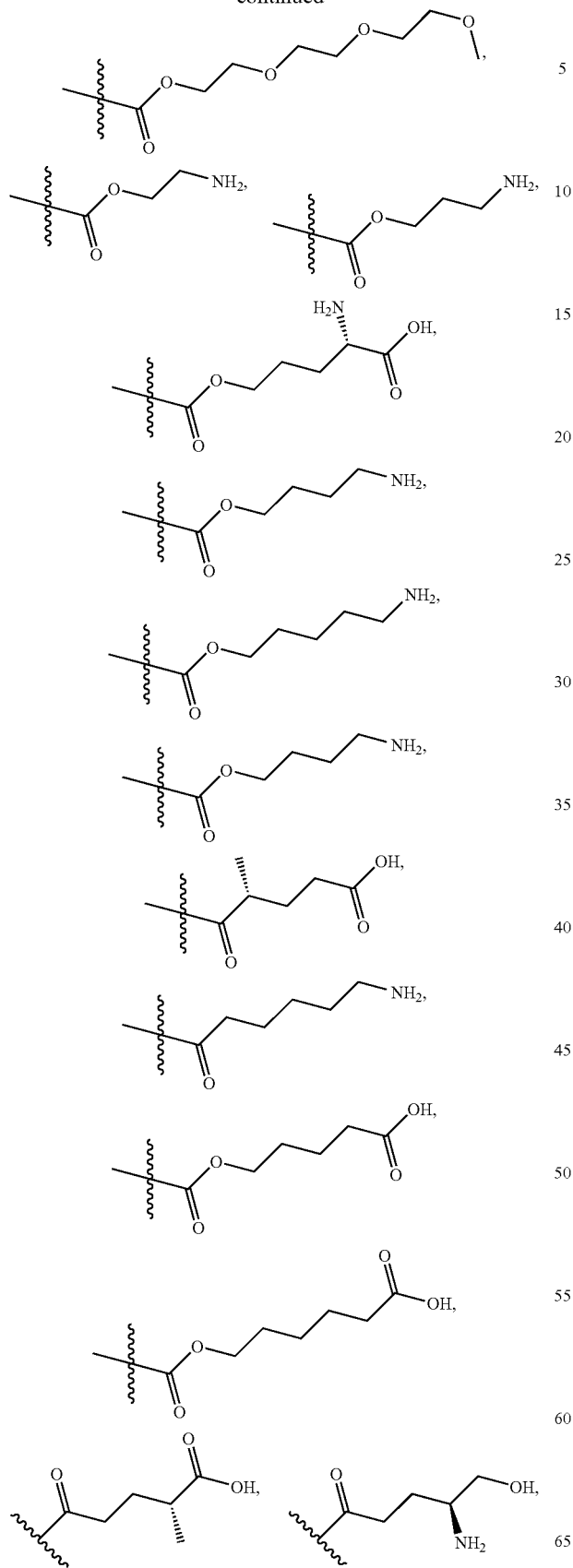
-continued
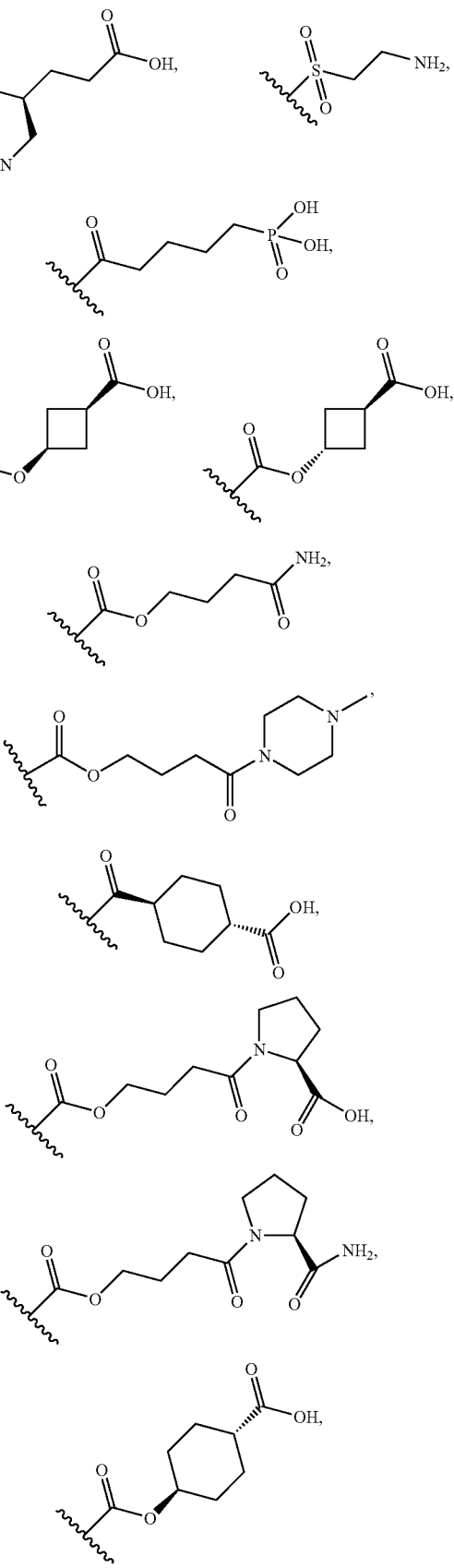

-continued
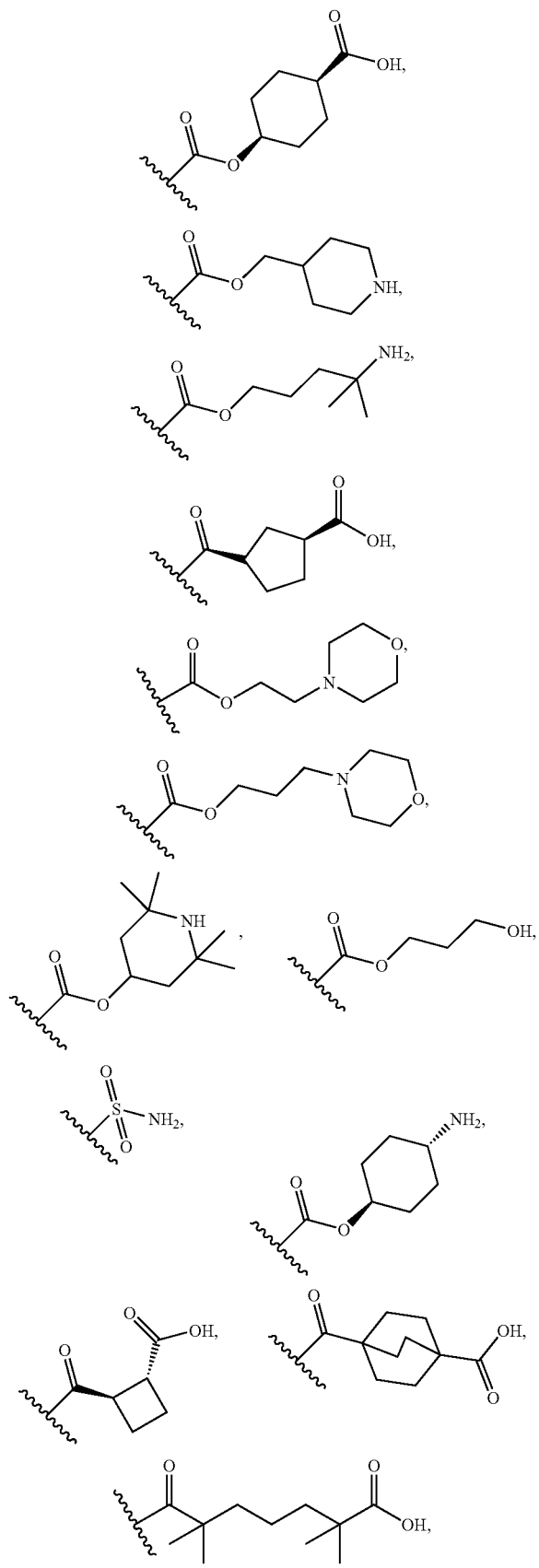
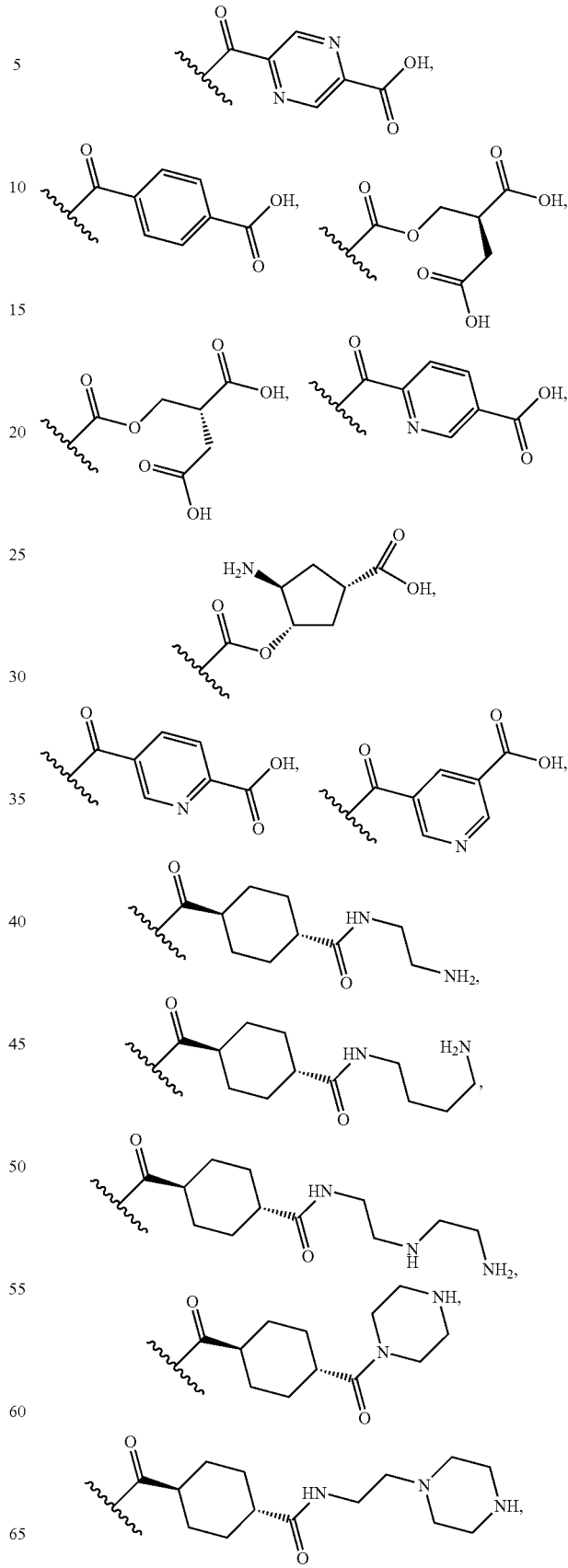

-continued

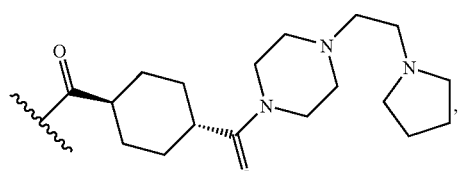

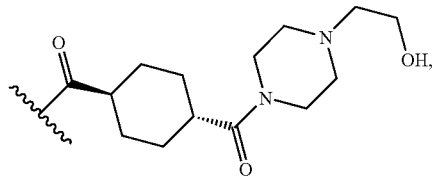

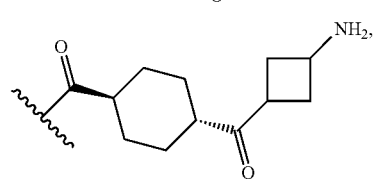

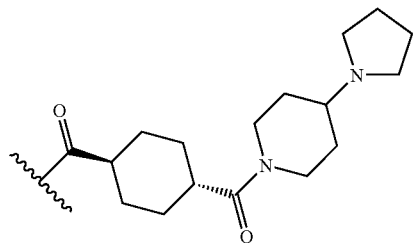

and

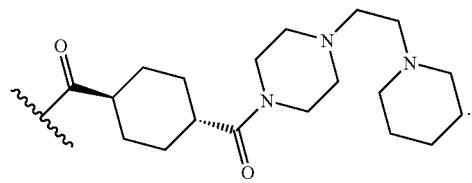

Still other compounds of Formula VIII include those compounds in which the

residue is an imidazolyl ring substituted with A-G-Q-J; and A-G-Q-J together form a functional group selected from the group consisting of

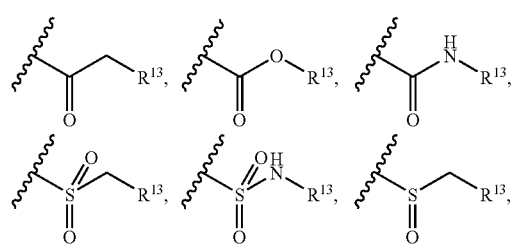

-continued

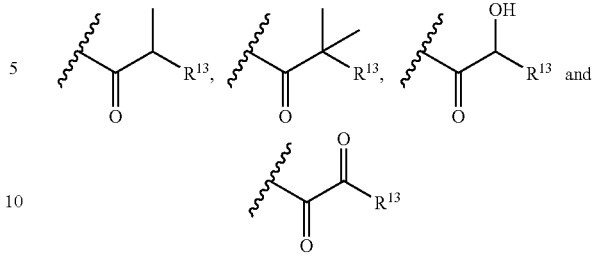

wherein $R^{13}$ is selected from the group consisting of hydrogen, hydroxymethyl, and aminomethyl or from the group consisting of:

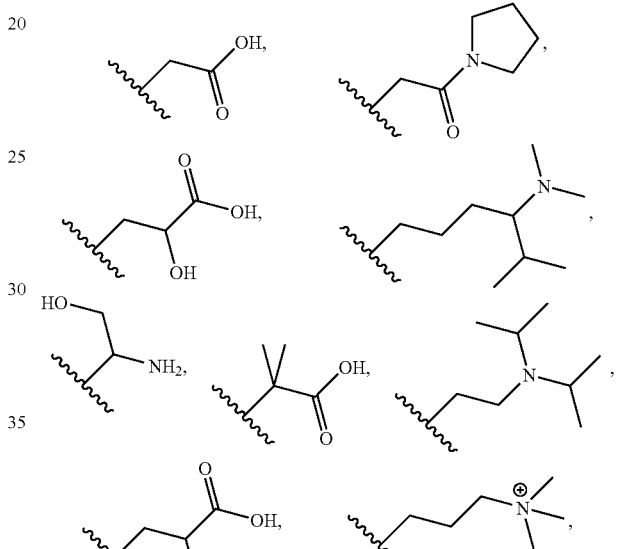

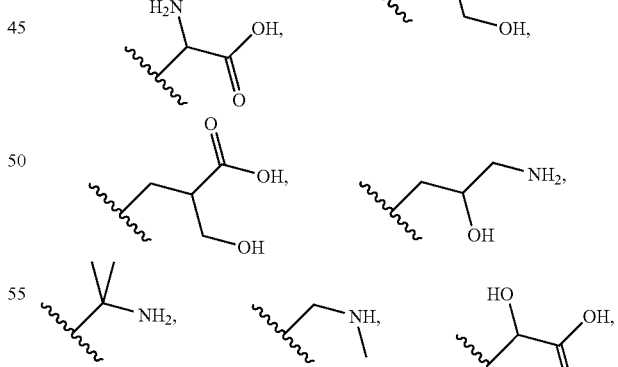

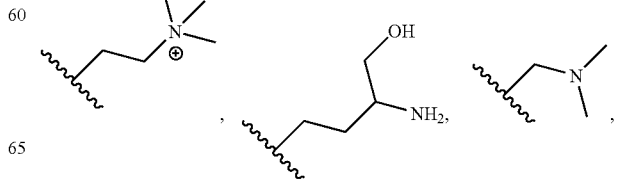

-continued
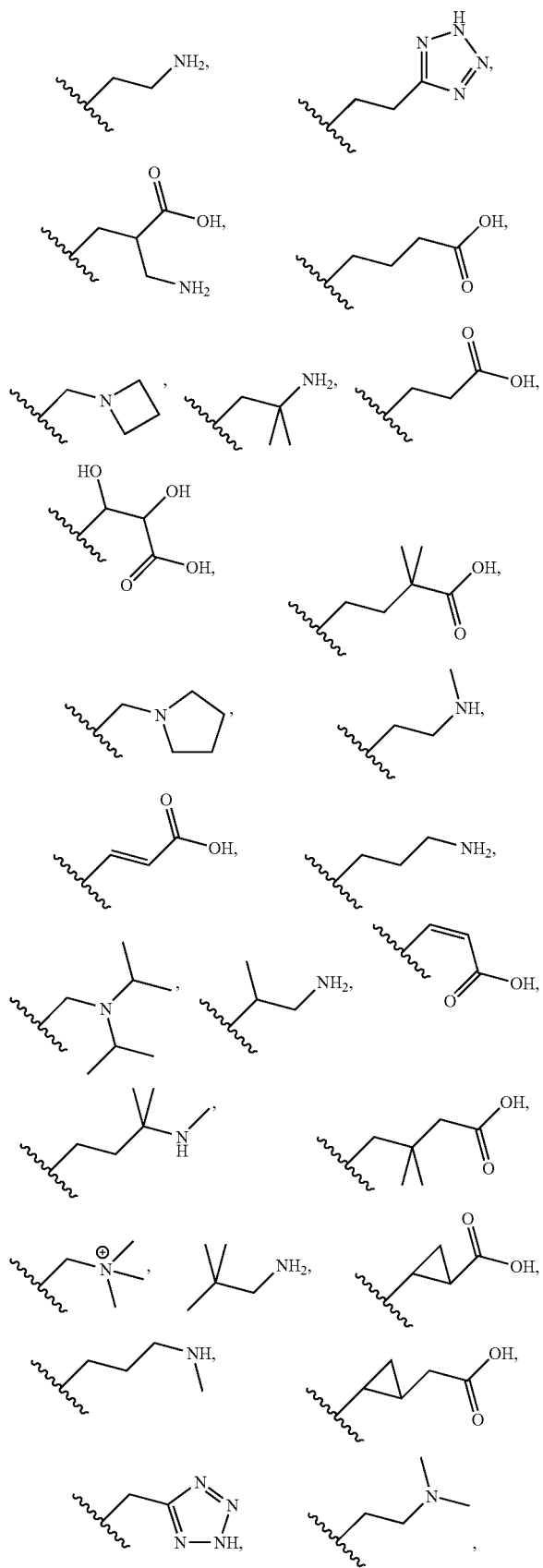
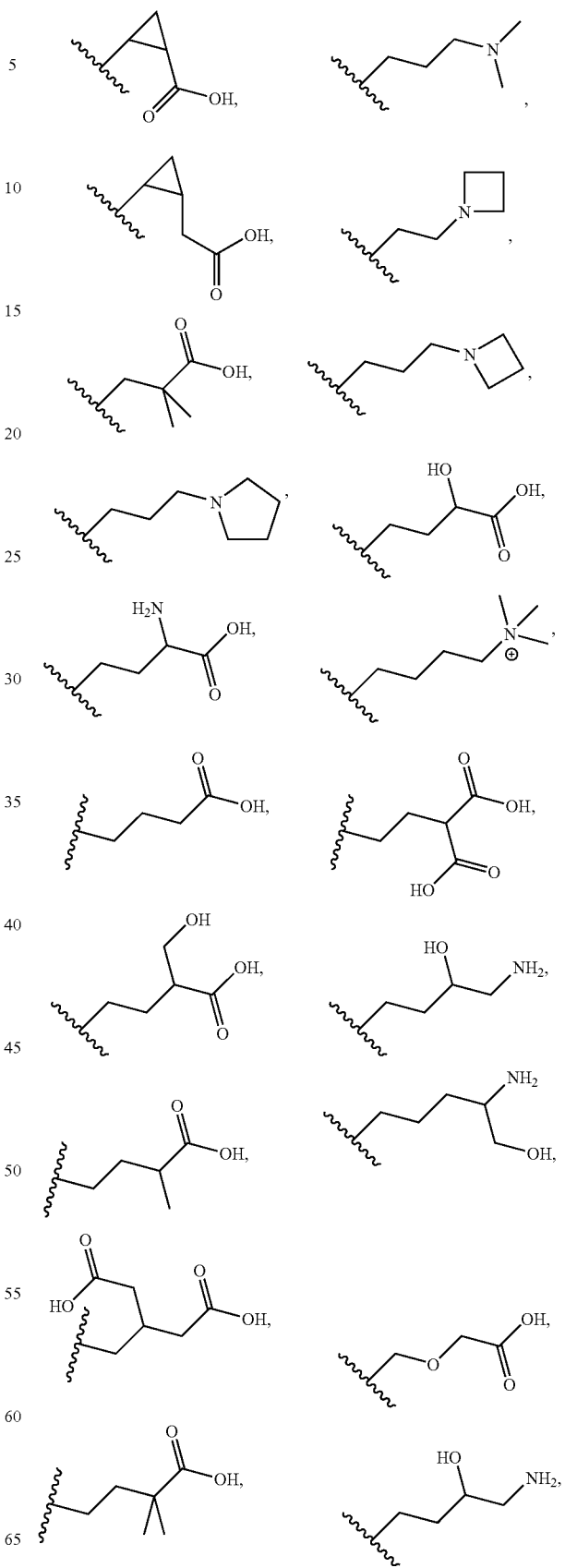

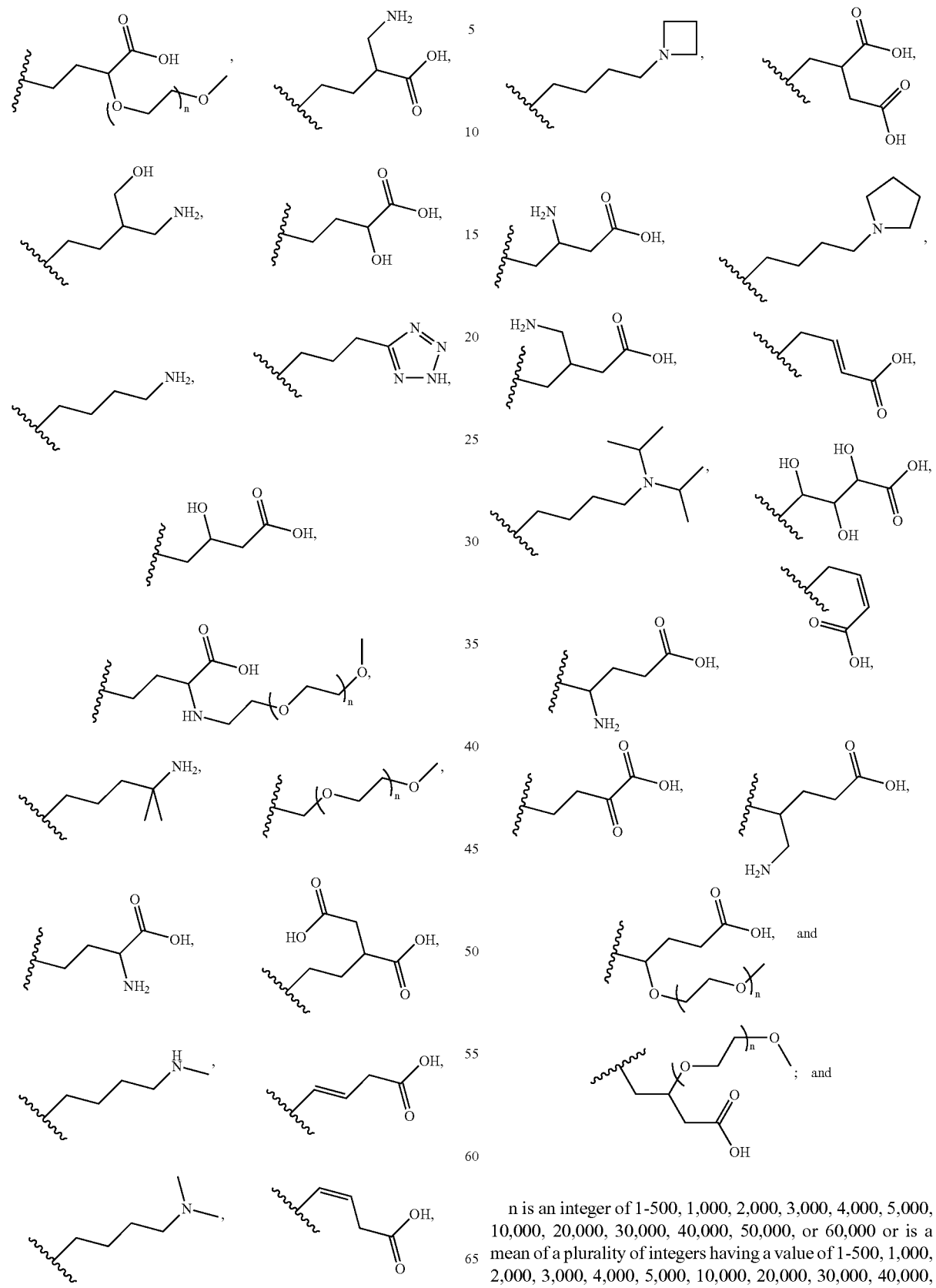
n is an integer of 1-500, 1,000, 2,000, 3,000, 4,000, 5,000, 10,000, 20,000, 30,000, 40,000, 50,000, or 60,000 or is a mean of a plurality of integers having a value of 1-500, 1,000, 2,000, 3,000, 4,000, 5,000, 10,000, 20,000, 30,000, 40,000, 50,000, or 60,000.

TABLE A
| Compound | Structure |
|---|---|
| 1 | 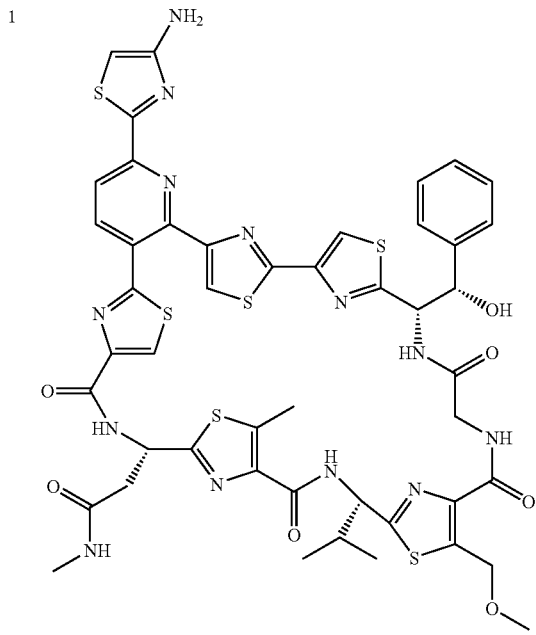 |
| 2 | 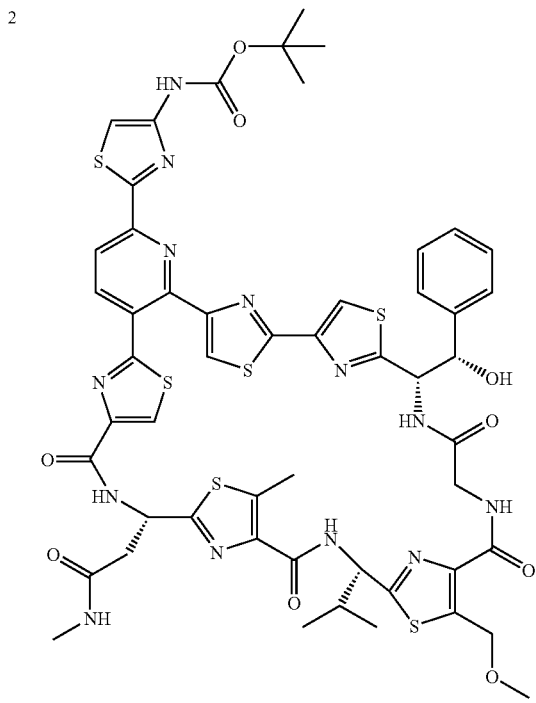 |
TABLE A-continued
| Compound | Structure |
|---|---|
| 3 | 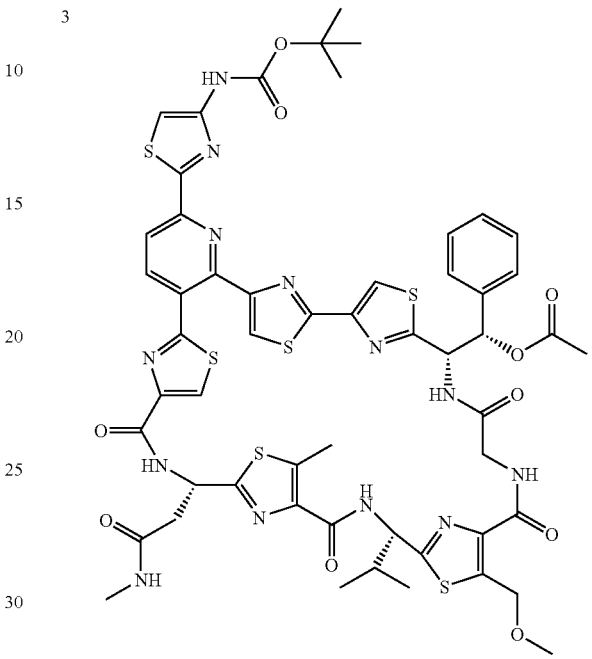 |
| 4 | 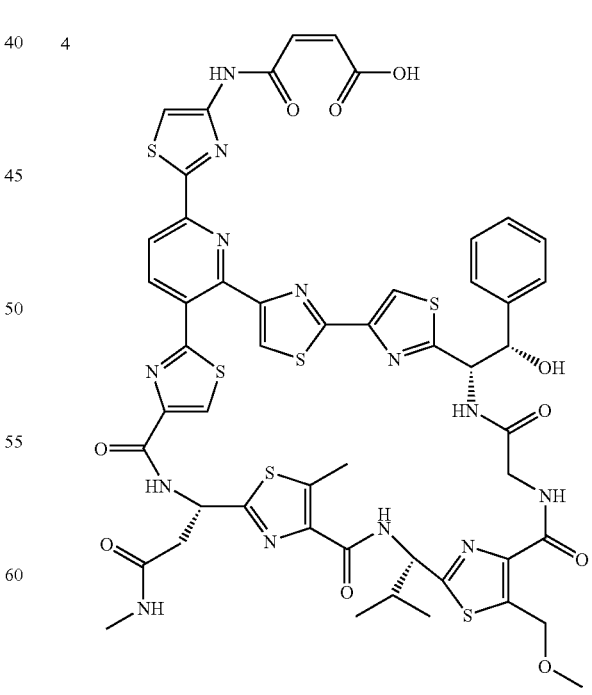 |

TABLE A-continued
| Compound | Structure |
|---|---|
| 5 | 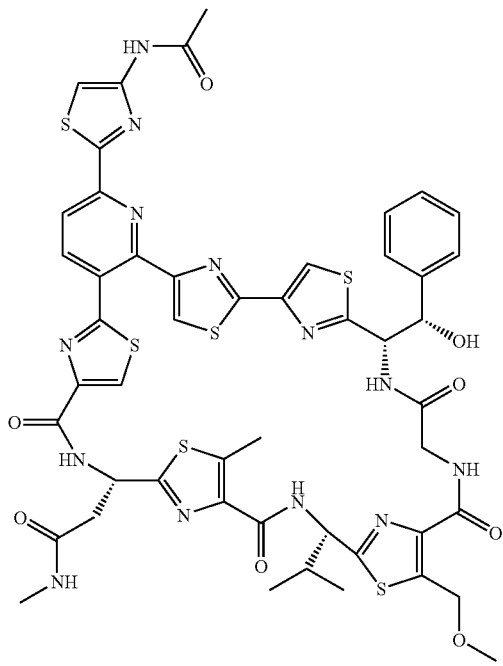 |
| 6 | 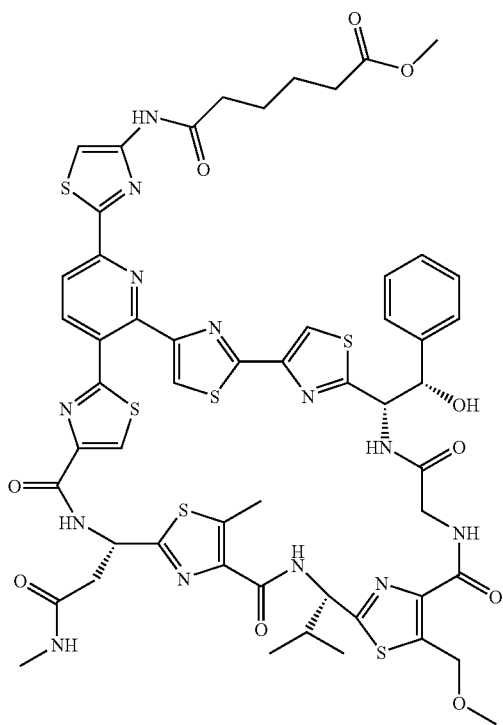 |
| 7 | 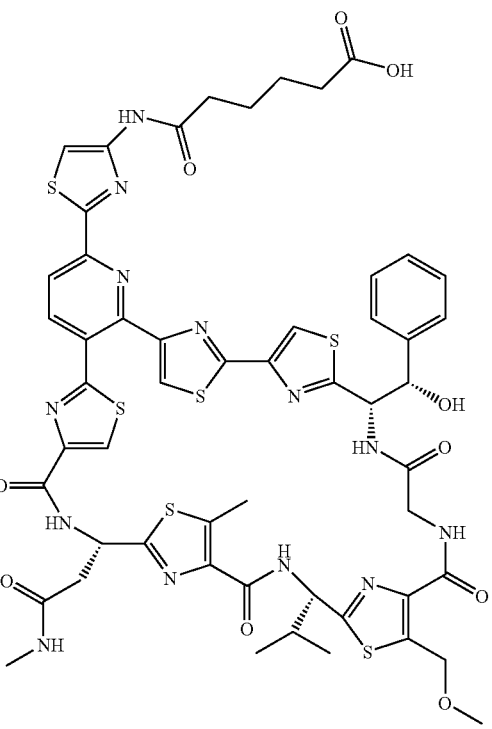 |
| 8 | 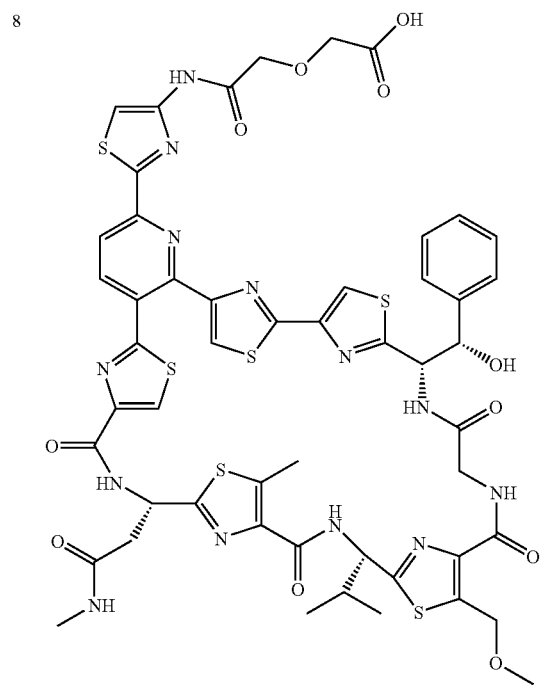 |

TABLE A-continued

| Compound | Structure |
|---|---|
| 9 | (chemical structure) |
| 10 | (chemical structure) |
| 11 | (chemical structure) |
| 12 | (chemical structure) |

TABLE A-continued
| Compound | Structure |
|---|---|
| 13 | 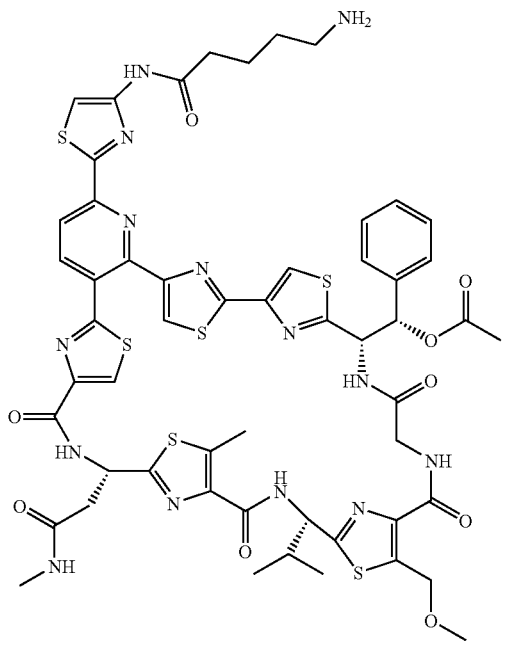 |
| 14 | 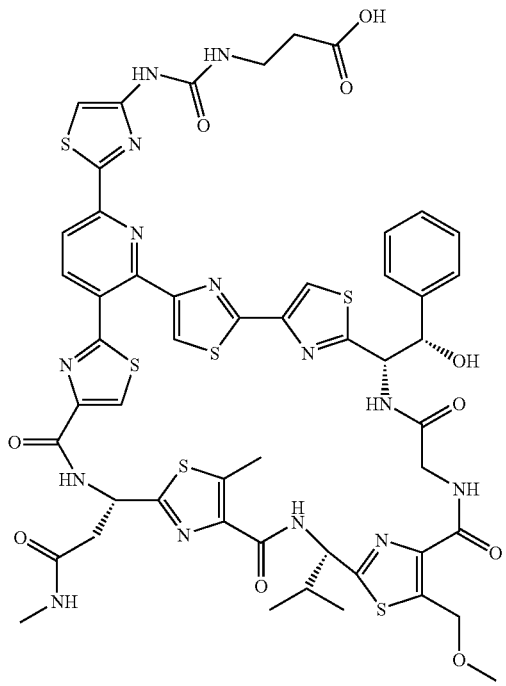 |
| 15 | 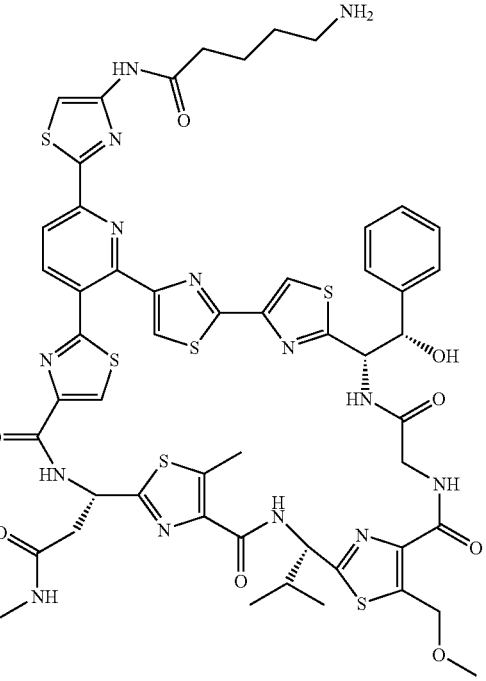 |
| 16 | 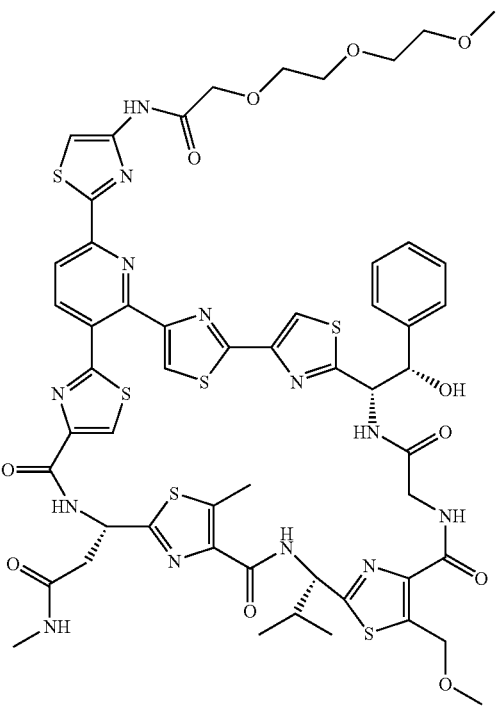 |

TABLE A-continued
| Compound | Structure |
|---|---|
| 17 | 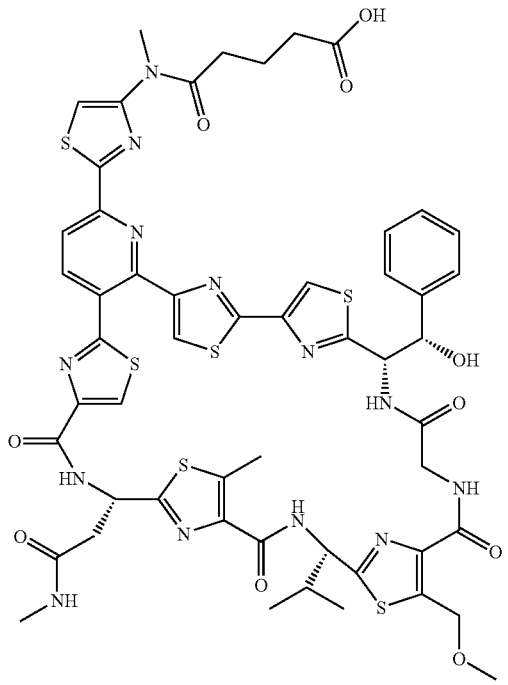 |
| 18 | 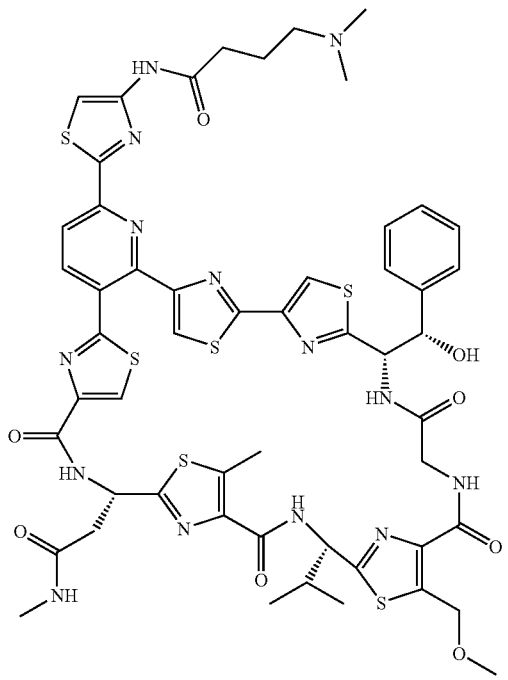 |
| 19 | 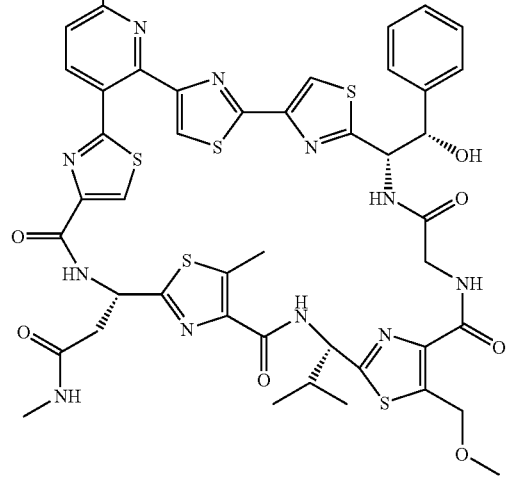 |
| 20 | 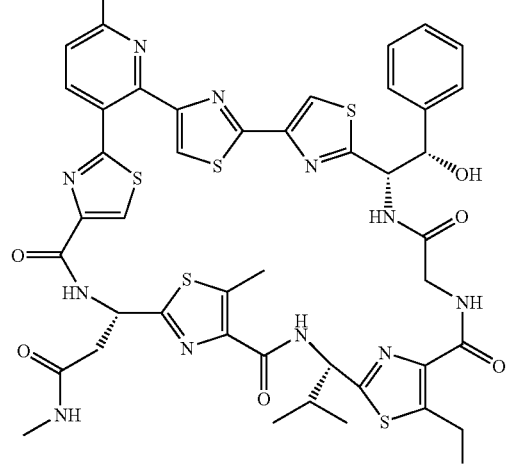 |

TABLE A-continued
| Compound | Structure |
|---|---|
| 21 | 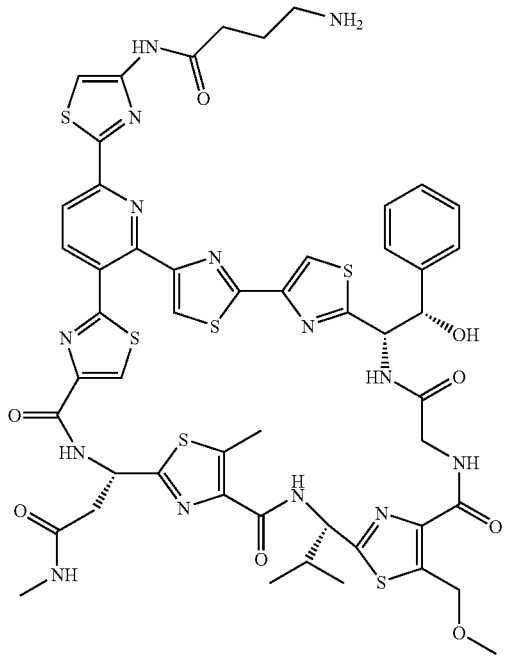 |
| 22 | 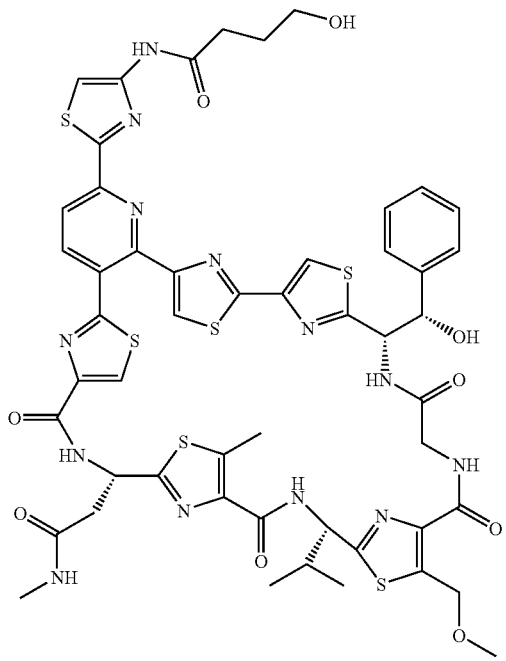 |
| 23 | 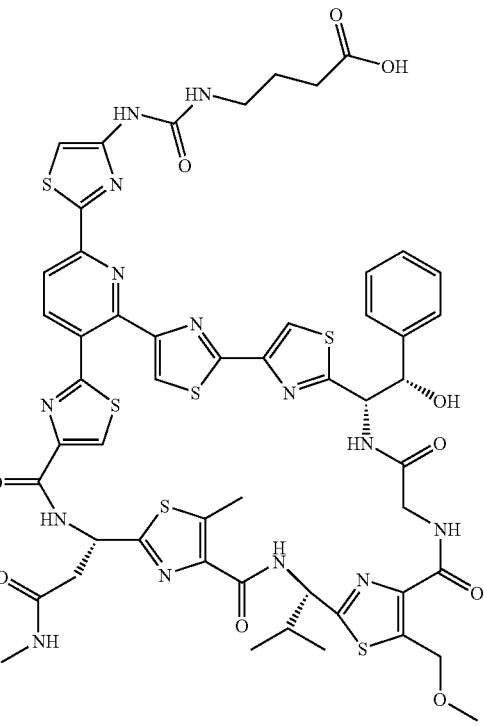 |
| 24 | 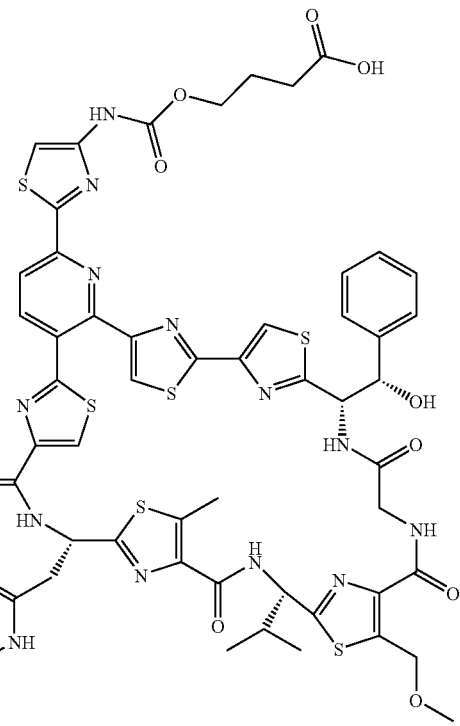 |

TABLE A-continued
| Compound | Structure |
|---|---|
| 25 | 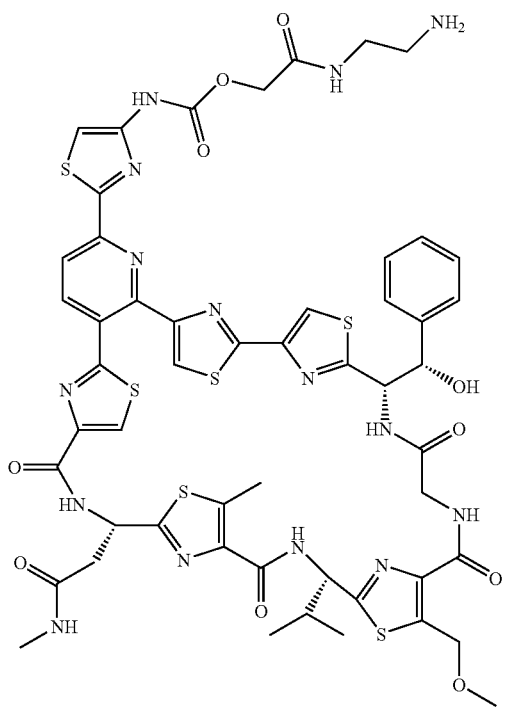 |
| 26 | 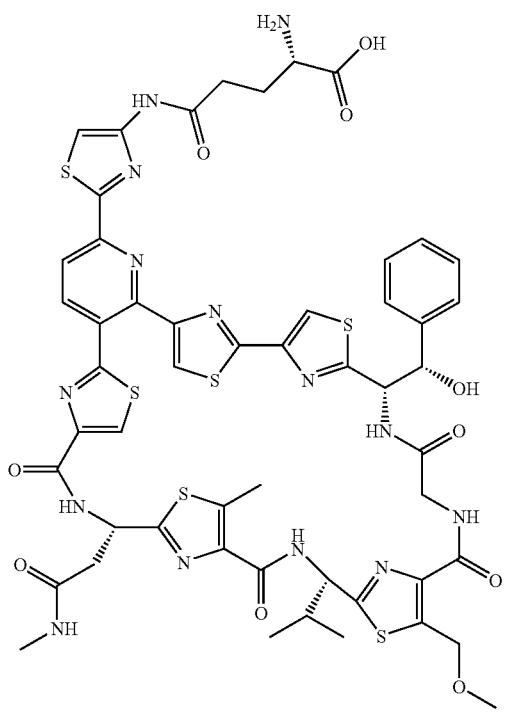 |
TABLE A-continued
| Compound | Structure |
|---|---|
| 27 | 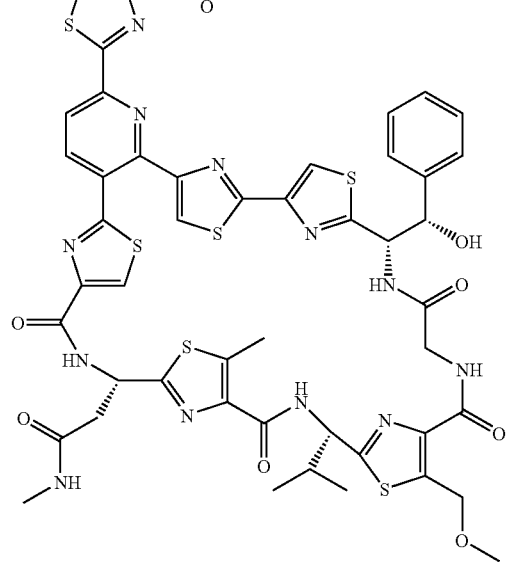 |
| 28 | 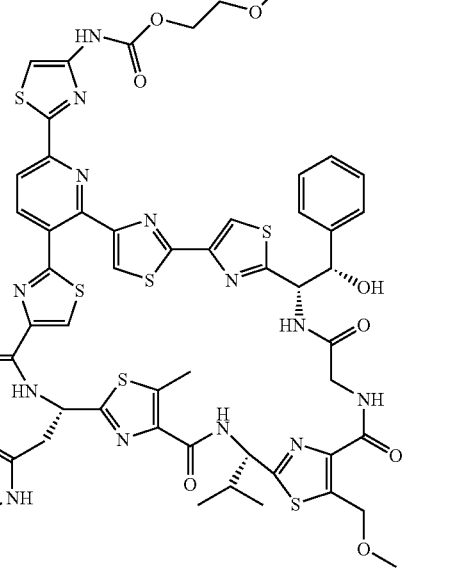 |

TABLE A-continued
| Compound | Structure |
|---|---|
| 29 | 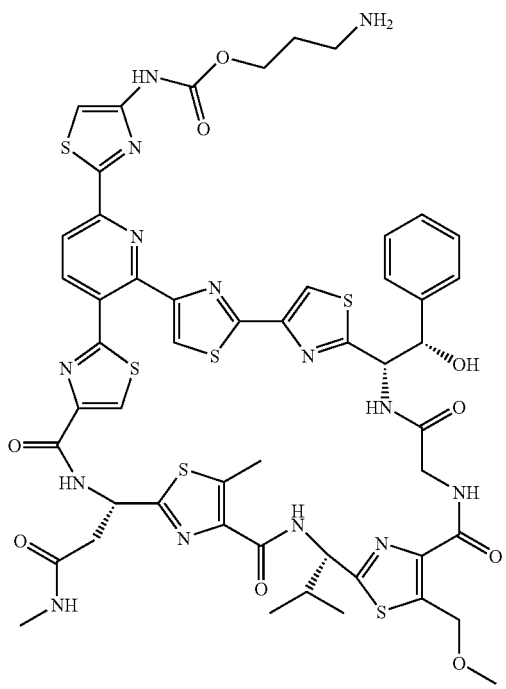 |
| 30 | 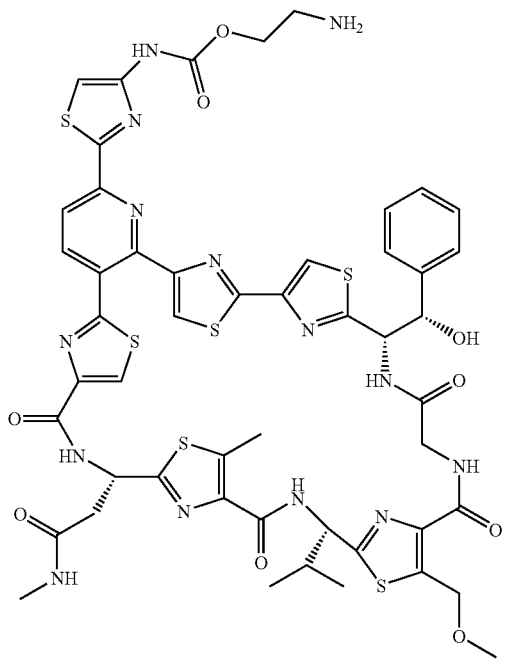 |
| 31 | 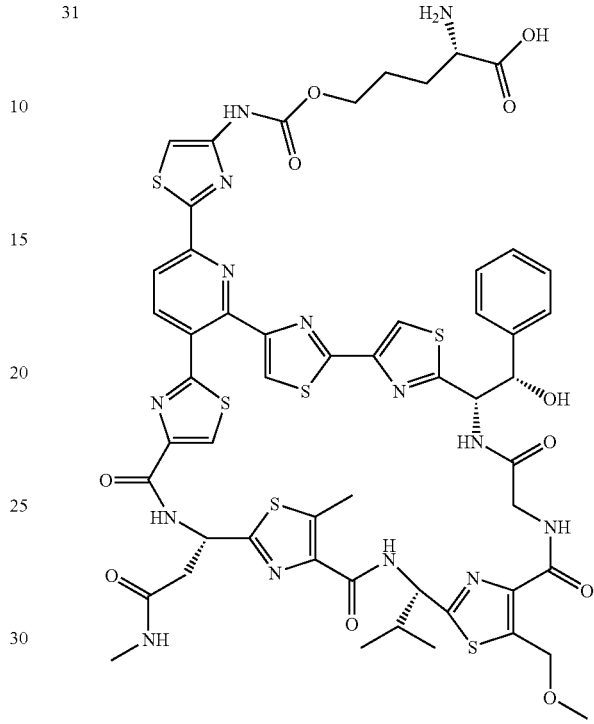 |
| 32 | 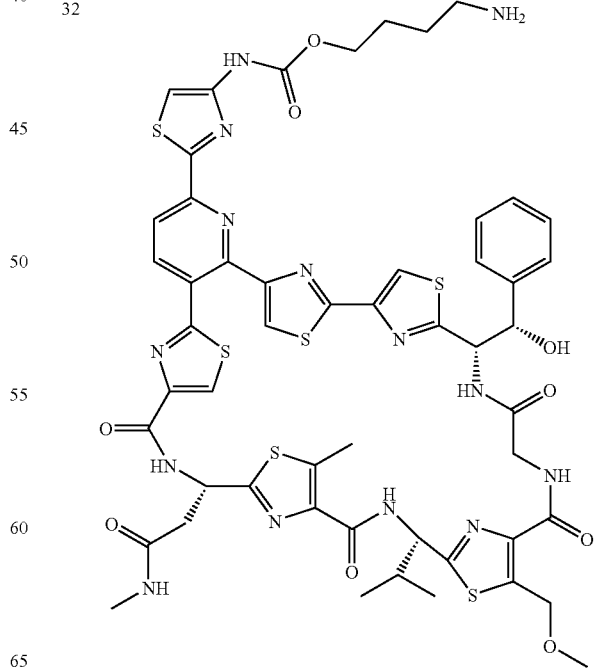 |

TABLE A-continued
Compound Structure
33
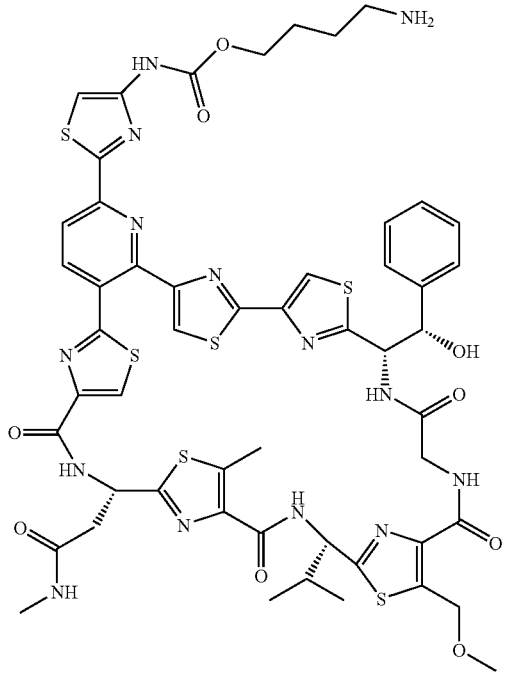
34
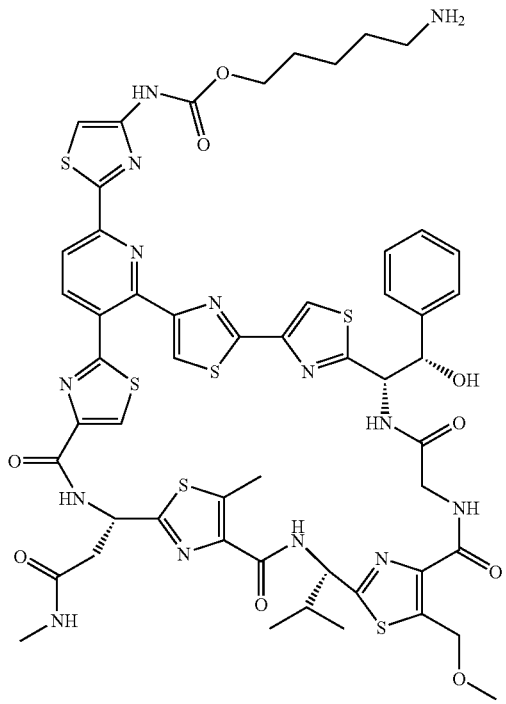
35
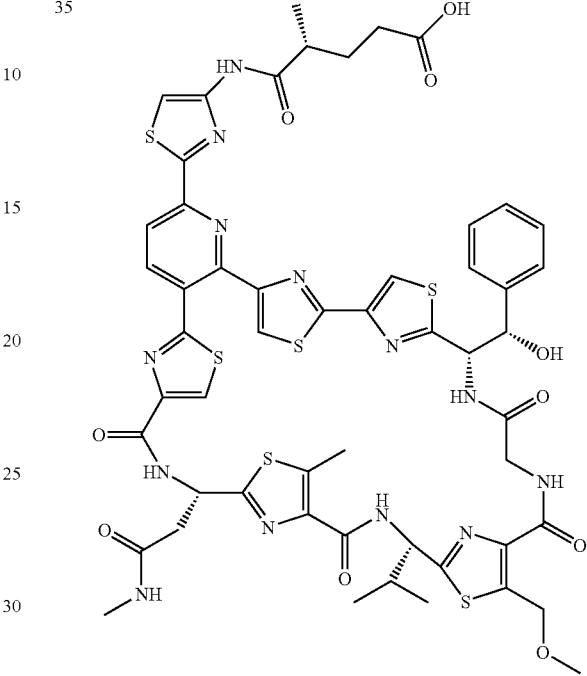
36
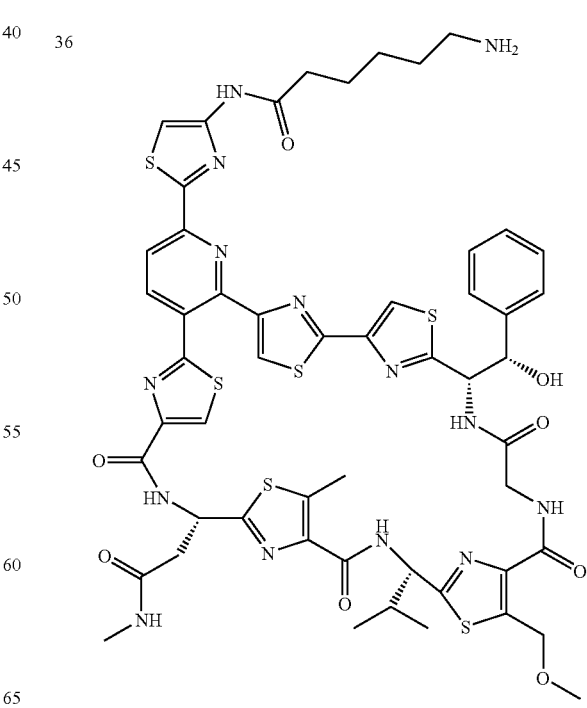

TABLE A-continued
| Compound | Structure |
|---|---|
| 37 | 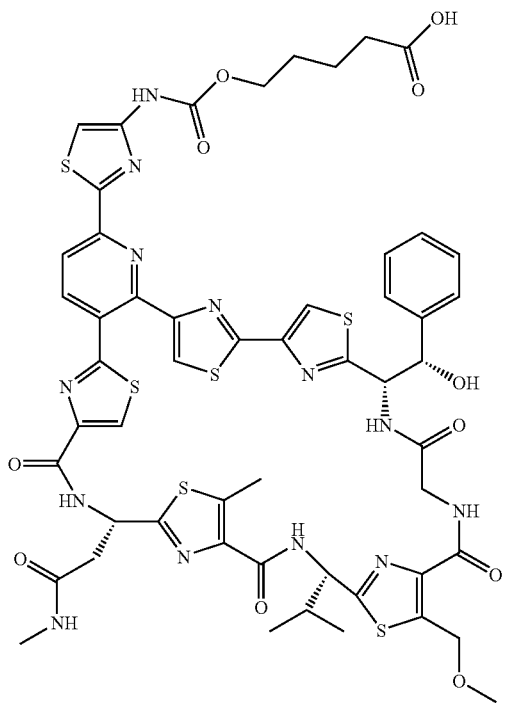 |
| 38 | 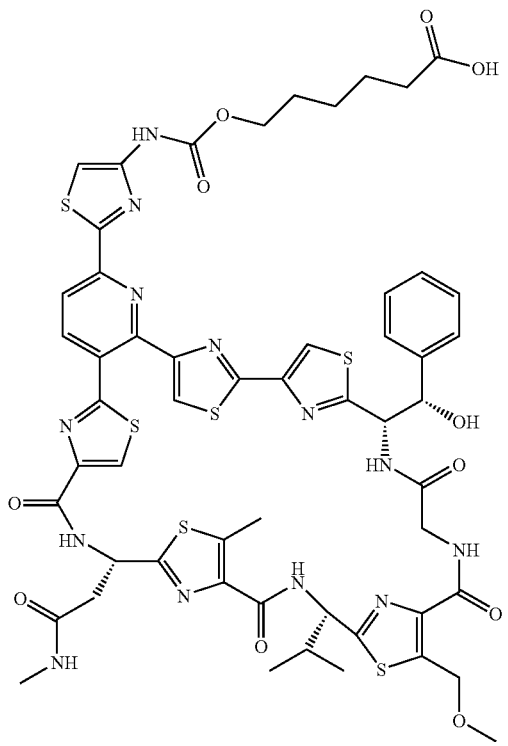 |
| 39 | 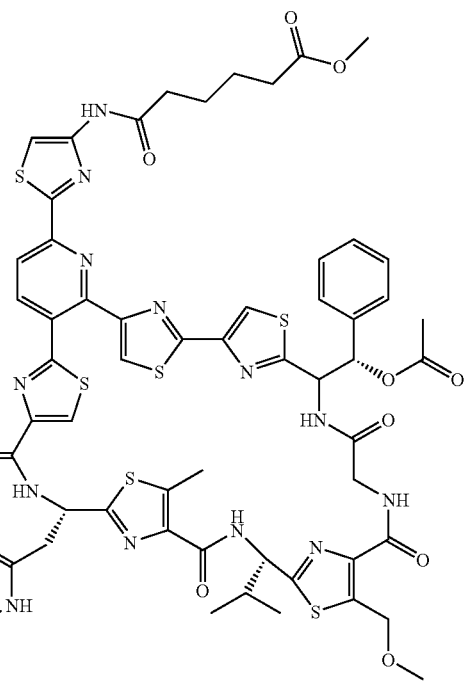 |
| 40 | 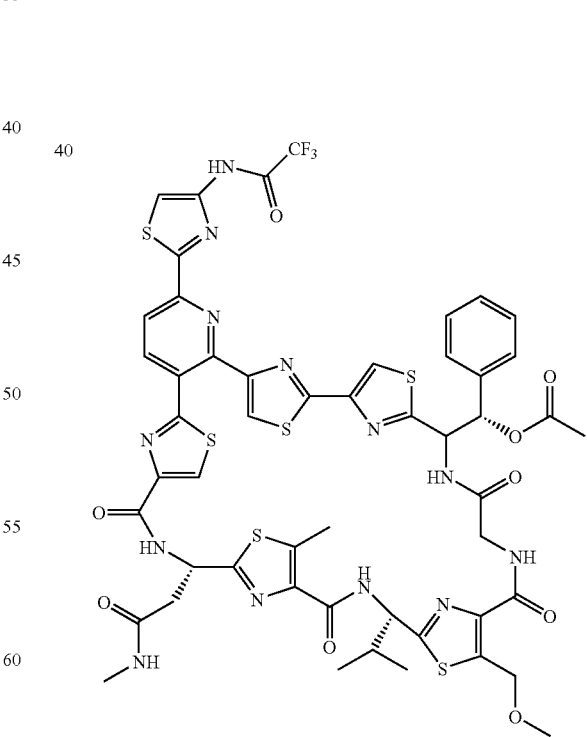 |

TABLE A-continued
| Compound | Structure |
|---|---|
| 41 | 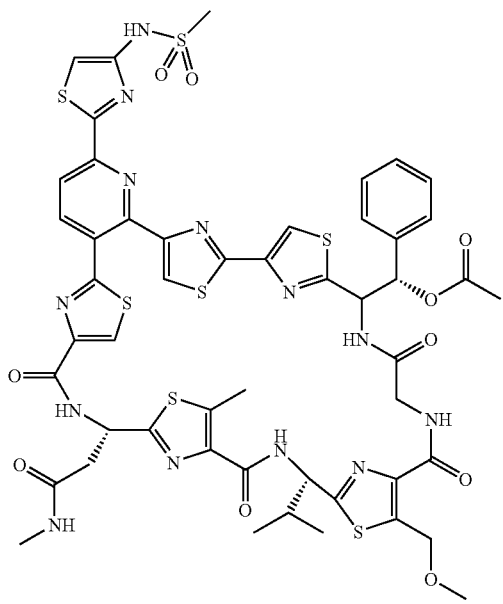 |
| 42 | 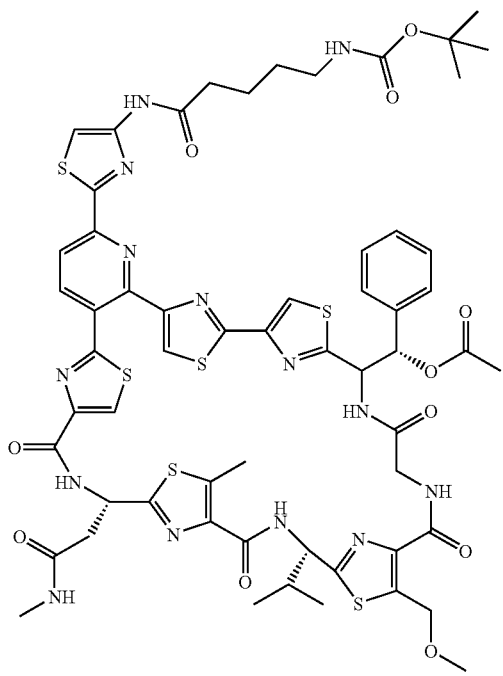 |
TABLE A-continued
| Compound | Structure |
|---|---|
| 43 | 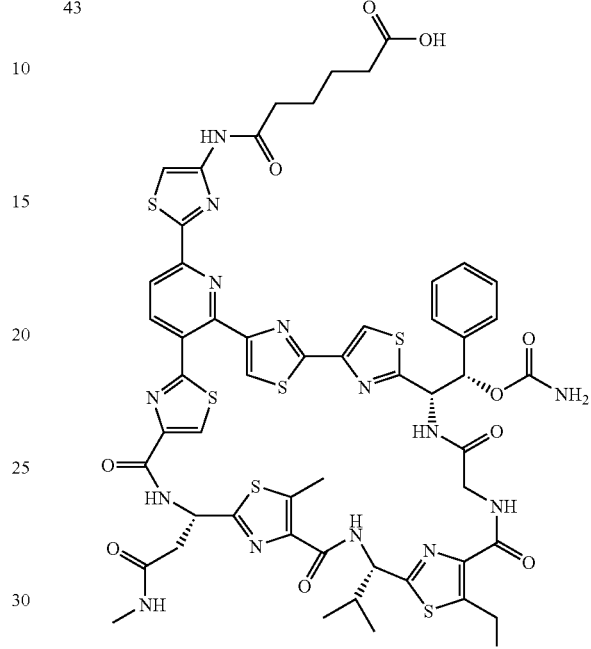 |
| 44 | 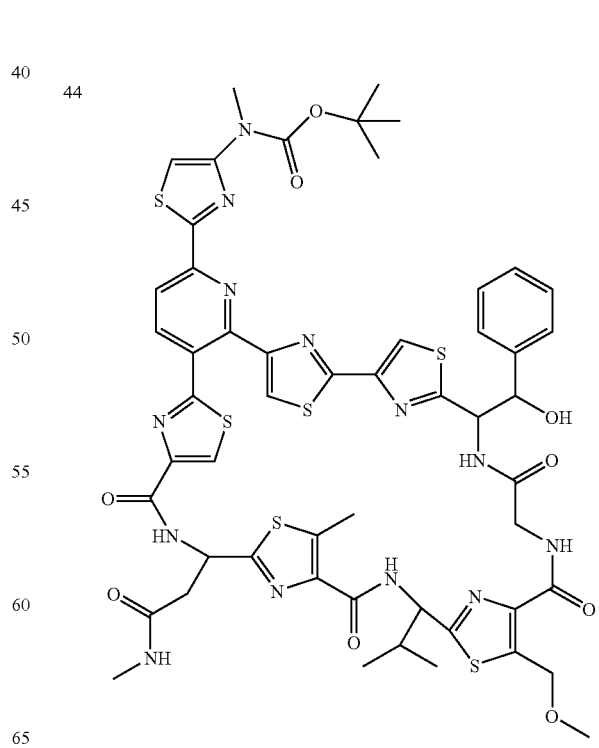 |

TABLE A-continued
| Com- |
| pound Structure |
45
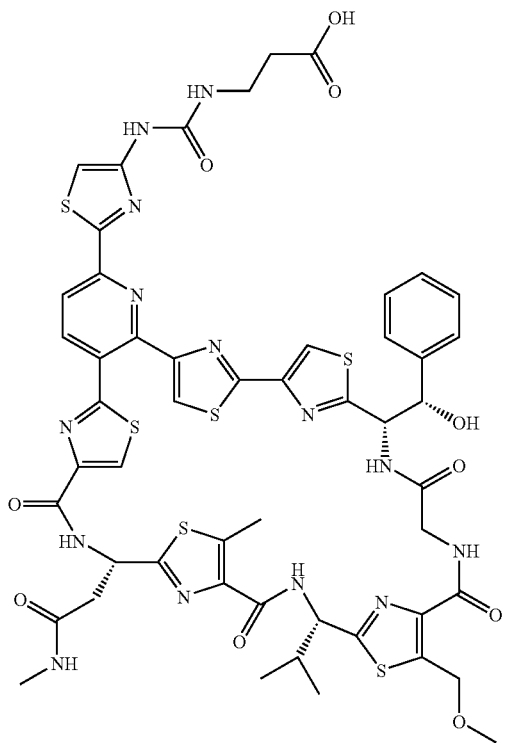
46
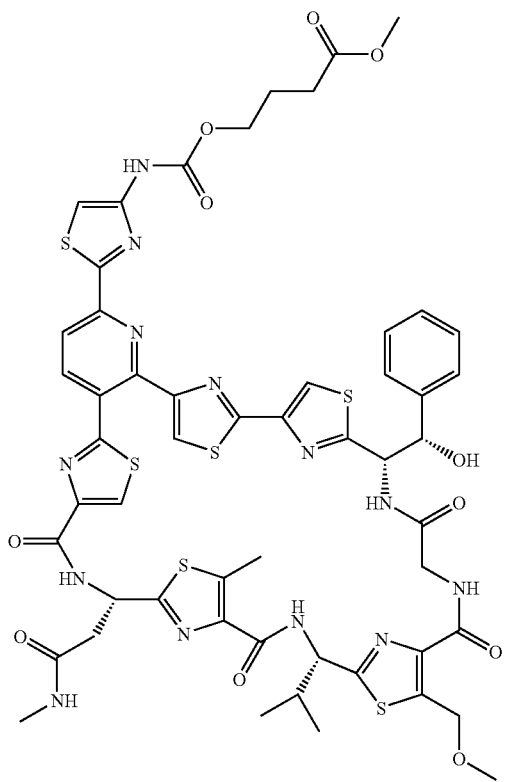
TABLE A-continued
| Com- |
| pound Structure |
47
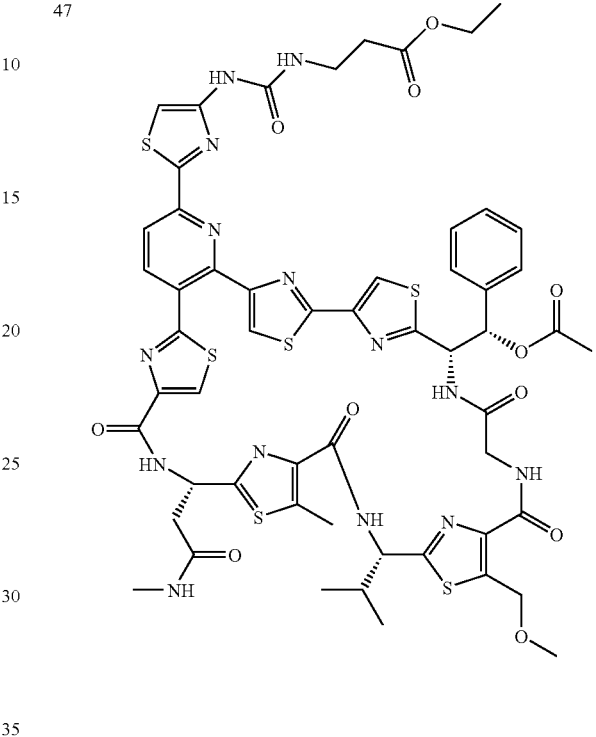
48
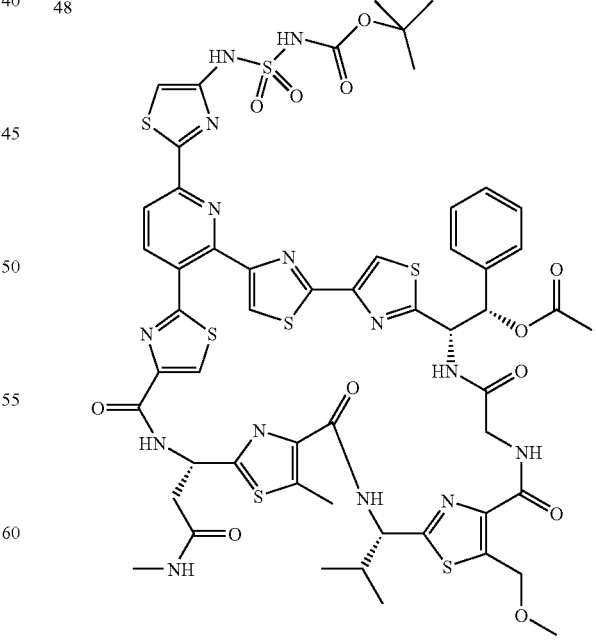

TABLE A-continued

| Compound | Structure |
|---|---|
| 49 | 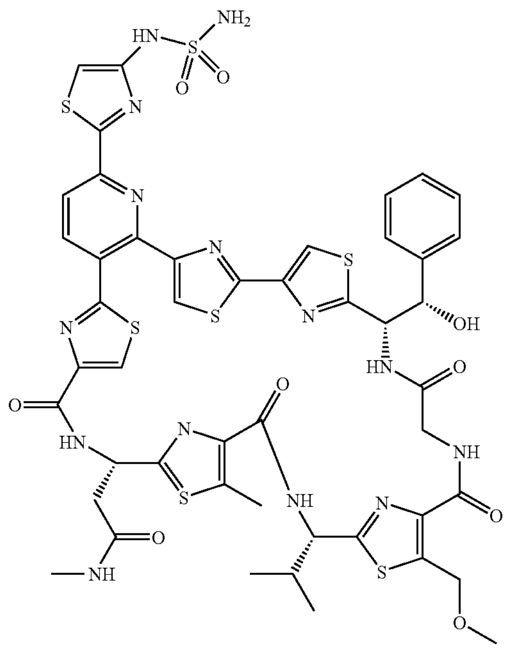 |
| 50 | 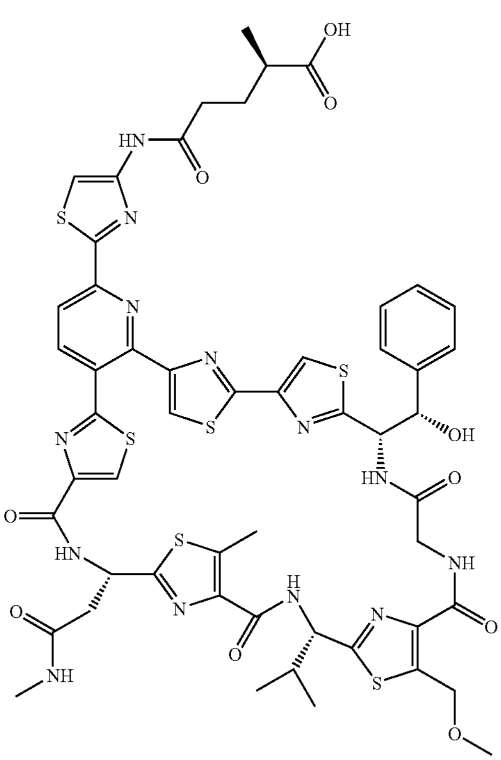 |
| 51 | |
| 52 | |

TABLE A-continued
| Compound | Structure |
|---|---|
| 53 | 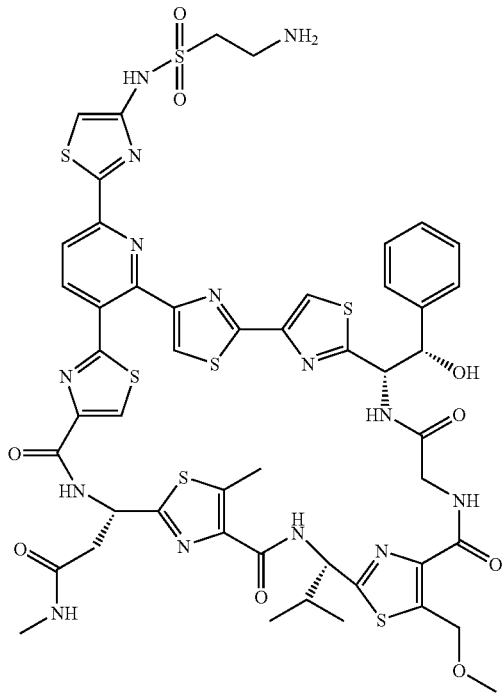 |
| 54 | 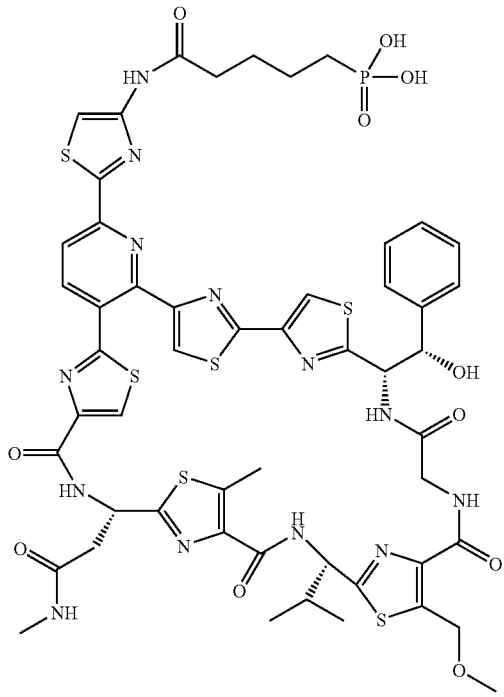 |
TABLE A-continued
| Compound | Structure |
|---|---|
| 55 | 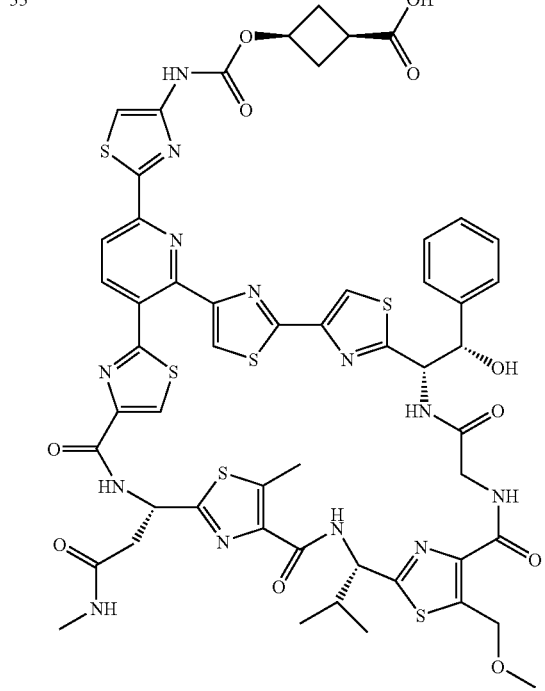 |
| 56 | 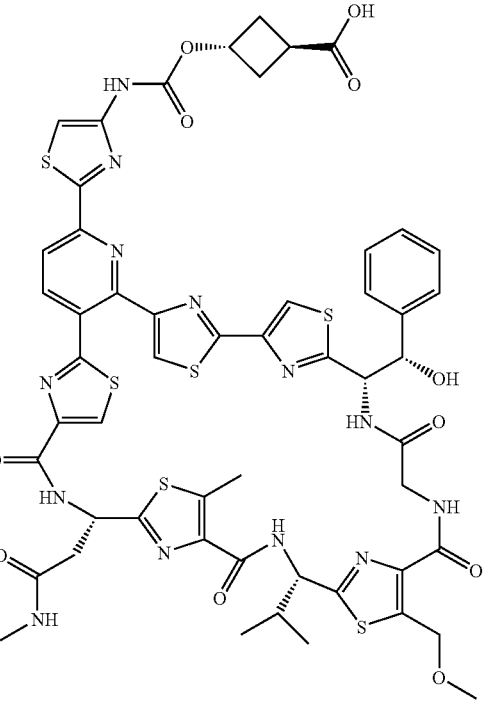 |

TABLE A-continued
| Compound | Structure |
|---|---|
| 57 | 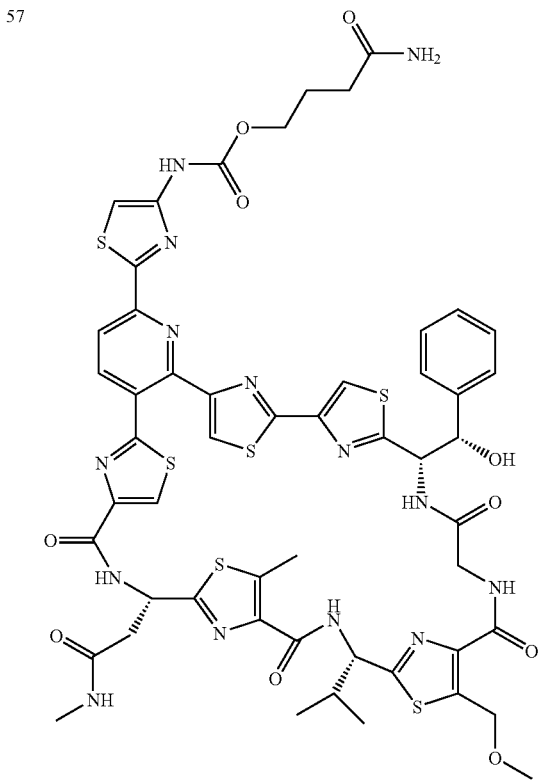 |
| 58 | 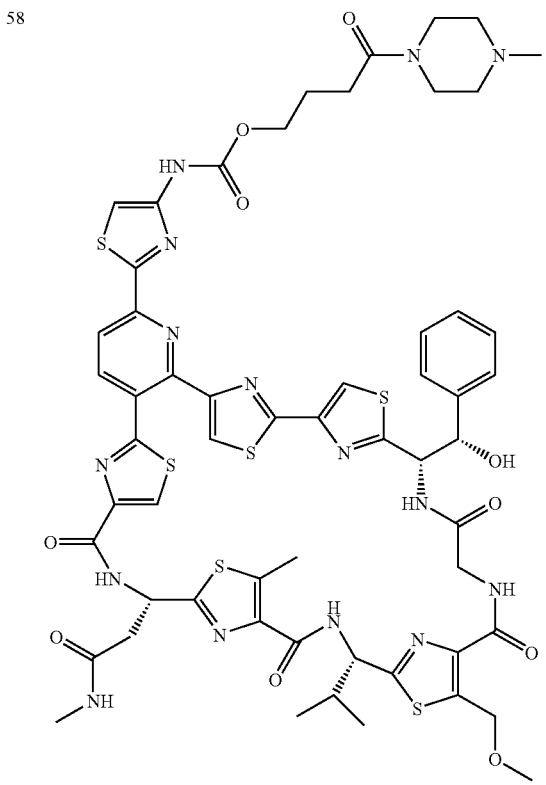 |
| 59 | 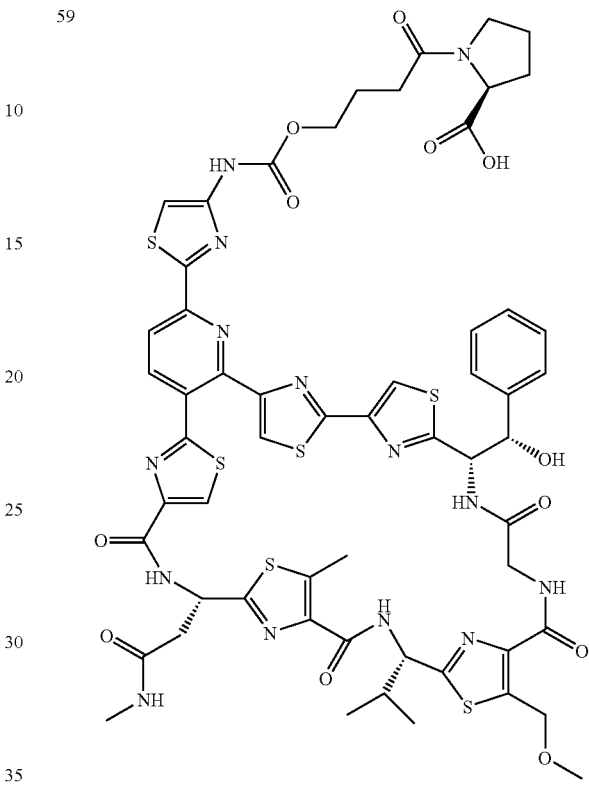 |
| 60 | 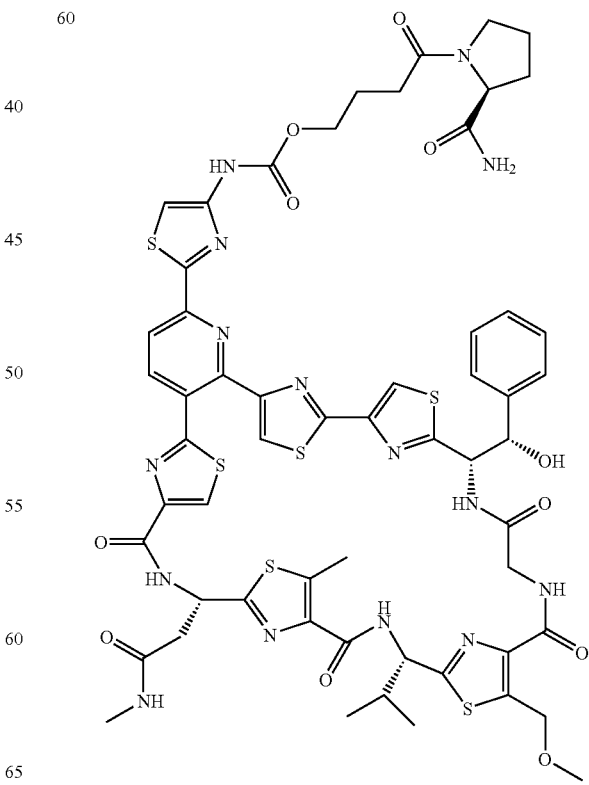 |

TABLE A-continued

| Compound | Structure |
|---|---|
| 61 | (chemical structure) |
| 62 | (chemical structure) |
| 63 | (chemical structure) |
| 64 | (chemical structure) |

TABLE A-continued
| Compound | Structure |
|---|---|
| 65 | 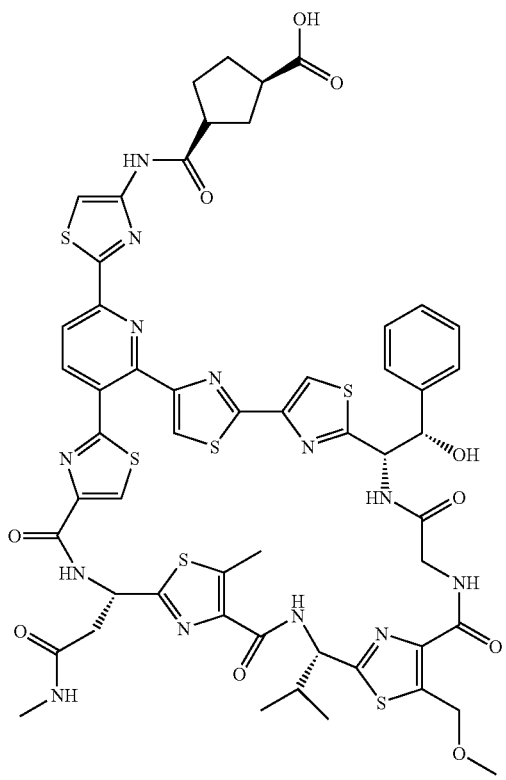 |
| 66 | 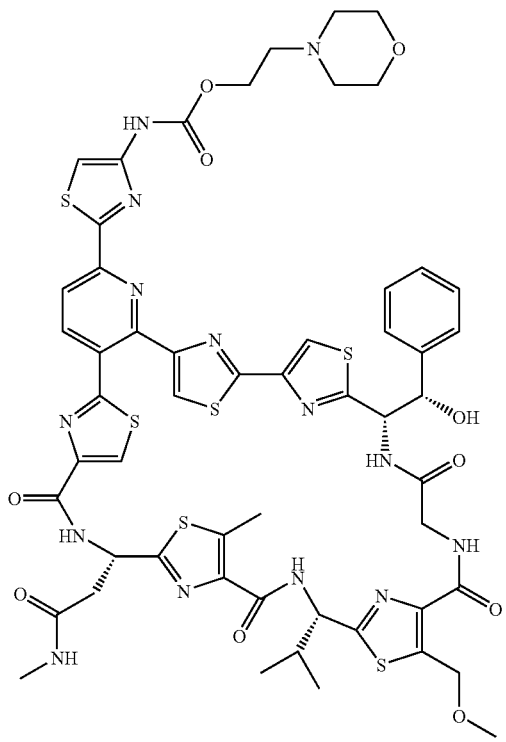 |
| 67 | 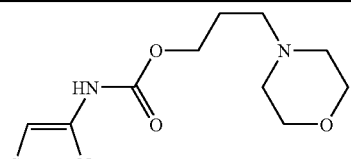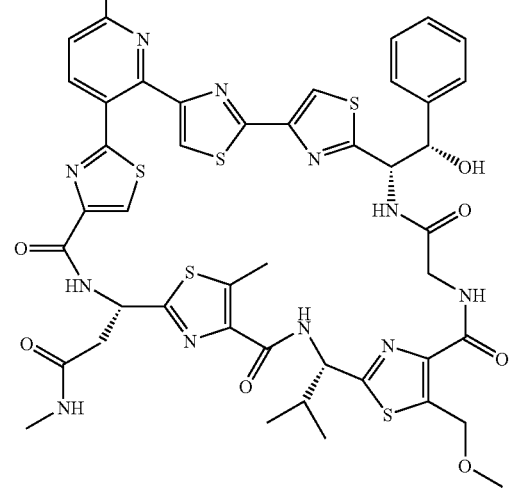 |
| 68 | 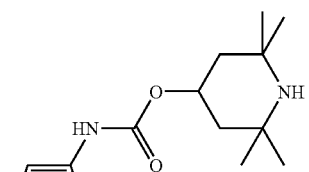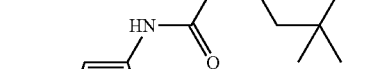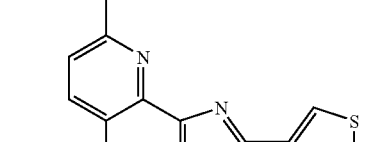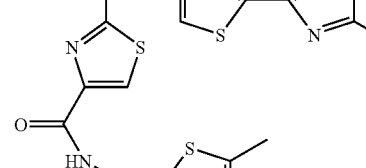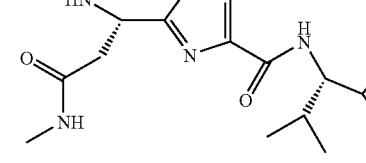 |

TABLE A-continued
| Compound | Structure |
|---|---|
| 69 | 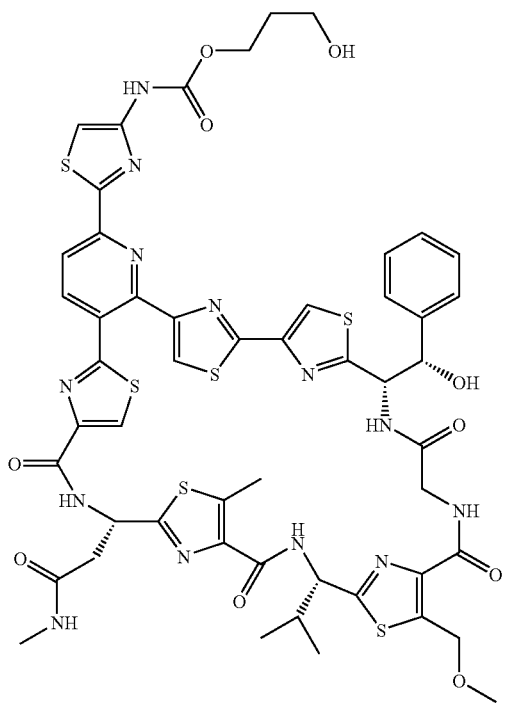 |
| 70 | 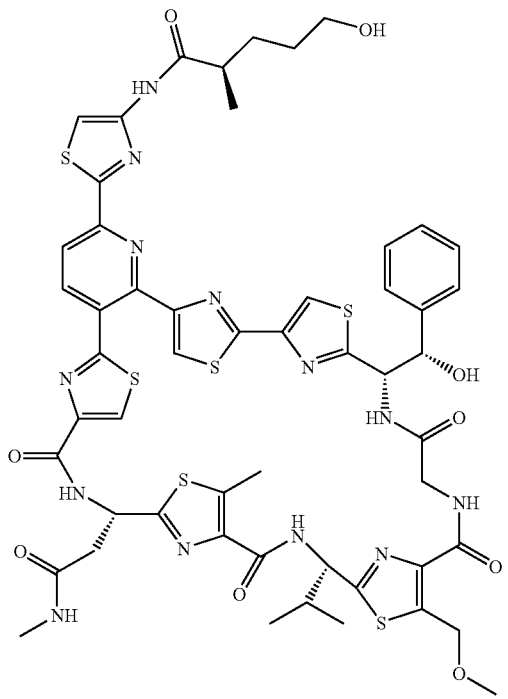 |
| 71 | 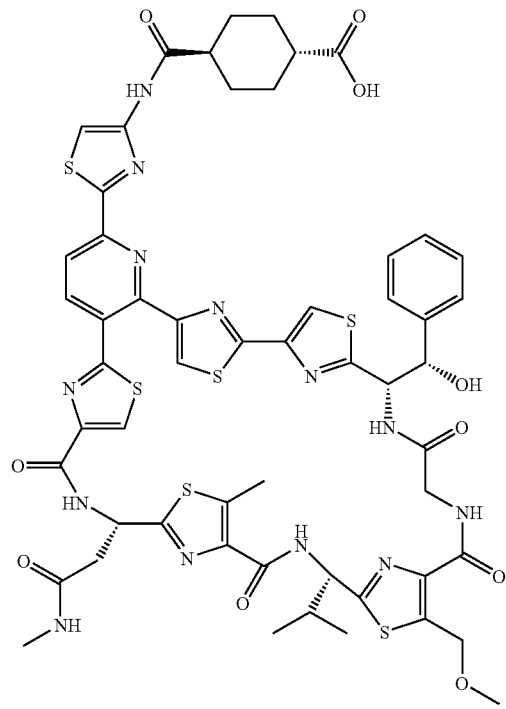 |
| 72 | 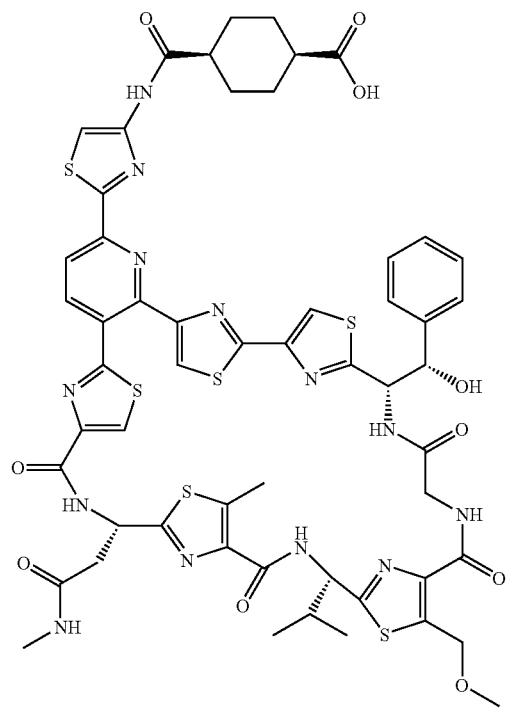 |

TABLE A-continued
| Compound | Structure |
|---|---|
| 73 | 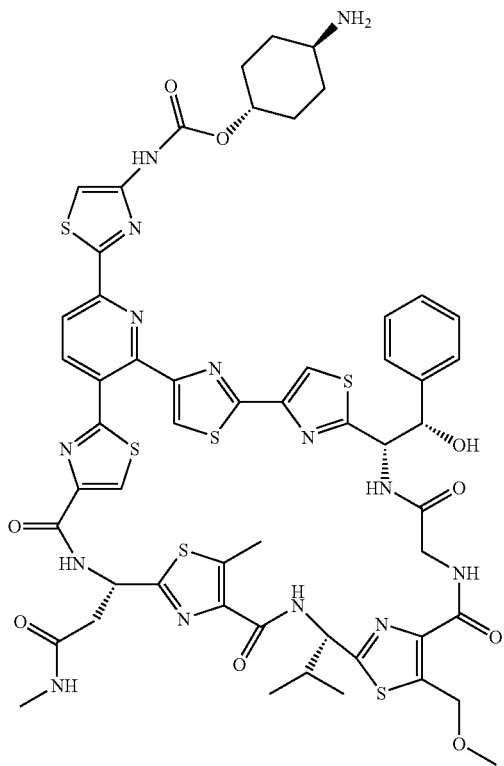 |
| 74 | 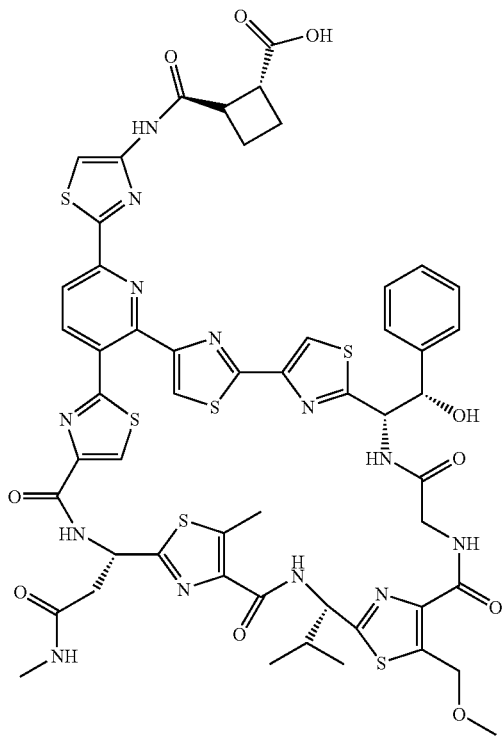 |
| 75 | 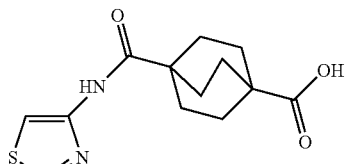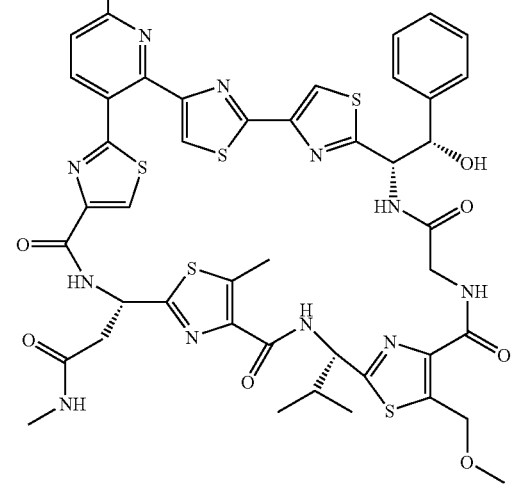 |
| 76 | 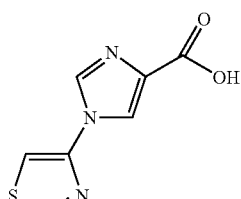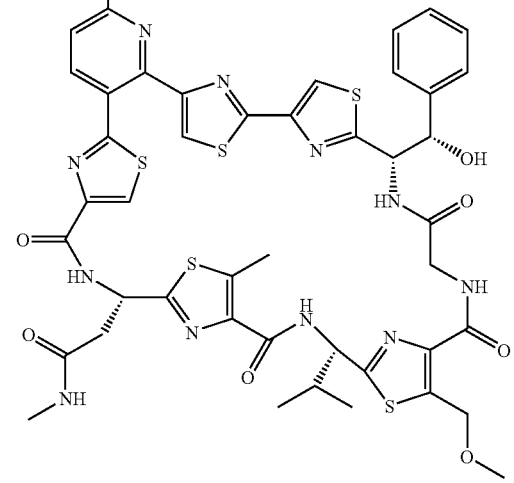 |

TABLE A-continued

| Compound | Structure |
|---|---|
| 77 | (chemical structure) |
| 78 | (chemical structure) |
| 79 | (chemical structure) |
| 80 | (chemical structure) |

TABLE A-continued
| Compound | Structure |
|---|---|
| 81 | 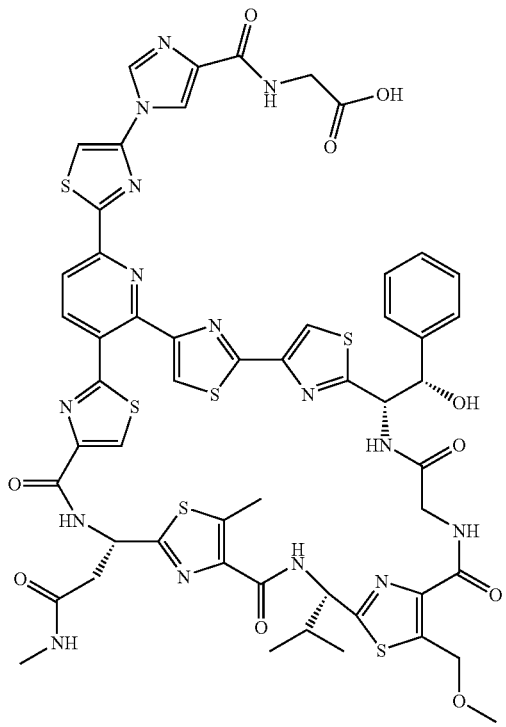 |
| 82 | 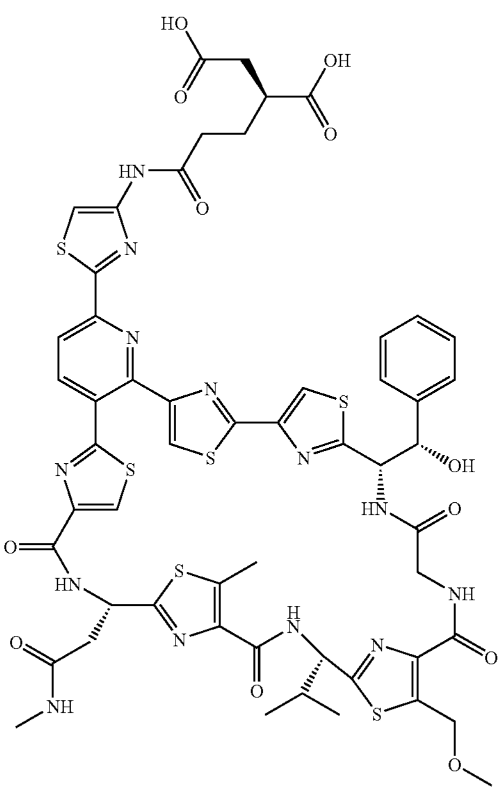 |
TABLE A-continued
| Compound | Structure |
|---|---|
| 83 | 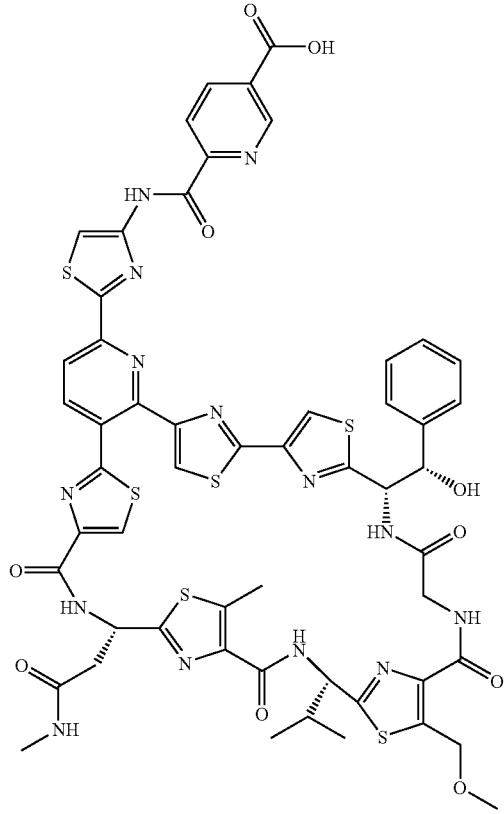 |
| 84 | |

TABLE A-continued
| Compound | Structure |
|---|---|
| 85 | 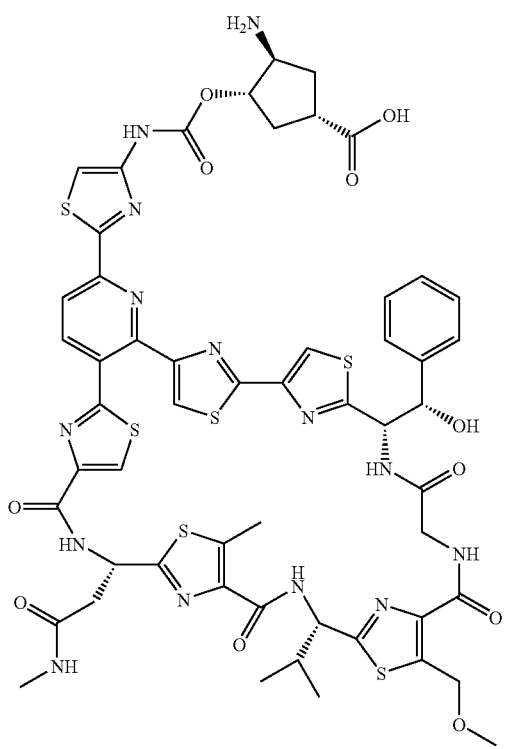 |
| 86 | 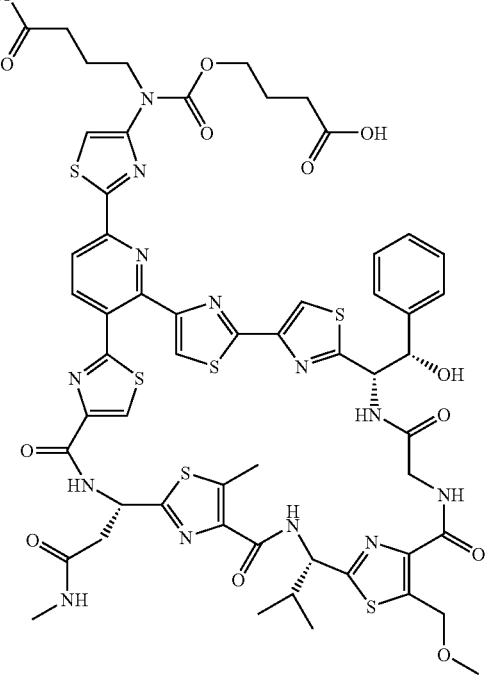 |
| 87 | 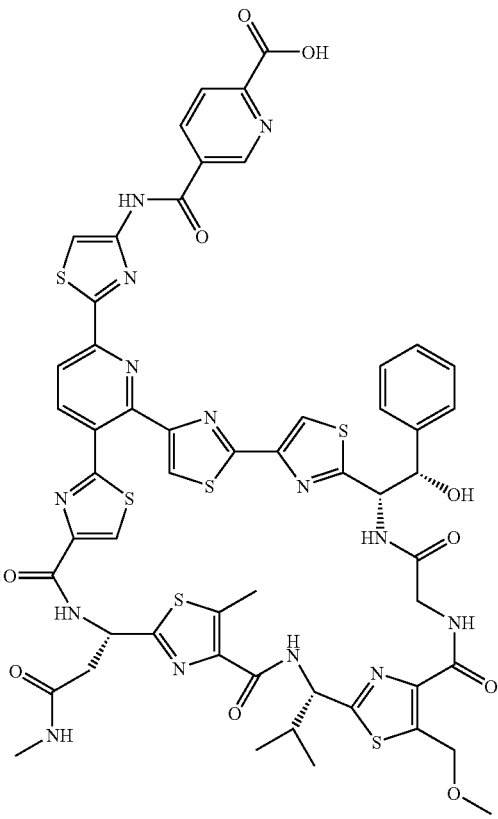 |
| 88 | 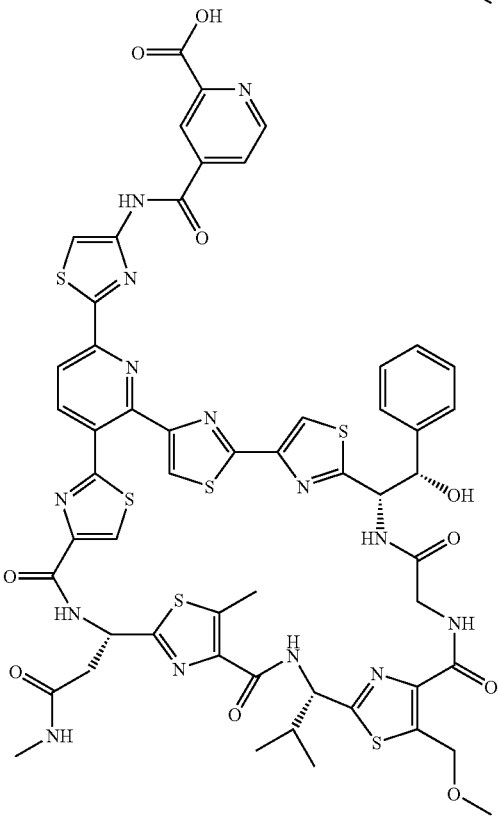 |

TABLE A-continued
| Compound | Structure |
|---|---|
| 89 | 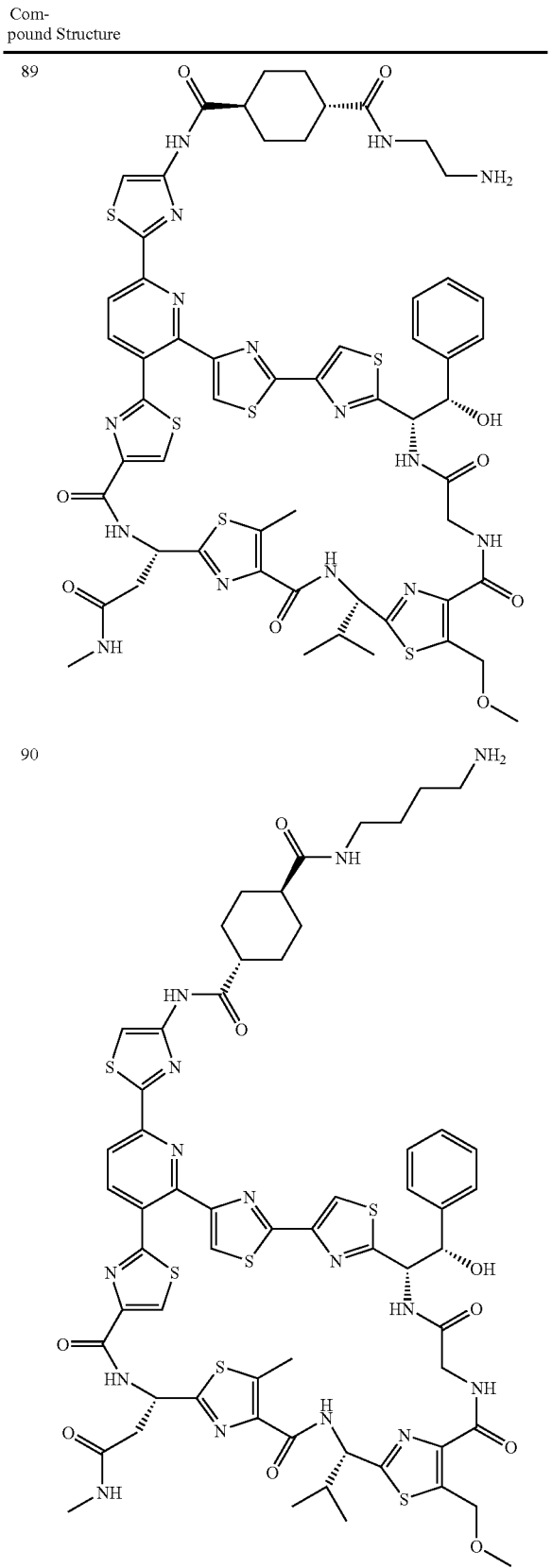 |
| 90 | 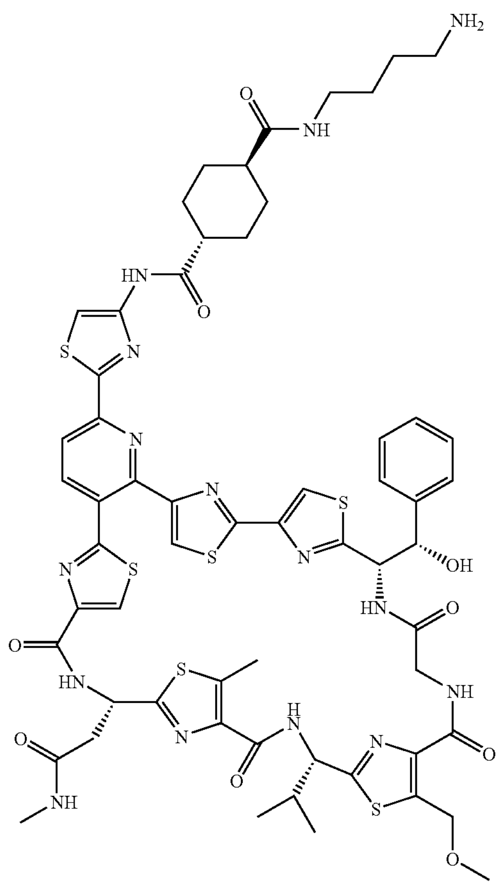 |
| 91 | 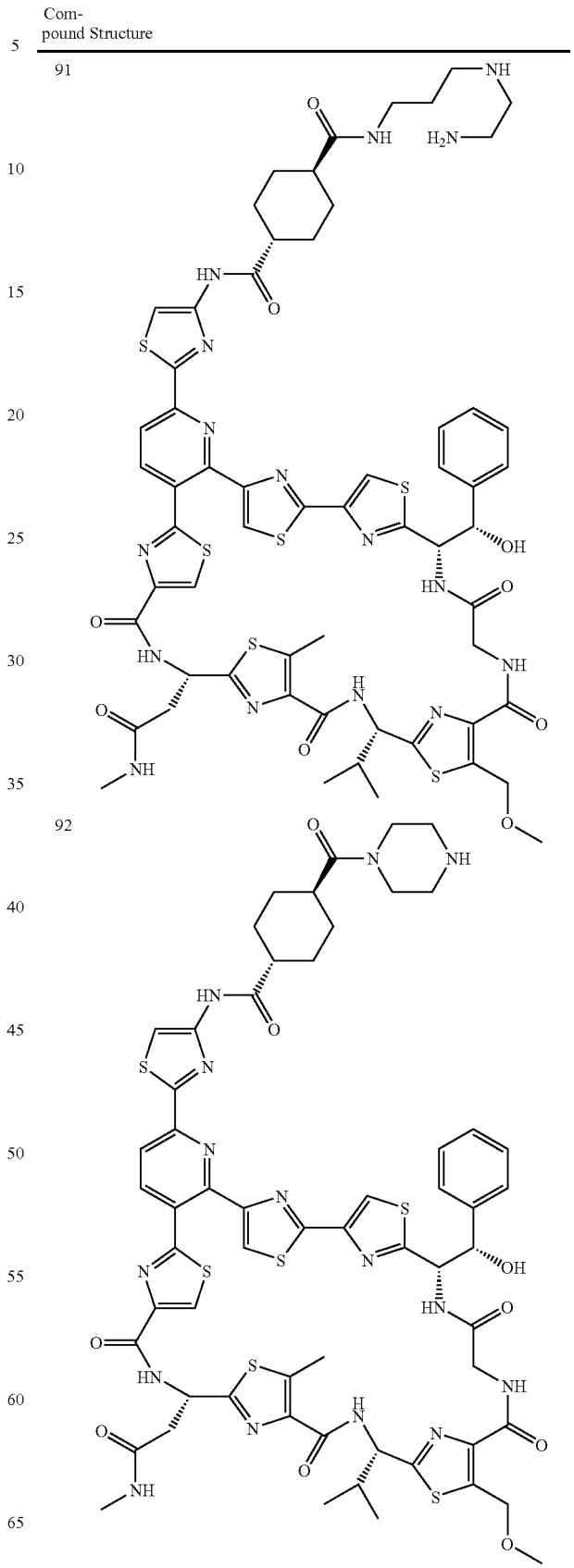 |
| 92 | 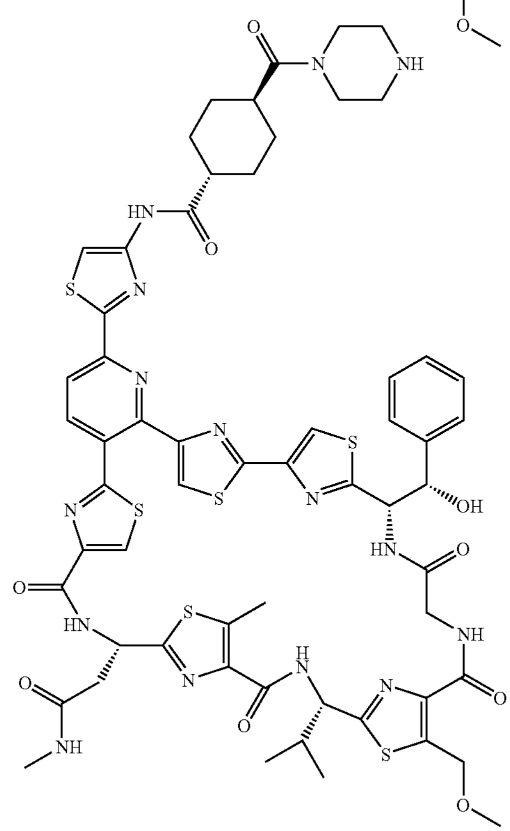 |

TABLE A-continued

| Compound | Structure |
|---|---|
| 93 | 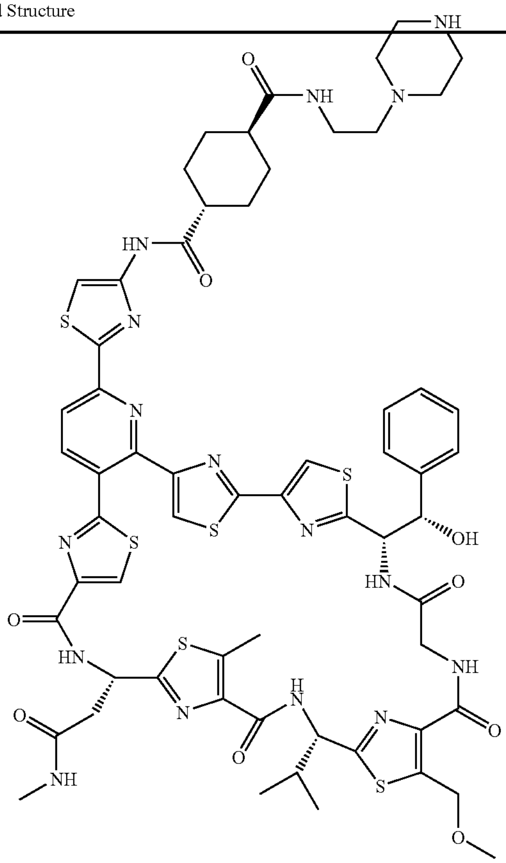 |
| 94 | 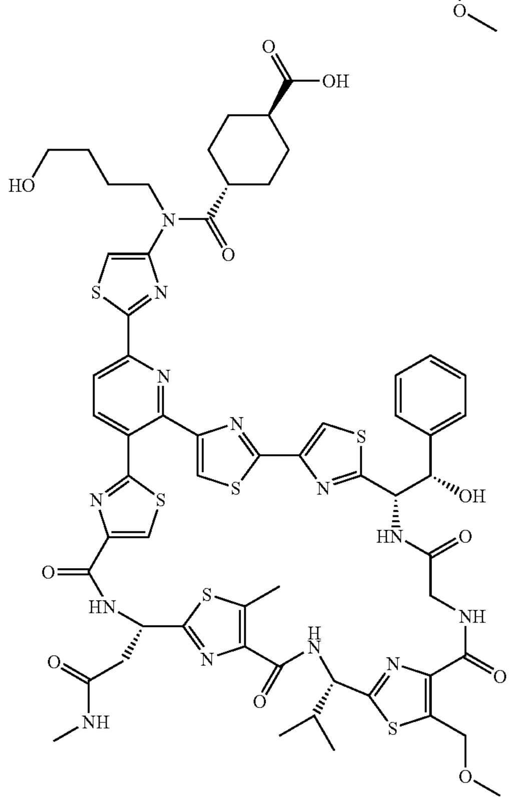 |
| 95 | |
| 96 | |

TABLE A-continued
| Compound | Structure |
|---|---|
| 97 | 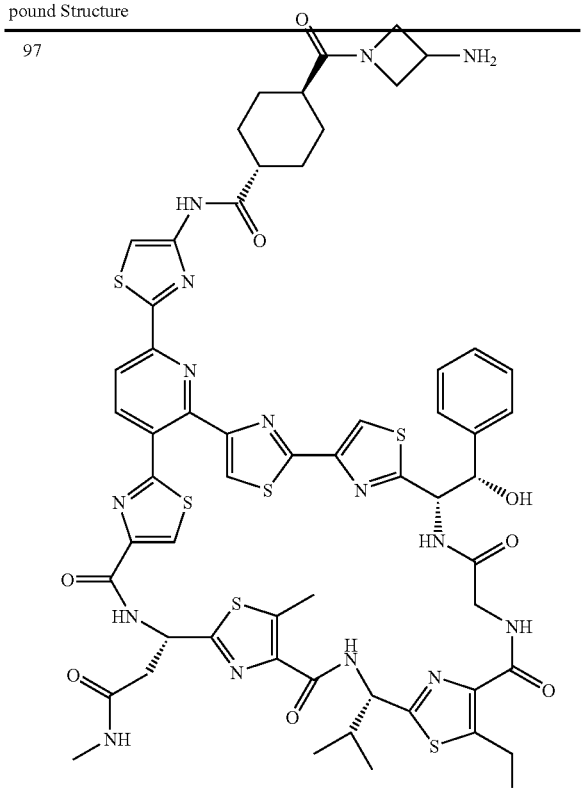 |
| 98 | 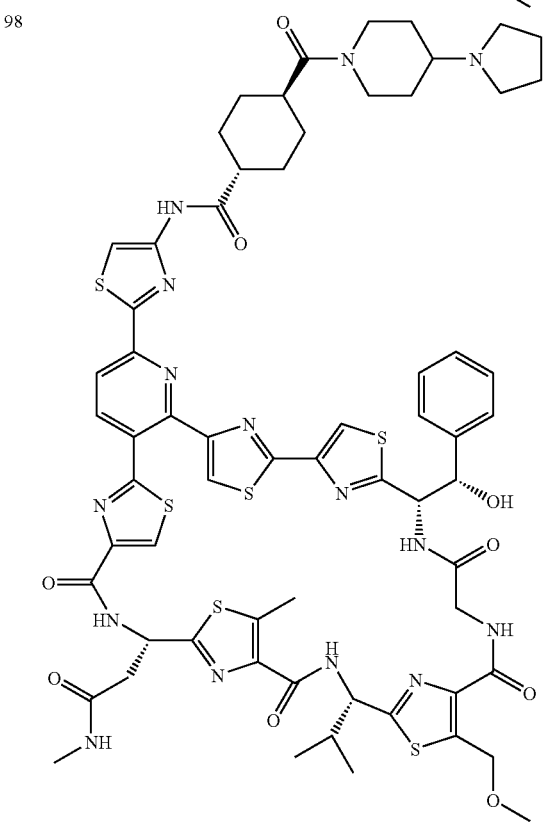 |
| 99 | 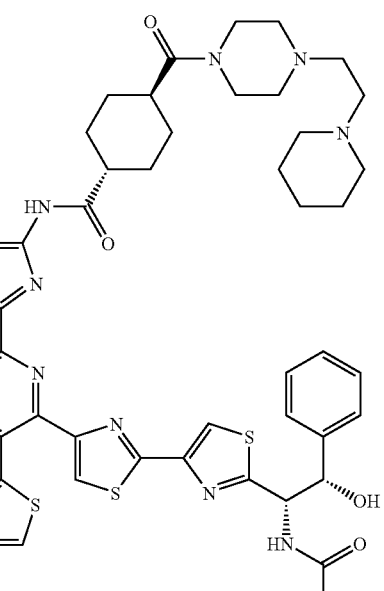 |
| 100 | |

TABLE B
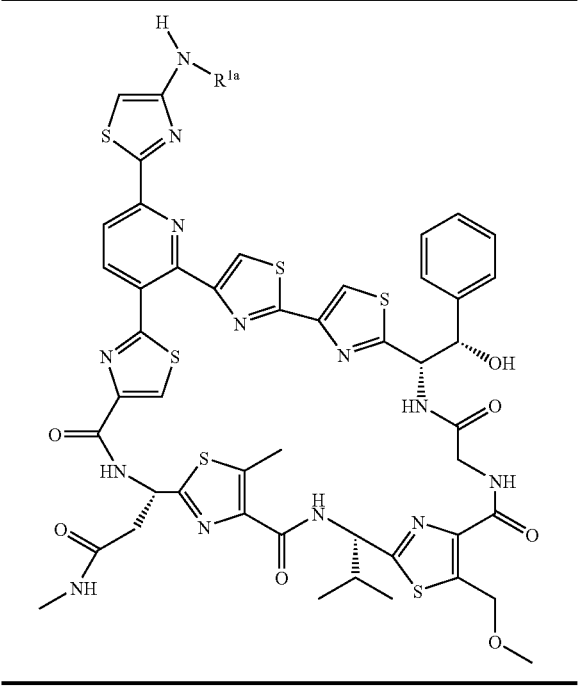
R$^{1a}$ =
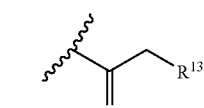 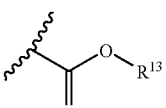
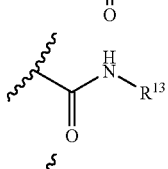 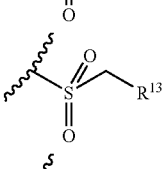
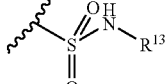 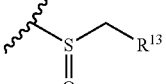
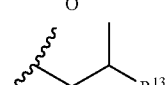 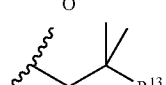
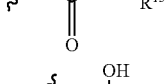 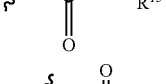
R$^{13}$ = 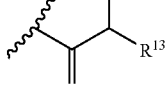 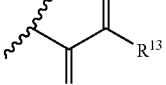
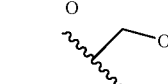 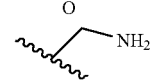
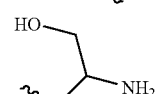 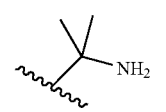
 
TABLE B-continued
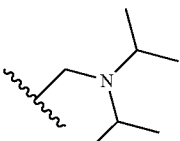 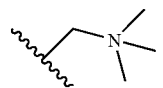
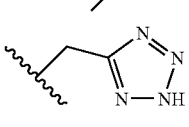 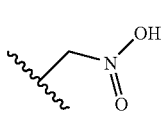
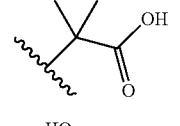 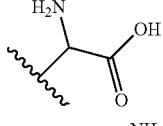
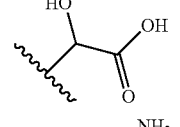 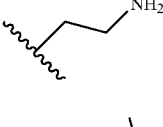
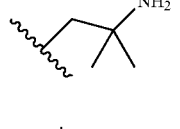 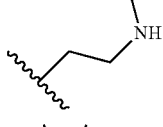
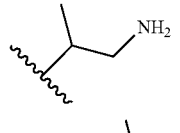 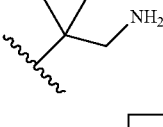
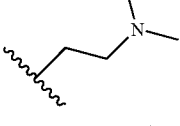 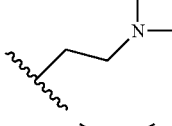
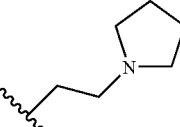 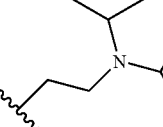
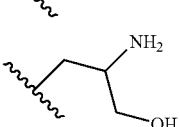 
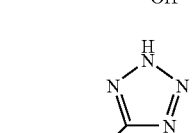 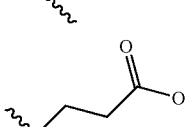
 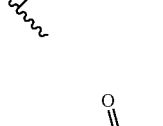
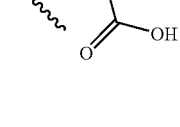 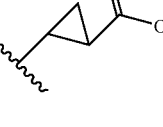
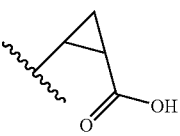 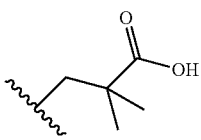

TABLE B-continued
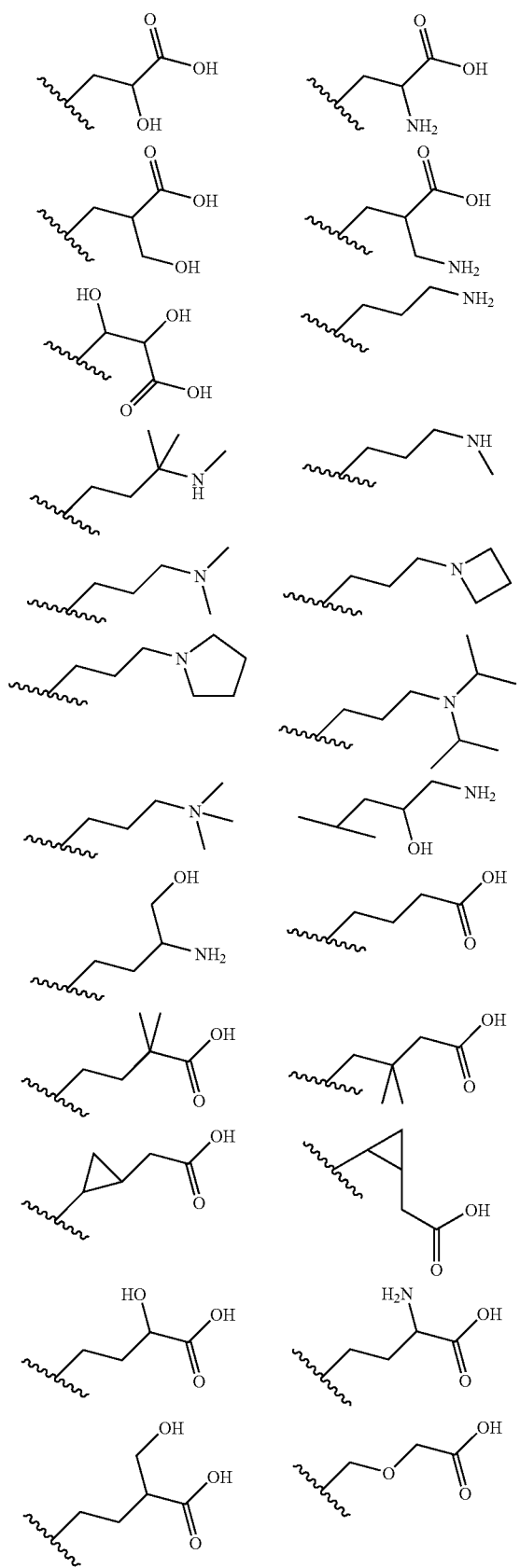
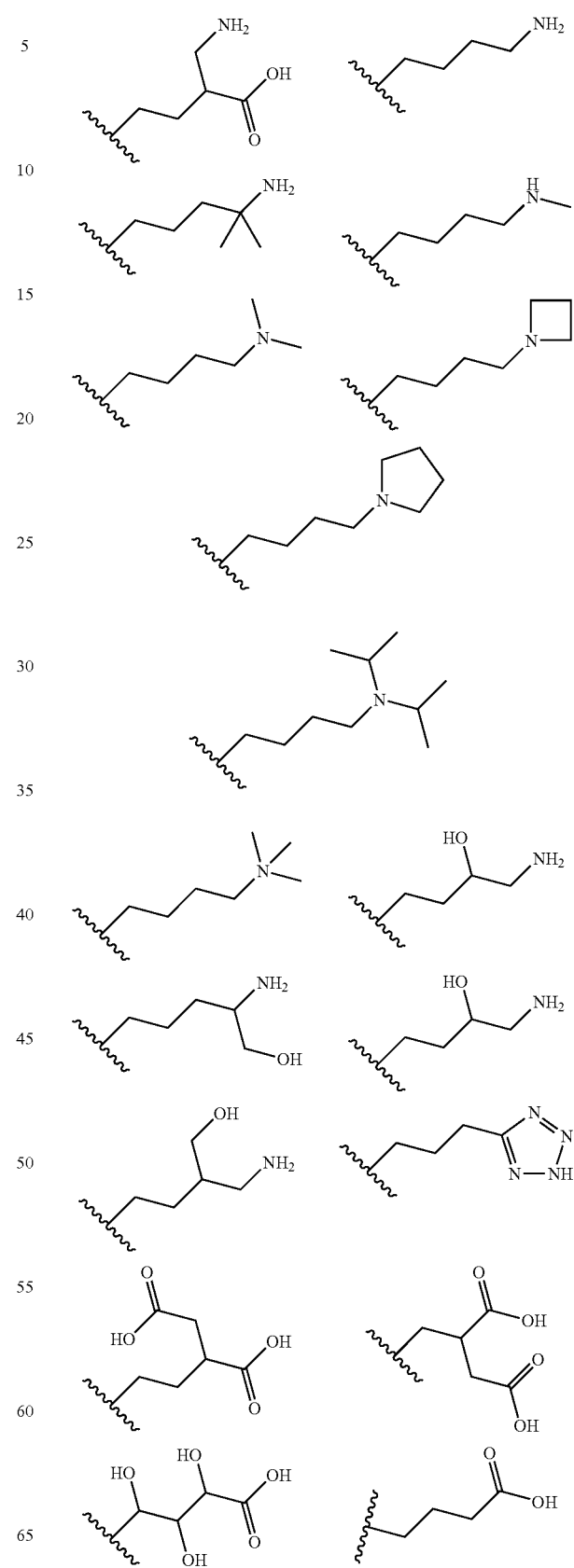

TABLE B-continued

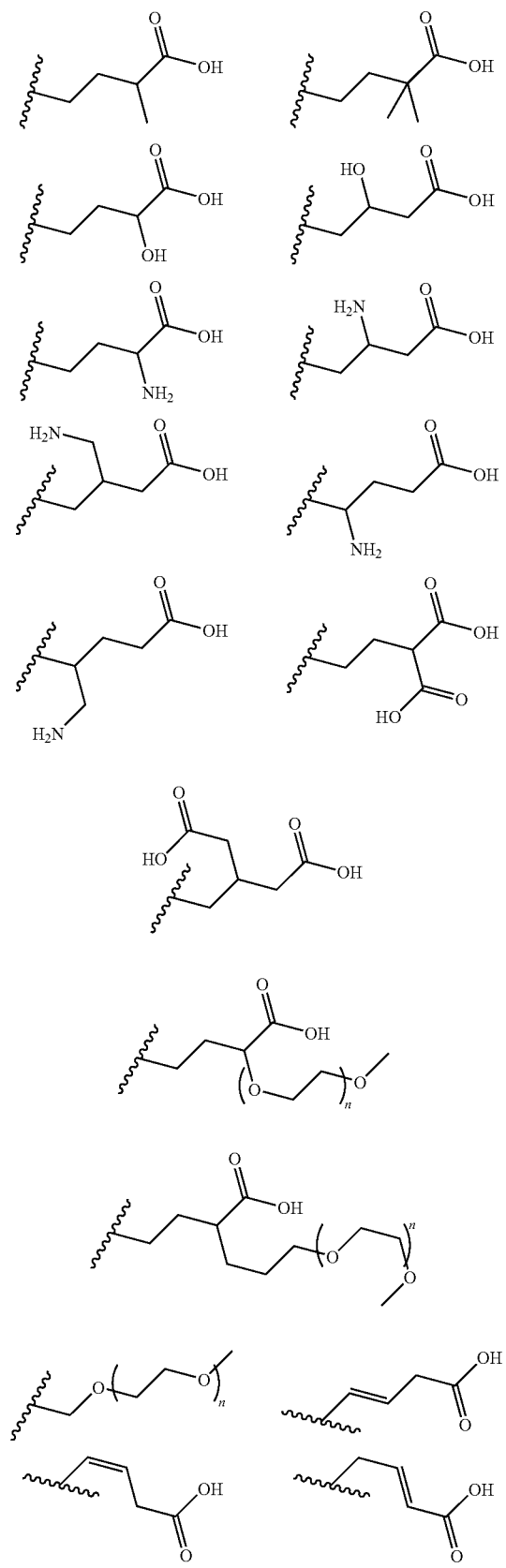
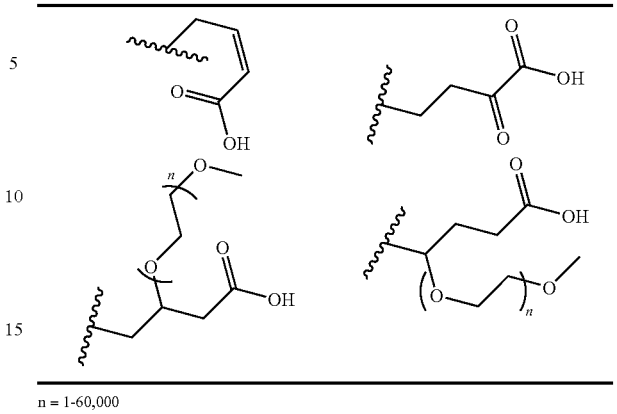

n = 1-60,000

In certain embodiments, the compound of the present invention is further characterized as a modulator of EF-Tu, including a prokaryotic EF-Tu, and especially including a bacterial EF-Tu. In a preferred embodiment, the compound of the invention is an EF-Tu inhibitor.

As used herein, the term "bacterial infection(s)" includes, but is not limited to, bacterial infections that occur in mammals, fish and birds as well as disorders related to bacterial infections that may be treated or prevented by administering antibiotics such as the compounds of the present invention. In addition to treating infections caused by multi-drug resistant strains of *Staphyloccocus aureus, Streptococcus pneumoniae, Mycobacterium tuberculosis* and Enterococci, the compounds of the present invention are useful in treating infections caused by other bacteria including, but not limited to, *Clostridium difficile, Propionibacterium acnes, Bacteroides fagiles, Neisseria gonorrhoeae, Branhamella catarrhalis, Haemophilus influenzae, E. coli, Pseudomonas aeruginosa, Proteus vulgaris, Klebsiella pneumonia,* and *Chlamydia trachomatis.*

Such bacterial infections and disorders related to such infections include, but are not limited to, the following: acne, rosacea, skin infection, pneumonia, otitis media, sinusitus, bronchitis, tonsillitis, and mastoiditis related to infection by *Streptococcus pneumoniae, Haemophilus influenzae, Moraxella catarrhalis, Staphylococcus aureus, Peptostreptococcus* spp. or *Pseudomonas* spp.; pharyngitis, rheumatic fever, and glomerulonephritis related to infection by *Streptococcus pyogenes,* Groups C and G streptococci, *Clostridium diptheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *S. pyogenes, S. agalactiae,* Streptococcal groups C-F (minute-colony streptococci), viridans streptococci, *Corynebacterium* spp., *Clostridium* spp., or *Bartonella henselae*; uncomplicated acute urinary tract infections related to infection by *S. saprophyticus* or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Nesseria gonorrheae*; toxin diseases related to infection by *S. aureus* (food poisoning and Toxic shock syndrome), or Groups A, S, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium* spp., odontogenic infection related to infection by viridans streptococci; persistent cough related to infection by *Bordetella pertussis*; gas gangrene related to infection by *Clostridium perfringens* or *Bacteroides* spp.; Skin infection by *S. aureus, Propionibacterium* acne; atherosclerosis related to infection by *Helicobacter pylori* or *Chlamydia pneumoniae*; or the like.

Further bacterial infections and disorders related to such infections that may be treated or prevented in animals include, but are not limited to, the following: bovine respiratory disease related to infection by *P. haemolytica., P. multocida, Mycoplasma bovis*, or *Bordetella* spp.; cow enteric disease related to infection by *E. coli* or protozoa (i.e., coccidia, cryptosporidia, etc.), dairy cow mastitis related to infection by *S. aureus, S. uberis, S. agalactiae, S. dysgalactiae, Klebsiella* spp., *Corynebacterium*, or *Enterococcus* spp.; swine respiratory disease related to infection by *A. pleuropneumoniae, P. multocida*, or *Mycoplasma* spp.; swine enteric disease related to infection by *E. coli, Lawsonia intracellularis, Salmonella* spp., or *Serpulina hyodyisinteriae*; cow footrot related to infection by *Fusobacterium* spp.; cow metritis related to infection by *E. coli*; cow hairy warts related to infection by *Fusobacterium necrophorum* or *Bacteroides nodosus*; cow pink-eye related to infection by *Moraxella bovis*, cow premature abortion related to infection by protozoa (i.e., neosporium); urinary tract infection in dogs and cats related to infection by *E. coli*; skin and soft tissue infections in dogs and cats related to infection by *S. epidermidis, S. intermedius*, coagulase neg. *Staphylococcus* or *P. multocida*; dental or mouth infections in dogs and goats related to infection by *Alcaligenes* spp., *Bacteroides* spp., *Clostridium* spp., *Enterobacter* spp., *Eubacterium* spp., *Peptostreptococcus* spp., *Porphfyromonas* spp., *Campylobacter* spp., *Actinomyces* spp., *Erysipelothrix* spp., *Rhodococcus* spp., *Trypanosoma* spp., *Plasmodium* spp., *Babesia* spp., *Toxoplasma* spp., *Pneumocystis* spp., *Leishmania* spp., *Trichomonas* spp. or *Prevotella* spp. Other bacterial infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996).

Further bacterial infections and disorders related to such infections that may be treated or prevented in animals include, but are not limited to, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, antibacterial prophylaxis in immunosuppressed patients, such as patients receiving cancer chemotherapy, or organ transplant patients and chronic diseases caused by infectious organisms, e.g., arteriosclerosis.

Bacterial protein synthesis requires EF-Tu chaperone proteins. EF-Tu is one of the most abundant proteins in bacteria, as well as one of the most highly conserved, and in a number of species the gene is duplicated with identical function. When bound to GTP, EF-Tu can form a complex with most aminoacylated tRNAs, loading the tRNA onto the ribosome. In one embodiment, the bacterial infection is associated with the activity of EF-Tu. Without being bound by theory, it is believed that the disruption of EF-Tu protein activity by the compounds of the invention will interfere with protein synthesis and thus bacterial function and/or proliferation. Because EF-Tu is highly conserved across Gram-positive and Gram-negative bacteria, the compounds of the present invention are useful for treating infections of both classes of bacteria.

As used herein, the term "EF-Tu-associated state" or "EF-Tu-associated disorder" include disorders and states (e.g., a disease state) that are associated with the activity of EF-Tu. A non-limiting example of an EF-Tu associated disorder is a bacterial infection in a subject.

The present invention includes treatment of bacterial infections, as well as EF-Tu-associated disorders, as described above, but the invention is not intended to be limited to the manner by which the compound performs its intended function of treatment of a disease. The present invention includes treatment of diseases described herein in any manner that allows treatment to occur, e.g., bacterial infection.

In certain embodiments, the invention provides a pharmaceutical composition of any of the compounds of the present invention. In a related embodiment, the invention provides a pharmaceutical composition of any of the compounds of the present invention and a pharmaceutically acceptable carrier or excipient of any of these compounds. In certain embodiments, the invention includes the compounds as novel chemical entities.

In one embodiment, the invention includes a packaged bacterial infection treatment. The packaged treatment includes a compound of the invention packaged with instructions for using an effective amount of the compound of the invention for an intended use.

The compounds of the present invention are suitable as active agents in pharmaceutical compositions that are efficacious particularly for treating bacterial infections. The pharmaceutical composition in various embodiments has a pharmaceutically effective amount of the present active agent along with other pharmaceutically acceptable excipients, carriers, fillers, diluents and the like. The phrase, "pharmaceutically effective amount" as used herein indicates an amount necessary to administer to a host, or to a cell, issue, or organ of a host, to achieve a therapeutic result, especially an anti-bacterial infection effect, e.g. inhibition of proliferation of a bacterium, or of any other bacterial infection.

In other embodiments, the present invention provides a method for inhibiting the activity of an EF-Tu protein. The method includes contacting a cell with any of the compounds of the present invention. In a related embodiment, the method further provides that the compound is present in an amount effective to selectively inhibit the activity of an EF-Tu protein.

In other embodiments, the present invention provides a use of any of the compounds of the invention for manufacture of a medicament to treat a bacterial infection in a subject.

In other embodiments, the invention provides a method of manufacture of a medicament, including formulating any of the compounds of the present invention for treatment of a subject.

DEFINITIONS

The term "treat," "treated," "treating" or "treatment" includes the diminishment or alleviation of at least one symptom associated or caused by the state, disorder or disease being treated. In certain embodiments, the treatment comprises the induction of a bacterial infection, followed by the activation of the compound of the invention, which would in turn diminish or alleviate at least one symptom associated or caused by the bacterial infection being treated. For example, treatment can be diminishment of one or several symptoms of a disorder or complete eradication of a disorder.

The term "subject" is intended to include organisms, e.g., prokaryotes and eukaryotes, which are capable of suffering from or afflicted with a bacterial infection. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from a bacterial infection, and for diseases or conditions described herein. In another embodiment, the subject is a cell.

The language "EF-Tu-modulating compound," "modulator of EF-Tu" or "EF-Tu inhibitor" refers to compounds that modulate, e.g., inhibit, or otherwise alter, the activity of EF-Tu. Examples of EF-Tu-modulating compounds include compounds of formula I, II, III, IV and V, as well as Table A and Table B (including pharmaceutically acceptable salts thereof, as well as enantiomers, stereoisomers, rotamers, tautomers, diastereomers, atropisomers or racemates thereof).

Additionally, a method of the invention includes administering to a subject an effective amount of an EF-Tu-modulating compound of the invention, e.g., EF-Tu-modulating compounds of Formula I, II, III, IV and V, as well as Table A and Table B (including pharmaceutically acceptable salts thereof, as well as enantiomers, stereoisomers, rotamers, tautomers, diastereomers, atropisomers or racemates thereof).

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term "alkyl" also includes alkenyl groups and alkynyl groups. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl, isobutyl and sec-butyl. Moreover, the term $C_{3-6}$-cycloalkyl includes, but is not limited to, cyclopropyl, cyclopentyl, and cyclohexyl. As discussed below, these alkyl groups, as well as cycloalkyl groups, may be further substituted. "$C_0$-$C_n$alkyl" refers to a single covalent bond ($C_0$) or an alkyl group having from 1 to n carbon atoms; for example "$C_0$-$C_4$alkyl" refers to a single covalent bond or a $C_1$-$C_4$alkyl group; "$C_0$-$C_8$alkyl" refers to a single covalent bond or a $C_1$-$C_8$alkyl group. In some instances, a substituent of an alkyl group is specifically indicated. For example, "$C_1$-$C_4$hydroxyalkyl" refers to a $C_1$-$C_4$alkyl group that has at least one hydroxy substituent.

"Alkylene" refers to a divalent alkyl group, as defined above. $C_0$-$C_4$alkylene is a single covalent bond or an alkylene group having from 1 to 4 carbon atoms; and $C_0$-$C_6$alkylene is a single covalent bond or an alkylene group having from 1 to 6 carbon atoms. "Alkenylene" and "Alkynylene" refer to divalent alkenyl and alkynyl groups respectively, as defined above.

A "cycloalkyl" is a group that comprises one or more saturated and/or partially saturated rings in which all ring members are carbon, such as cyclopropyl, cyclobutyl, cyclopentyl, cyclohexyl, cycloheptyl, cyclooctyl, adamantyl, decahydro-naphthalenyl, octahydro-indenyl, and partially saturated variants of the foregoing, such as cyclohexenyl. Cycloalkyl groups do not comprise an aromatic ring or a heterocyclic ring. Certain cycloalkyl groups are $C_3$-$C_8$cycloalkyl, in which the group contains a single ring with from 3 to 8 ring members. A "($C_3$-$C_8$cycloalkyl)$C_0$-$C_4$alkyl" is a $C_3$-$C_8$cycloalkyl group linked via a single covalent bond or a $C_1$-$C_4$alkylene group. In certain aspects, $C_{3-6}$-cycloalkyl groups are substituted one or more times (or preferably between one and five times) with substitutents independently selected from a halogen atom, aryl, heteroaryl, trihalomethyl, $C_{1-4}$-alkoxy or $C_{1-4}$-alkyl.

Moreover, alkyl (e.g., methyl, ethyl, propyl, butyl, pentyl, hexyl, etc.) include both "unsubstituted alkyl" and "substituted alkyl", the latter of which refers to alkyl moieties having substituents replacing a hydrogen on one or more carbons of the hydrocarbon backbone, which allow the molecule to perform its intended function.

The term "substituted" is intended to describe moieties having substituents replacing a hydrogen on one or more atoms, e.g. C, O or N, of a molecule. Such substituents can include, for example, oxo, alkyl, alkoxy, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, morpholino, phenol, benzyl, phenyl, piperizine, cyclopentane, cyclohexane, pyridine, 5H-tetrazole, triazole, piperidine, or an aromatic or heteroaromatic moiety, and any combination thereof.

Further examples of substituents of the invention, which are not intended to be limiting, include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g. benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., —$NH_2$), $(CR'R'')_{0-3}CN$ (e.g. —CN), —$NO_2$, halogen (e.g., —F, —Cl, —Br, or —I), $(CR'R'')_{0-3}C(halogen)_3$ (e.g., —$CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., —$SO_3H$, —$OSO_3H$), $(CR'R'')_{0-3}O(CR'R'')_{0-3}H$ (e.g., —$CH_2OCH_3$ and —$OCH_3$), $(CR'R'')_{0-3}S(CR'R'')_{0-3}H$ (e.g., —SH and —$SCH_3$), $(CR'R'')_{0-3}OH$ (e.g. —OH), $(CR'R'')_{0-3}COR'$, (CR'R")$_{0-3}$(substituted or unsubstituted phenyl), (CR'R")$_{0-3}$ (C$_3$-C$_8$ cycloalkyl), (CR'R")$_{0-3}$CO$_2$R' (e.g., —CO$_2$H), or (CR'R")$_{0-3}$OR' group, or the side chain of any naturally occurring amino acid; wherein R' and R" are each independently hydrogen, a C$_1$-C$_5$ alkyl, C$_2$-C$_5$ alkenyl, C$_2$-C$_5$ alkynyl, or aryl group. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, oxime, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety, and any combination thereof. In certain embodiments, a carbonyl moiety (C=O) may be further derivatized with an oxime moiety, e.g. an aldehyde moiety may be derivatized as its oxime (—C=N—OH) analog. It will be understood by those skilled in the art that the moieties substituted on the hydrocarbon chain can themselves be substituted, if appropriate. Cycloalkyls can be further substituted, e.g. with the substituents described above. An "aralkyl" moiety is an alkyl substituted with an aryl (e.g., phenylmethyl (i.e., benzyl)).

The term "alkenyl" includes unsaturated aliphatic groups analogous in length and possible substitution to the alkyls described above, but which contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups that include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., C$_2$-C$_6$ for straight chain, C$_3$-C$_6$ for branched chain). Likewise, cycloalkenyl groups may have from 3-8 carbon atoms in their ring structure, and more preferably have 5 or 6 carbons in the ring structure. The term C$_2$-C$_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g. ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., C$_2$-C$_6$ for straight chain, C$_3$-C$_6$ for branched chain). The term C$_2$-C$_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "amine" or "amino" should be understood as being broadly applied to both a molecule, or a moiety or functional group, as generally understood in the art, and may be primary, secondary, or tertiary. The term "amine" or "amino" includes compounds where a nitrogen atom is covalently bonded to at least one carbon, hydrogen or heteroatom. The terms include, for example, but are not limited to, "alkylamino," "arylamino," "diarylamino," "alkylarylamino," "alkylaminoaryl," "arylaminoalkyl," "alkaminoalkyl," "amide," "amido," and "aminocarbonyl." The term "alkyl amino" comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "aryl" includes groups, including 5- and 6-membered single-ring aromatic groups that may include from zero to four heteroatoms, for example, phenyl, pyrrole, furan, thiophene, thiazole, isothiaozole, imidazole, triazole, tetrazole, pyrazole, oxazole, isoxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, anthryl, phenanthryl, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics." The aromatic ring can be substituted at one or more ring positions with such substituents as described above, as for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

The term "acyl" includes compounds and moieties which contain the acyl radical ($CH_3CO-$) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "carbonyl" or "carboxy" includes compounds and moieties which contain a carbon connected with a double bond to an oxygen atom, and tautomeric forms thereof. Examples of moieties that contain a carbonyl include aldehydes, ketones, carboxylic acids, amides, esters, anhydrides, etc. The term "carboxy moiety" or "carbonyl moiety" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety. For example, the term includes moieties such as, for example, aminocarbonyl moieties, (wherein a nitrogen atom is bound to the carbon of the carbonyl group, e.g., an amide), aminocarbonyloxy moieties, wherein an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. moieties.

The term "thiocarbonyl" or "thiocarboxy" includes compounds and moieties which contain a carbon connected with a double bond to a sulfur atom. The term "thiocarbonyl moiety" includes moieties that are analogous to carbonyl moieties. For example, "thiocarbonyl" moieties include aminothiocarbonyl, wherein an amino group is bound to the carbon atom of the thiocarbonyl group, furthermore other thiocarbonyl moieties include, oxythiocarbonyls (oxygen bound to the carbon atom), aminothiocarbonylamino groups, etc.

The term "ether" includes compounds or moieties that contain an oxygen bonded to two different carbon atoms or heteroatoms. For example, the term includes "alkoxyalkyl" which refers to an alkyl, alkenyl, or alkynyl group covalently bonded to an oxygen atom that is covalently bonded to another alkyl group.

The term "ester" includes compounds and moieties that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom that is bonded to an alkyl group. Similarly, the term "alkthioalkenyls" and "alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" include moieties with two or more rings (e.g., cycloalkyls, cycloalkenyls, cycloalkynyls, aryls and/or heterocyclyls) in which two or more carbons are common to two adjoining rings, e.g. the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

Additionally, the phrase "any combination thereof" implies that any number of the listed functional groups and molecules may be combined to create a larger molecular architecture. For example, the terms "phenyl," "carbonyl" (or "=O"), "—O—," "—OH," and $C_{1-6}$ (i.e., —$CH_3$ and —$CH_2CH_2CH_2$—) can be combined to form a 3-methoxy-4-propoxybenzoic acid substituent. It is to be understood that when combining functional groups and molecules to create a larger molecular architecture, hydrogens can be removed or added, as required to satisfy the valence of each atom.

It is to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms: carbon: four bonds; nitrogen: three bonds; oxygen: two bonds; and sulfur: two-six bonds.

It will be noted that the structures of some of the compounds of this invention include asymmetric carbon atoms. It is to be understood accordingly that the isomers arising from such asymmetry (e.g., all enantiomers, stereoisomers, rotamers, tautomers, diastereomers, or racemates) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein may be obtained through art recognized synthesis strategies.

It will also be noted that the substituents of some of the compounds of this invention include isomeric cyclic structures. It is to be understood accordingly that constitutional isomers of particular substituents are included within the scope of this invention, unless indicated otherwise. For example, the term "tetrazole" includes tetrazole, 2H-tetrazole, 3H-tetrazole, 4H-tetrazole and 5H-tetrazole.

Use in Bacterial Infection

The compounds of the present invention have valuable pharmacological properties and are useful in the treatment of diseases. In certain embodiments, compounds of the invention are useful in the treatment of bacterial infections.

The term "use" includes any one or more of the following embodiments of the invention, respectively: the use in the treatment of bacterial infections; the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. In particular, diseases to be treated and are thus preferred for use of a compound of the present invention are selected from bacterial infections, as well as those diseases that depend on the activity of EF-Tu. The term "use" further includes embodiments of compositions herein which bind to an EF-Tu protein sufficiently to serve as tracers or labels, so that when coupled to a fluor or tag, or made radioactive, can be used as a research reagent or as a diagnostic or an imaging agent.

In certain embodiments, a compound of the present invention is used for treating EF-Tu-associated diseases, and use of the compound of the present invention as an inhibitor of any one or more EF-Tu proteins. It is envisioned that a use can be a treatment of inhibiting one or more isoforms of EF-Tu.

Assays

The inhibition of antibacterial activity by the compounds of the invention may be measured using a number of assays available in the art. An example of such an assay is the standard minimum inhibitory concentration (MIC) test conducted according to CSLI guidelines.

Pharmaceutical Compositions

The language "effective amount" of the compound is that amount necessary or sufficient to treat or prevent a bacterial infection, e.g. prevent the various morphological and somatic symptoms of a bacterial infection, and/or a disease or condition described herein. In an example, an effective amount of the compound of the invention is the amount sufficient to treat a bacterial infection in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a bacterial infection. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical compositions for use in the treatment of these diseases. Methods of use of compounds of the present invention in the treatment of these diseases, or pharmaceutical preparations having compounds of the present invention for the treatment of these diseases.

The language "pharmaceutical composition" includes preparations suitable for administration to mammals, e.g. humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof, and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral and/or IV administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a bacterial infection.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

Synthetic Procedure

Compounds of the present invention are prepared from commonly available compounds using procedures known to those skilled in the art, including any one or more of the following conditions without limitation:

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g. Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosauren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g. a free carboxy group and a free amino group, may be formed, e.g., by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by, e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

General Process Conditions

The following applies in general to all processes mentioned throughout this disclosure.

The process steps to synthesize the compounds of the invention can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g., in the $H^+$ form, depending on the nature of the reaction and/or of the reactants at reduced, normal or elevated temperature, for example in a temperature range of from about $-100°$ C. to about $190°$ C., including, for example, from approximately $-80°$ C. to approximately $150°$ C., for example at from $-80$ to $-60°$ C., at room temperature, at from $-20$ to $40°$ C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described in Science of Synthesis: Houben-Weyl Methods of Molecular Transformation. Georg Thieme Verlag, Stuttgart, Germany. 2005.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

Prodrugs

This invention also encompasses pharmaceutical compositions containing, and methods of treating bacterial infections through administering, pharmaceutically acceptable prodrugs of compounds of the compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy) ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Any reference to a compound of the present invention is therefore to be understood as referring also to the corresponding pro-drugs of the compound of the present invention, as appropriate and expedient.

Combinations

A compound of the present invention may also be used in combination with other agents, e.g., an additional antibacterial compound that is or is not a compound of the invention, for treatment of a bacterial infection in a subject.

By the term "combination" is meant either a fixed combination in one dosage unit form, or a kit of parts for the combined administration where a compound of the present invention and a combination partner may be administered independently at the same time or separately within time intervals that especially allow that the combination partners show a cooperative, e.g. synergistic, effect, or any combination thereof.

A compound of the present invention may be used in combination with another antibacterial agent. The term "antibacterial agent" refers to any substance that is either bactericidal or bacteriostatic, i.e., capable of killing or inhibiting the growth of bacterial cells. Antibacterial agents include antibiotics, biocides, antimicrobials, and bacteriostatic agents. The known types of antibiotics include, e.g., cell wall synthesis inhibitors, cell membrane inhibitors, protein synthesis inhibitors and inhibitors that bind to or affect the synthesis of DNA or RNA. Numerous antibiotic agents suitable for use in the treatment of bacteria-related diseases and disorders, are known and disclosed, e.g. in The Physician's Desk Reference (PDR), Medical Economics Company (Montvale, N.J.), (53.sup.rd Ed.), 1999; Mayo Medical Center Formulary, Unabridged Version, Mayo Clinic (Rochester, Minn.), January 1998; Merck Index: An Encyclopedia of Chemicals, Drugs and Biologicals, (11.sup.th Ed.), Merck & Co., Inc. (Rahway, N.J.), 1989; University of Wisconsin Antimicrobial Use Guide, http://www.medsch.wisc.edu/clinsci/5amcg/amcg.html; Introduction on the Use of the Antibiotics Guideline, of Specific Antibiotic Classes, Thomas Jefferson University, http://jeffiine.tju.edu/CWIS/OAC/antibiotics_guide/intro.html; and references cited therein.

Examples of antibiotics for use in combination with the compounds of the invention include, but are not limited to, quinolone, macrolide, glycopeptide, oxazolidinone, β-lactams (including amoxicillin, ampicillin, bacampicillin, carbenicillin, cloxacillin, dicloxacillin, flucloxacillin, methicillin, mezlocillin, nafcillin, oxacillin, penicillin G, penicillin V, piperacillin, pivampicillin, pivmecillinam, ticarcillin, sulbactam, tazobactam, clavulanate), cephalosporins (cefaclor, cefadroxil, cefamandole, cefazolin, cefdinir, cefditoren, cefepime, cefixime, cefonicid, cefoperazone, cefotaxime, cefotetan, cefoxitin, cefpodoxime, cefprozil, ceftazidime, ceftibuten, ceftizoxime, ceftriaxone, cefuroxime, cephalexin, cephalothin, cephapirin, cephradine), aminoglycosides (including gentamycin, streptomycin, amikacin, kanamycin, viomycin, capreomycin), ethionamide, prothionamide, cycloserine, dapsone, clofazimine, tetracyclines (tetracycline, doxycycline, chlortetracycline, oxytetracycline, minocycline demeclocycline), oxazolidinones (linezolid, eperezolid), metronidazole, rifabutin, isoniazonid, ethambutol, and combinations thereof.

Examples of anti-viral agents for use in combination with the compounds of the invention include, but are not limited to, zidovudine, lamivudine, didanosine, zalcitabine, stavudine, abacavir, nevirapine, delavirdine, emtricitabine, efavirenz, saquinavir, ritonavir, indinavir, nelfinavir, amprenavir, tenofovir, adefovir, atazanavir, fosamprenavir, hydroxyurea, AL-721, ampligen, butylated hydroxytoluene; polymannoacetate, castanospermine; contracan; creme pharmatex, CS-87, penciclovir, famciclovir, acyclovir, cytofovir, ganciclovir, dextran sulfate, D-penicillamine trisodium phosphonoformate, fusidic acid, HPA-23, eflornithine, nonoxynol, pentamidine isethionate, peptide T, phenyloin, isoniazid, ribavirin, rifabutin, ansamycin, trimetrexate, SK-818, suramin, UA001, enfuvirtide, gp41-derived peptides, antibodies to CD4, soluble CD4, CD4-containing molecules, CD4-IgG2, and combinations thereof.

Further examples of agents the compounds of the present invention can be used in combination with include, but are not limited to, free radical scavengers, ascorbic acid, Vitamin C, anti-cancer agents, chemotherapeutic agents, non-steroidal anti-inflammatory drugs, steroidal anti-inflammatory drugs, anti-fungal agents, detoxifying agents, analgesics, bronchodilators, drugs for the treatment of vascular ischemia antibody monoclonal agent, minoxidil for topical application for hair growth, diuretics, immunosuppressants, lymphokynes, α-and-β-interferon and combinations thereof.

The compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention comprises an additional agent as described herein. Each component may be present in individual compositions, combination compositions, or in a single composition.

EXEMPLIFICATION OF THE INVENTION

The invention is further illustrated by the following examples, which should not be construed as further limiting. The practice of the present invention will employ, unless otherwise indicated, conventional techniques of cell biology, cell culture, molecular biology, transgenic biology, microbiology and immunology, which are within the skill of the art.

General Synthesis Methods

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

EXAMPLES

| Definitions | |
|---|---|
| AcOH | acetic acid |
| aq | aqueous |
| Boc | tert-butoxycarbonyl |
| DMF | N,N-dimethylformamide |
| DCC | N,N-dicyclohexylcarbodiimide |
| DCE | dichloroethane |
| DCM | dichloromethane |
| DMAP | 4-dimethylaminopyridine |
| DMSO | dimethylsulfoxide |
| EtOAc | ethyl acetate |
| EtOH | ethanol |
| eq | equivalents |
| LC | liquid chromatography |
| LCMS | liquid chromatography mass spectrum |
| MeOH | methanol |
| MHz | megahertz |
| PS | polystyrene |
| RT | room temperature |
| $R_t$ | retention time |
| s | solid |
| sat. | saturated |
| TEA | triethylamine |
| TFA | trifluoroacetic acid |
| THF | tetrahydrofuran |
| h | hours |
| min | minutes |
| m/z | mass to charge |
| MS | mass spectrum |
| HRMS | high resolution mass spectrum |
| NMR | nuclear magnetic resonance |

Analytical Methods

NMR: proton spectra are recorded on a Bruker 400 MHz ultrashield spectrometer. Chemical shifts are reported relative to methanol ($\delta$3.31), dimethyl sulfoxide ($\delta$ 2.50), or chloroform ($\delta$ 7.26).

LCMS: compounds are analyzed on an Inertsil ODS-3 column (C18, 50×4.6 mm, 3 µm) with a 2 min gradient elution (25% acetonitrile/$H_2O$/5 mM ammonium formate) and a flow rate of 4 ml/min.

HPLC purification utilizes a C8 or C18 column (30×100 mm, 5 µm, brand: Sunfire or XTerra) and is performed according to two methods. Method 1 consists of 0.1% TFA in 10%-95% ACN in $H_2O$. Method 2 consists of 10 mM $NH_4OH$ in 40%-95% ACN in $H_2O$.

LC analysis utilizes an Atlantis brand C18 column (150 mm) with gradient elution (0-95% acetonitrile in water+0.1% TFA).

General Scheme 1:

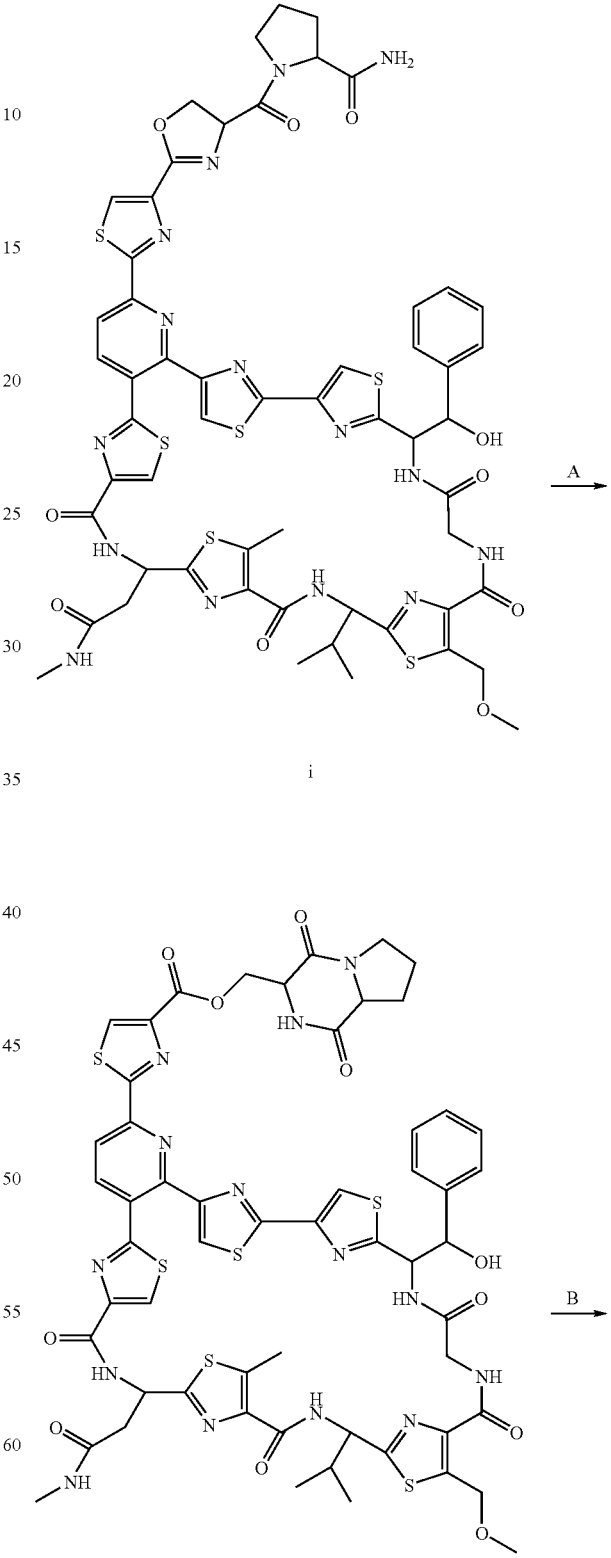

i ii

129
-continued
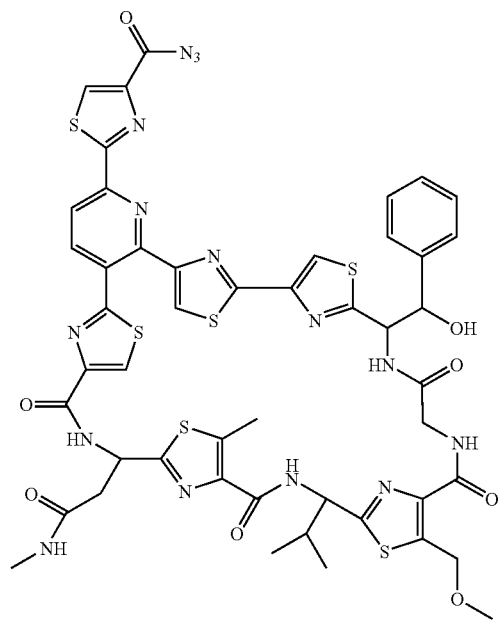
iii
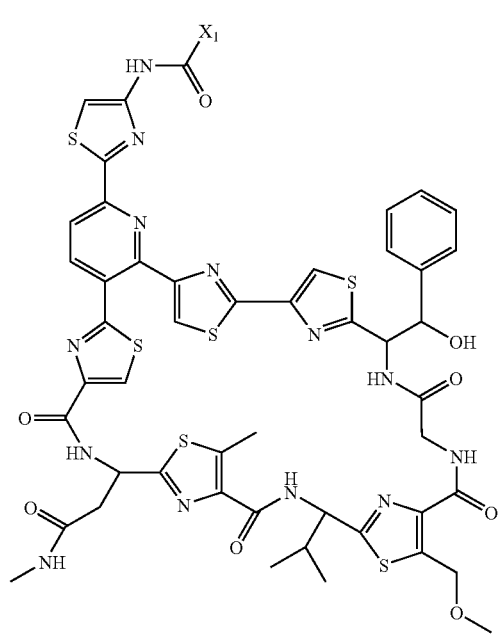
iv
130
-continued
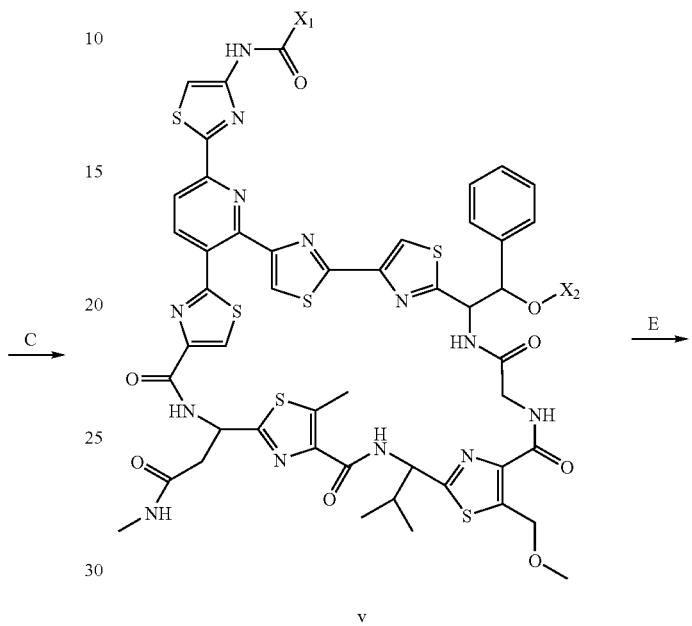
v
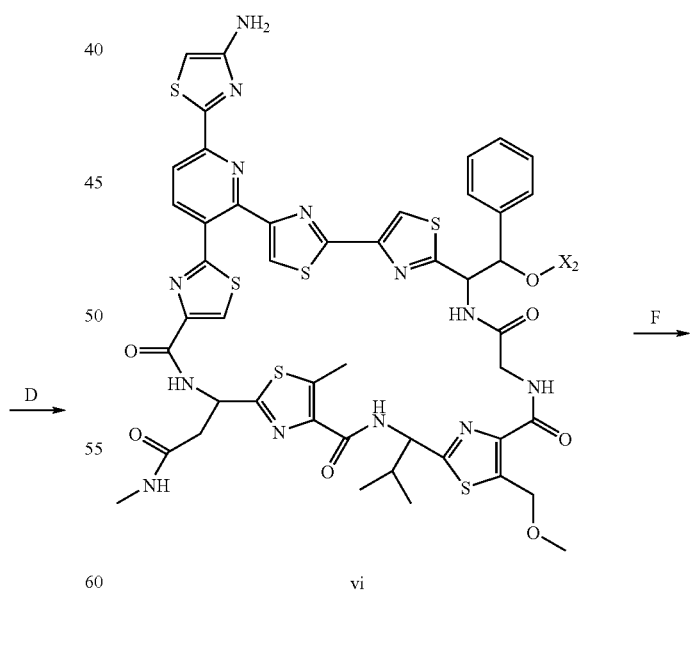
vi -continued

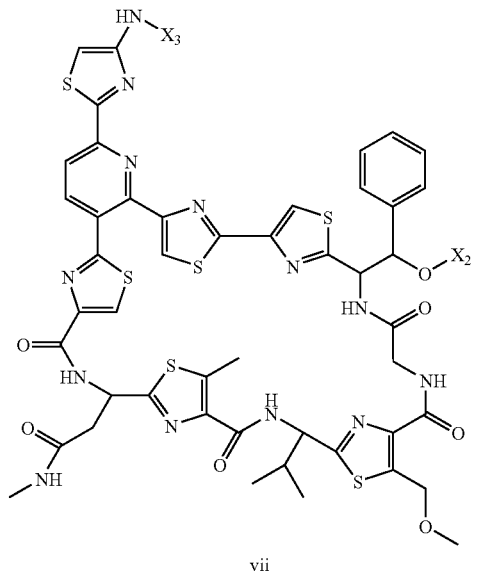

vii

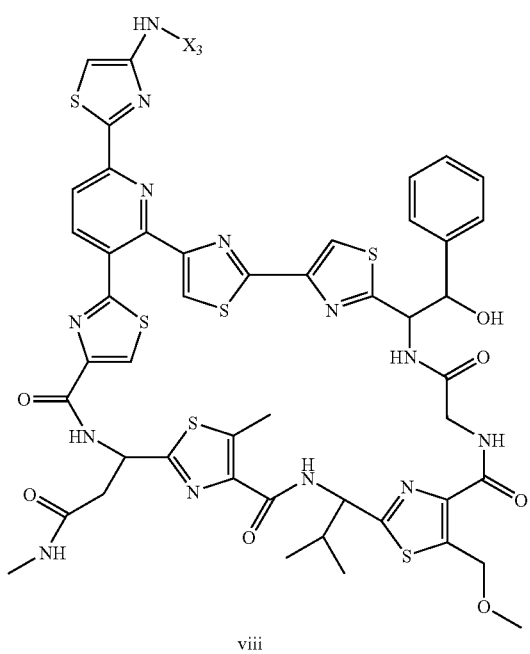

viii

The compound of general formula (i) may be prepared via synthetic methods well known to those skilled in the art, or alternatively isolated from a fermentation broth. See, for example, U.S. Pat. No. 5,202,241, which is incorporated herein in its entirety. The compound of general structural formula (ii) may be prepared by process A by the acid or base mediated rearrangement of compound (i) in the presence of water and a suitable acid or base. The compound of general formula (iii) may be prepared in process B from (ii) directly via reaction with azide or alternatively through a multi step process which includes removal of the ester functionality through hydrolysis with a suitable base or acid, activation of the carboxylic acid moiety using a suitable activation agent, and reaction with a suitable reagent such as azide. Azides represented by formula (iii) are known in the art and are readily synthesized by standard procedures commonly employed in the art. The compound of general formula (iv) may be prepared by reaction of the azide (iii) with a nucleophile, alcohol, amine, or protecting group ($X_1$). A suitable protecting group can be selected by those skilled in the art. Protecting groups are selected so that they are suitable for the depicted transformations and can be removed following the synthesis with little or no loss of yield. The introduction and selective removal of protecting groups are taught in Greene and Wuts, "Protective Groups in Organic Synthesis", John Wiley & Sons (1991). The compound of general structural formula (v) may be prepared by reacting compound (iv) with a reactive reagent such as an electrophile, alkylating agent, acylating agent, or protecting group ($X_2$) to afford compound (v). The compound of general structure (vi) can be prepared by reacting compound (v) with acid, base, a nucleophile, or electrophile to remove the protecting group ($X_1$). The compound of general structure (vii) can be prepared by reacting compound (vi) with a suitable electrophile, alkylating agent, or acylating agent ($X_3$). The compound of general structure (viii) can be prepared by reacting compound (vii) with acid, base, a nucleophile, or electrophile to remove the protecting group ($X_2$). Alternatively, any of these steps (A-G) may be performed in a different order, or with some steps removed or slightly altered, which is obvious to those skilled in the art.

Scheme 2: Preparation of Common Intermediate, Boc-Amine (4):
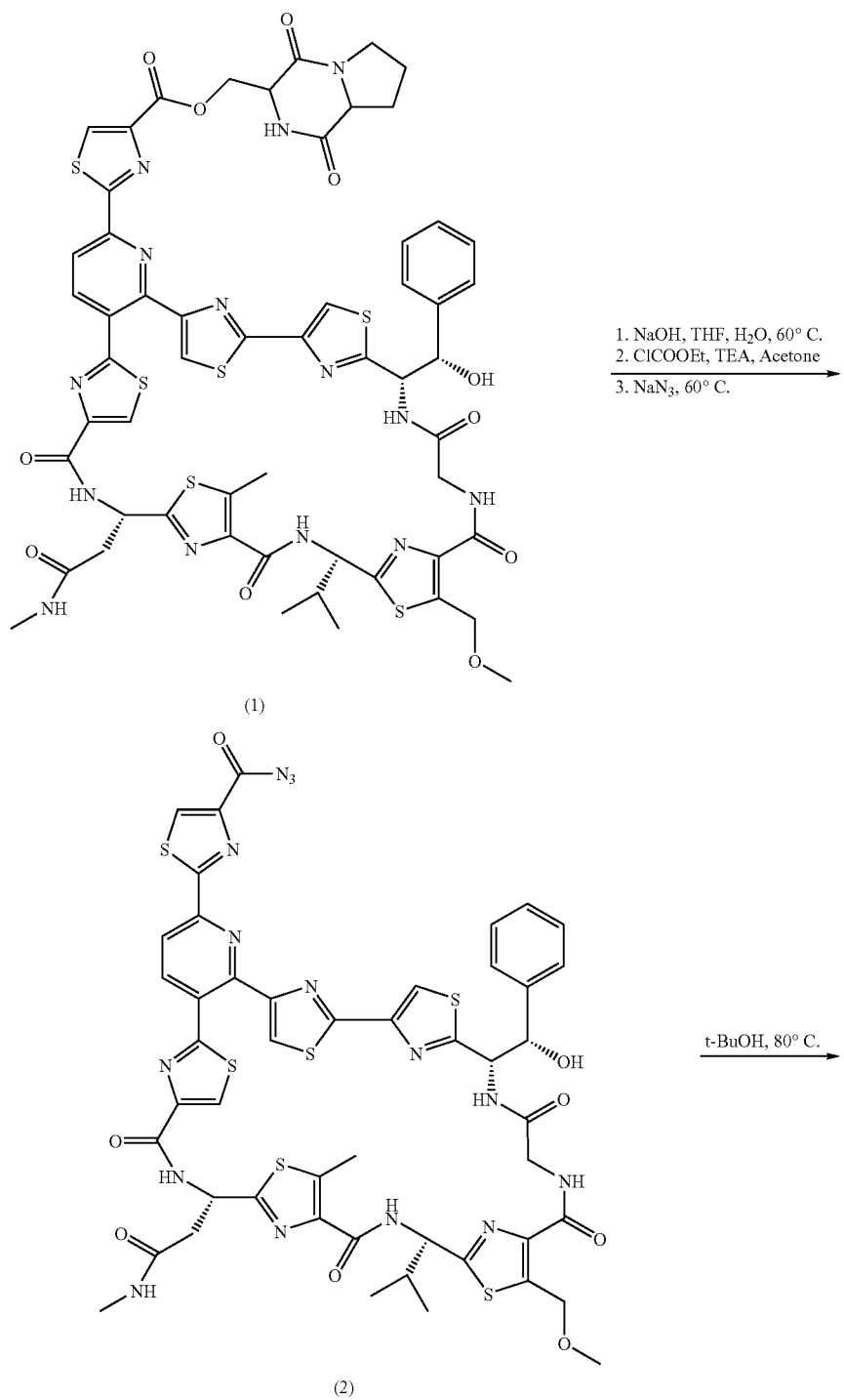

-continued
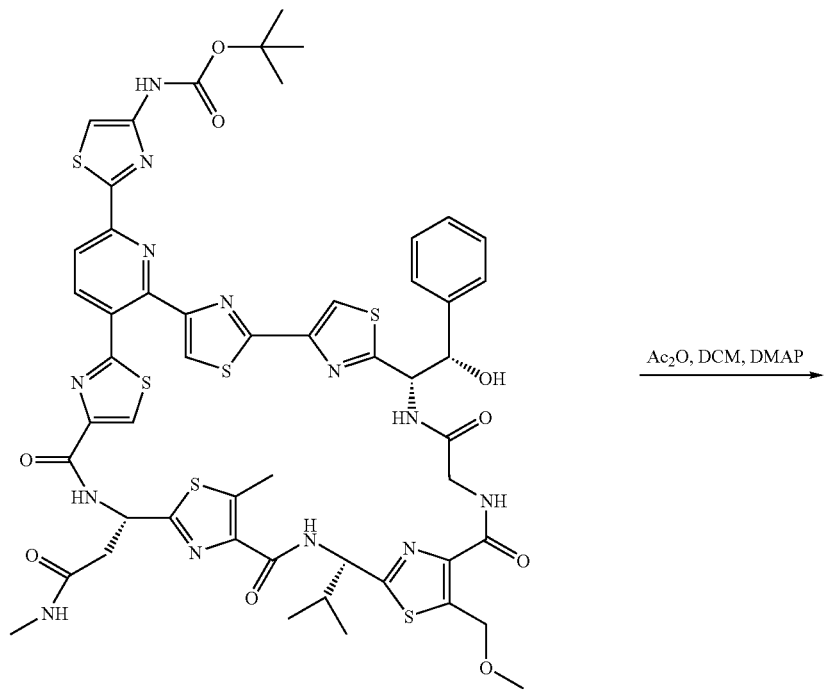
(3)
Ac₂O, DCM, DMAP →
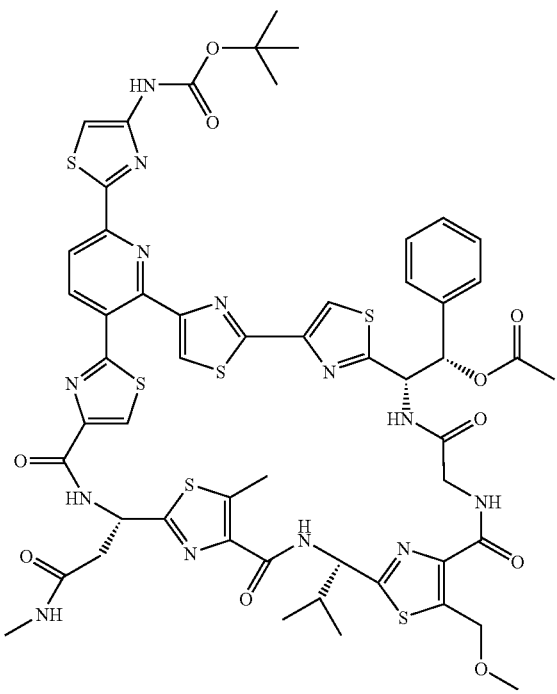
(4)

Preparation of Common Intermediate (4):

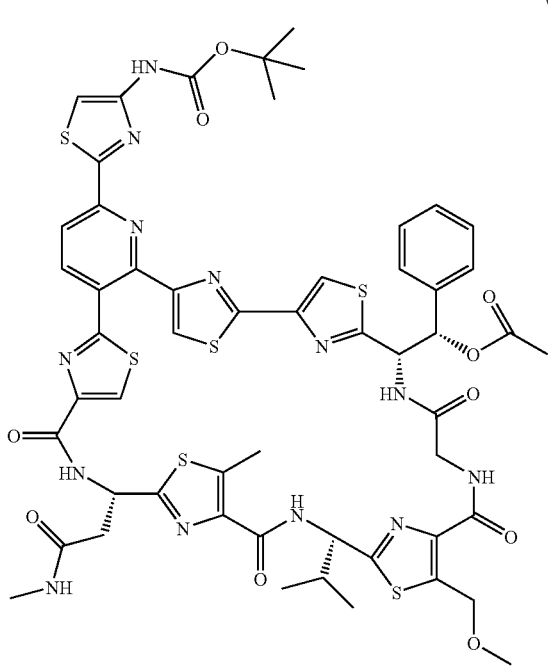
(4)

Steps 1-3, Preparation of Acylazide (2):

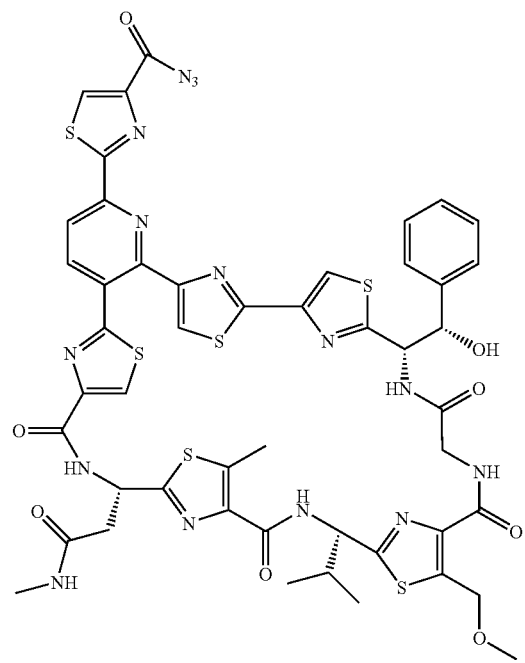
(2)

To a solution of the ester (1, 1.5 g, 1.16 mmol) in THF (300 mL) is added 20 mL H$_2$O and NaOH (60 mg, 1.50 mmol). The reaction is stirred at 60° C. for 1.5 h and monitored by TLC (10% MeOH/DCM) and LCMS. After completion, the reaction is concentrated to dryness. The off-white solid is suspended in toluene (100 mL) and concentrated to dryness (repeat 3×), which affords the acid, an off-white solid. The crude solid is stored in vacuo (0.1 Torr) for 12 h. LCMS: R$_t$=1.12 min, [M+H]$^+$1125.

The crude acid is suspended in 300 mL acetone. The flask is sonicated and the solid scraped down the sides of the flask for 15 min. To this suspension is added TEA (2.0 mL, 14.2 mmol) and ethyl chloroformate (2.0 mL, 20.91 mmol). The reaction appears to slowly dissolve. Further sonication, and vigorous stirring is used to break up all particles. After 1 h, the reaction appears complete via LCMS and NaN$_3$ (500 mg, 7.69 mmol) is added. The suspension (white/yellow in appearance) is stirred for 1 h at 60° C. and monitored by LCMS. Two more aliquots of NaN$_3$ (500 mg, 7.69 mmol) is added and the reaction stirs for 20 min. The reaction is concentrated onto SiO$_2$ and purified by flash chromatography (1.5"×1.5" SiO$_2$ column, 3 L EtOAc). This affords 920 mg of crude acyl-azide (2), a white solid. The crude material is taken on to the next step with no further purification. LCMS: R$_t$=1.55 min, [M+H]$^+$ 1150.

Step 4, Preparation of Boc-amine (3):

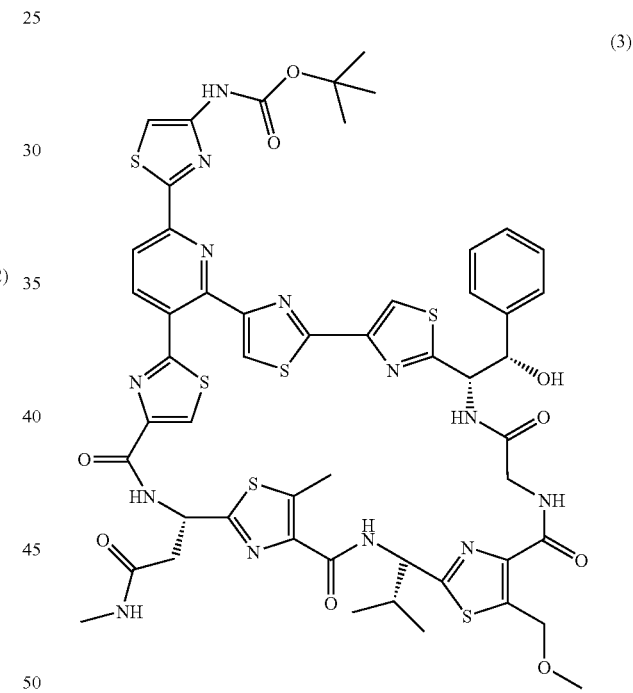
(3)

A suspension of acyl-azide (2, 920 mg) is heated (80° C.) in t-BuOH (100 g). After 2 h complete dissolution occurs and after 12 h the reaction appears complete by LCMS. The solution is concentrated directly onto SiO$_2$ and chromatographed (gradient elution: 50-70% EtOAc/hexanes) which affords 600 mg of Boc-amine (3), a white solid. $^1$H NMR (400 MHz, d$_6$-DMSO) δ 10.38 (br s, 1H), 9.00 (d, 1H), 8.70 (app d, 2H), 8.58 (s, 1H), 8.44-8.41 (m, 1H), 8.38 (d, 1H), 8.23 (s, 1H), 8.11 (d, 1H), 7.48 (br s, 1H), 7.38-7.23 (m, 7H), 6.02 (br s, 1H), 5.31-5.18 (m, 3H), 5.01-5.00 (m, 1H), 4.97 (s, 2H), 4.30-4.24 (dd, 1H), 3.79 (dd, 1H), 3.38 (s, 3H), 2.75-2.68 (m, 1H), 2.47 (d, 3H), 2.22-2.13 (m, 1H), 1.49 (s, 9H), 1.37-1.31 (m, 1H), 0.87 (d, 3H), 0.84 (d, 3H). LCMS: R$_t$=1.72 min, [M+H]$^+$ 1196.

Step 5, Preparation of Boc-amine-acetate (4):

(4)

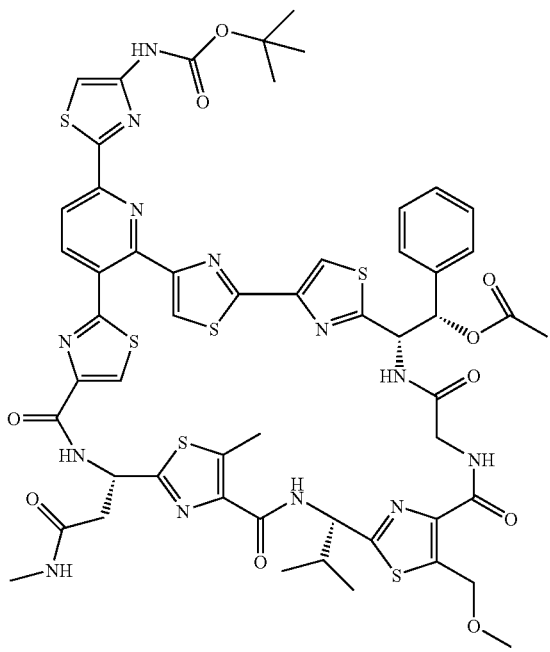

To a solution of the Boc-amine (3, 540 mg, 0.451 mmol) in DCM (250 mL) is added acetic anhydride (0.100 mL, 0.979 mmol), pyridine (1.0 mL, 12.4 mmol) and DMAP (20 mg, 0.169 mmol). The reaction is stirred for 3 h, concentrated directly onto SiO$_2$ and chromatographed (gradient elution: 50-70% EtOAc/hexanes) which provides 465 mg of Boc-amine-acetate (4). $^1$H NMR (400 MHz, d$_6$-DMSO) δ 10.38 (br s, 1H), 9.20 (br d, 1H), 8.79 (br d, 1H), 8.61 (br d, 1H), 8.56 (s, 1H), 8.44-8.41 (m, 1H), 8.38 (d, 1H), 8.24 (s, 1H), 8.11 (d, 1H), 7.48 (br s, 1H), 7.42 (s, 2H), 7.35-7.29 (m, 6H), 6.14 (s, 1H), 5.47 (t, 1H), 5.31-5.26 (m, 1H), 5.19 (dd, 1H), 4.97 (s, 3H), 4.26 (dd, 1H), 3.72 (dd, 1H), 3.38 (s, 3H), 2.70-2.65 (m, 1H), 2.59 (s, 3H), 2.45 (d, 3H), 2.22-2.14 (m, 1H), 1.96 (s, 3H), 1.57-1.50 (m, 1H), 1.49 (s, 9H), 0.88 (d, 3H), 0.84 (d, 3H). LCMS: R$_t$=1.81 min, [M+H]$^+$ 1238.

Example 1

Preparation of Amide (5)

(5)

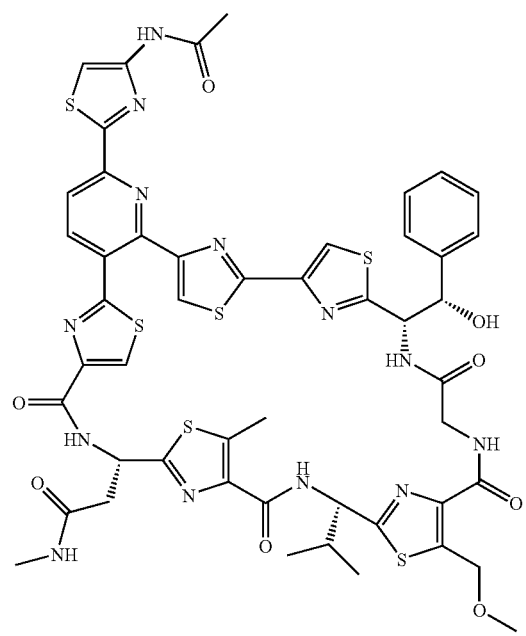

To a solution of the Boc-amine (3, 10 mg, 0.0083 mmol) in DCM (10 mL) is added TFA (1 mL, 13.46 mmol). The reaction is stirred for 30 min and concentrated. The resultant yellow foam is dissolved in DCM (10 mL) and concentrated (repeat 3×). The crude amine salt is taken on with no further purification. LCMS: R$_t$=1.33 min, [M+H]$^+$ 1096.

To a solution of the amine (0.0083 mmol) in pyridine (1 mL) is added acetic anhydride (0.100 mL, 0.979 mmol). The solution is stirred at RT for 10 min and poured into a saturated aq solution of sodium bicarbonate (100 mL). The mixture is extracted with EtOAc (3×) and the combined organic extracts are dried over MgSO$_4$, filtered, and concentrated directly onto SiO$_2$. The crude product is purified by flash chromatography (gradient elution: 0-5% MeOH/DCM) to afford 6 mg of amide (5) as a white solid. $^1$H NMR (400 MHz, d$_6$-DMSO) δ 11.14 (br s, 1H), 9.00 (br d, 1H), 8.68-8.66 (m, 2H), 8.59 (s, 1H), 8.45-8.42 (m, 1H), 8.40 (d, 1H), 8.24 (s, 1H), 8.13 (d, 1H), 7.80 (s, 1H), 7.38-7.21 (m, 7H), 6.01 (br d, 1H), 5.32-5.17 (m, 3H), 5.01-4.99 (m, 1H), 4.97 (s, 2H), 4.27 (dd, 1H), 3.79 (dd, 1H), 3.38 (s, 3H), 2.73-2.68 (m, 1H), 2.46 (d, 3H), 2.19-2.14 (m, 1H), 2.10 (s, 3H), 1.35-1.28 (m, 1H), 0.87 (d, 3H), 0.84 (d, 3H). LCMS: R$_t$=1.35 min, [M+H]$^+$ 1138.

Example 2

Preparation of Methyl Ester (6)

(6)

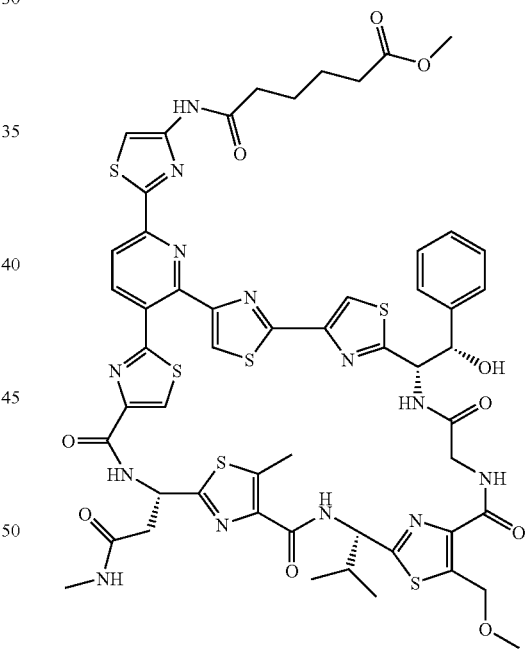

Methyl ester (6) is prepared according to the procedures described in example 1, except adipic acid monomethylester chloride is used as an acylating agent. $^1$H NMR (400 MHz, d$_6$-DMSO) δ 11.11 (br s, 1H), 9.00 (br s, 1H), 8.68-8.66 (m, 2H), 8.59 (s, 1H), 8.44-8.41 (m, 1H), 8.40 (d, 1H), 8.24 (s, 1H), 8.13 (d, 1H), 7.83 (s, 1H), 7.38-7.22 (m, 8H), 6.02 (br d, 1H), 5.31-5.17 (m, 3H), 5.01-4.99 (m, 1H), 4.97 (s, 2H), 4.28 (dd, 1H), 3.78 (dd, 1H), 3.59 (s, 3H), 3.38 (s, 3H), 2.70 (m, 1H), 2.58 (s, 3H), 2.46 (d, 3H), 2.40 (app t, 2H), 2.34 (app t, 2H), 2.20-2.12 (m, 1H), 1.65-1.54 (m, 4H), 1.35-1.32 (m, 1H), 0.87 (d, 3H), 0.84 (d, 3H). LCMS: R$_t$=1.47 min, [M+H]$^+$ 1238.

Example 3

Preparation of Acid (7)

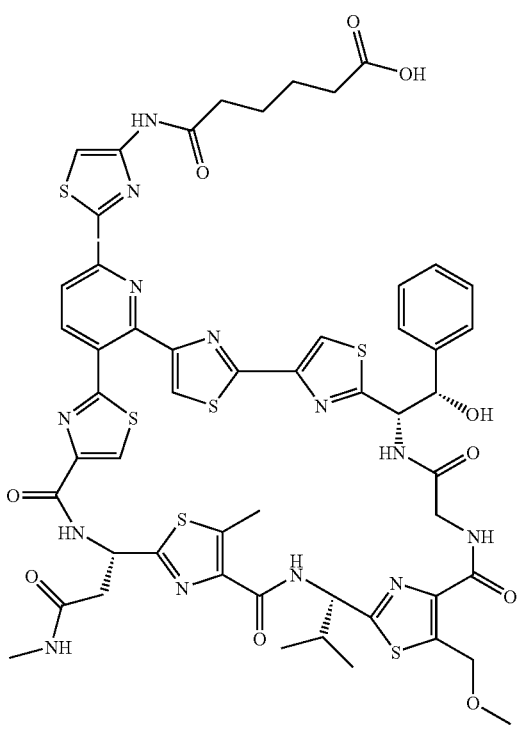

Steps 1-2, Preparation of Methylester-acetate (8):

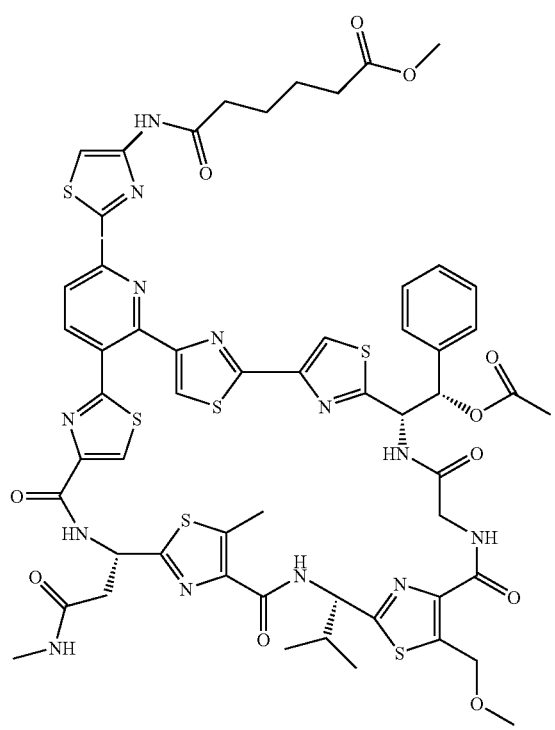

To a solution of Boc-amine-acetate (4,190 mg, 0.153 mmol) in DCM (10 mL) is added TFA (5 mL, 67.3 mmol). The reaction is stirred for 30 min and concentrated. The resultant yellow foam is dissolved in DCM (10 mL) and concentrated (repeat 3×). The crude amine salt is taken on with no further purification. LCMS: $R_t$=1.45 min, $[M+H]^+$ 1138.

To a solution of the amine salt in pyridine (5 mL) is added adipic acid monomethyl ester chloride (0.200 mL, 1.285 mmol). The solution is stirred at RT for 10 min and poured into a saturated aq solution of sodium bicarbonate (100 mL). The mixture is extracted with EtOAc (3×) and the combined organic extracts were dried over $MgSO_4$, filtered, and concentrated directly onto $SiO_2$. The crude product is purified by flash chromatography (gradient elution: 50-80% EtOAc/hexanes) which affords 170 mg of ester-acetate (8). LCMS: $R_t$=1.58 min, $[M+H]^+$ 1280.

Step 3, Preparation of Acid (7):

To a solution of the methylester-acetate (8, 170 mg, 0.133 mmol) in MeOH (100 mL) is added $H_2O$ (5 mL) and NaOH (100 mg, 2.5 mmol). The solution is heated to 50° C., stirred for 2 h, and concentrated onto $SiO_2$. Flash chromatography (gradient elution: 0-5% MeOH/DCM) provides 95 mg of the title compound, a tan solid. $^1H$ NMR (400 MHz, $d_6$-DMSO) δ 12.05 (br s, 1H), 11.13 (br s, 1H), 9.44 (br d, 1H), 8.70-8.65 (m, 2H), 8.59 (s, 1H), 8.45-8.42 (m, 1H), 8.39 (d, 1H), 8.23 (s, 1H), 8.13 (d, 1H), 7.82 (s, 1H), 7.42-7.38 (m, 1H), 7.32 (s, 1H), 7.29-7.17 (m, 6H), 6.13 (br s, 1H), 5.33-5.17 (m, 3H), 5.03 (d, 1H), 4.98 (s, 3H), 4.32 (dd, 1H), 3.83-3.76 (m, 1H), 3.38 (s, 3H), 2.74-2.68 (m, 1H), 2.58 (s, 3H), 2.47 (d, 3H), 2.40 (t, 2H), 2.23 (t, 2H), 2.19-2.14 (m, 1H), 1.66-1.52 (m, 4H), 1.34-1.29 (m, 1H), 0.87 (d, 3H), 0.74 (d, 3H). LCMS: $R_t$=1.24 min, $[M+H]^+$ 1224.

Example 4

Preparation of Trifluoroacetate (9)

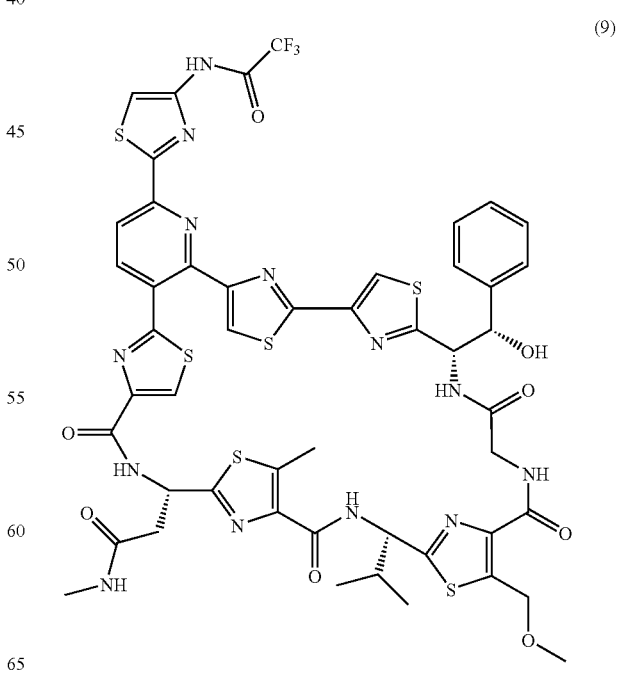

Steps 1-2, Preparation of Acetate (10):

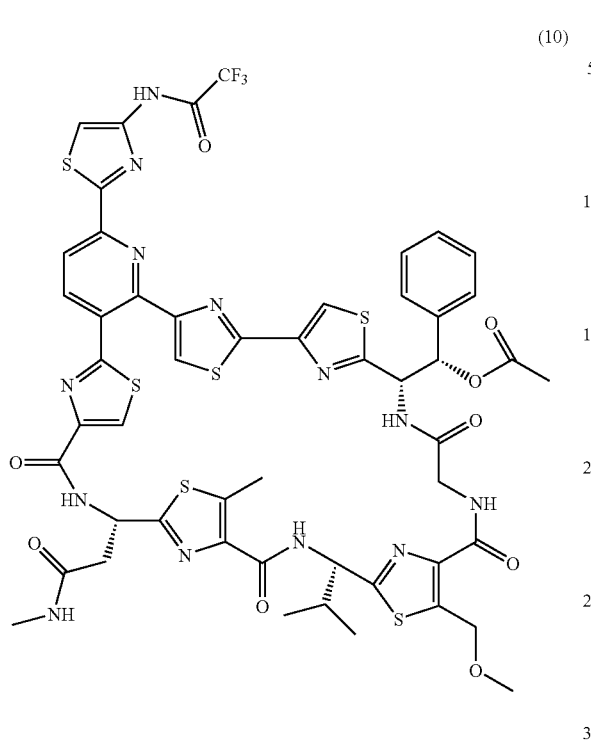

To a solution of Boc-amine-acetate (4, 400 mg, 0.323 mmol) in DCM (25 mL) is added TFA (5 mL, 67.3 mmol). The reaction is stirred for 30 min and concentrated. The resultant yellow foam is dissolved in DCM (10 mL) and concentrated (repeat 3×). The crude amine salt is taken on with no further purification. LCMS: $R_t$=1.45 min, [M+H]$^+$ 1138.0.

To a solution of the amine (0.323 mmol) in pyridine (5 mL) is added methanesulfonylchloride (0.050 mL, 0.646 mmol). The solution is stirred for 30 min and poured into a saturated aq solution of sodium bicarbonate (100 mL). The mixture is extracted with EtOAc (3×) and the combined organic extracts are dried over MgSO$_4$, filtered, and concentrated directly onto SiO$_2$. The crude product is purified by flash chromatography (gradient elution: 50-80% EtOAc/hexanes) which afforded 330 mg of acetate (10). LCMS: $R_t$=1.67 min, [M+H]$^+$ 1234.0.

Step 3, Preparation of Trifluoroacetate (9):

To a solution of the acetate (10, 200 mg, 0.162 mmol) in MeOH (50 mL) is added K$_2$CO$_3$ (50 mg, 0.362 mmol). The reaction is stirred for 10 min and concentrated. The solid is suspended in EtOAc and poured into a saturated aq solution of sodium bicarbonate (100 mL). The mixture is extracted with EtOAc (3×) and the combined organic extracts are dried over MgSO$_4$, filtered, and concentrated directly onto SiO$_2$. The crude product is purified by HPLC (method 1) which affords 55 mg of acetate (9). $^1$H NMR (400 MHz, d$_6$-DMSO) δ 12.78 (br s, 1H), 9.00 (br d, 1H), 8.69-8.67 (m, 2H), 8.59 (s, 1H), 8.43-8.41 (m, 2H), 8.27 (s, 1H), 8.19 (d, 1H), 8.02 (s, 1H), 7.39-7.21 (m, 7H), 5.32-5.17 (m, 3H), 5.00 (d, 1H), 4.97 (s, 2H), 4.28 (dd, 1H), 3.79 (dd, 1H), 3.38 (s, 3H), 2.70 (m, 1H), 2.71 (m, 1H), 2.58 (s, 3H), 2.47 (d, 3H), 2.20-2.12 (m, 1H), 1.34-1.27 (m, 1H), 0.87 (d, 3H), 0.84 (d, 3H). LCMS: $R_t$=1.56 min, [M+H]$^+$ 1192.

Example 5

Preparation of Sulfonamide (11)

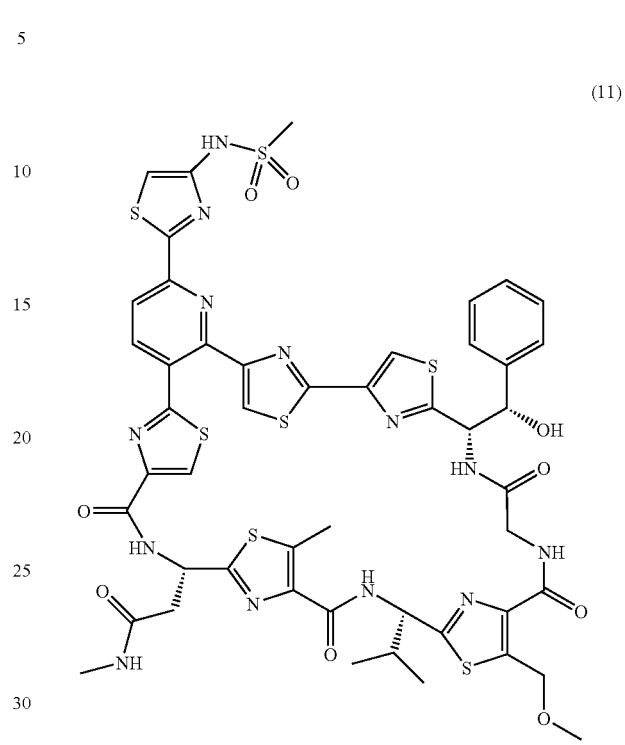

Steps 1-2, Preparation of Acetate (12):

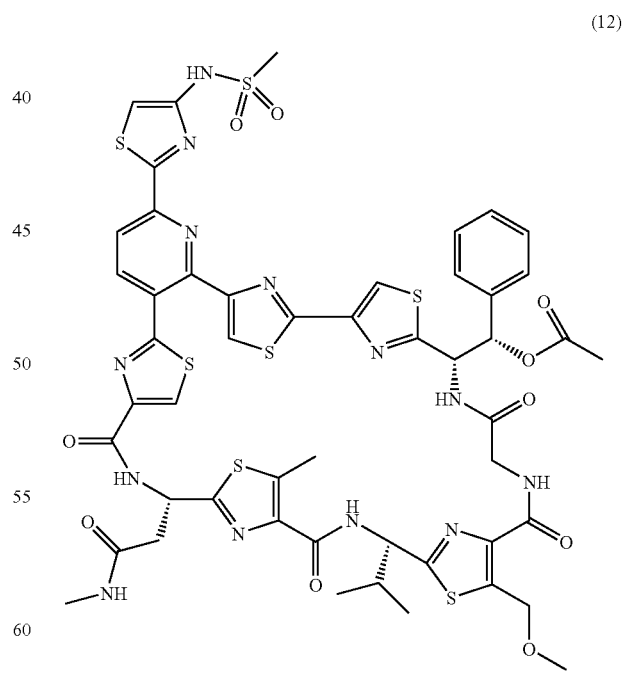

To a solution of Boc-amine-acetate (4, 100 mg, 0.081 mmol) in DCM (25 mL) is added TFA (5 mL, 67.3 mmol). The reaction is stirred for 30 min and concentrated. The resultant yellow foam is dissolved in DCM (10 mL) and concentrated (repeat 3×). The crude amine salt is dissolved in EtOAc and poured into a saturated aq solution of sodium bicarbonate (100 mL). The mixture is extracted with EtOAc (3×) and the combined organic extracts are dried over MgSO$_4$, filtered, and concentrated. The crude free-based amine is taken on with no further purification. LCMS: R$_t$=1.45 min, [M+H]$^+$ 1138.

To a solution of the amine (0.081 mmol) in pyridine (5 mL) is added methanesulfonylchloride (0.050 mL, 0.646 mmol). The solution is stirred for 30 min and poured into a saturated aq solution of sodium bicarbonate (100 mL). The mixture is extracted with EtOAc (3×) and the combined organic extracts are dried over MgSO$_4$, filtered, and concentrated directly onto SiO$_2$. The crude acetate (12) is taken on to the next step without any further purification. LCMS: R$_t$=1.42 min, [M+H]$^+$ 1216.

Step 3, Preparation of Sulfonamide (11):

To a solution of the sulfonamide (12) in MeOH (10 mL) is added K$_2$CO$_3$ (50 mg, 0.362 mmol). The reaction is stirred 5 min, concentrated, and purified by HPLC (method 2) to afford 15 mg of sulfonamide 11. $^1$H NMR (400 MHz, d$_6$-DMSO) δ 10.62 (br s, 1H), 9.00 (br d, 1H), 8.68-8.66 (m, 2H), 8.58 (s, 1H), 8.44-8.41 (m, 1H), 8.37 (d, 1H), 8.23 (s, 1H), 8.15 (d, 1H), 7.39-7.20 (m, 7H), 7.07 (br s, 1H), 6.02 (d, 1H), 5.31-5.18 (m, 3H), 5.01-4.98 (m, 1H), 4.97 (s, 2H), 4.27 (dd, 1H), 3.77 (dd, 1H), 3.38 (s, 3H), 3.12 (s, 3H), 2.73-2.67 (m, 1H), 2.58 (s, 3H), 2.47 (d, 3H), 2.19-2.13 (m, 1H), 1.36-1.28 (m, 1H), 0.87 (d, 3H), 0.84 (d, 3H). LCMS: R$_t$=1.31 min, [M+H]$^+$ 1174.

Example 6

Preparation of Amine (13)

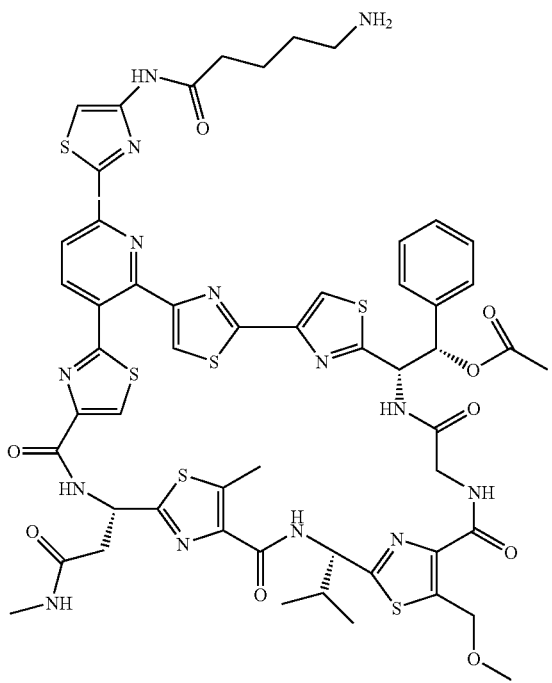

Steps 1-2, Preparation of Boc-amine (14):

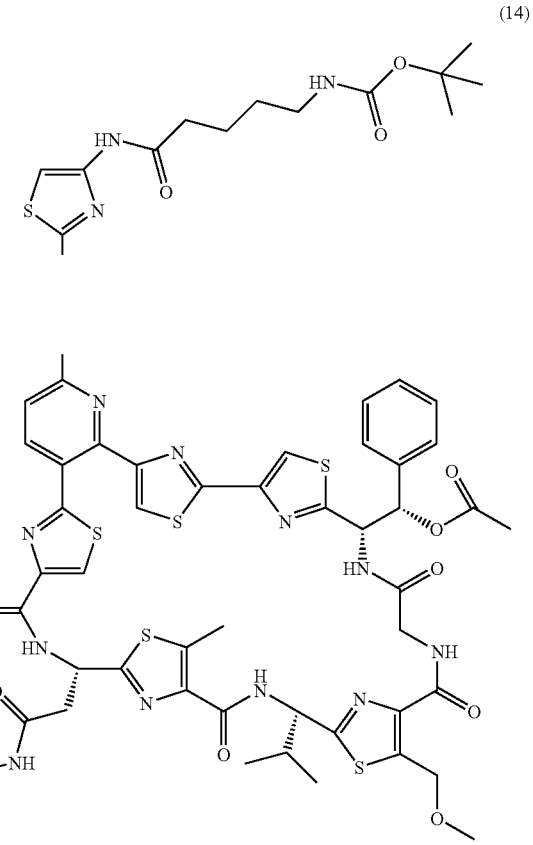

The preparation of Boc-amine (14) is performed according to the method described in example 3, except the acid chloride of 5-(tert-butoxycarbonylamino)-valeric acid is used as an acylating agent. LCMS: R$_t$=1.66 min, [M+2H]$^+$ 1338.

Step 3, Preparation of Amine (13):

To a solution of Boc-amine (14, 150 mg, 0.112 mmol) in DCM (5 mL) is added TFA (2 mL, 26.9 mmol). The solution is stirred for 30 min and concentrated directly onto SiO$_2$. Flash chromatography (gradient elution: 0-10% MeOH/DCM, then 100% DCM, then 0-10% MeOH/DCM with 0.1% AcOH) furnishes 90 mg of amine 13. $^1$H NMR (400 MHz, d$_6$-DMSO) δ 11.16 (br s, 1H), 9.23 (br d, 1H), 8.77 (br d, 1H), 8.62 (br d, 1H), 8.58 (s, 1H), 8.44-8.42 (m, 1H), 8.40 (d, 1H), 8.25 (s, 1H), 8.14 (d, 1H), 7.84 (s, 1H), 7.73-7.64 (m, 2H), 7.41 (s, 1H), 7.35-7.31 (m, 5H), 7.28-6.95 (m, 2H), 6.14 (d, 1H), 5.46 (t, 1H), 5.29-5.25 (m, 1H), 5.19 (dd, 1H), 4.97 (s, 2H), 4.26 (dd, 1H), 3.72 (dd, 1H), 3.38 (s, 3H), 2.85-2.79 (m, 2H), 2.71-2.65 (m, 2H), 2.59 (s, 1H), 2.46 (d, 3H), 2.44-2.42 (m, 2H), 2.22-2.15 (m, 1H), 1.96 (s, 3H), 1.70-1.56 (m, 4H), 1.50-1.42 (m, 1H), 0.88 (d, 3H), 0.84 (d, 3H). LCMS: R$_t$=1.06 min, [M+2H]$^+$ 1238.

Example 7

Preparation of Amine (15)

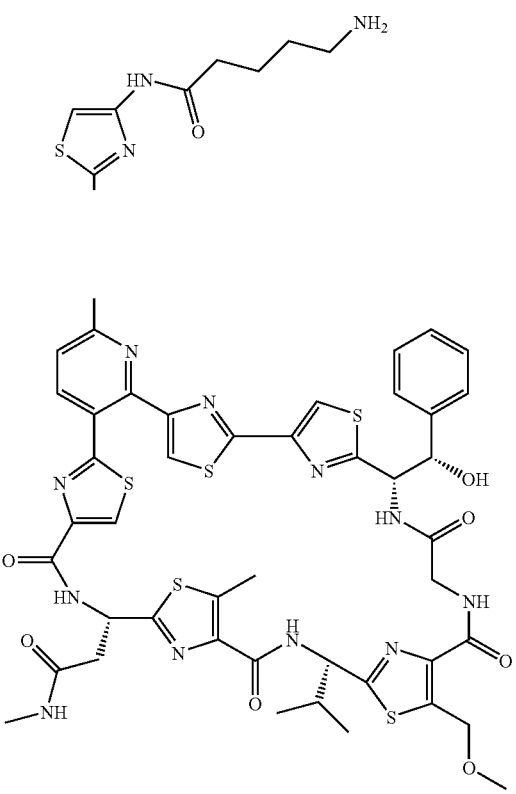

Boc-amine (14) is prepared as described in example 6. The acetate protecting group is then removed according to the procedures described in example 4. The boc protecting group is removed according to the procedures described in example 6. HPLC purification (method 1) furnishes the amine (15). $^1$H NMR (400 MHz, d$_6$-DMSO) δ 11.16 (s, 1H), 9.02, (br d, 1H), 8.70-8.65 (m, 2H), 8.60 (s, 1H), 8.45-8.41 (m, 1H), 8.40 (d, 1H), 8.24 (s, 1H), 8.13 (d, 1H), 7.84 (s, 1H), 7.69-7.62 (br s, 3H), 7.38-7.20 (m, 7H), 6.03 (br s, 1H), 5.31-5.18 (m, 3H), 5.02-4.99 (m, 1H), 4.97 (s, 2H), 4.28 (dd, 1H), 3.78 (dd, 1H), 3.38 (s, 3H), 3.12-3.06 (m, 4H), 2.84-2.79 (m, 2H), 2.73-2.69 (m, 1H), 2.58 (s, 3H), 2.47 (d, 3H), 2.46-2.42 (d, 3H), 2.20-2.12 (m, 1H), 1.70-1.54 (m, 4H), 1.29-1.22 (m, 1H), 1.17 (t, 6H), 0.87 (d, 3H), 0.84 (d, 3H). LCMS: R$_t$=0.93 min, [M+2H]$^+$ 1196.

Example 8

Preparation of Amide (16)

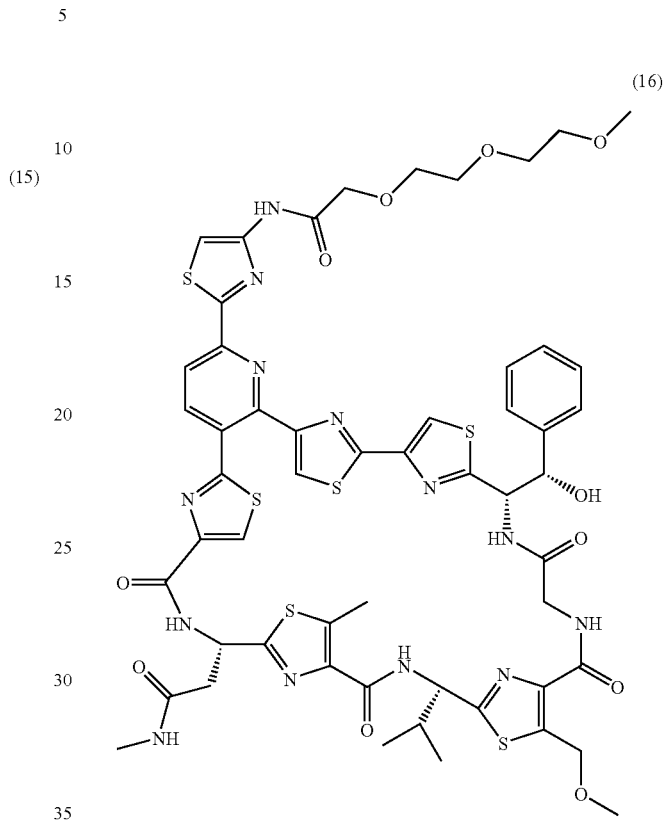

Amide (16) is prepared according to the procedures described in example 3. $^1$H NMR (400 MHz, d$_6$-DMSO) δ 10.69 (s, 1H), 9.00 (br d, 1H), 8.68-8.66 (m, 2H), 8.59 (s, 1H), 8.45-8.41 (m, 1H), 8.40 (d, 1H), 8.25 (s, 1H), 8.16 (d, 1H), 7.87 (s, 1H), 7.39-7.21 (m, 7H), 6.03 (br s, 1H), 5.31-5.18 (m, 3H), 5.01-4.99 (m, 1H), 4.97 (s, 2H), 4.27 (dd, 1H), 4.18 (s, 2H), 3.78 (dd, 1H), 3.70-3.68 (m, 2H), 3.63-3.59 (m, 4H), 3.52-3.50 (m, 2H), 3.38 (s, 3H), 3.24 (s, 3H), 2.73-2.68 (m, 1H), 2.58 (s, 3H), 2.47 (d, 3H), 2.20-2.12 (m, 1H), 1.35-1.28 (m, 1H), 0.87 (d, 3H), 0.84 (d, 3H). LCMS: R$_t$=1.45 min, [M+H]$^+$ 1256.

Example 9

Preparation of Acid (17)

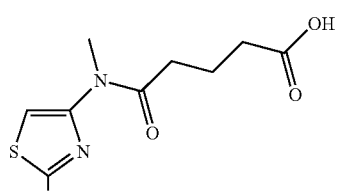

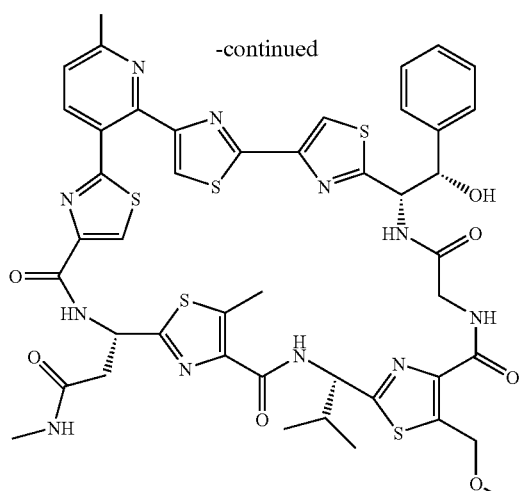

Step 1: Preparation of Amide (18)

(18)

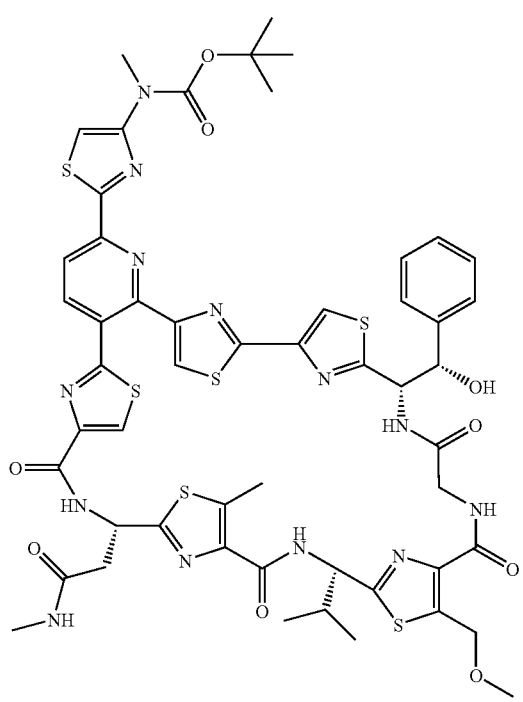

To a solution of Boc-amine-acetate (3, 200 mg, 0.167 mmol) in DMF (5 mL) is added $Cs_2CO_3$ (100 mg, 0.309 mmol) and iodomethane (0.100 mL, 1.61 mmol, neutralized with $Al_2O_3$). The solution is stirred for 2 h, concentrated, and taken on to the next step with no further purification. LCMS: $R_t$=1.85, [M+H]$^+$ 1210.

Steps 2-4: Preparation of Acid (17).

Acid (17) is prepared according to the procedures described in example 3. $^1$H NMR (400 MHz, d$_6$-DMSO) δ 9.01 (br d, 1H), 8.69-8.66 (m, 2H), 8.59 (s, 1H), 8.45-8.41 (m, 1H), 8.38 (d, 1H), 8.26 (s, 1H), 8.22 (d, 1H), 7.92 (br s, 1H), 7.39-7.20 (m, 8H), 5.31-5.18 (m, 3H), 5.00-4.99 (m, 1H), 4.97 (s, 2H), 4.27 (dd, 1H), 3.81-3.76 (dd, 1H), 3.38 (s, 3H), 3.34 (br s, 3H), 2.73-2.68 (m, 1H), 2.58 (s, 3H), 2.47 (d, 3H), 2.46-2.40 (m, 2H), 2.26-2.41 (m, 2H), 2.19-2.12 (m, 1H), 1.80-1.73 (m, 2H), 1.33-1.25 (m, 1H), 0.88 (d, 3H), 0.84 (d, 3H). LCMS: $R_t$=1.27, [M+H]$^+$ 1224.

Example 10

Preparation of Acid (19)

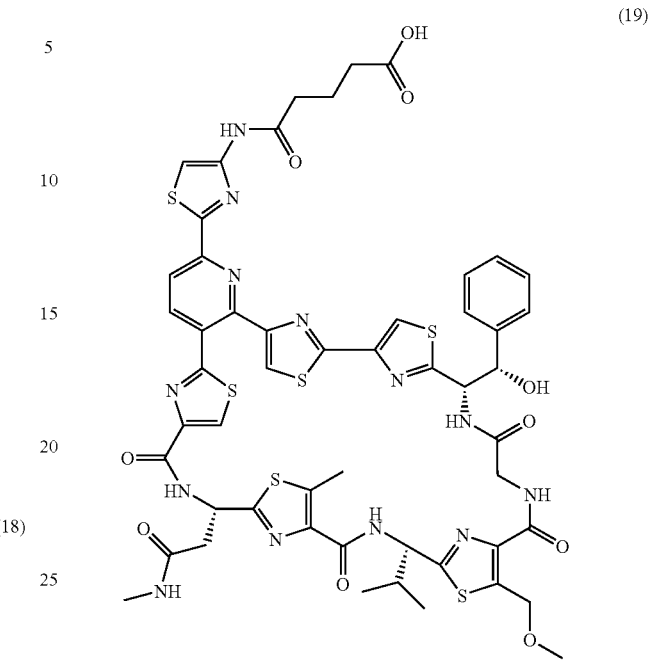

(19)

Acid (19) is prepared according to the procedures described in example 3. $^1$H NMR (DMSO-d$_6$) δ 11.22 (s, 1H), 9.27 (d, 1H), 8.65-8.69 (m, 2H), 8.58 (s, 1H), 8.42-8.45 (m, 1H), 8.38 (d, 1H), 8.23 (s, 1H), 8.13 (d, 1H), 7.83 (s, 1H), 7.19-7.46 (m, 8H), 6.42 (br s, 1H), 5.18-5.30 (m, 3H), 5.02 (d, 1H), 4.98 (s, 2H), 4.27-4.34 (m, 1H), 3.77-3.82 (m, 1H), 3.38 (s, 3H), 2.69-2.74 (m, 2H), 2.58 (s, 3H), 2.41-2.46 (m, 5H), 2.14-2.23 (m, 3H), 1.79-1.85 (m, 2H), 1.28-1.34 (m, 1H), 0.83-0.88 (m, 6H). LCMS: $R_t$=1.18, [M+H]$^+$ 1210.

Example 11

Preparation of Acid (20)

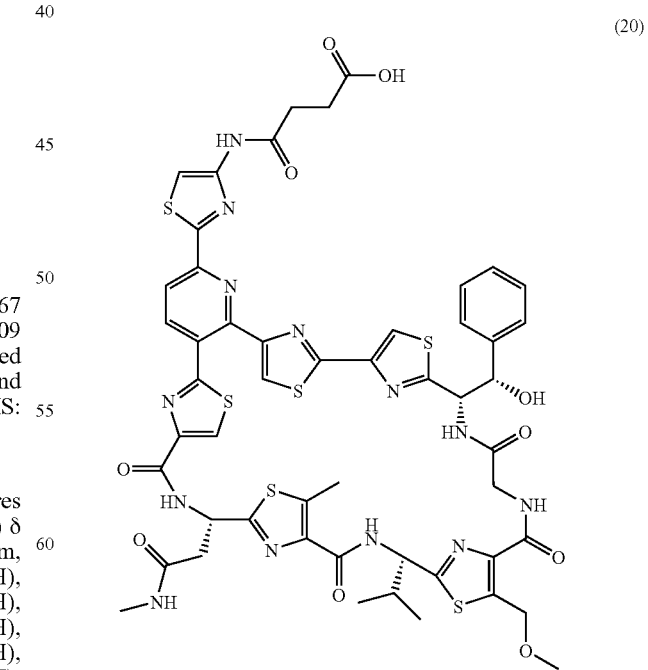

(20)

Acid (20) is prepared according to the procedures described in example 3. $^1$H NMR (DMSO-d$_6$) δ 11.18 (s, 1H), 9.00 (d, 1H), 8.67 (d, 2H), 8.59 (s, 1H), 8.42 (d, 2H), 8.24 (s, 1H), 8.14 (d, 1H), 7.80 (s, 1H), 7.22-7.38 (m, 8H), 5.18-5.31 (m, 3H), 5.00 (d, 1H), 4.97 (s, 2H), 4.24-4.30 (m, 1H), 3.75-3.81 (m, 1H), 3.38 (s, 3H), 2.63-2.73 (m, 2H), 2.58 (s, 3H), 2.53-2.56 (m, 1H), 2.46-2.48 (m, 5H), 2.13-2.19 (m, 1H), 1.29-1.35 (m, 1H), 0.83-0.88 (m, 6H). LCMS: $R_t$=1.22 min, $[M+H]^+$ 1196.

Example 12
Preparation of Amine (21)

(21)

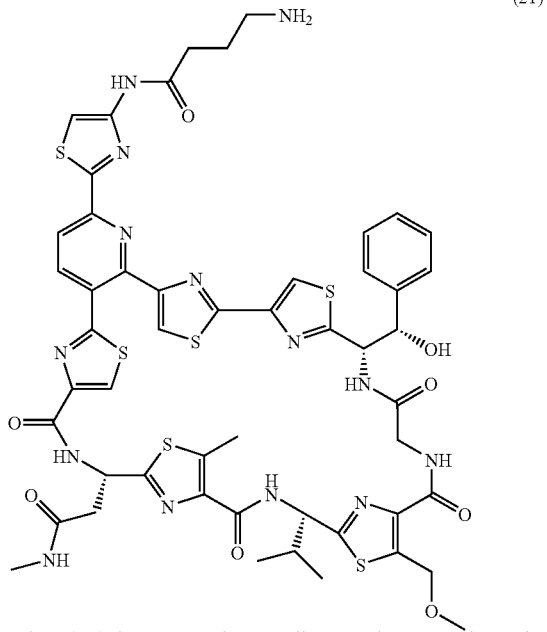

Amine (21) is prepared according to the procedures in example 7. $^1$H NMR (DMSO-$d_6$) δ 9.01 (d, 1H), 8.65-8.69 (m, 2H), 8.59 (s, 1H), 8.39-8.44 (m, 2H), 8.24 (s, 1H), 8.13 (d, 1H), 7.83 (s, 1H), 7.20-7.37 (m, 8H), 6.02 (d, 1H), 5.18-5.31 (m, 3H), 5.00 (d, 1H), 4.97 (s, 2H), 4.24-4.30 (m, 1H), 3.76-3.81 (m, 1H), 3.38 (s, 3H), 2.66-2.72 (m, 3H), 2.58 (s, 3H), 2.44-2.4 (m, 5H), 2.14-2.18 (m, 1H), 1.72-1.79 (m, 2H), 1.24-1.33 (m, 1H), 0.83-0.88 (m, 6H). LCMS: $R_t$=0.86, $[M+H]^+$ 1181.

Example 13
Preparation of Aminothiazole Hydrochloric Acid (22)

(22)

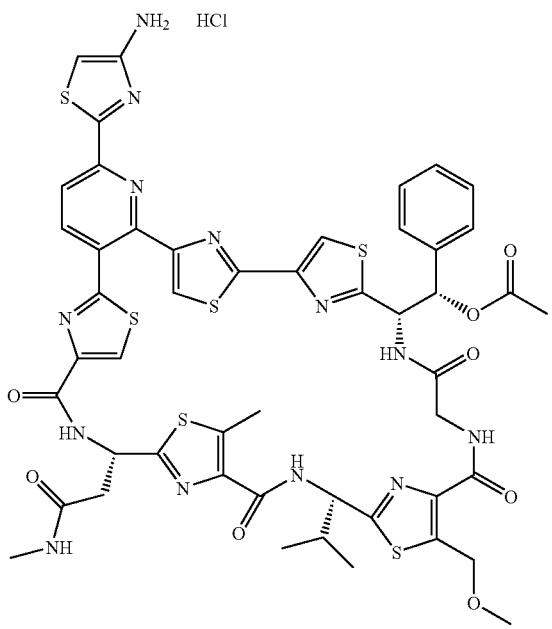

Hydrochloric acid is bubbled through a solution of Boc protected amine (4, 1.4 g, 1.1 mmol) in DCM (20 mL) for thirty min. The reaction mixture is then tightly capped and stirred for thirty minutes after which the reaction mixture is sparged with nitrogen. The mixture loses its gel like appearance. DCM (5 mL) is added to the solution, and HCl gas is bubbled through it for an additional 20 min, followed by nitrogen for 30 min. Crude product (1.32 g) is obtained after concentration as a bright orange solid, and taken on to the next step with no further purification. LCMS: $R_t$=1.5 min, $[M+H]^+$ 1138.

Example 14

Preparation of Acid (23)

(23)

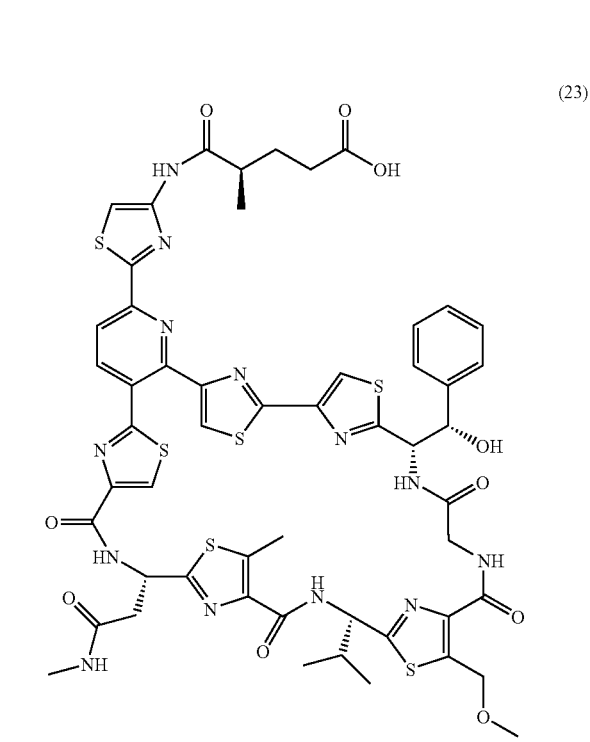

Step 1, Coupling Reactions Using N-Cyclohexylcarbodiimide, N'-Methyl Polystyrene.

To a solution of aminothiazole hydrochloric acid (22, 348 mg, 1 eq) in DCM (20 mL) and pyridine (0.5 mL) is added R-(−)-4-methylglutaric acid 1-monomethyl ester (72.0 μL, 0.45 mmol, 2 eq) and N-cyclohexylcarbodiimide, N'-methyl polystyrene (348 mg, 0.90 mmol, 3 eq). The reaction mixture is stirred for 4 h, then the solution is filtered through Celite and concentrated.

Step 2, Deprotection of Acetate and Saponification to Acid.

The concentrate is dissolved in THF (5.0 mL), MeOH (5.0 mL), and water (2.0 mL). To this solution is added 4 M LiOH (0.34 mL, 3.96 mmol). Ammonium chloride (sat. aq) is added to neutralize excess LiOH, and the solution is concentrated onto silica. The crude residue is first chromatographed with 10% MeOH in DCM (isochratic). A second chromatography (gradient elution: 0-10% MeOH/DCM) affords product 23. HRMS $[M+H]^+$ 1224.2688. LC $R_t$=14.85 min.

Example 15
Preparation of Amino-acid (24)

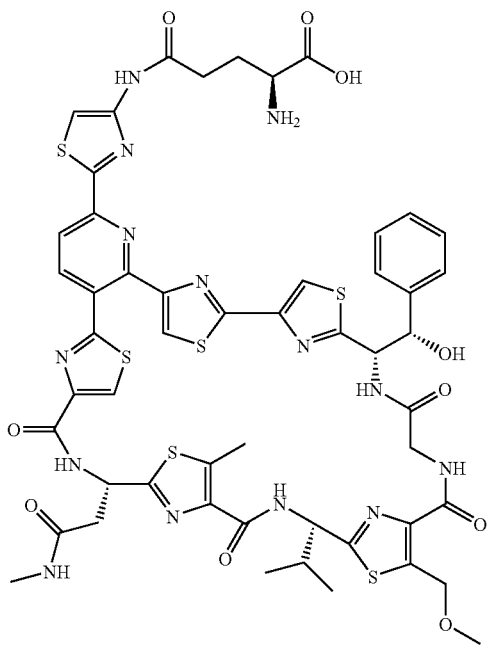
(24)

Step 1:
Conditions for the amide coupling for 24 are the same as example 14, step 1 with Boc-(L) glutamic acid t-butyl ester (27.3 mg, 0.09 mmol).

Step 2:
The procedure in example 5 is used to remove the acetate protecting group. Flash chromatography (50-80% ethylacetate/hexanes) yields 239 mg yellow solid.

Step 3: Deprotection of Boc and t-butyl Groups.

The material is dissolved in DCM (50 mL) and HCl gas is bubbled through the solution for 10 min. The solution is then sparged with nitrogen to remove excess acid. Purification via HPLC yields 24 (9 mg). LCMS: $R_t$=0.99 min, $[M+2H]^+$ 1226

Example 16
Preparation of Sulfonamide (25)

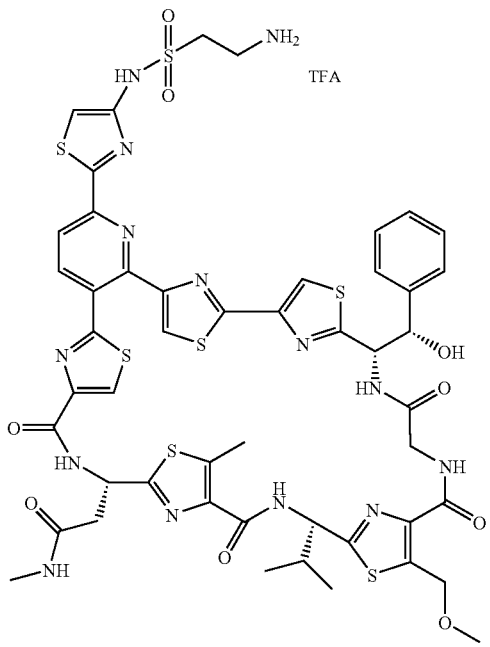
(25)

Step 1:
To a solution of the aminothiazole hydrochloride salt (22, 1.0 g, 0.85 mmol) in pyridine (30 mL) is added 2-phthalimidoethanesulfonyl chloride (700 mg, 2.6 mmol). The reaction is stirred for 2 h. Additional sulfonyl chloride is added (236 mg, 1.3 mmol). After stirring 30 min the mixture is concentrated onto silica gel and purified via flash chromatography (gradient elution: 50-100% EtOAc/hexanes) affording product (500 mg).

Step 2: Deprotection of Phthalimide Amine

To a solution of the sulfonamide in MeOH (30 mL) is added hydrazine hydrate (0.5 mL). The reaction is stirred for 1 h and the mixture is concentrated onto silica gel and purified first via flash chromatography (gradient elution: 0-10% MeOH/DCM then 1% $NH_4OH$+10% MeOH/DCM). A second purification is performed with a Biotage column C18 (gradient elution: 10-70% $CH_3CN/H_2O$ with 0.01% TFA) providing the TFA salt (10.4 mg) as a white solid. HRMS: 1203.1965, LC $R_t$=12.33 min.

Example 17
Preparation of Phosphoric-acid (26)

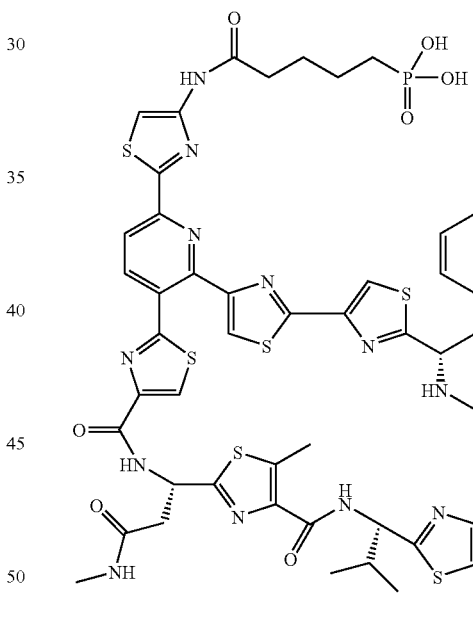
(26)

Step 1:
The amide synthesis of compound 26 is performed according to the procedure described above using diethylphosphonopentanoic acid (0.2 mL) and PS-DCC.

Step 2: Deprotecting the Phosphoric Acid.

To a cooled solution of the phosphoric ester (275 mg, 0.21 mmol) in DCM (50 mL) at 0° C. is added TMSBr (1 mL, >100 eq). The mixture is stirred for 1 h, then warmed to RT. TMSBr (2 mL, >100 eq) is added and the solution is stirred at RT for 1 h. The mixture is concentrated to dryness, and the crude phosphoric acid is taken forward with no further purification.

155

Step 3:

The acetate removal is performed according to the procedure described above. Purification is performed on a C18 biotage column. Two purifications are performed (gradient elution: 20-80% acetonitrile/water with 0.1% TFA; second column 20-80% acetonitrile/water with 0.1%) to afford product 26. HRMS: m/2=630.6124, LC $R_t$=13.24 min.

Example 18

Preparation of Alcohol (27)

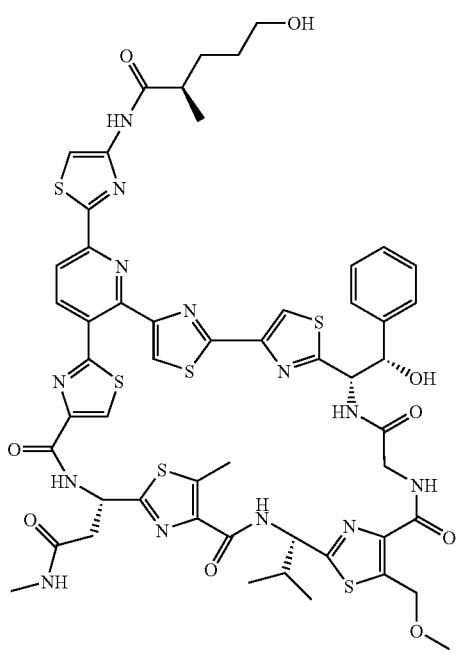

(16)

To a 0° C. solution of acid 23 (1.0 g, 0.82 mmol) in THF (20 mL) is added $Et_3N$ (0.11 mL, 0.82 mmol) followed by ethylchloroformate (0.08 mL, 0.89 mmol). The mixture is stirred for 30 min, then warmed to RT and stirred for an additional 30 min. The triethylamine hydrochloride salt is filtered off and the solution is cooled again to 0° C. $NaBH_4$ (68 mg, 1.8 mmol) in water (3 mL) is added. The mixture is stirred for 30 min, warmed to RT and stirred for an additional 30 min. The mixture is neutralized with 1 N HCl and partitioned with DCM. The organic extract is collected and concentrated. The product is purified via chromatography: column 1, Biotage C18 column, gradient elution 20-70% acetonitrile/water with 0.1% TFA. A second purification repeats the conditions of column 1. A third purification uses a Biotage C18 column (gradient elution: 20-70% acetonitrile/water with 0.1% ammonium formate) to provide product. LCMS $R_t$=1.37 min, [M+H]$^+$ 1210.

156

Example 19

Preparation of Acid (28)

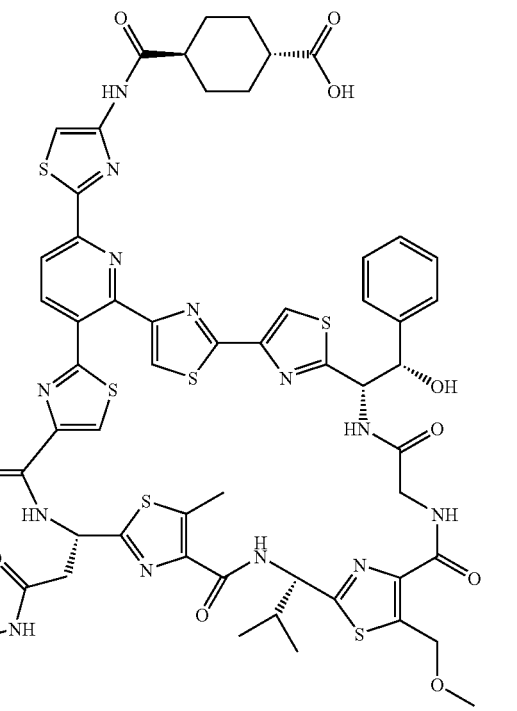

(28)

Step 1:

The amide synthesis of compound 28 is performed according to the PS-DCC procedure described above using trans-4-carbomethoxycyclohexane-1-carboxylic acid (316 mg, 1.70 mmol).

Step 2:

Deprotection of the acetate and saponification for the synthesis of 28 is performed according to the procedures described above. Purification via flash chromatography (isochratic elution: 10% MeOH/DCM), then via HPLC provides 28 (100 mg) as a light yellow solid. LCMS: $R_t$=1.37 min, [M+H]$^+$=1250.

Example 20

Preparation of Amino-Amide (29)

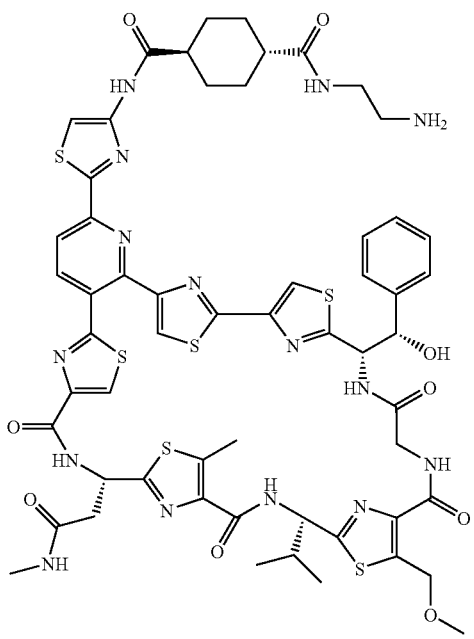

(29)

To a solution of 28 (470 mg, 0.38 mmol) in acetone (20 mL), water (30 μL) and Et₃N (0.2 mL, 1.5 mmol) is added ethylchloroformate (0.07 mL, 0.75 mmol). The solution is stirred for 1 h and ethylenediamine (0.5 mL, 7.5 mmol) is added. The crude solution is then concentrated onto silica gel and purified via flash chromatography (gradient elution: 0-20% MeOH/DCM) then via HPLC to yield product as a yellow solid. LCMS: $R_t$=0.94 min, $[M-H]^+$ 1290.

Example 21

Preparation of Carbamate (30)

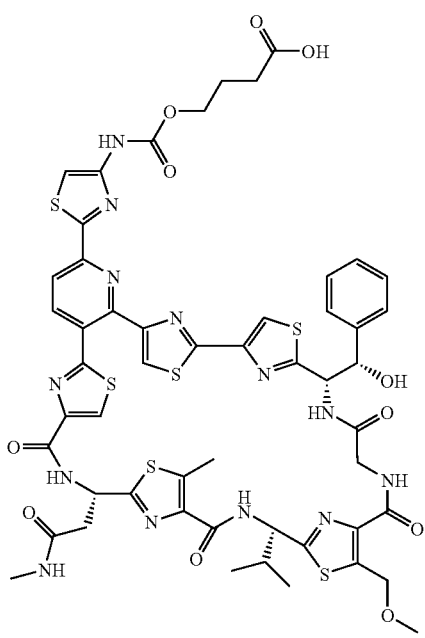

(30)

Step 1:

To a suspension of acylazide 2 (1.15 g, 1.00 mmol) in toluene (60 mL) is added alcohol (0.354 g, 3.00 mmol) and the mixture is stirred at 80° C. for 4 h. The reaction is concentrated in vacuo and the crude product is purified by flash chromatography (heptane/EtOAc) to yield 1.01 g (0.815 mmol, 81.5%) of the intermediate ester.

Step 2:

To a solution of the ester (1.01 g, 0.815 mmol) in MeOH (25 mL) and water (3 mL) is added sodium hydroxide (0.325 g, 8.13 mmol) and the mixture is stirred at 22° C. for 16 h. The reaction is concentrated in vacuo and the crude product is purified by flash chromatography (MeOH/DCM) to yield 0.705 g (0.575 mmol, 71%) of 30. LC: $R_t$=14.83 min, HRMS: $[M+H]^+$ 1226.2257.

Example 22

Preparation of Carbamoyl-Acid (31)

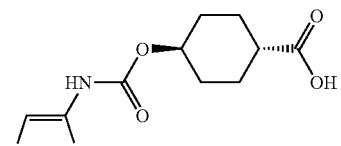

(31)

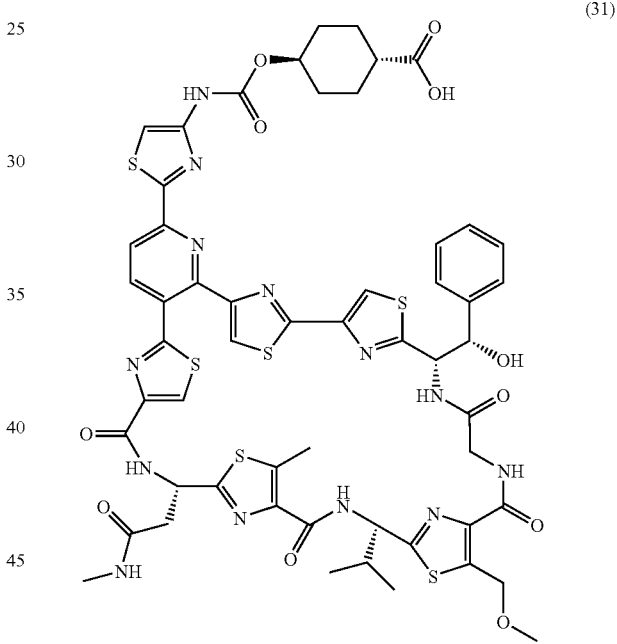

Step 1:

To a suspension of acylazide (2, 0.600 g, 0.522 mmol) in toluene (20 mL) is added trans-4-hydroxy-cyclohexanecarboxylic acid ethylester (0.134 g, 0.778 mmol) and the mixture is stirred at 80° C. for 5 h. The reaction is concentrated in vacuo and the crude product is purified by flash chromatography (MeOH/DCM) to yield 0.236 g (0.182 mmol, 35%) of the ester.

Step 2:

To a solution of the ester (0.236 g, 0.182 mmol) in THF (3.6 mL) and H₂O (1.2 mL) is added lithium hydroxide (0.045 g, 1.29 mmol) and the mixture is stirred at 22° C. for 48 h. The reaction is concentrated in vacuo and the crude product is purified by flash chromatography (MeOH/DCM) to yield 0.119 g (0.094 mmol, 52%) of 31. Further purification via HPLC (30×100 mm C18 Waters Sunfire, gradient elution 30-80% ACN/H₂O, 0.1% TFA, 6 mL/min for 9 min) affords 31. LC: R$_t$=12.98 min. HRMS: m/2, [M+2H]⁺ 633.6321.

Example 23

Preparation of Urea (32)

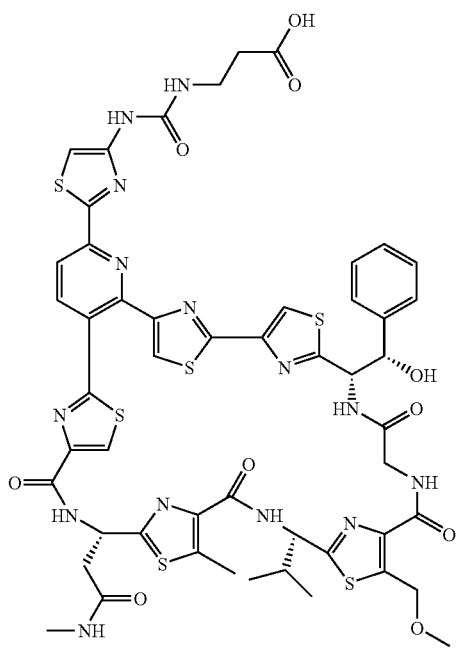

Step 1:

To a solution of amine 22 (0.115 g, 0.101 mmol) in pyridine (4 mL) is added the 3-isocyanaopropionic acid ethylester (0.452 mL, 0.343 mmol) and the mixture is stirred at 22° C. for 1 h. The reaction is concentrated in vacuo and the residue is azeotroped with toluene to provide 0.129 g (0.101 mmol) of the acetate-ester of 32. LCMS: m/2 [M+2H]⁺ 641.

Step 2:

To a solution of the acetate (0.129 g, 0.101 mmol) in MeOH (4 mL) is added K₂CO₃ (42 mg, 0.303 mmol) and the mixture is stirred for 2 h at 22° C. NaOH (s, 100 mg, 2.5 mmol) in H₂O (2 mL) is added via syringe and reaction mixture is stirred for 24 h. The volatiles are removed under reduced pressure. The residue is purified by HPLC (30-80% ACN/H₂O, 0.1% TFA) to provide 30 mg (25%) of yellow solid, 32. LC: R$_t$=16.69 min, MS [M+H]⁺ 1211.

Example 24

Preparation of Sulfonylurea (33)

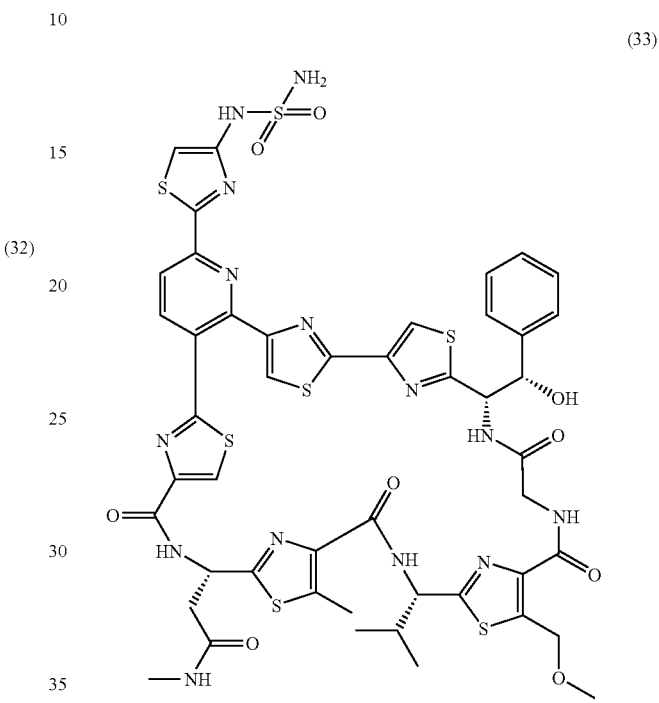

Step 1:

To a solution of chlorosulfonylisocyanate (1.35 g, 9.6 mmol) in DCM (50 mL) at 0° C., is added t-BuOH (918 uL, 9.6 mmol) and stirred for 30 min while maintaining temperature at 0° C. To a solution of amine 22 (820 mg, 0.72 mmol) in pyridine (12 mL) is added 0.2 M solution of sulfonyl chloride (1.44 mmol, 0.72 mL). The reaction is stirred for 5 min at 0° C. The solvents were evaporated in vacuo and the solid is purified by basic alumina flash chromatography (gradient elution: 0-10% MeOH/DCM to provide 220 mg of the boc-sulfonylurea. MS (M+H)⁺ 1317.

Step 2:

To a solution of the intermediate boc-sulfonylurea (106 mg, 0.08 mmol) in MeOH (10 mL) is added K₂CO₃ (111 mg, 0.8 mmol). The reaction is stirred for 2 h at 22° C. 1 g of SiO₂ is added to the reaction and the solvents are evaporated in vacuo. The solid is purified by flash chromatography (gradient elution: 0-10% MeOH/DCM) to provide 102 mg of a yellow solid. The yellow solid (120 mg, 0.09 mmol) is dissolved in DCM (20 mL), cooled to 0° C. and HCl (g) is bubbled into the solution for 10 min. The reaction is capped and stirred for 2 h. N2 gas is bubbled into reaction to remove excess HCl gas. The solvents are evaporated in vacuo to provide 140 mg crude yellow solid. The solid was purified by HPLC purification (gradient elution: 30-50% ACN/H₂O, 0.1% TFA) to provide 11 mg of 60% pure solid. Second HPLC purification (gradient elution: 50-55% ACN/H₂O, 0.1% TFA) provides 6.7 mg of product 33. LCMS: R$_t$ 1.24 min, (M+H)⁺ 1175.

Scheme 3: Synthesis of Imidazoles
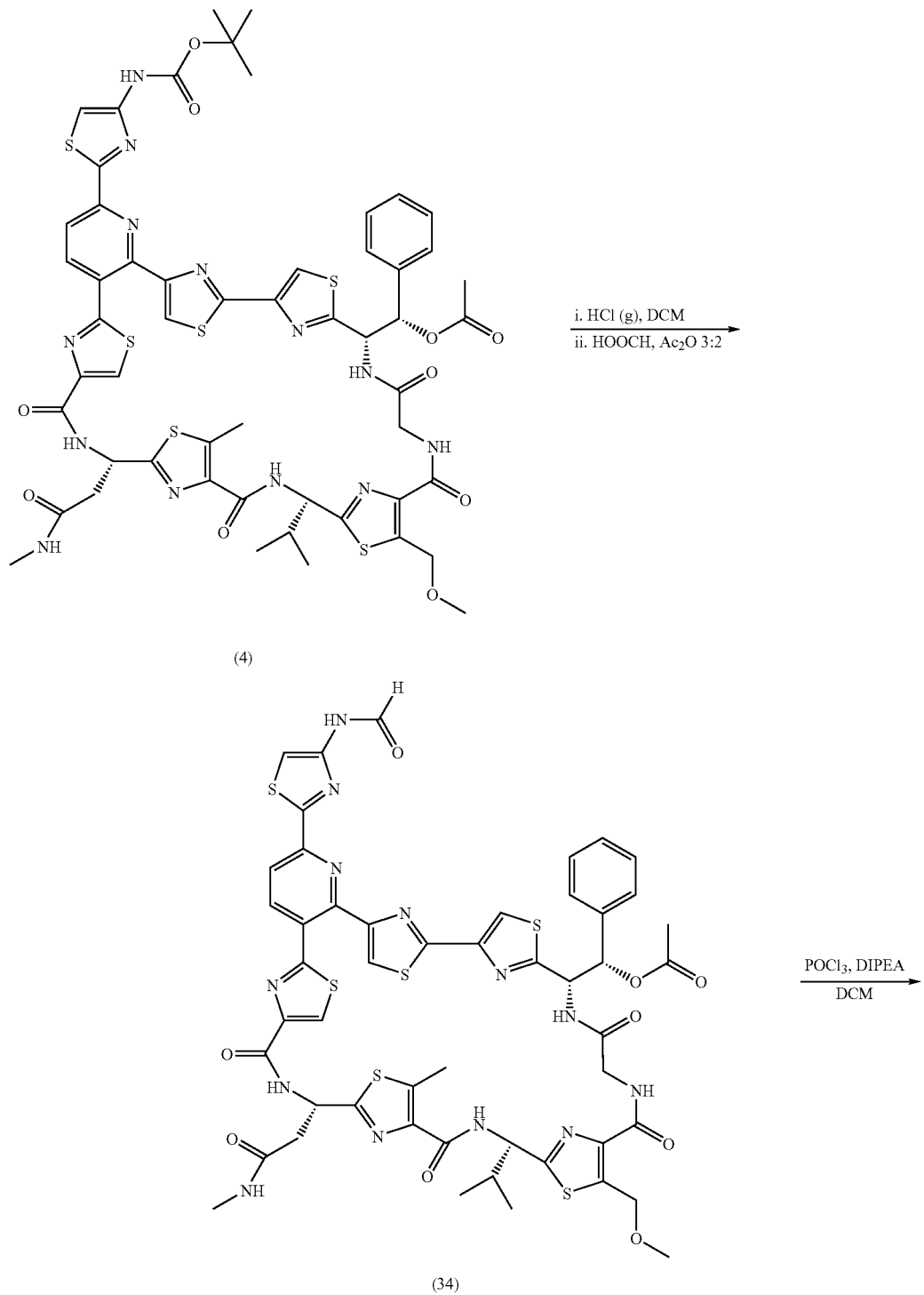

-continued
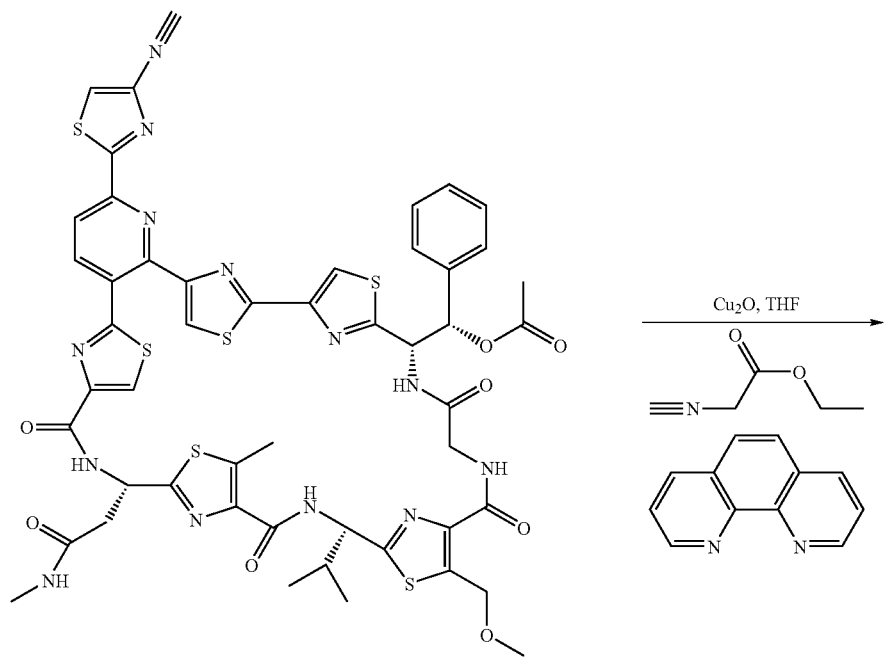
(35)
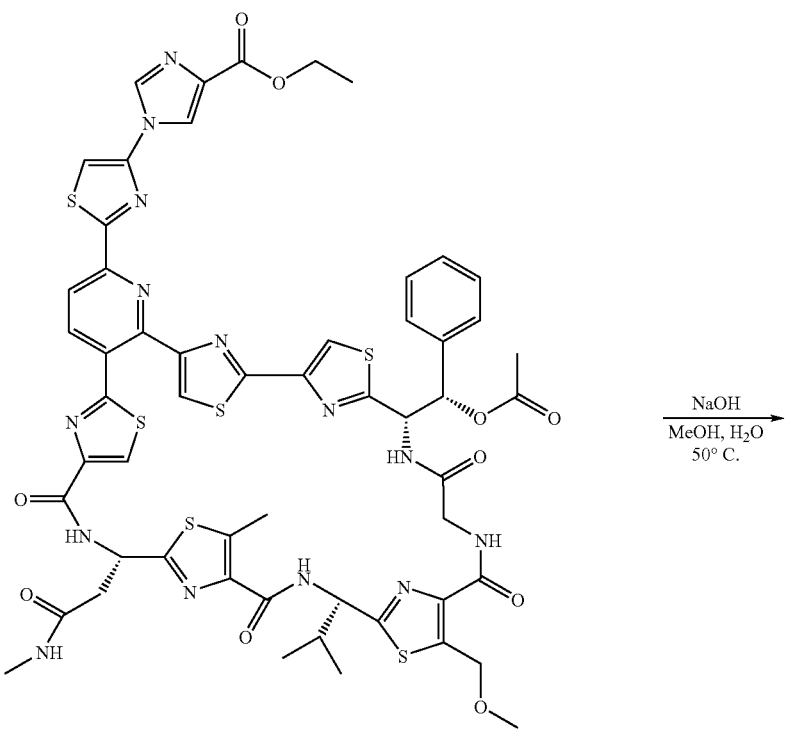
(36)

-continued
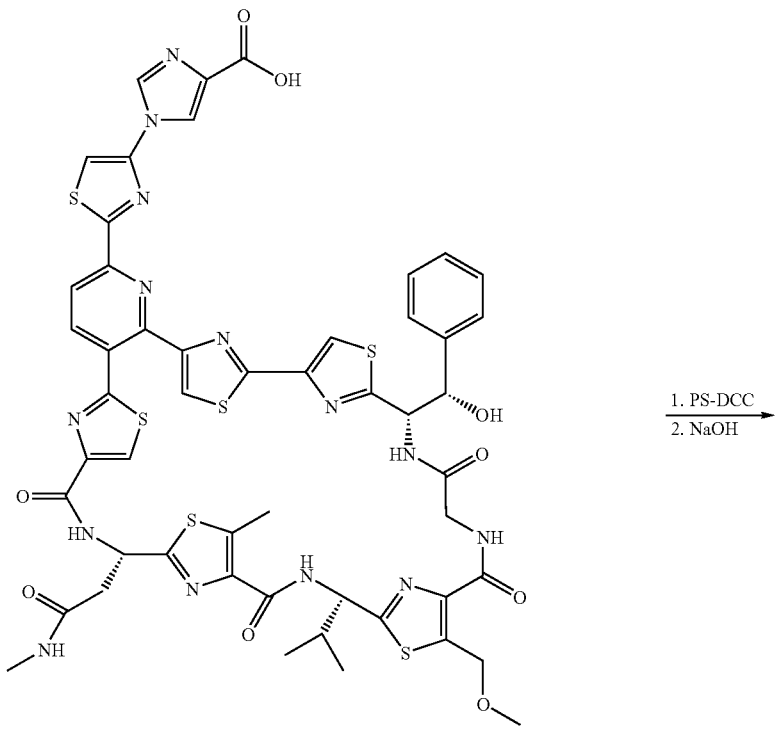
(37)
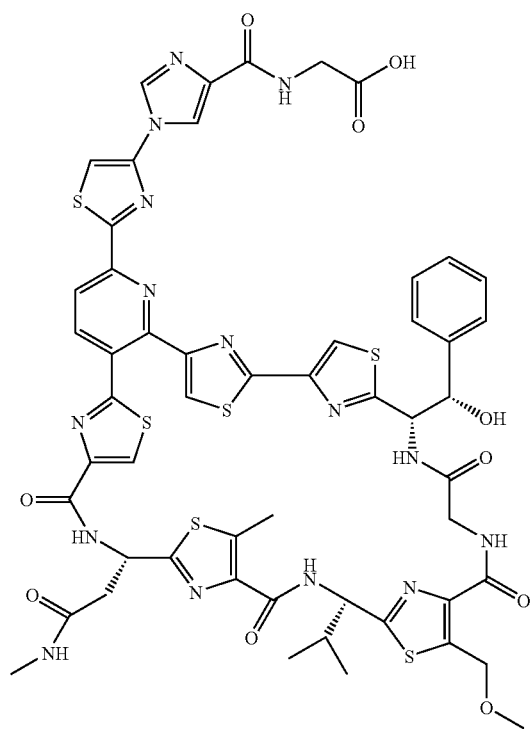
(38)
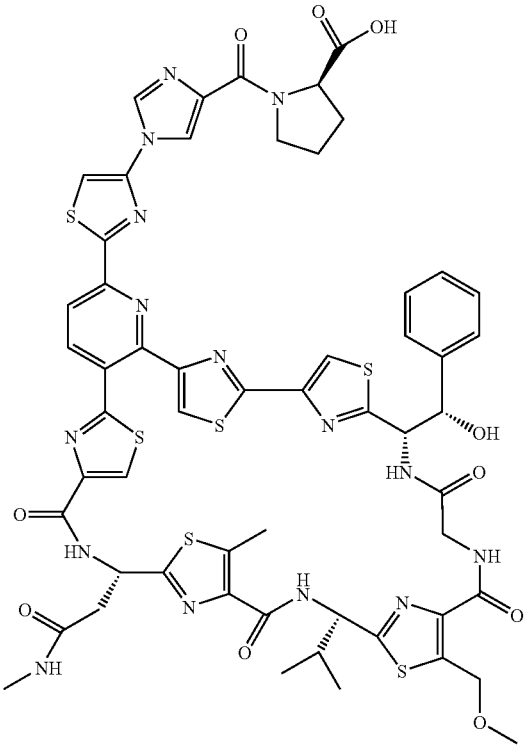
(39)

Example 25

Preparation of Imidazole (37)

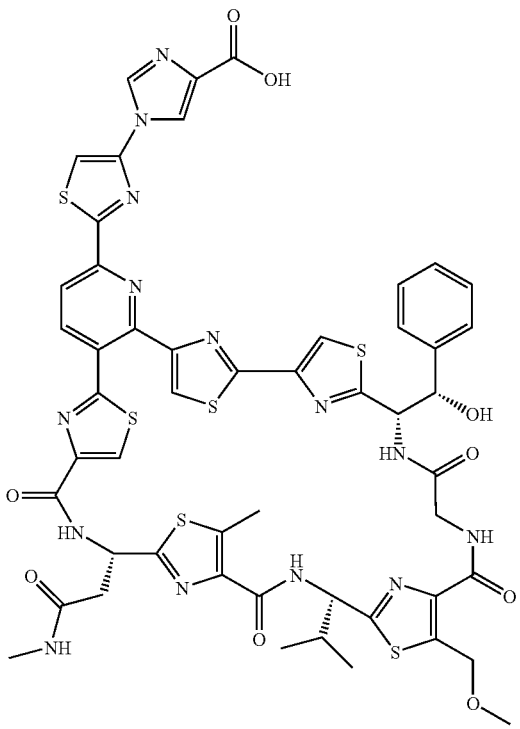

(37)

Step 1:

To a suspension of boc-amine 4 (800 mg, 0.647 mmol) in DCM (150 mL) is added HCl (g, stream) for 20 min. The reaction is capped and stirred for 30 min. The reaction is concentrated to dryness and taken to the next step with no further purification. The residue is suspended in DCM (150 mL) and a solution of formic acid in acetic anhydride (1 mL, 3:2) is added followed by stirring at RT for 2 h. The crude formamide (34) is concentrated to dryness and stored in vacuo for 12 h. LCMS: $R_t$ 1.46 min, [M+H]$^+$ 1166.

Step 2:

To a suspension of the intermediate formamide (34, 670 mg) in DCM (100 mL) is added DIPEA (1 mL, 5.74 mmol) and POCl$_3$ (100 µL, 1.27 mmol). The reaction is stirred at RT for 30 min and a second addition of DIPEA (1 mL, 5.74 mmol) and POCl$_3$ (100 µL, 1.27 mmol) is added. The reaction is stirred an additional 30 min and then concentrated onto silica gel. Purification by flash chromatography (gradient elution: 60-100% EtOAc in heptane) affords 150 mg of isonitrile (35). LCMS: $R_t$ 1.72 min, [M] 1148.

Step 3:

To a solution of isonitrile (35, 100 mg, 0.087 mmol) in THF (8 mL) is added Cu$_2$O (cat.), ethyl isocyanoacetate (13.8 mg, 0.122 mmol) and phenanthroline (3.1 mg, 0.017 mmol). The reaction is placed in a sealed tube and heated to 80° C. for 2 h, then cooled to RT. The reaction is concentrated and is purified by flash chromatography (gradient elution: 50-100% EtOAc in heptane); second column: (gradient elution: 0-10% MeOH in DCM) to furnish imidzole-ester 36. LCMS: $R_t$ 1.62 min, [M+2H]$^+$ 1262. Step 4: To a solution of imidazole 36 in MeOH (8 mL) and H$_2$O (2 mL) is added NaOH (s, 10 mg, 0.25 mmol) and reaction is heated to 40° C. for 12 h. The reaction is cooled to RT and concentrated to dryness. Final purification by HPLC (gradient elution: 45-55% acetonitrile in H$_2$O with 0.1% TFA) generates 3 mg of 37 as a TFA salt. LCMS: $R_t$ 1.13 min, [M+H]$^+$ 1191.

Example 26

Preparation of Imidazole (38)

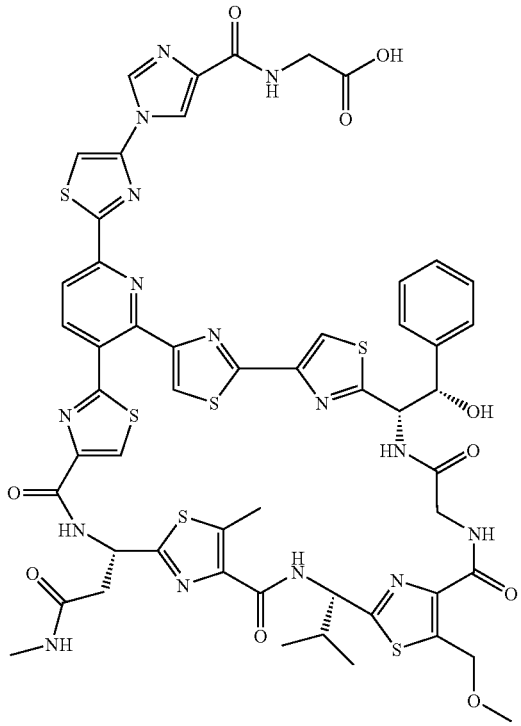

(38)

Step 1:

To a suspension of crude imidazole 37 (180 mg, 0.151 mmol) in DCM (10 mL) and pyridine (500 mL) is added PS-DCC (0.453 mmol) and amino-acetic acid methyl ester (20 mg, 0.227 mmol). The reaction is stirred at RT for 48 h and then heated to 40° C. for 2 h. The residue is concentrated onto silica gel and purified by flash chromatography (gradient elution: 50-100% EtOAc in heptanes) to generate 77 mg of methyl ester intermediate. LCMS: $R_t$ 1.35 min, [M+H]$^+$ 1262.

Step 2:

The methyl ester (77 mg, 0.061 mmol) is suspended in MeOH (5 mL) and H$_2$O (1 mL) NaOH (s, 40 mg, 1.00 mmol) is added. The reaction is stirred at RT for 12 h and then concentrated onto silica gel for purification by flash chromatography (gradient elution: 0-10% MeOH in DCM+0.1% acetic acid) to generate 4.2 mg of imidazole acid 38. LCMS: $R_t$ 1.18 min, [M+2H]$^+$ 1249.

Example 26

Preparation of Imidazole (39)

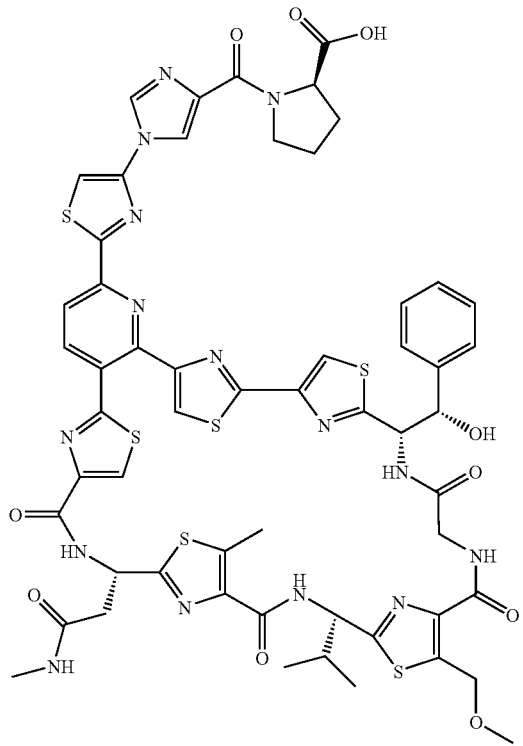

(39)

Step 1:

To a suspension of crude imidazole acid 37 (276 mg, 0.232 mmol) in DCM (20 mL) and pyridine (1.0 mL) is added PS-DCC (0.695 mmol) and (R)-pyrrolidine-2-carboxylic acid methyl ester (60 mg, 0.463 mmol). The reaction is stirred and heated to 40° C. for 24 h. The reaction is concentrated onto silica gel and purified (twice) by flash chromatography (gradient elution: 0-5% MeOH in DCM) to generate 170 mg of methyl ester intermediate. LCMS: $R_t$ 1.45 min, $[M+2H]^+$ 1303.

Step 2:

The methyl ester (170 mg, 1.305 mmol) is suspended in MeOH (10 mL) and $H_2O$ (2 mL) and NaOH (s, 40 mg 1.00 mmol) are added. The reaction is stirred at RT for 18 h then heated to 40° C. for 12 h. The reaction is mounted onto silica gel for purification by flash chromatography (gradient elution: 0-10% MeOH in DCM) followed by HPLC purification (gradient elution: 40-60% acetonitrile in $H_2O$ with 0.1% TFA) to generate 5 mg of imidazole acid 39. LCMS: $R_t$ 1.11 min, $[M+H]^+$ 1288.

Biological Results:

Using the standard MIC test described above with the bacteria *Enterococcus faecalis, Enterococcus faecium* or *Staphylococcus aureus*, compounds 5-7, 9, 11, 13, 15-17, 19-21, 23-25, 27-33, 37-39 demonstrate a minimum inhibitory concentration ranging from 0.0010 μg/mL to 128 μg/mL.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

INCORPORATION BY REFERENCE

The entire contents of all patents, published patent applications and other references cited herein are hereby expressly incorporated herein in their entireties by reference.

The invention claimed is:

1. A compound of the formula VII:

VII

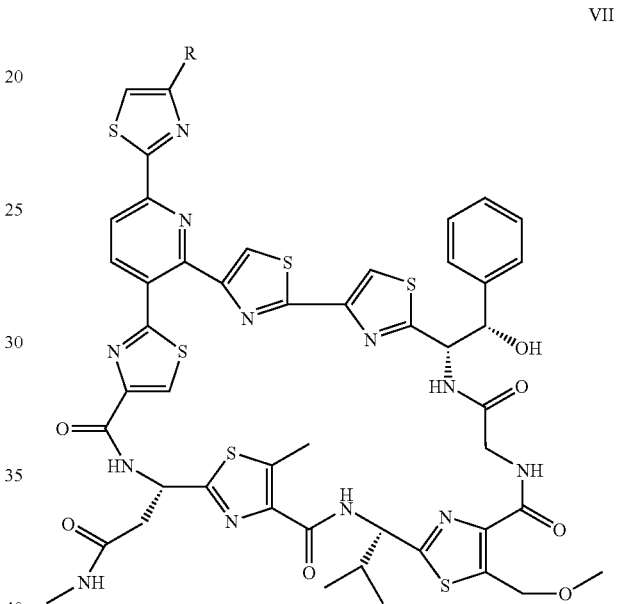

and pharmaceutically acceptable salts,
wherein
R is selected from the group consisting of $N(R^1)$ and $N(R^1)$-A-G-Q-J;
A is a bond or is selected from the group consisting of —C(O)—, —C(O)C(O)—, —C(O)O—, —C(O)N($R^{8a}$)—, —S(O)$_2$—, —S(O)—, —S(O)$_2$N($R^{8a}$)—, —S(O)N($R^{8a}$)—, —C(=$NR^8$)N($R^{8a}$)—, —C(=$NR^8$)N($R^{8a}$)C(O)—, —C(=$NR^8$)—, —C=C—C(O)—, —C=C—C(O)O—, —C=C—C(O)N($R^{8a}$)—;
G is absent, selected from the group consisting of —[C($R^a$)($R^b$)]$_x$—, —[C($R^{8a}$)($R^b$)]$_x$—C($R^a$)=C($R^a$)—[(C($R^a$)($R^b$)]$_y$—, —[C($R^a$)($R^b$)]$_x$—O—[C($R^a$)($R^b$)]$_y$—, and —[C($R^a$)($R^b$)]$_x$—N($R^{8a}$)—[C($R^a$)($R^b$)]$_y$—, or is selected from the group consisting of -(cycloalkyl)-, -(heterocycle)-, -(aryl)-, and -(heteroaryl)- each of which has 0-4 substituents;
Q is absent, selected from the group consisting of —C(O)—[C($R^a$)($R^b$)]$_x$—, —C(O)—[C($R^a$)($R^b$)]$_x$—C($R^a$)=C($R^a$)—[C($R^a$)($R^b$)]$_y$—, —C(O)—[C($R^a$)($R^b$)]$_x$—O—[C($R^a$)($R^b$)]$_y$—, and —C(O)—{N($R^{8a}$)—[C($R^a$)($R^b$)]$_y$}$_p$—, or is selected from the group consisting of -(cycloalkyl)-, -(heterocycle)-, -(aryl)-, -(heteroaryl)-, —C(O)-(cycloalkyl)-, —C(O)-(heterocycle)-, —C(O)-(aryl)-, and —C(O)-(heteroaryl)-, each of which has 0-4 substituents;

J is selected from the group consisting of H, $C_{1-4}$alkyl, halogen, $C_{1-4}$alkoxy, hydroxy, amino, mono- and di-$C_{1-4}$alkylamino, tri$C_{1-4}$alkylammonium, $N(R^{8a})C(O)$ $C_{1-4}$alkyl, $CO_2H$, $C(=O)N(R^{8a})_2$, $CH_2CO_2H$, $CH_2C(=O)N(R^{8a})_2$, $CO_2$—$C_{1-4}$alkyl, $C(O)C_{1-4}$alkyl, $P(O)(OH)_2$, $P(O)(O$—$C_{1-4}$alkyl$)_2$, $C_{0-4}$alkylene-(cycloalkyl) and $C_{0-4}$alkylene-(heterocycle), which heterocycle may be substituted 0-4 times;

$R^a$ is selected from the group consisting of H, alkyl, F, $CO_2H$, $CO_2$-alkyl, —$N(R^1)_2$, —$OR^1$, —$(CH_2)_{0-4}$-J and —$R^{4b}$;

$R^b$ is selected from the group consisting of H, alkyl, and F;

p is 0, 1, 2, or 3;

x and y are each, independently selected at each occurrence from integers from 0-10;

$R^1$ is independently selected at each occurrence from —H, alkyl substituted with J, and —$R^{4b}$;

$R^{4b}$ is selected from the group consisting of alkyl and —$(CH_2$—$CH_2$—$O$—$)_n$—$R^9$, wherein n is an integer of 1-500, 1,000, 2,000, 3,000, 4,000, 5,000, 10,000, 20,000, 30,000, 40,000, 50,000, or 60,000 or is a mean of a plurality of integers having a value of 1-500, 1,000, 2,000, 3,000, 4,000, 5,000, 10,000, 20,000, 30,000, 40,000, 50,000, or 60,000;

$R^8$ is selected from the group consisting of H, CN, $NO_2$, $C_{1-6}$alkyl, $C_{3-7}$cycloalkyl, and $SO_2$—$C_{1-6}$alkyl; and $R^{8a}$ is absent, or selected from the group consisting of H, $C_{1-6}$alkyl, $C_{3-7}$cycloalkyl, $C_{1-6}$alkyl substituted with J, and $R^{4b}$, or two $R^{8a}$ residues, taken in combination may form a saturated, unsaturated or aromatic ring having 3 to 7 ring atoms, which ring may be substituted 0-4 times.

2. The compound of claim 1, wherein R is $N(R^1)$-A-G-Q-J, $R^1$ is H and A-G-Q-J together form H, or together form a functional group selected from the group consisting of

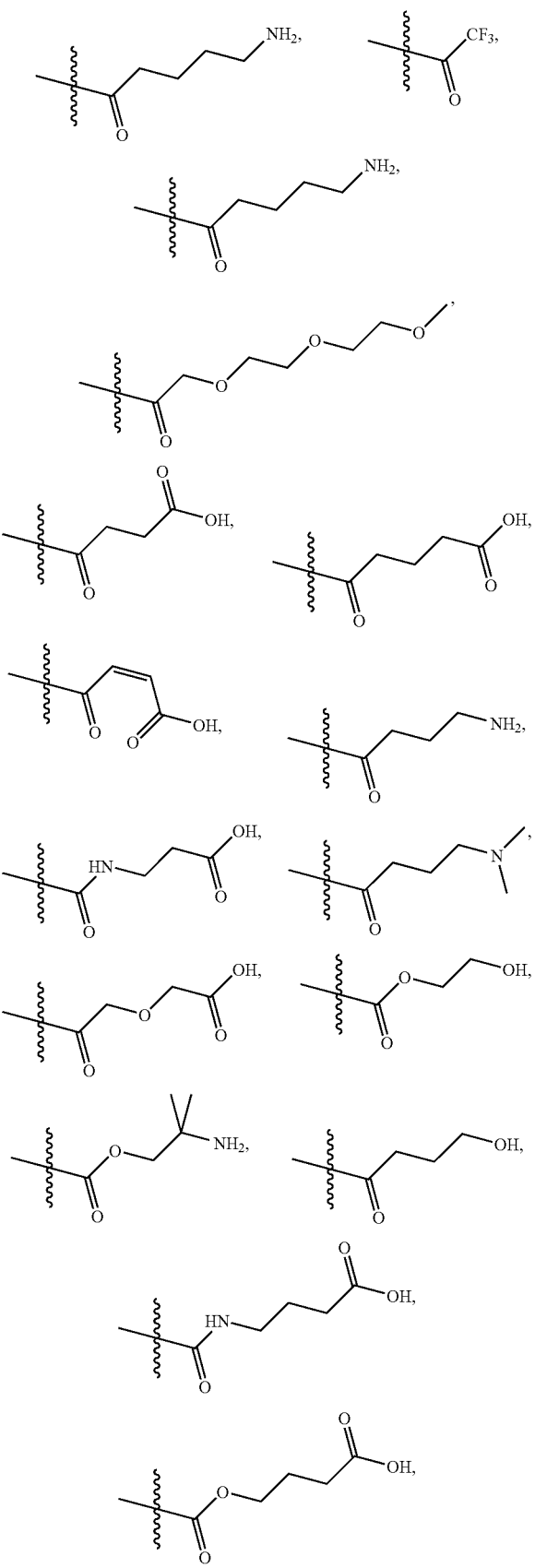

-continued

-continued
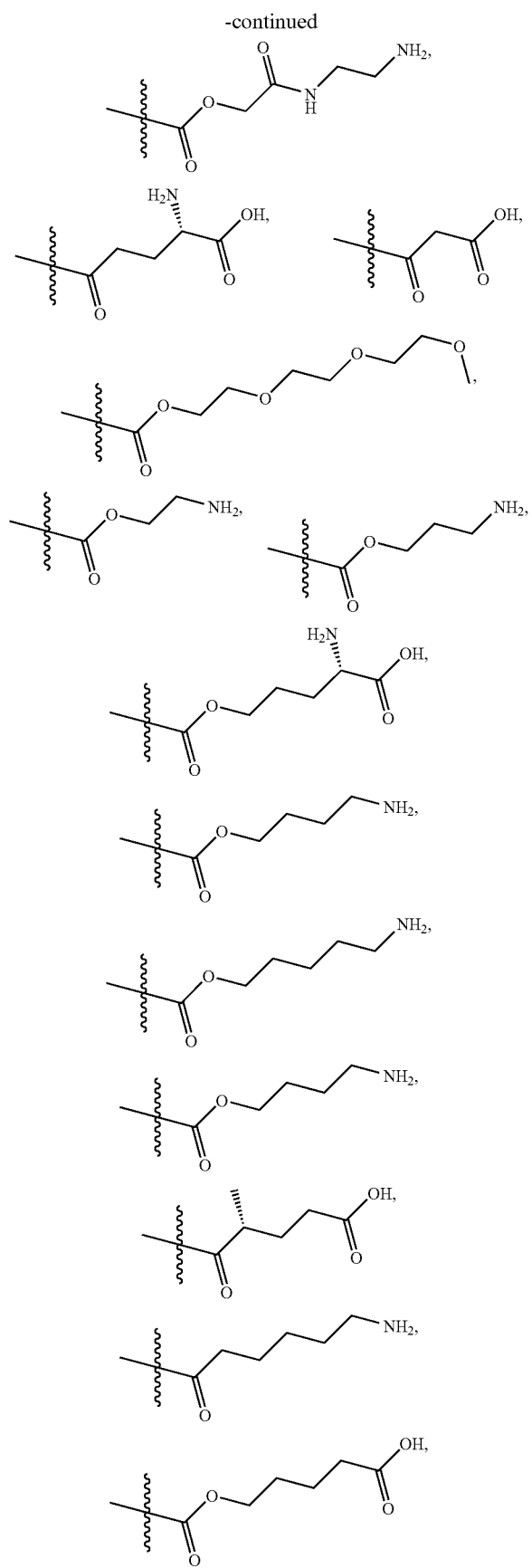
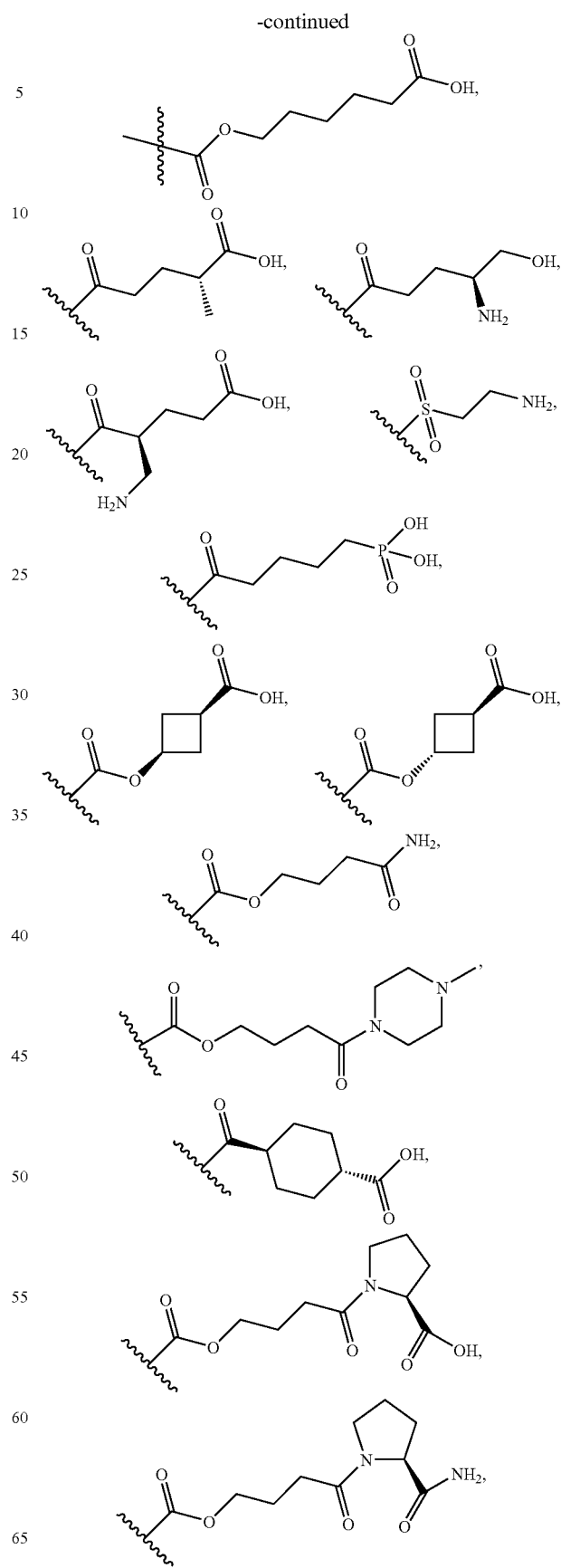

-continued
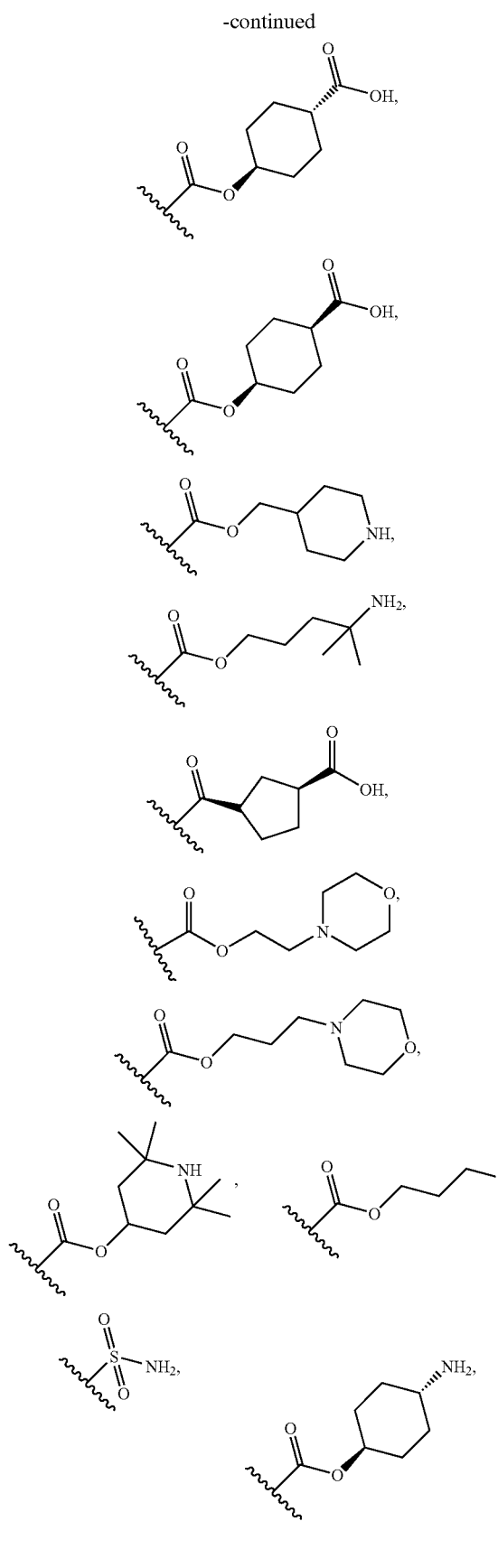
-continued
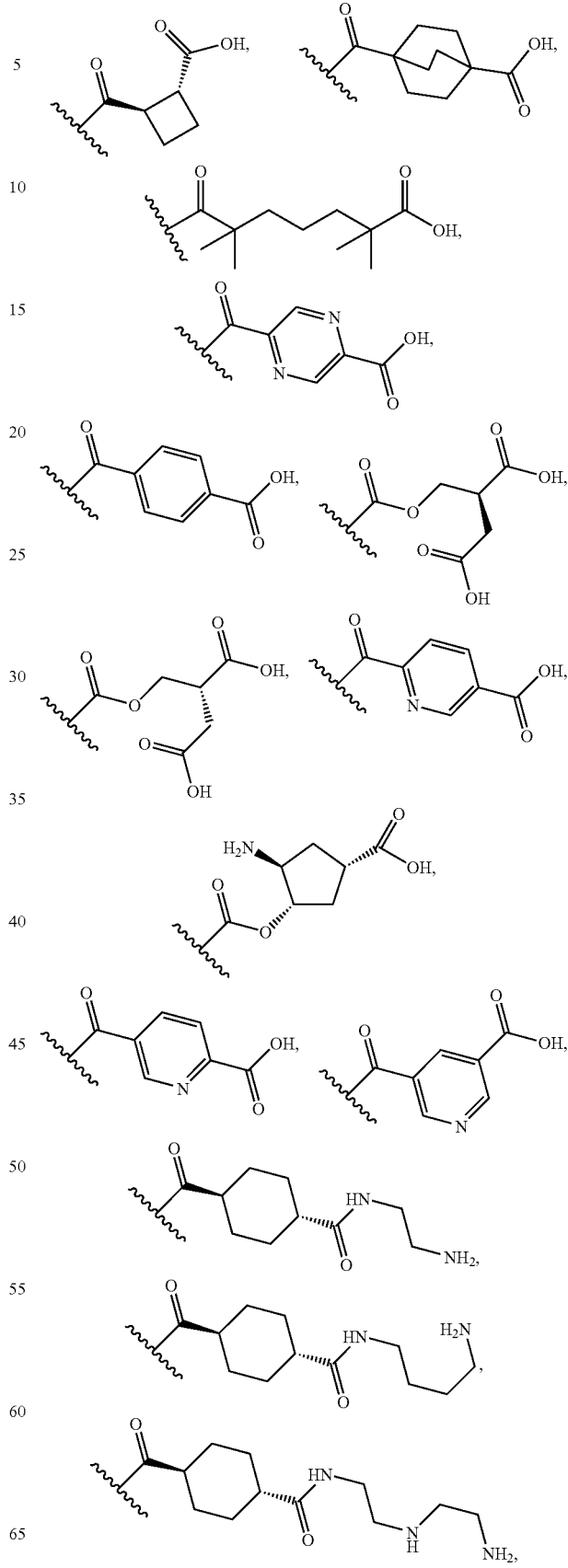

-continued
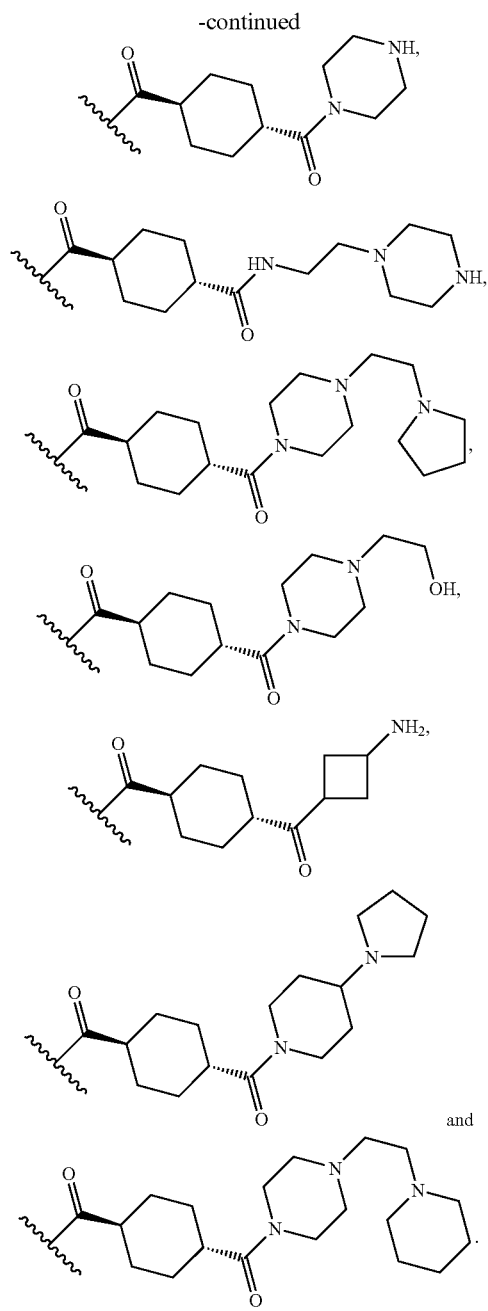
3. The compound of claim 1, wherein R is N(R¹)-A-G-Q-J, R¹ is H and A-G-Q-J together form a functional group selected from the group consisting of
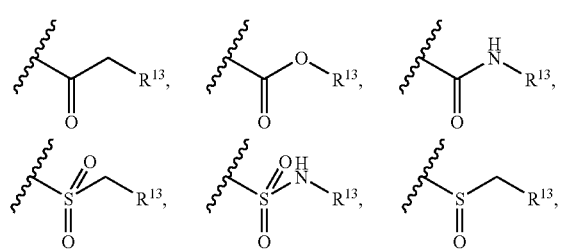
-continued
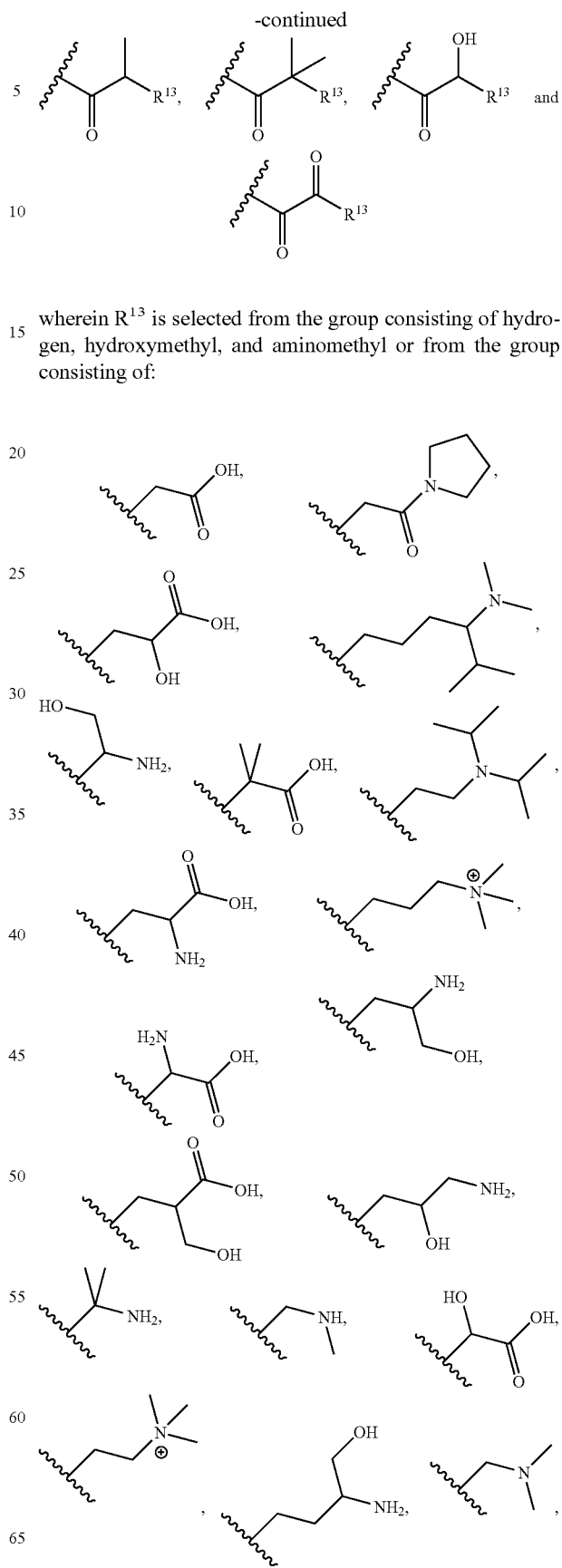
wherein $R^{13}$ is selected from the group consisting of hydrogen, hydroxymethyl, and aminomethyl or from the group consisting of:

-continued
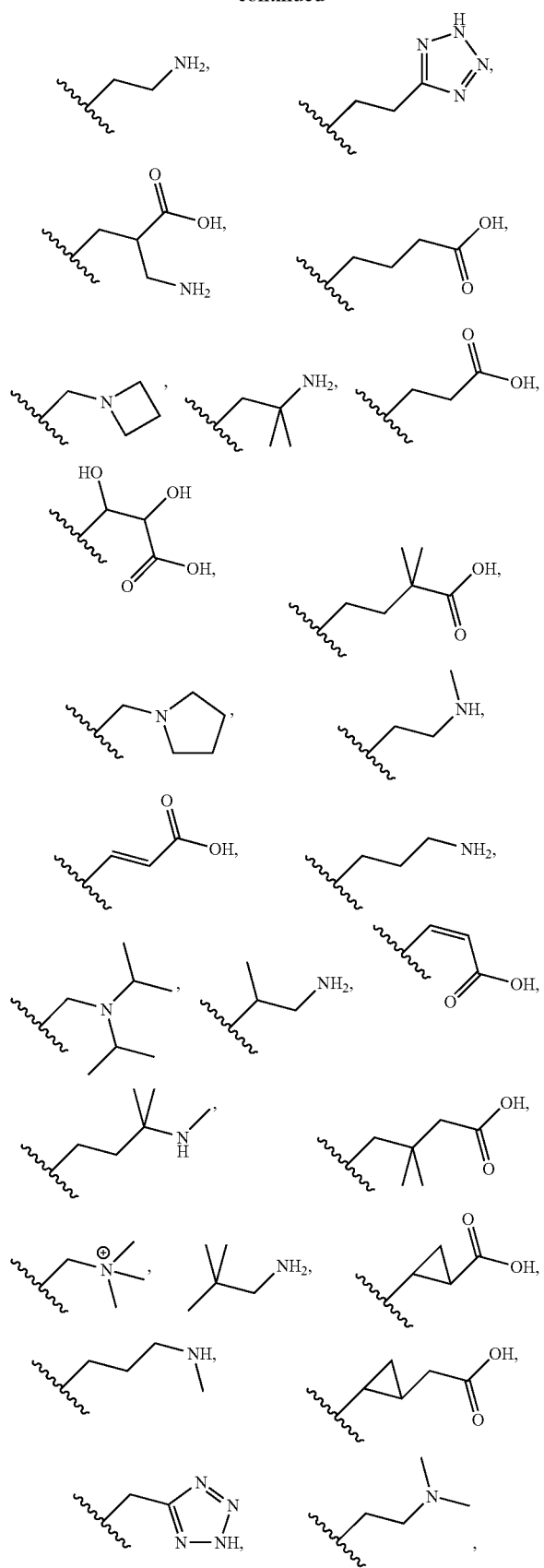
-continued
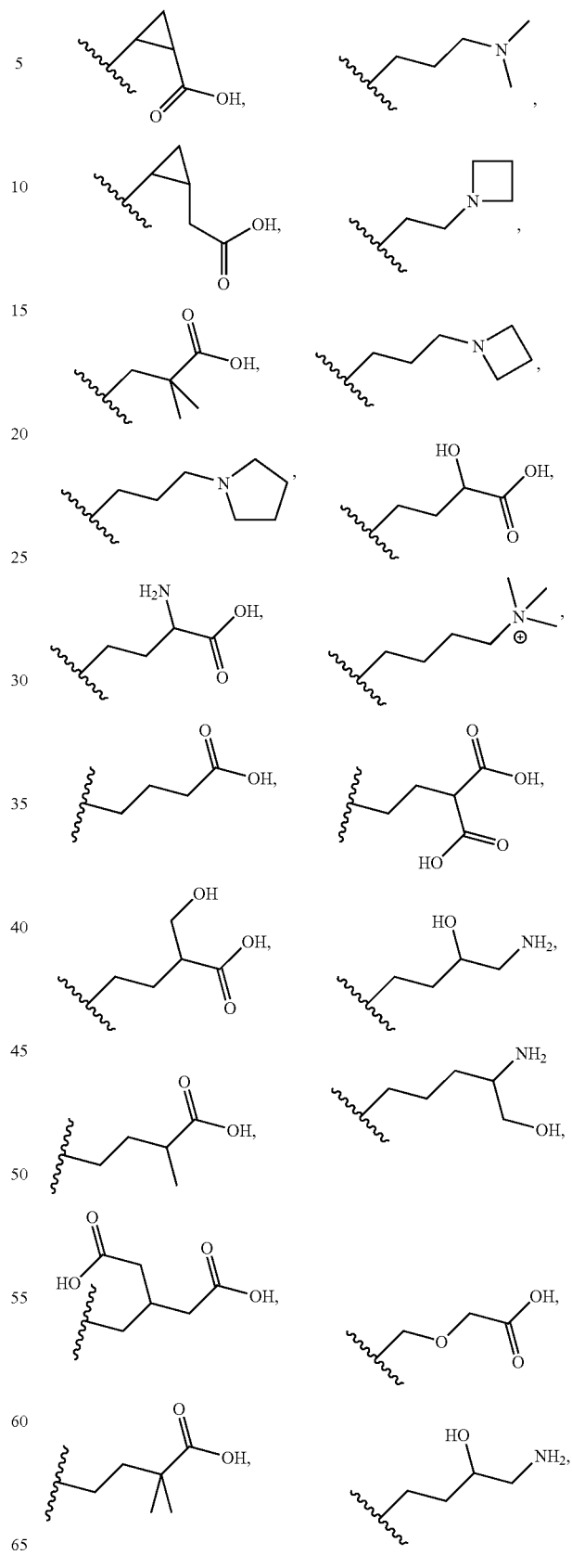

-continued
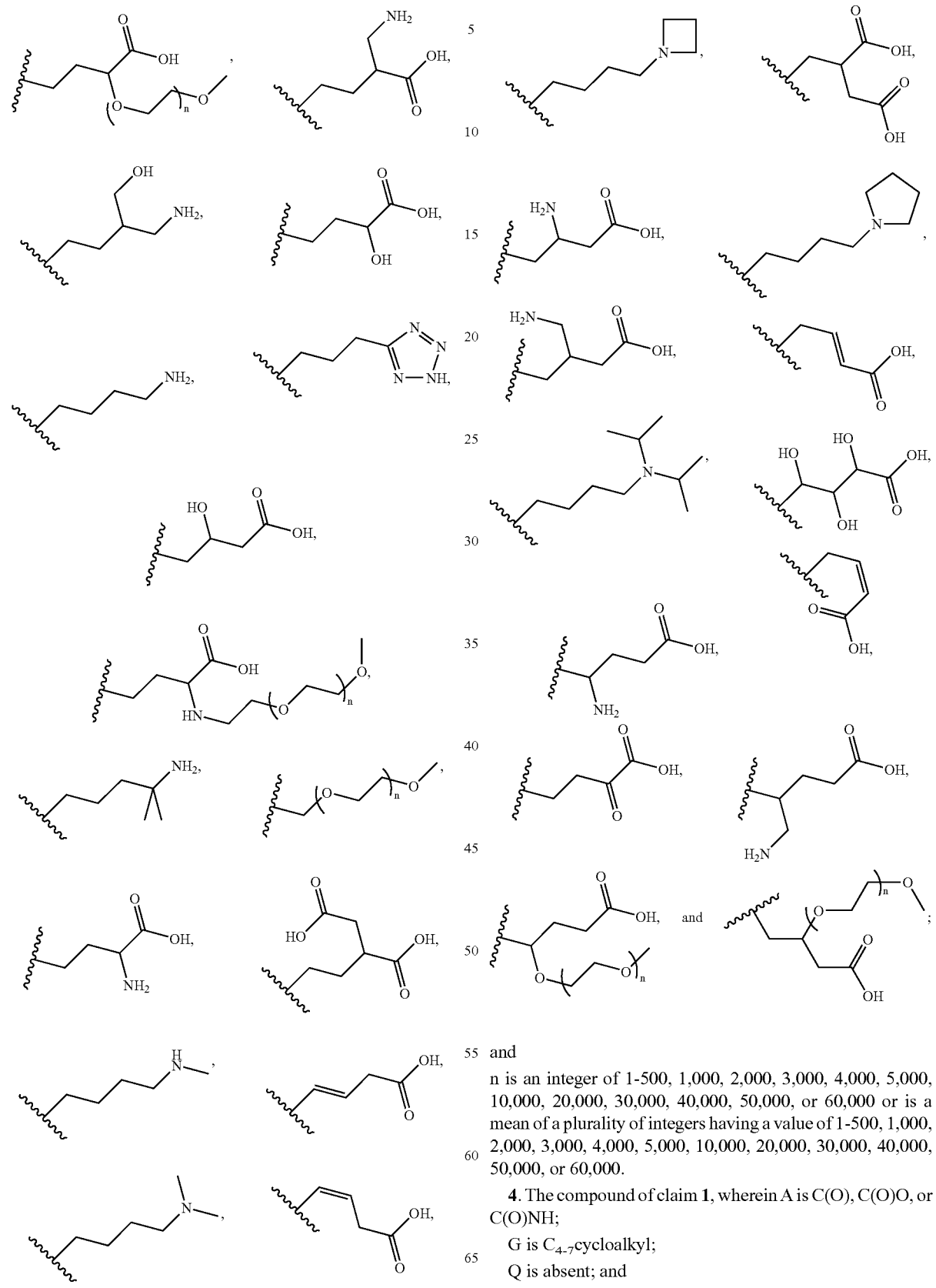
and
n is an integer of 1-500, 1,000, 2,000, 3,000, 4,000, 5,000, 10,000, 20,000, 30,000, 40,000, 50,000, or 60,000 or is a mean of a plurality of integers having a value of 1-500, 1,000, 2,000, 3,000, 4,000, 5,000, 10,000, 20,000, 30,000, 40,000, 50,000, or 60,000.
4. The compound of claim 1, wherein A is C(O), C(O)O, or C(O)NH;
G is $C_{4-7}$cycloalkyl;
Q is absent; and
J is $CO_2H$ or $CO_2C_{1-4}$alkyl.

5. A compound selected from the group consisting of:
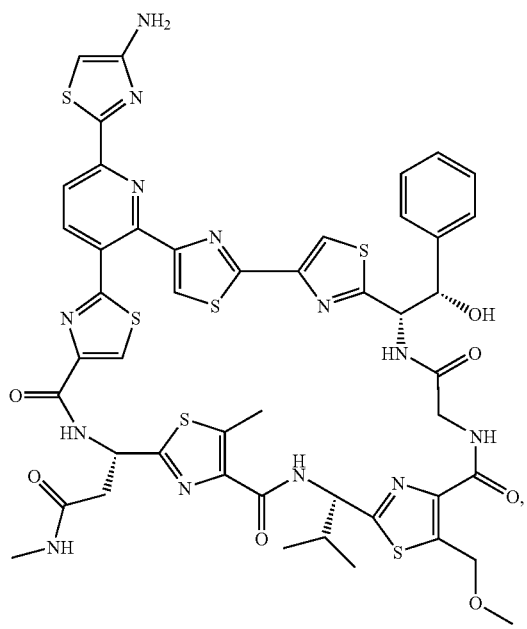
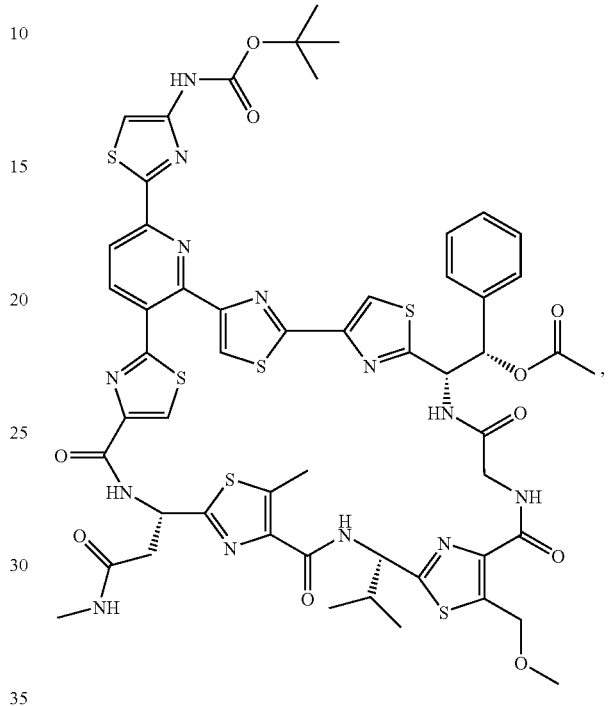
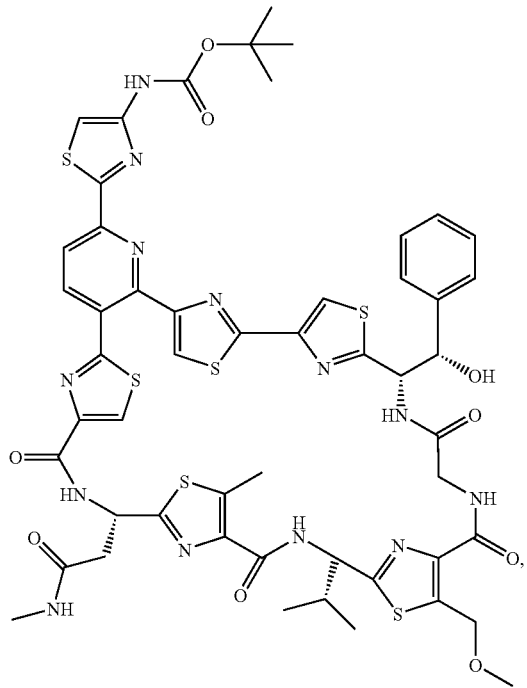
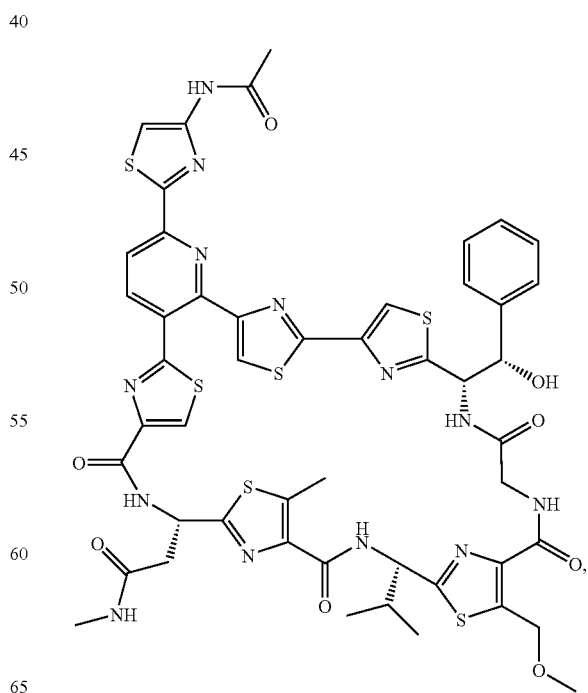

185
-continued
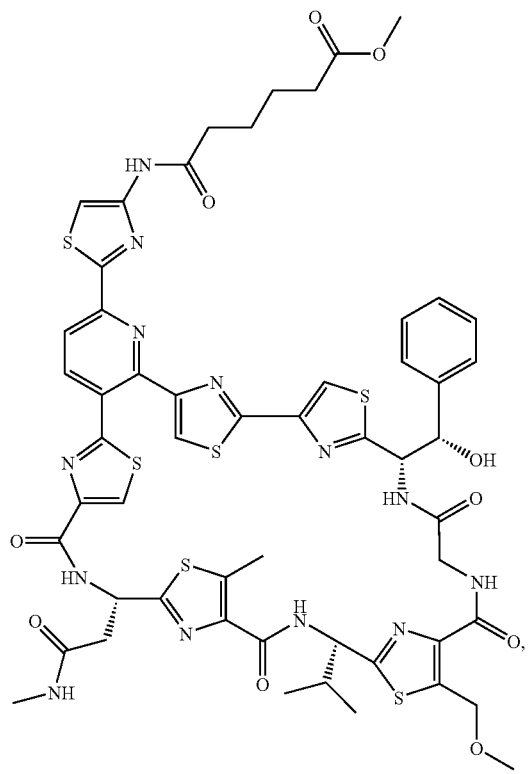
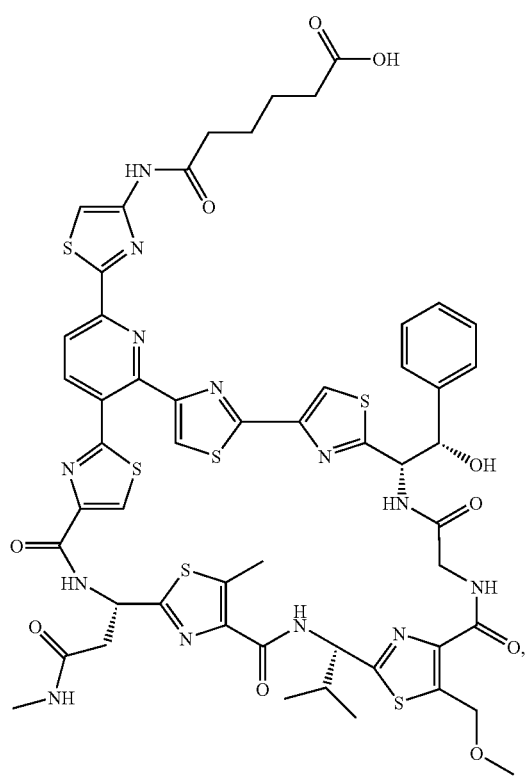
186
-continued
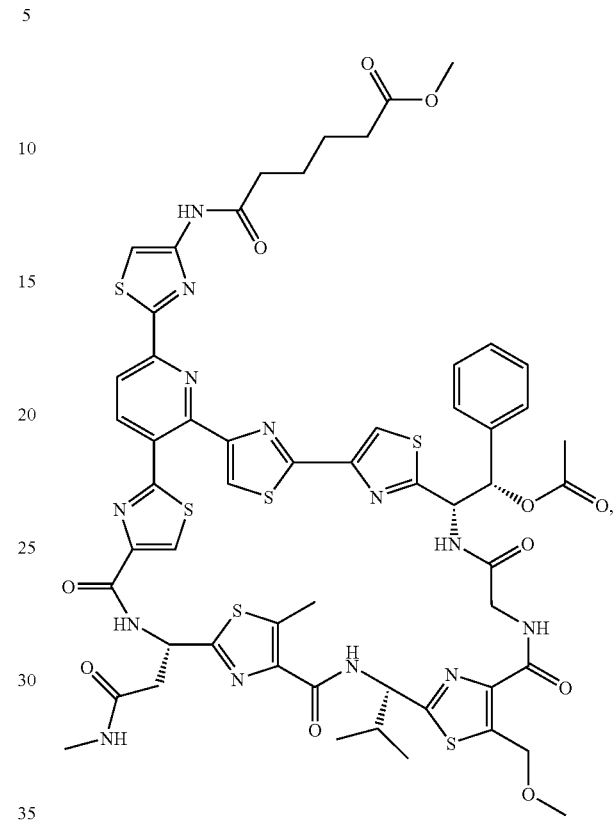
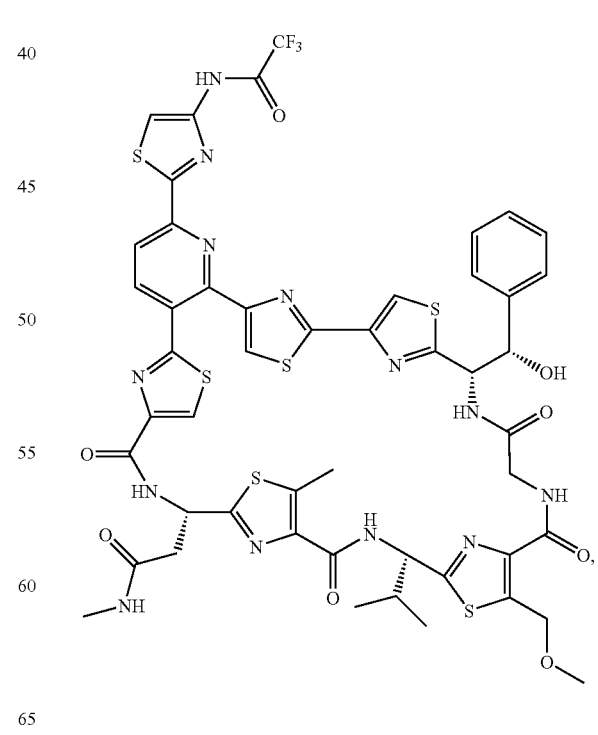

187
-continued
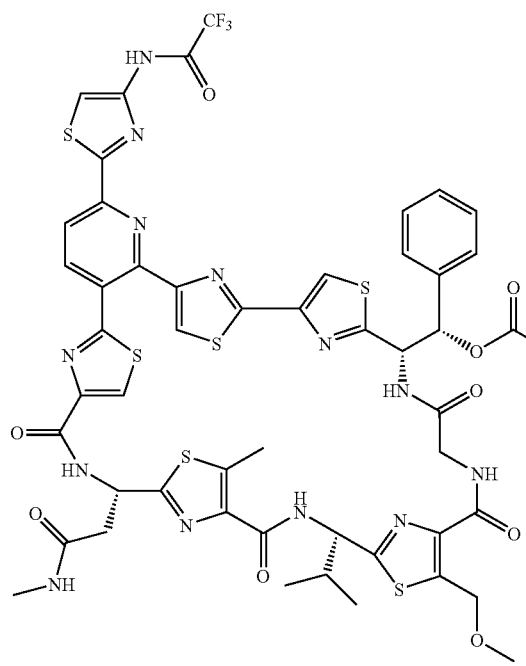
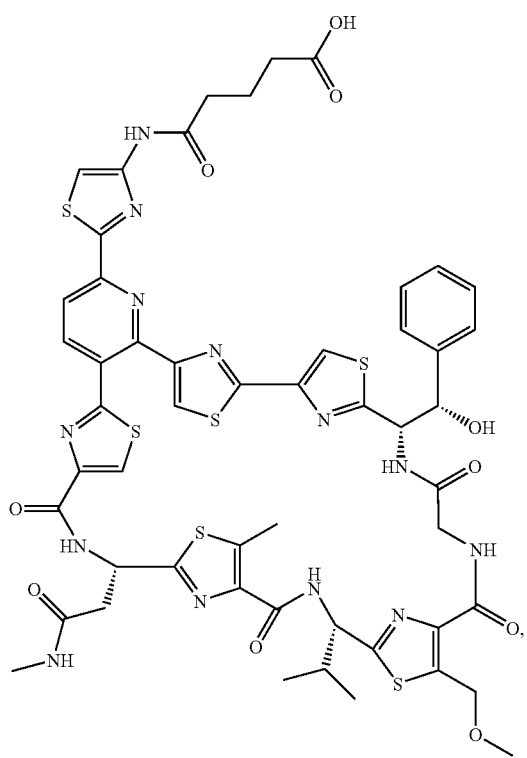
188
-continued
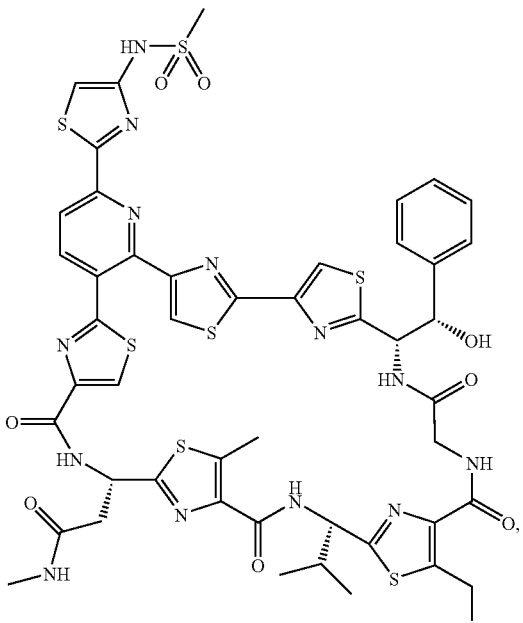
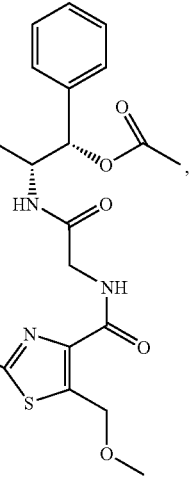

189
190
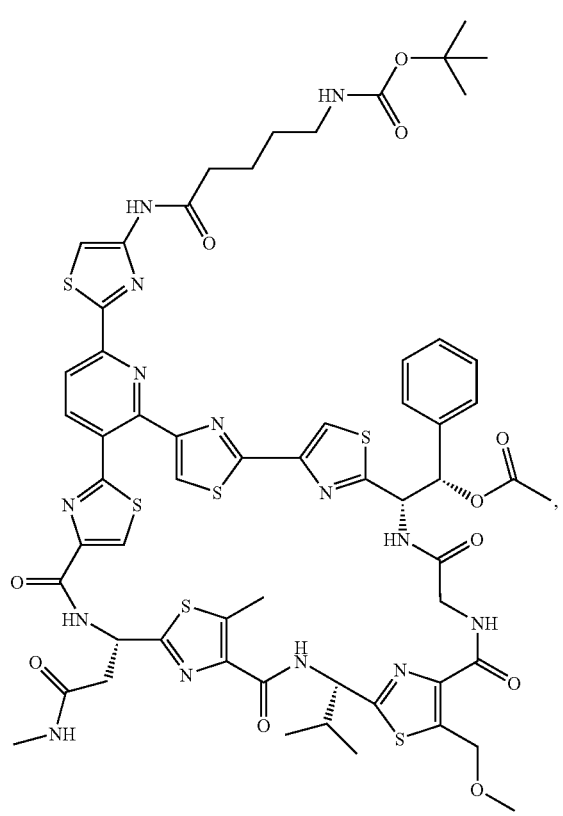
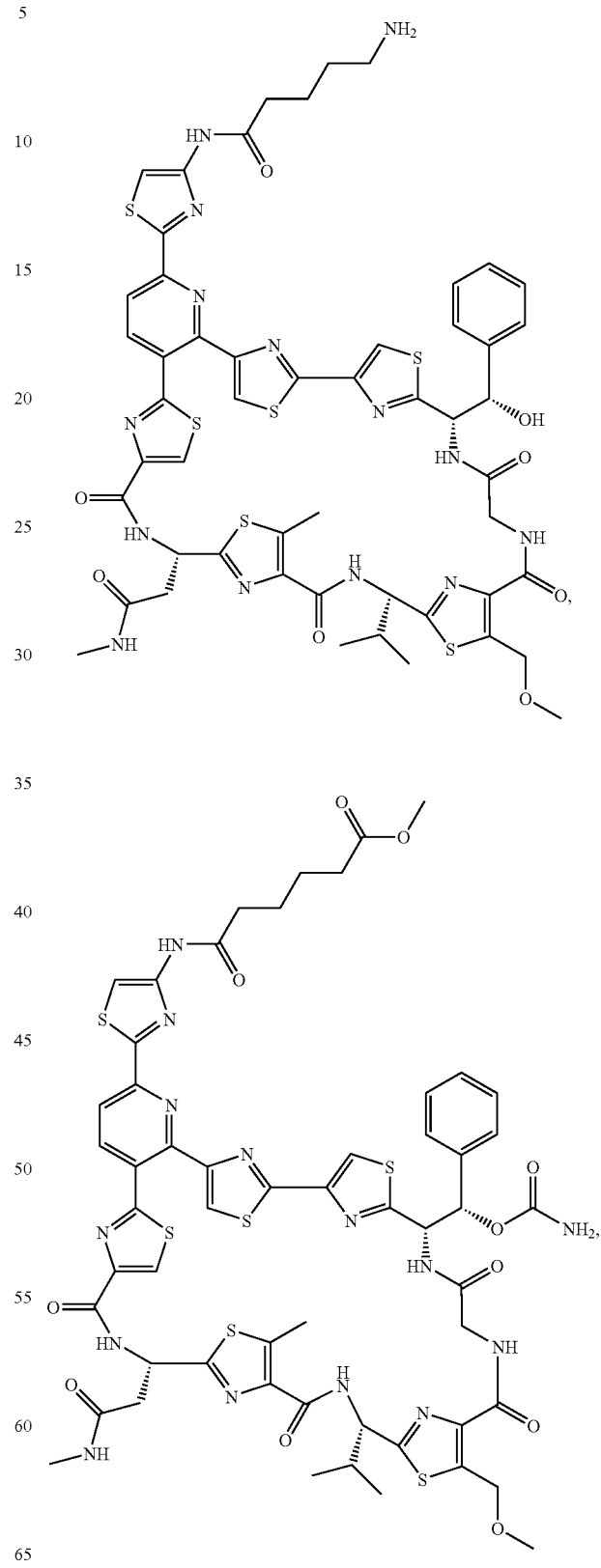

191
192
-continued
-continued
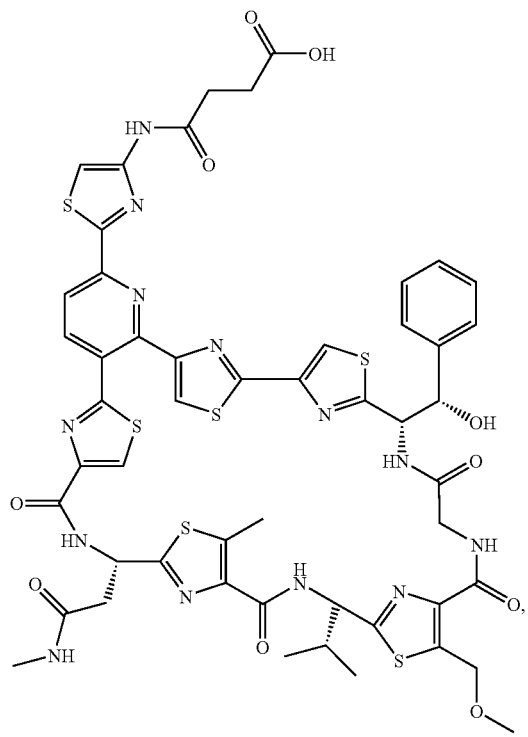
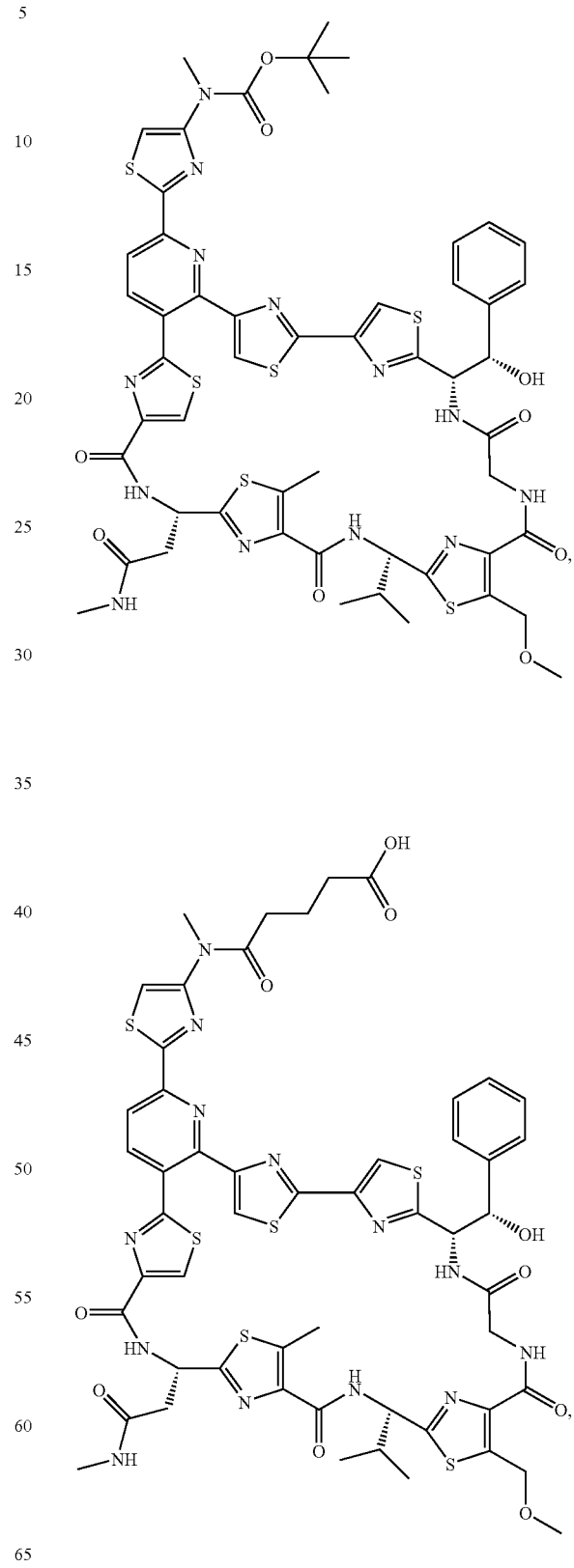

193 194
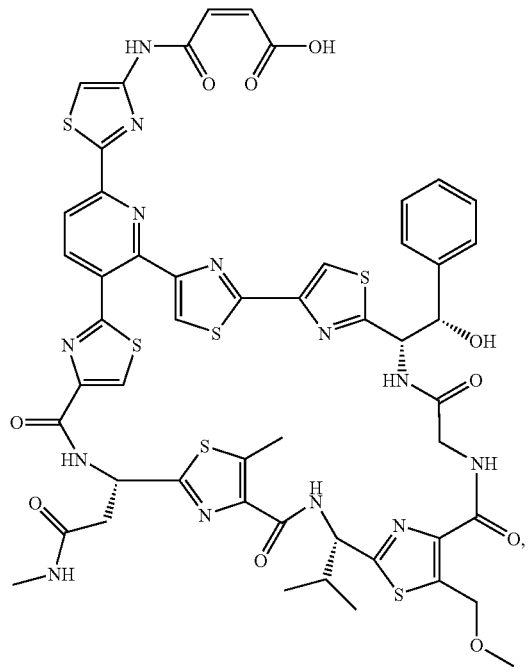
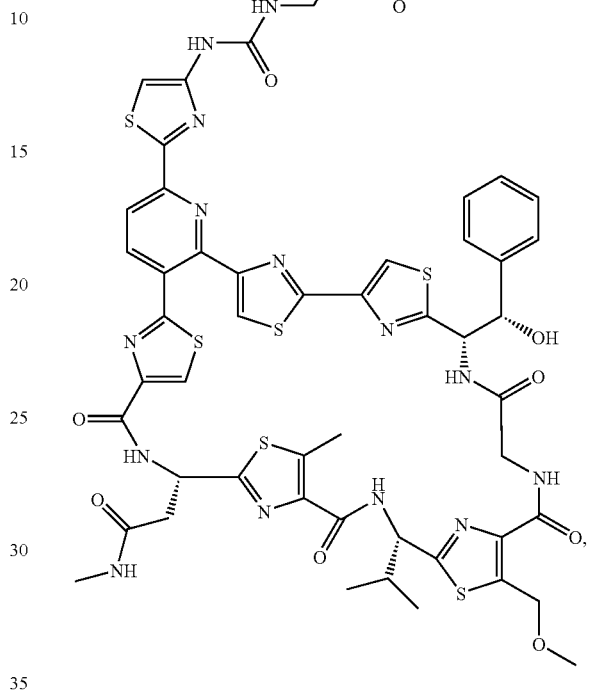
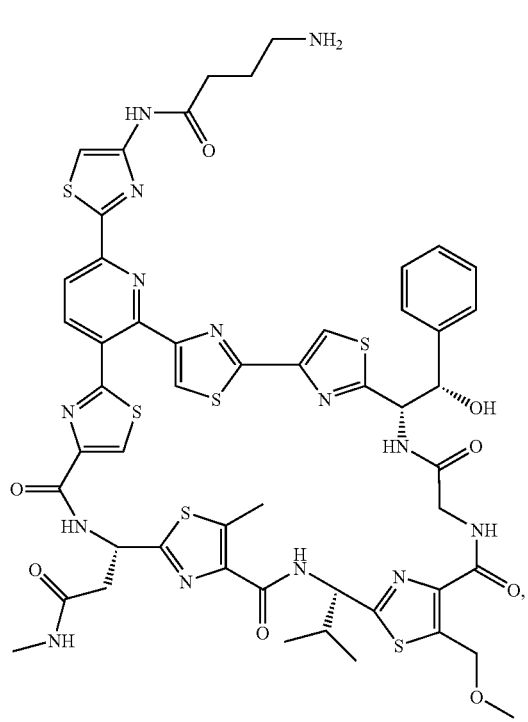

195
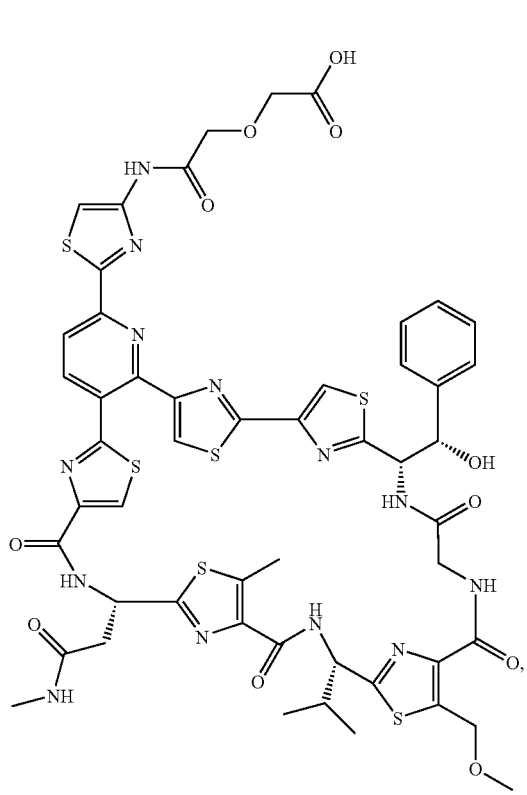
196
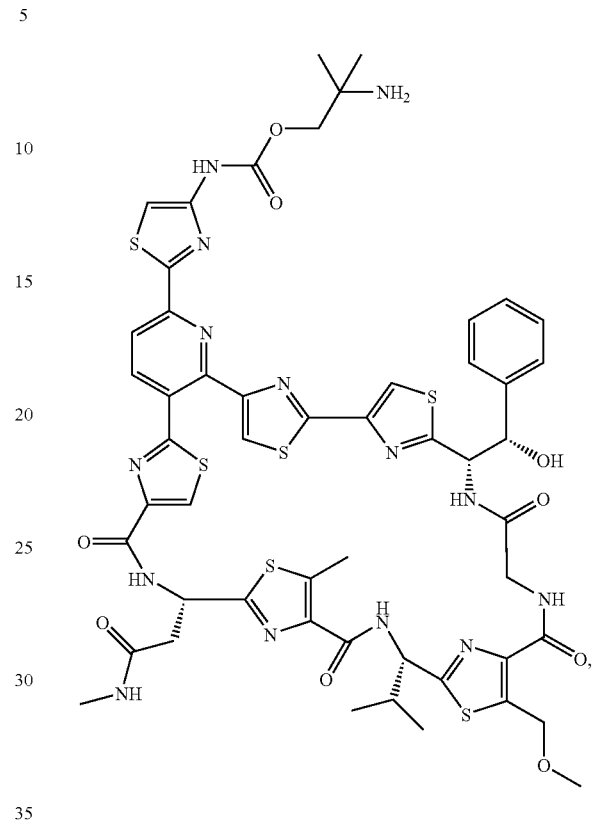
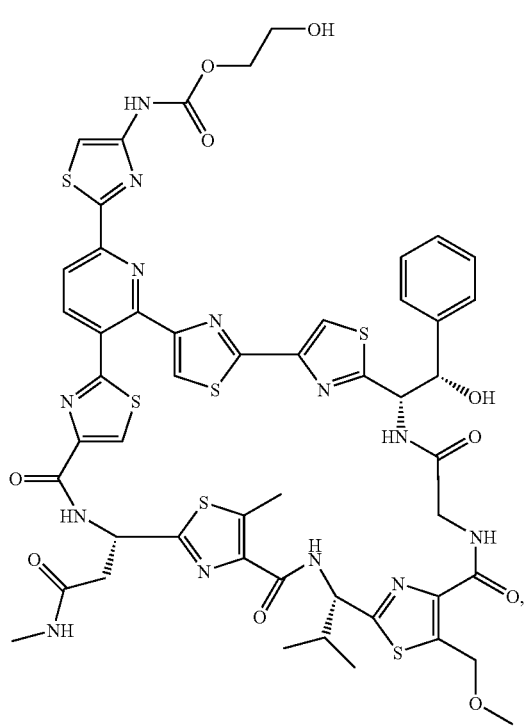
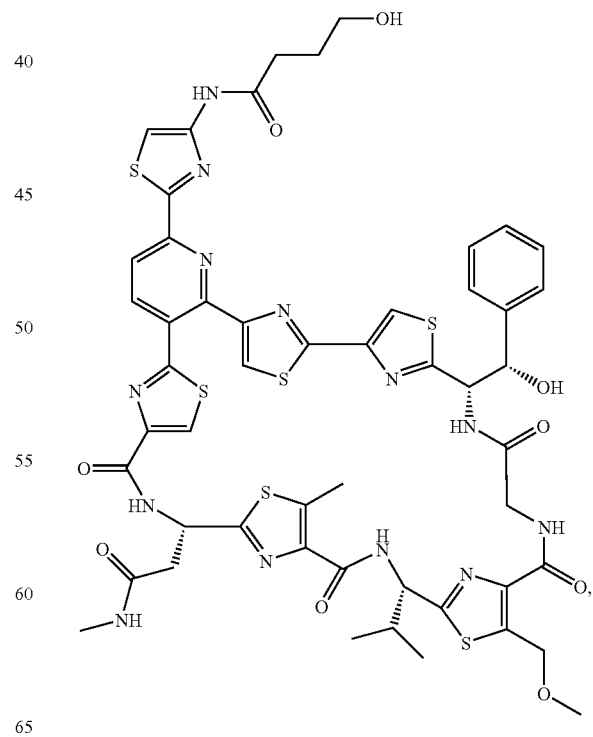

197
198
-continued
-continued
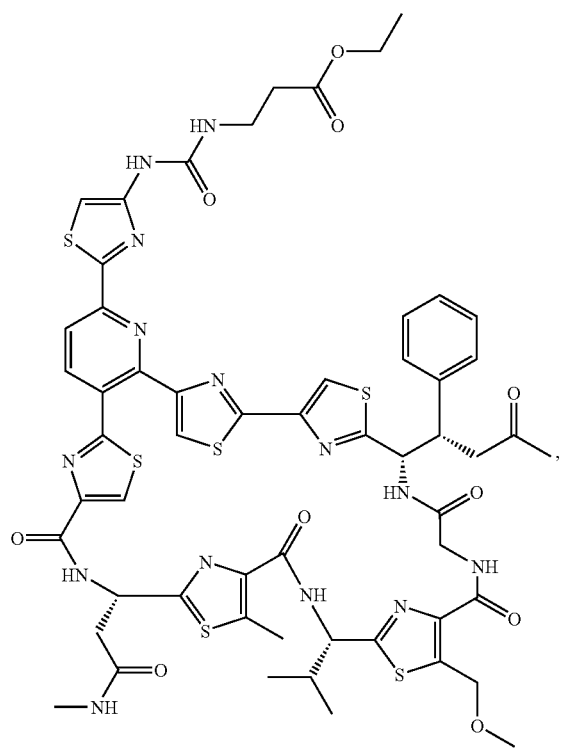
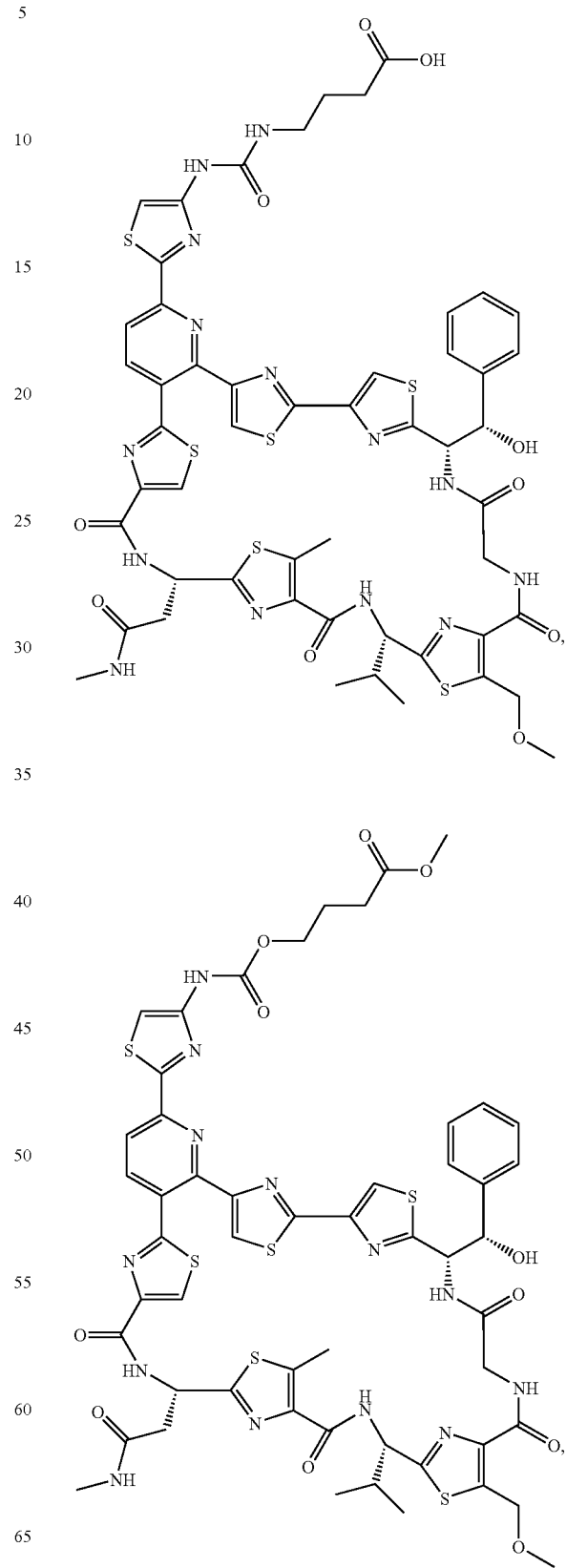

199
-continued
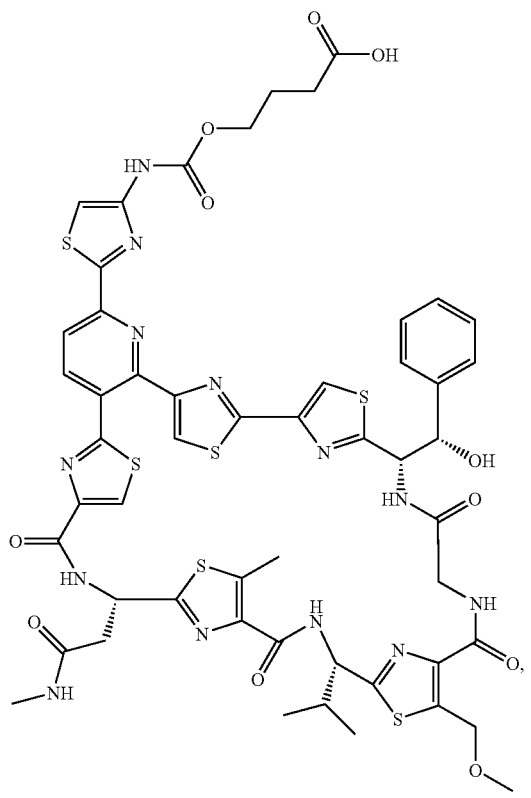
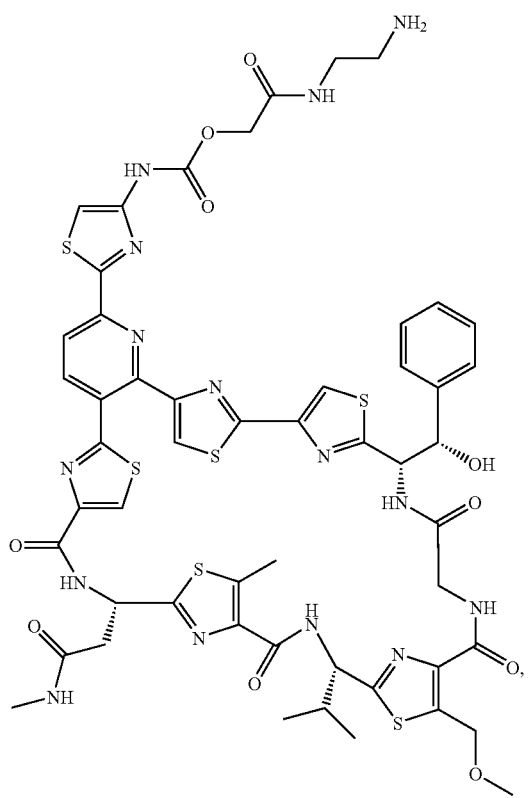
200
-continued
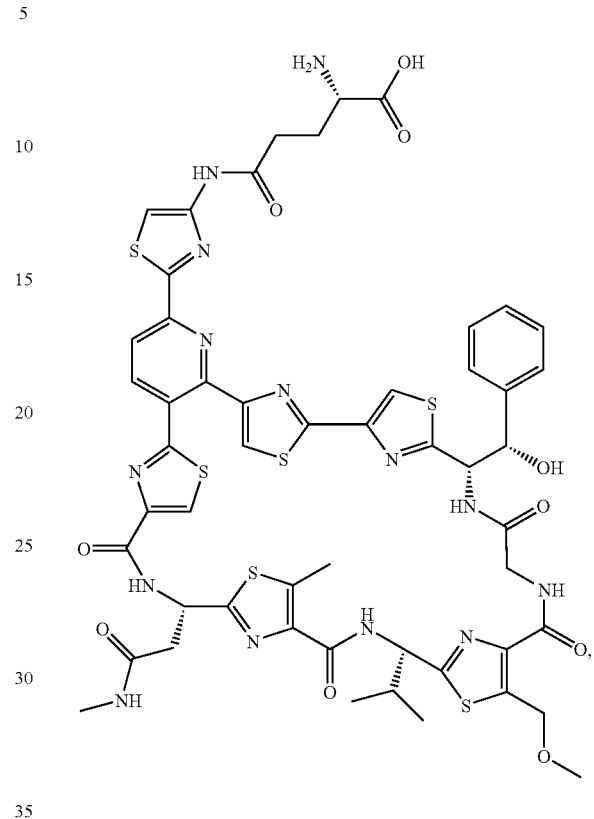
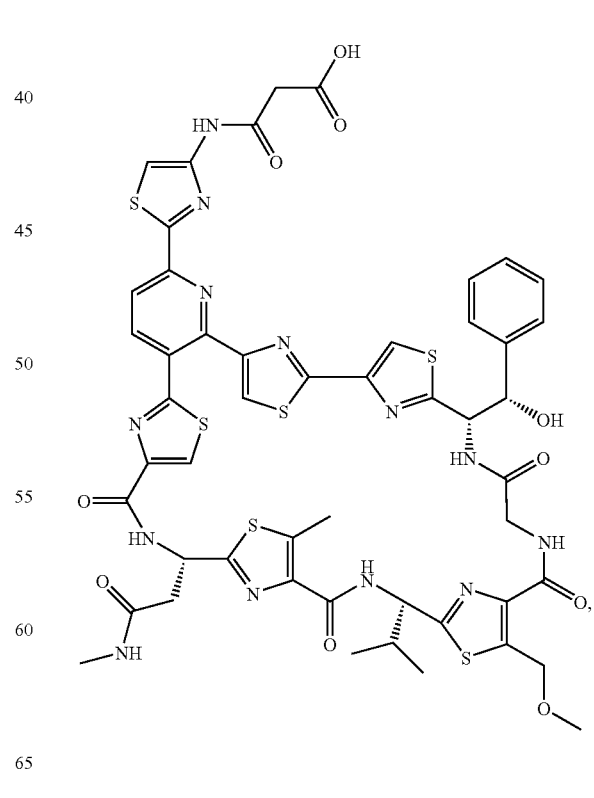

201
-continued
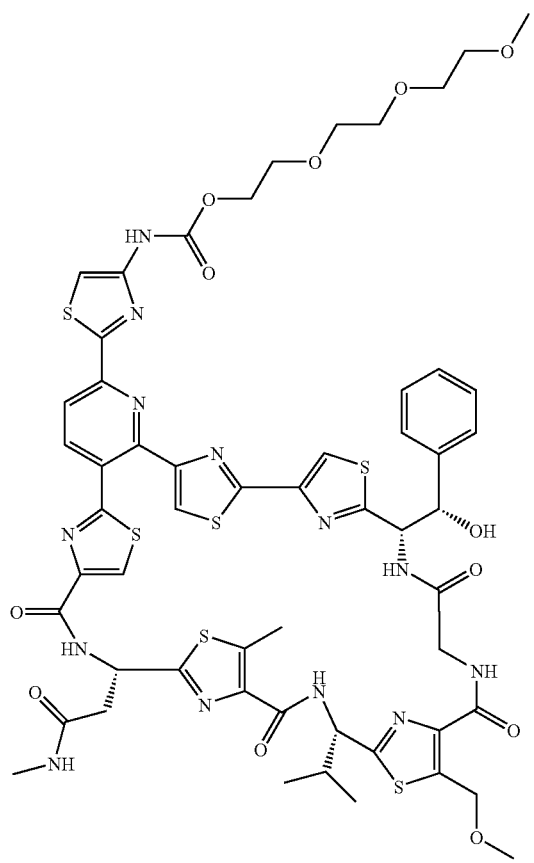
202
-continued
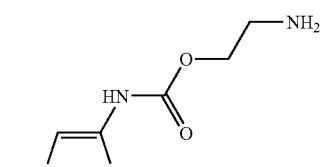
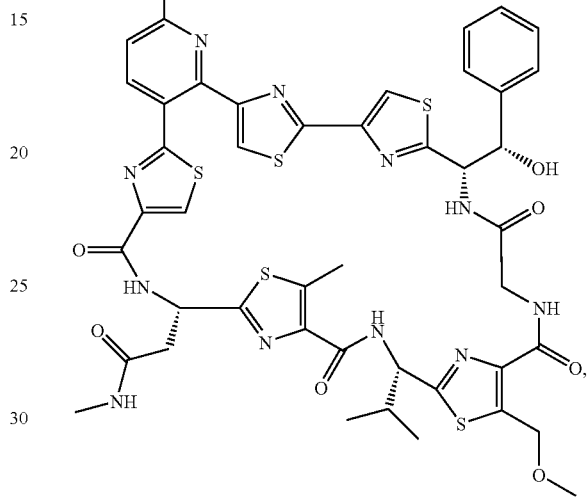
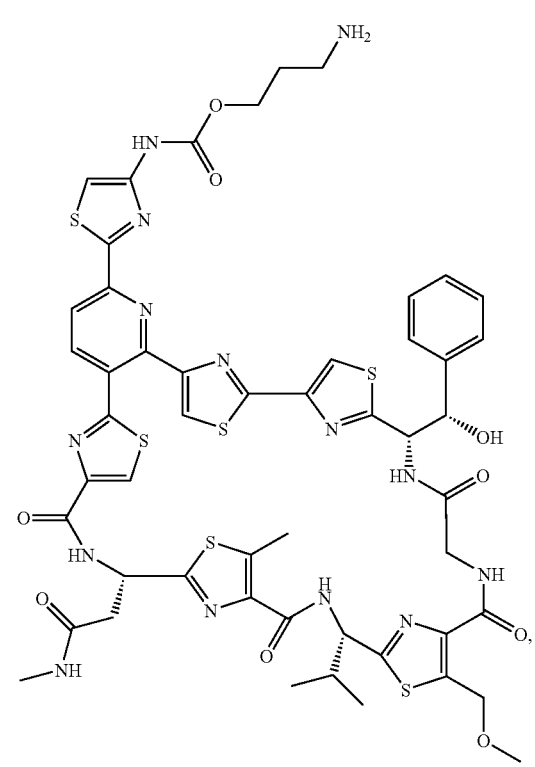
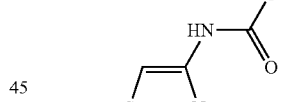
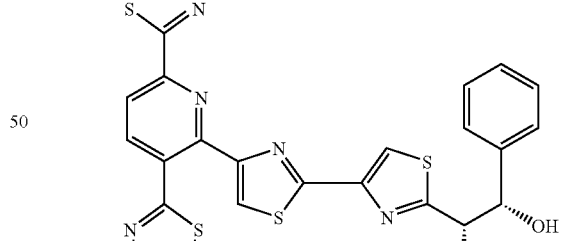
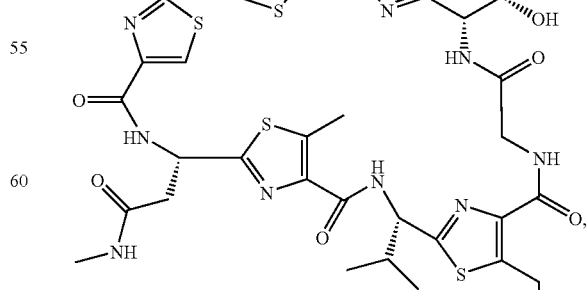

203
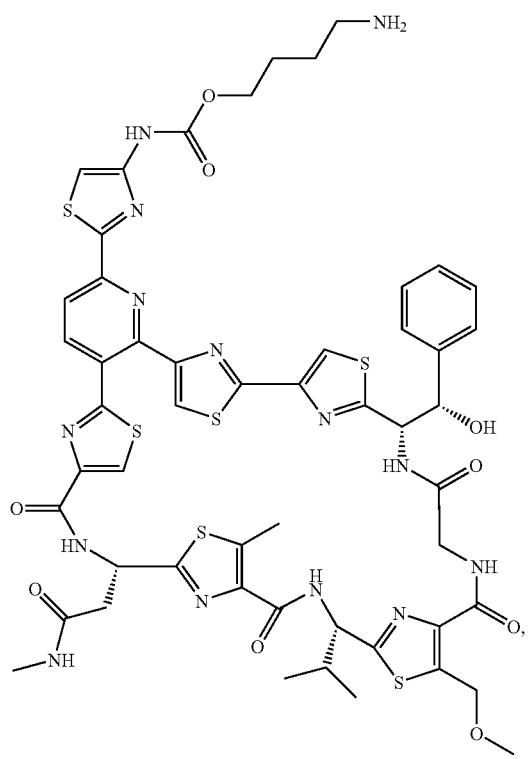
204
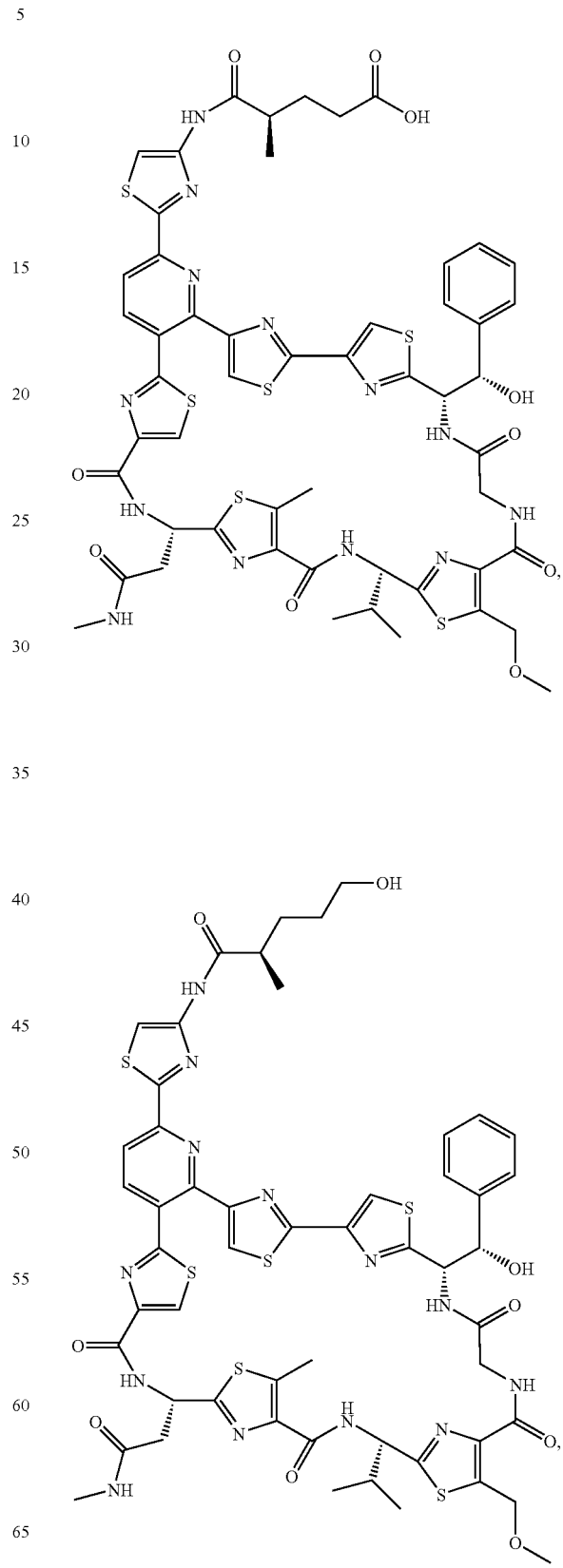

205
206
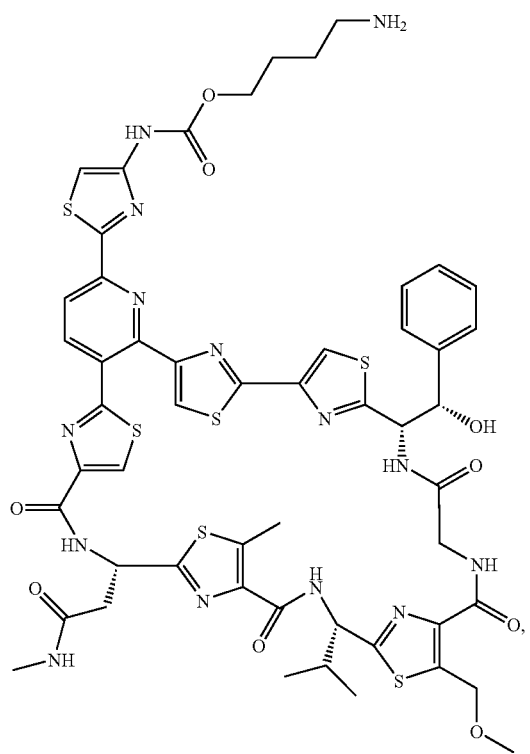
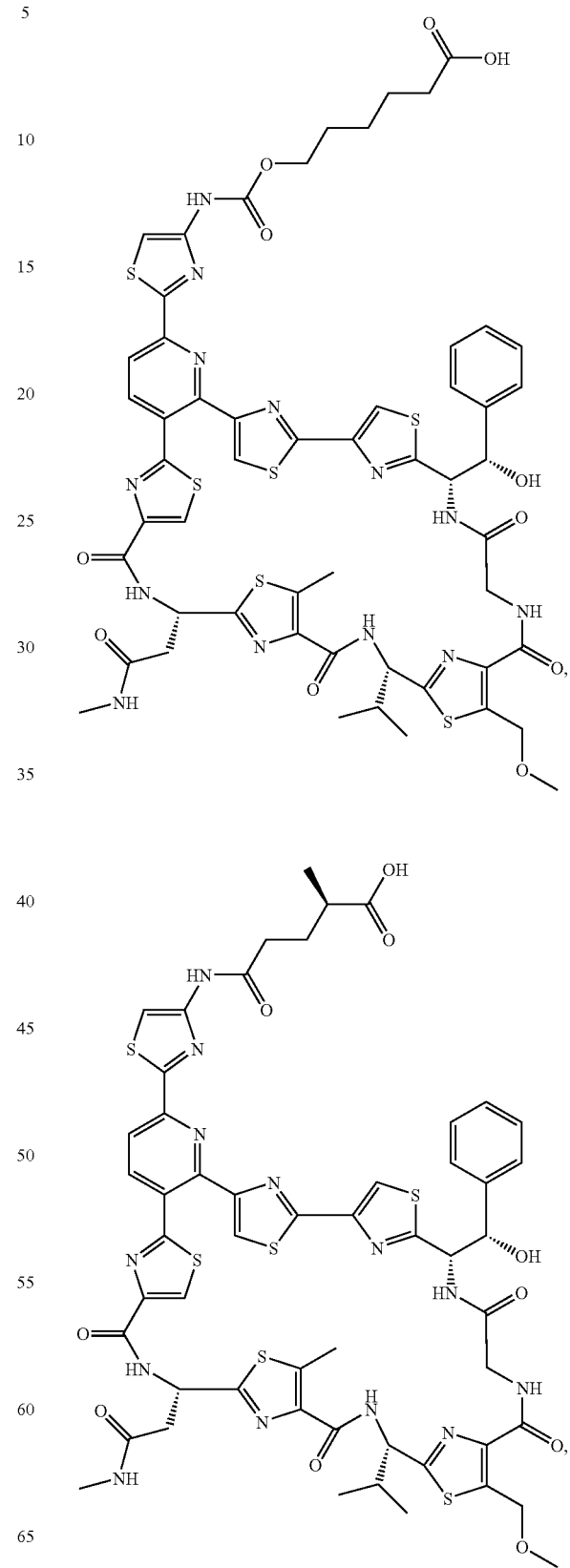

207
-continued
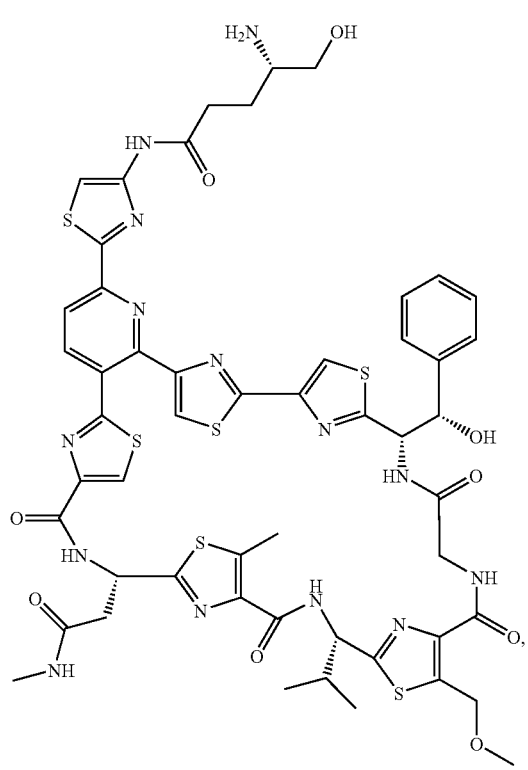
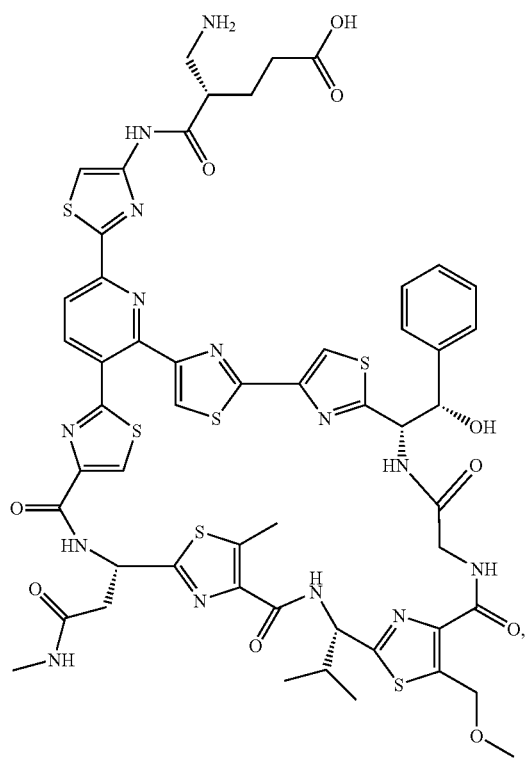
208
-continued
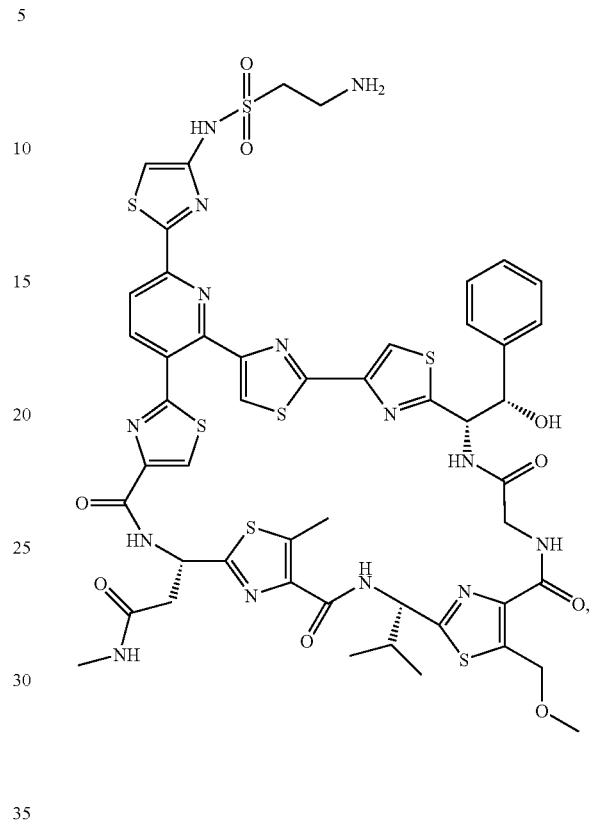
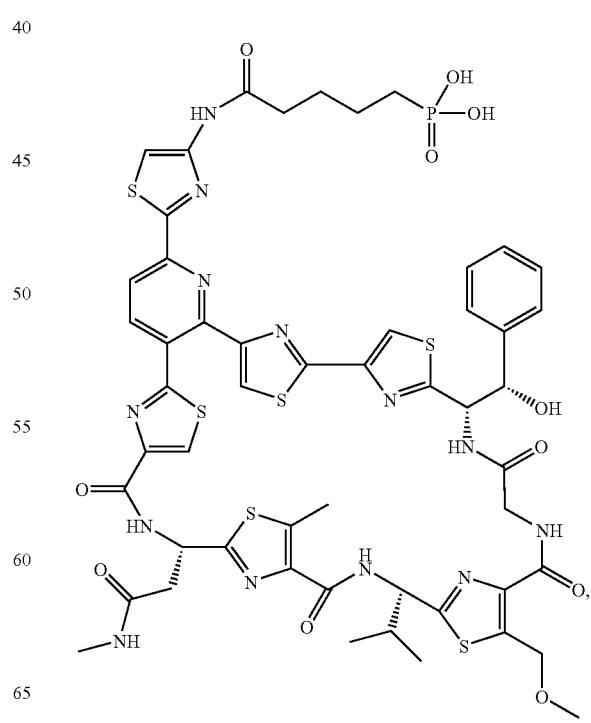

209
-continued
210
-continued
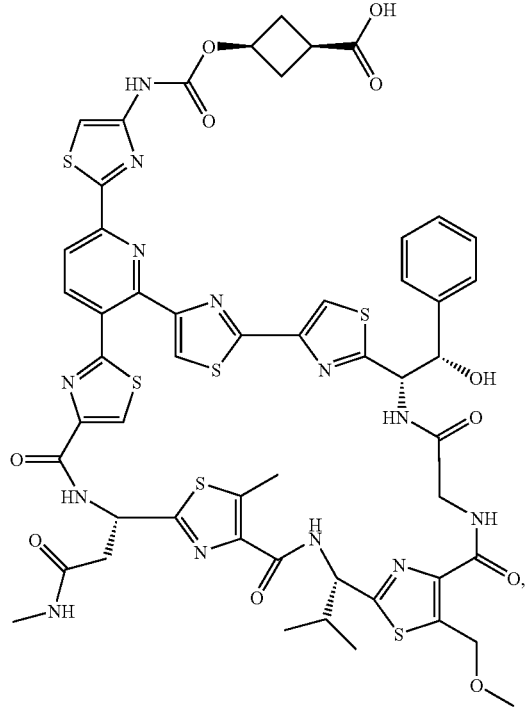
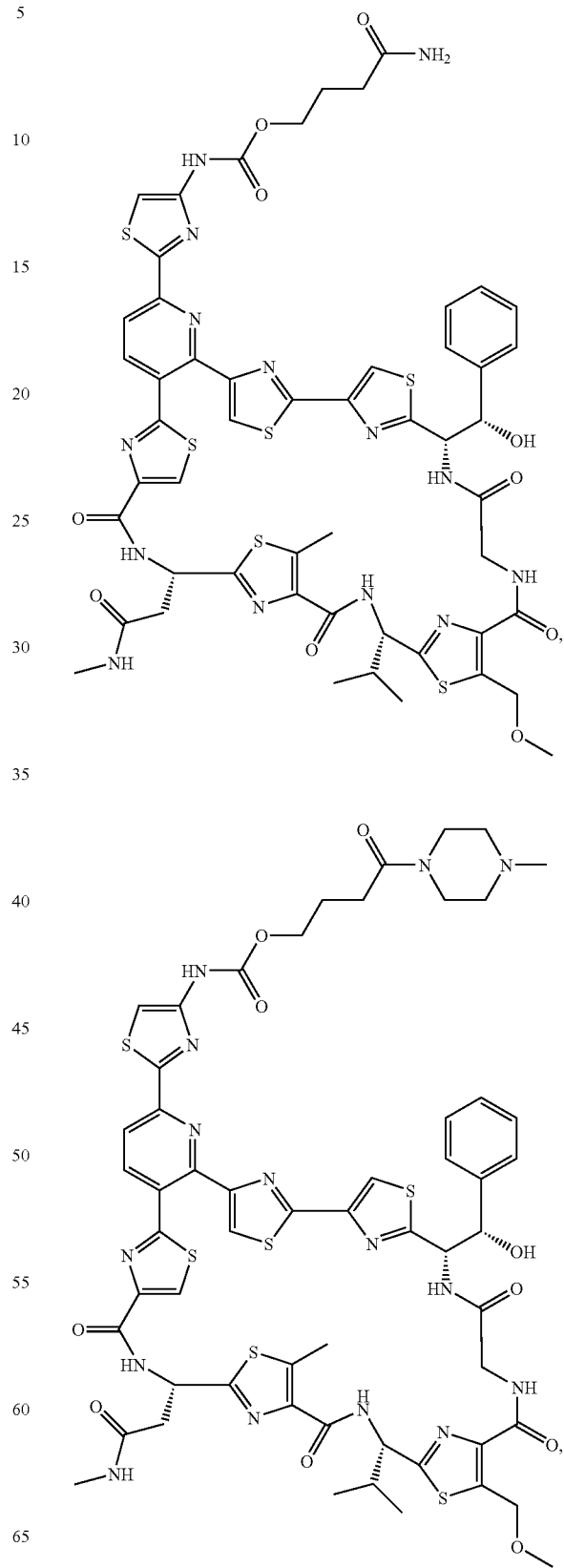

211
-continued
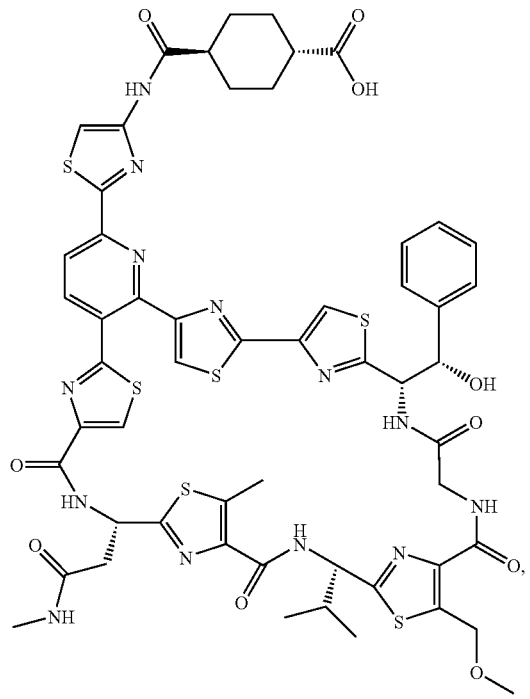
212
-continued
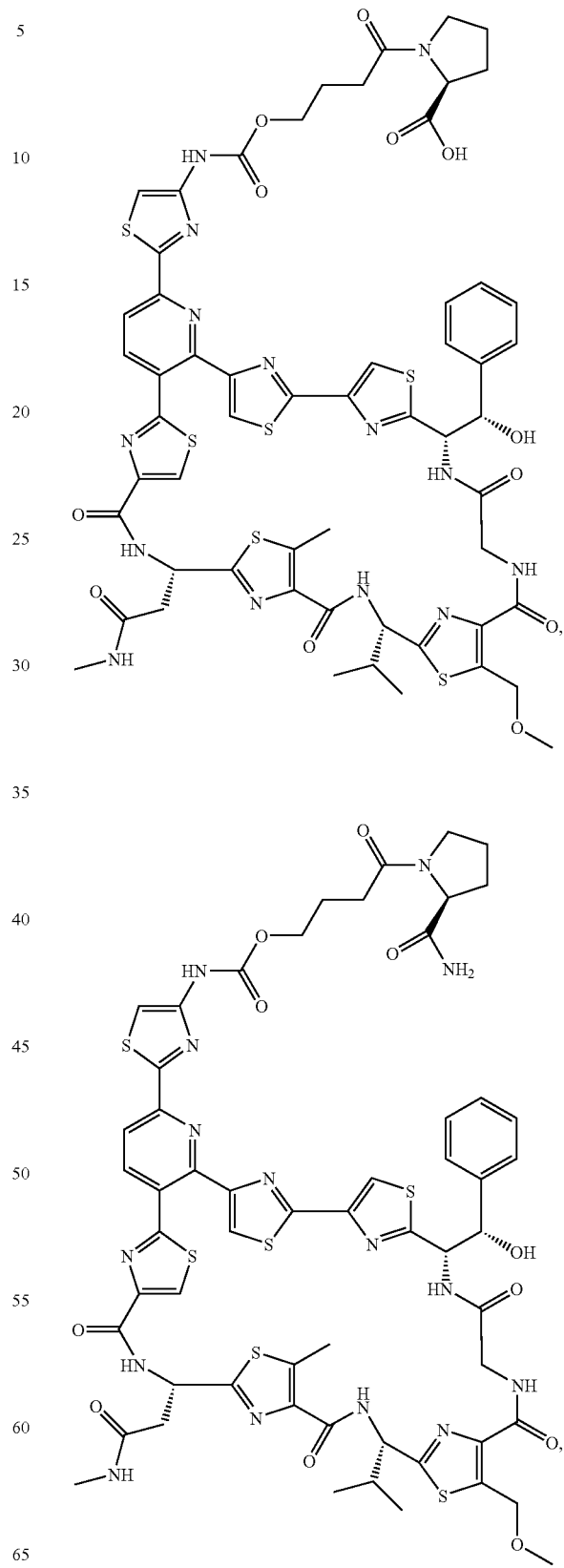

213
-continued
214
-continued
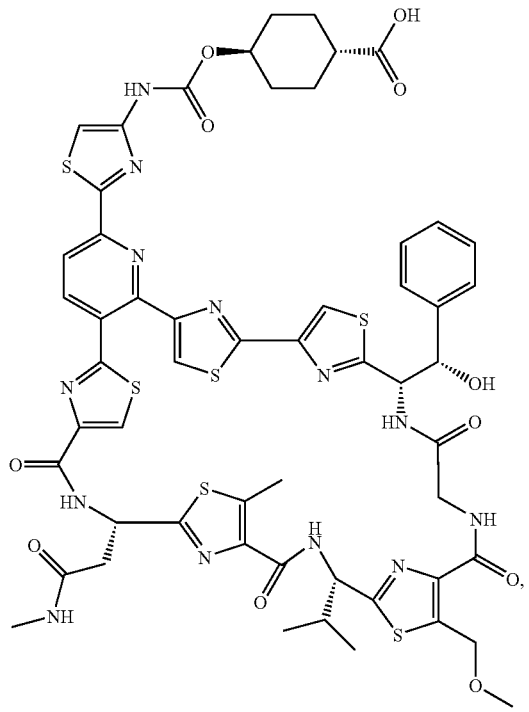
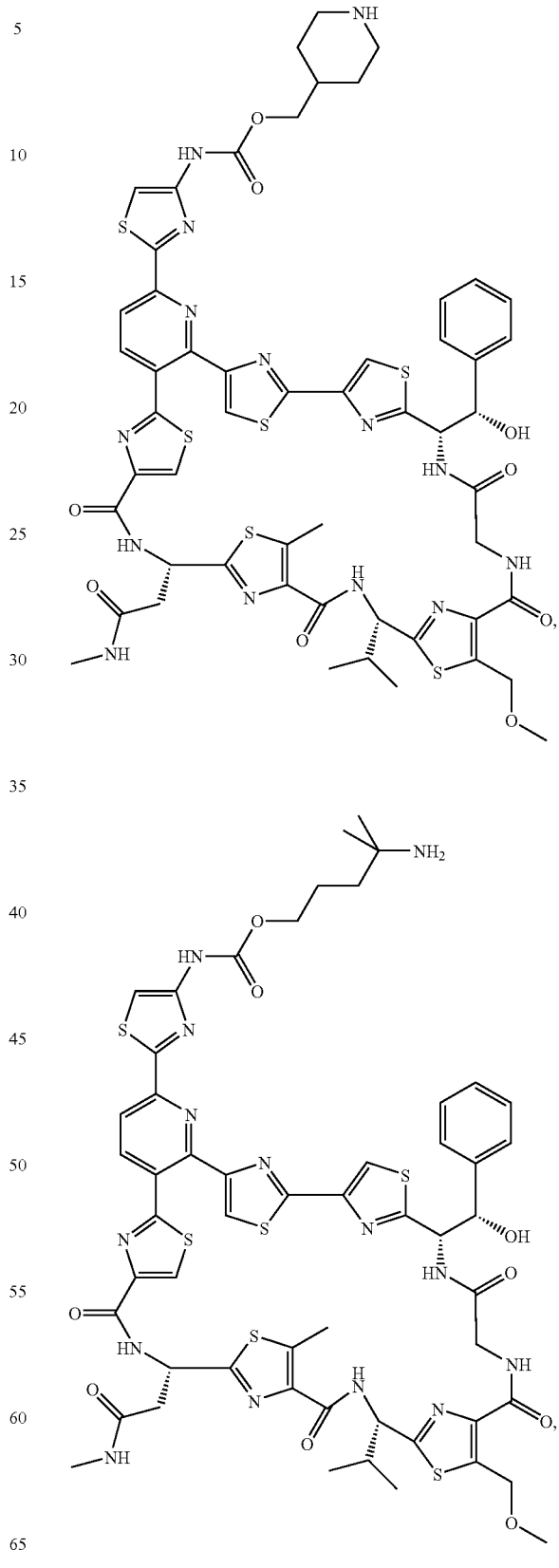

215
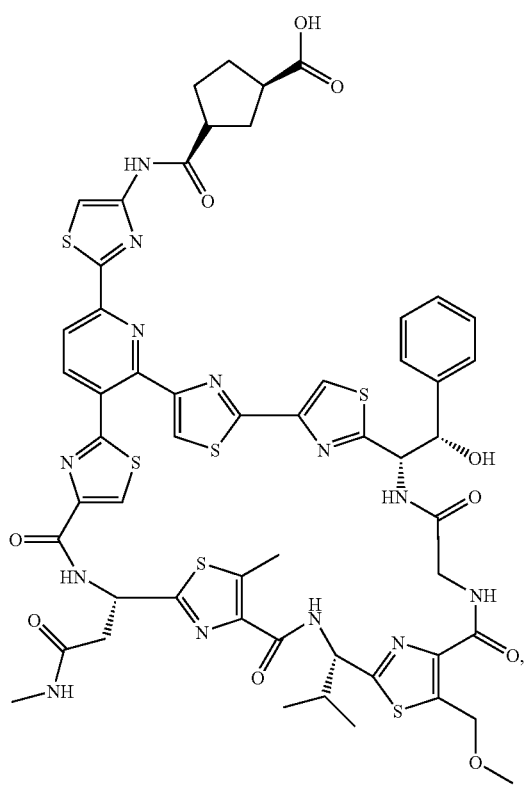
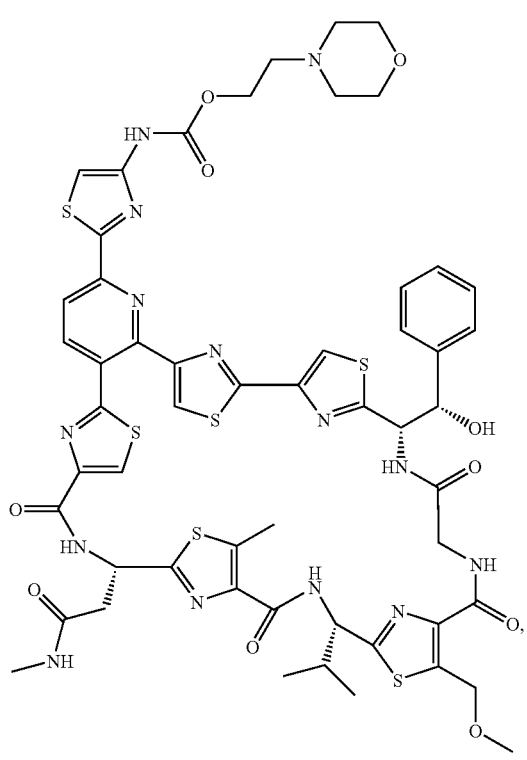
216
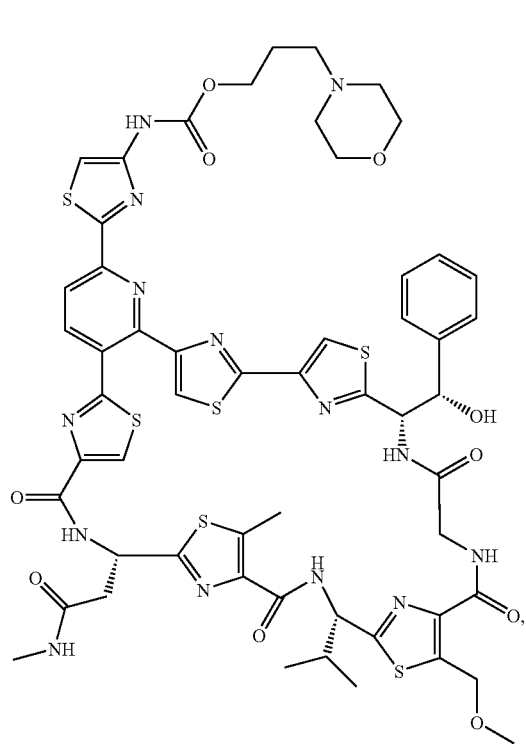
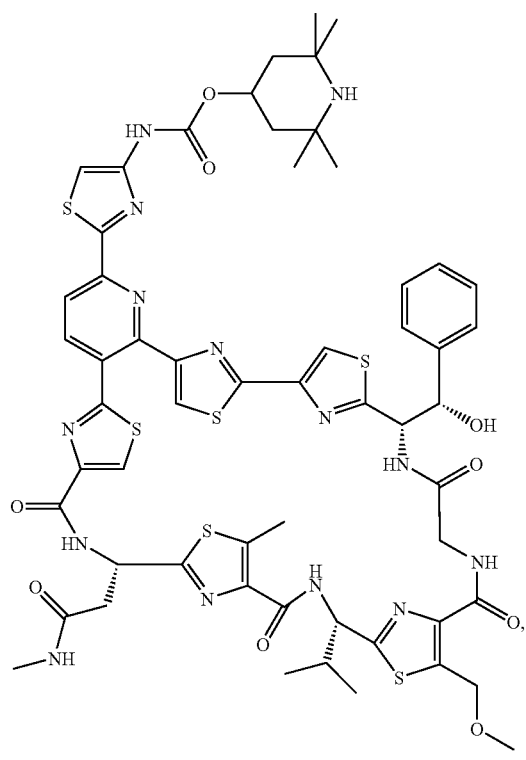

217
-continued
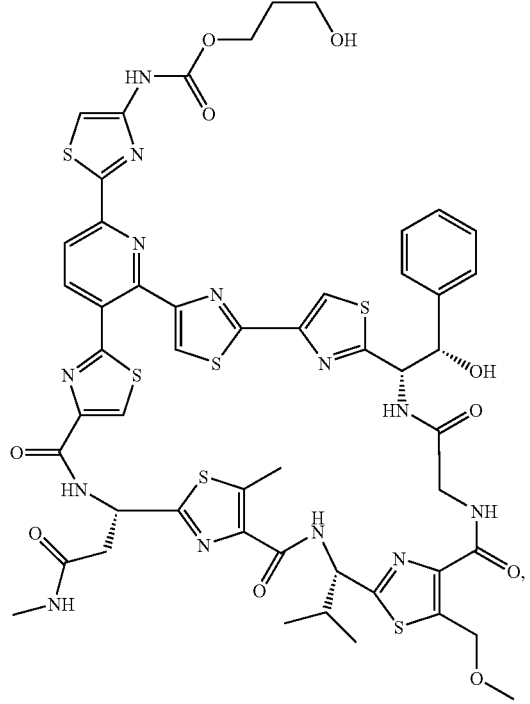
218
-continued
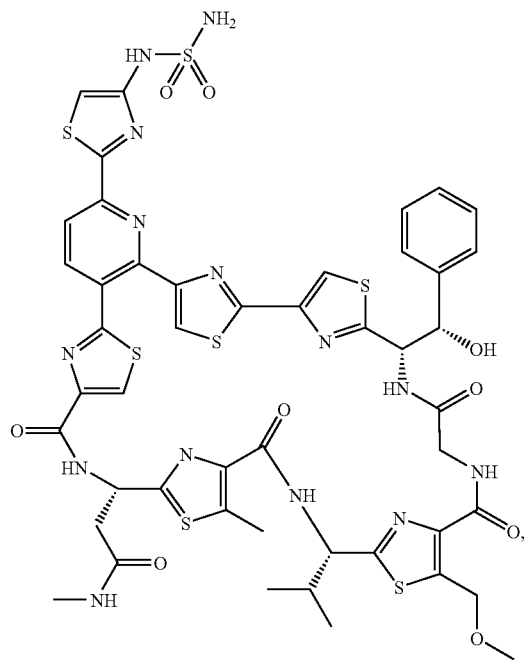
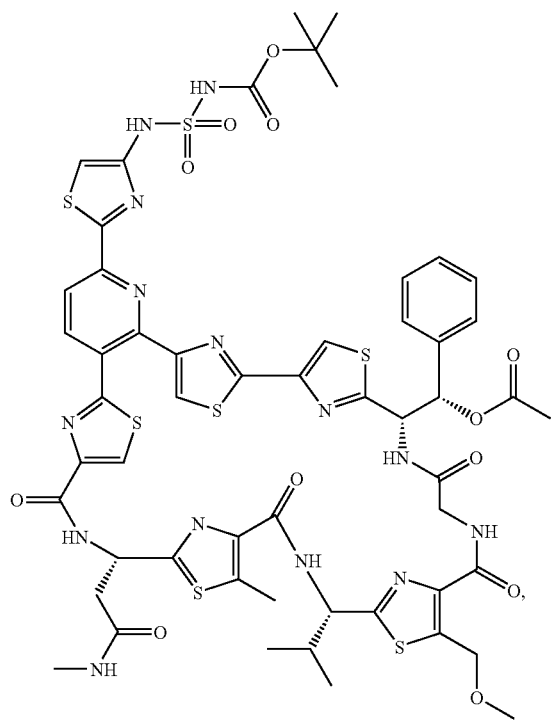
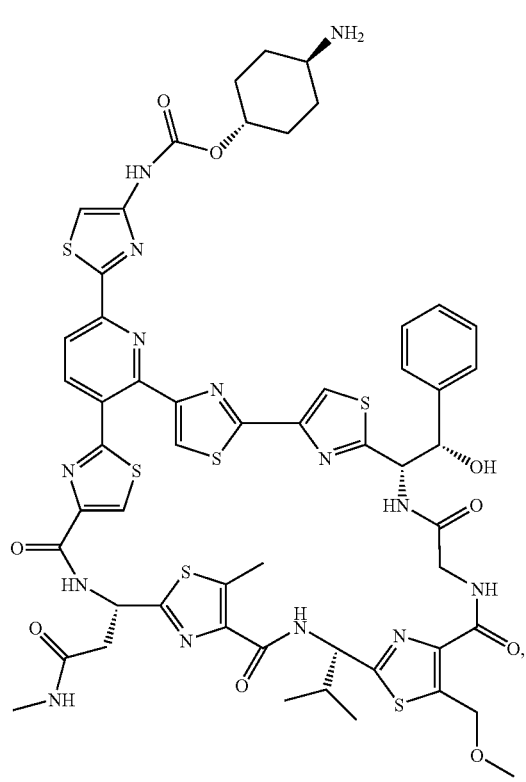

-continued
219
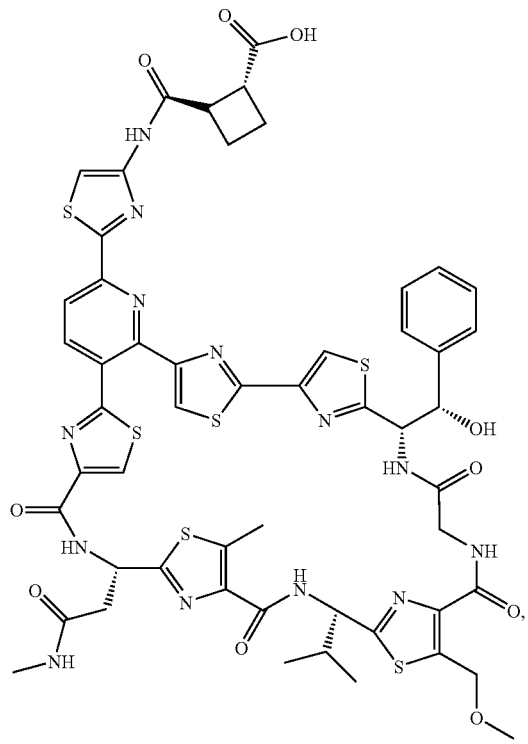
220
-continued
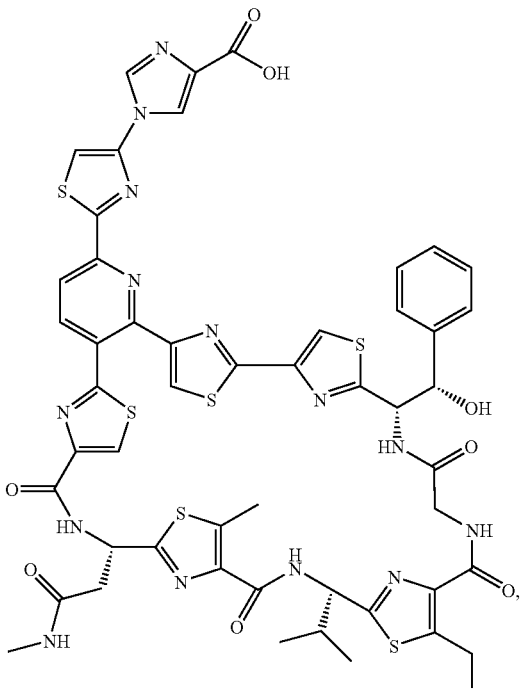
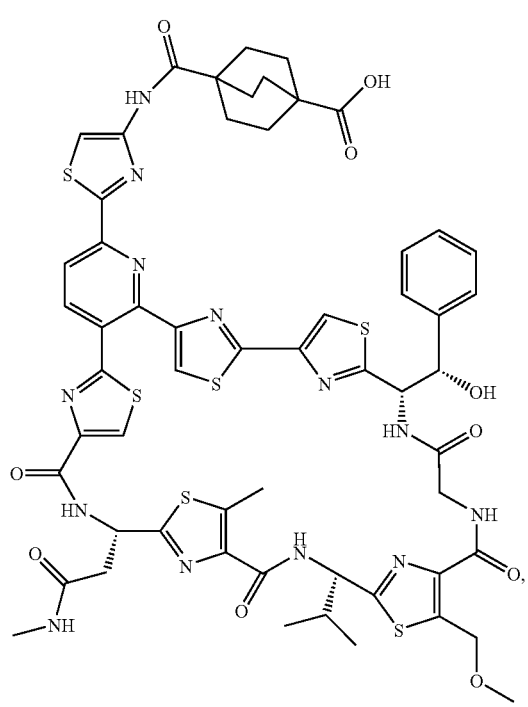
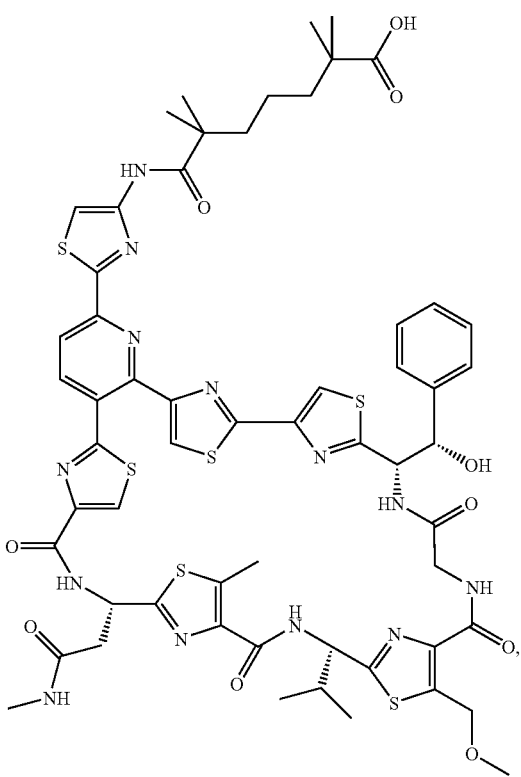

221
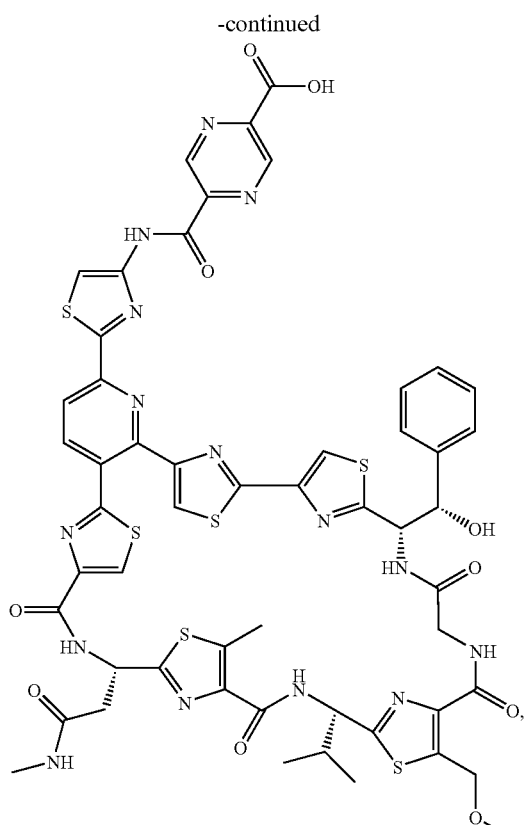
222
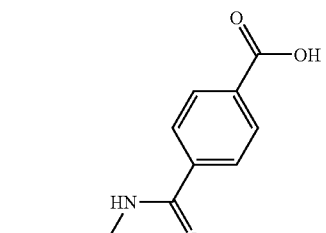
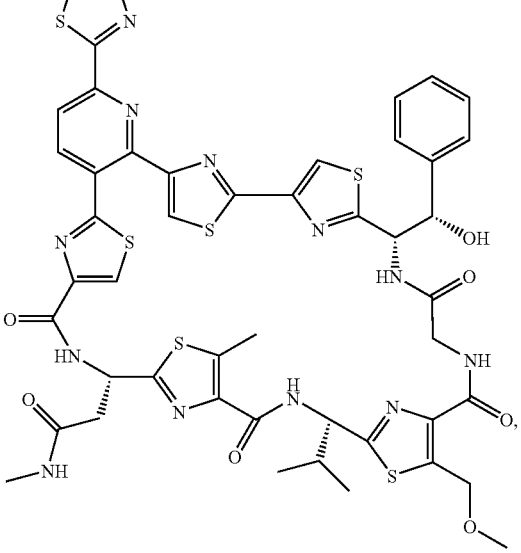
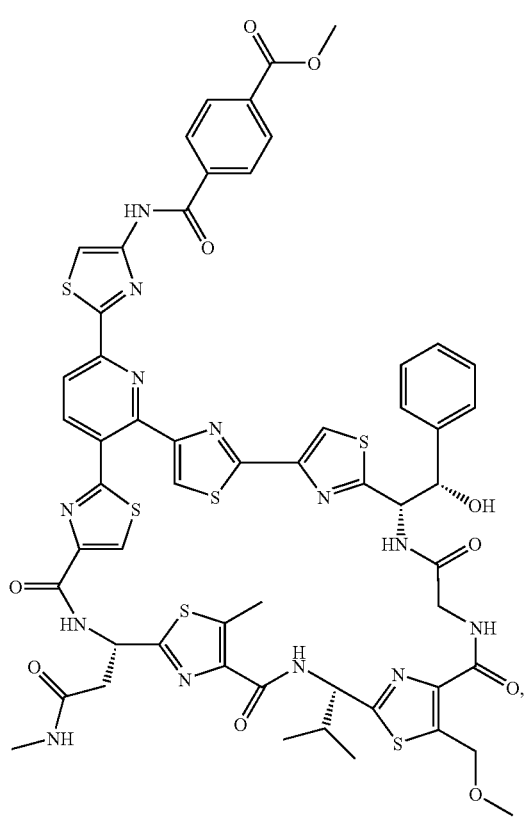
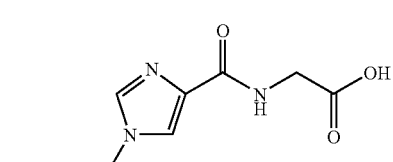
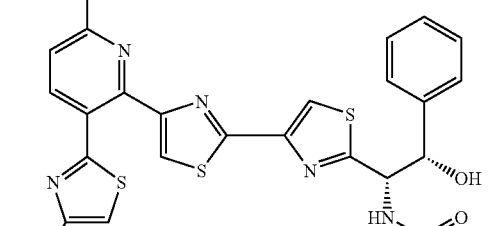
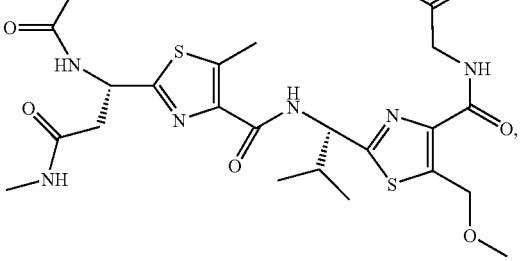

223
-continued
224
-continued
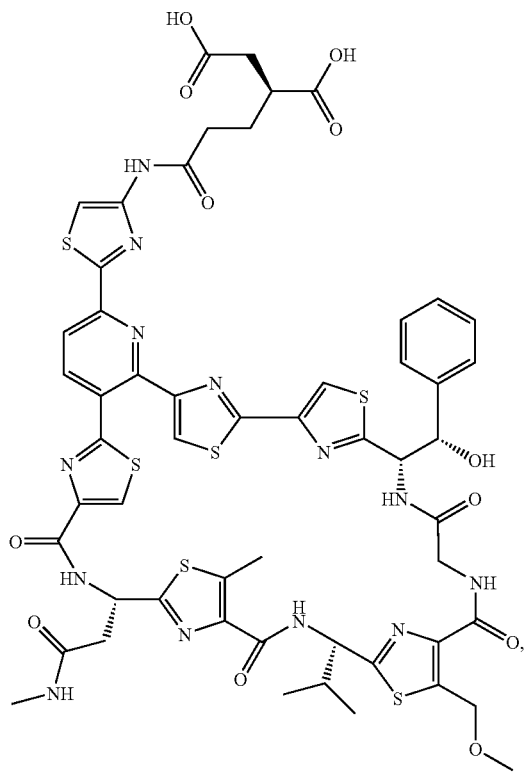
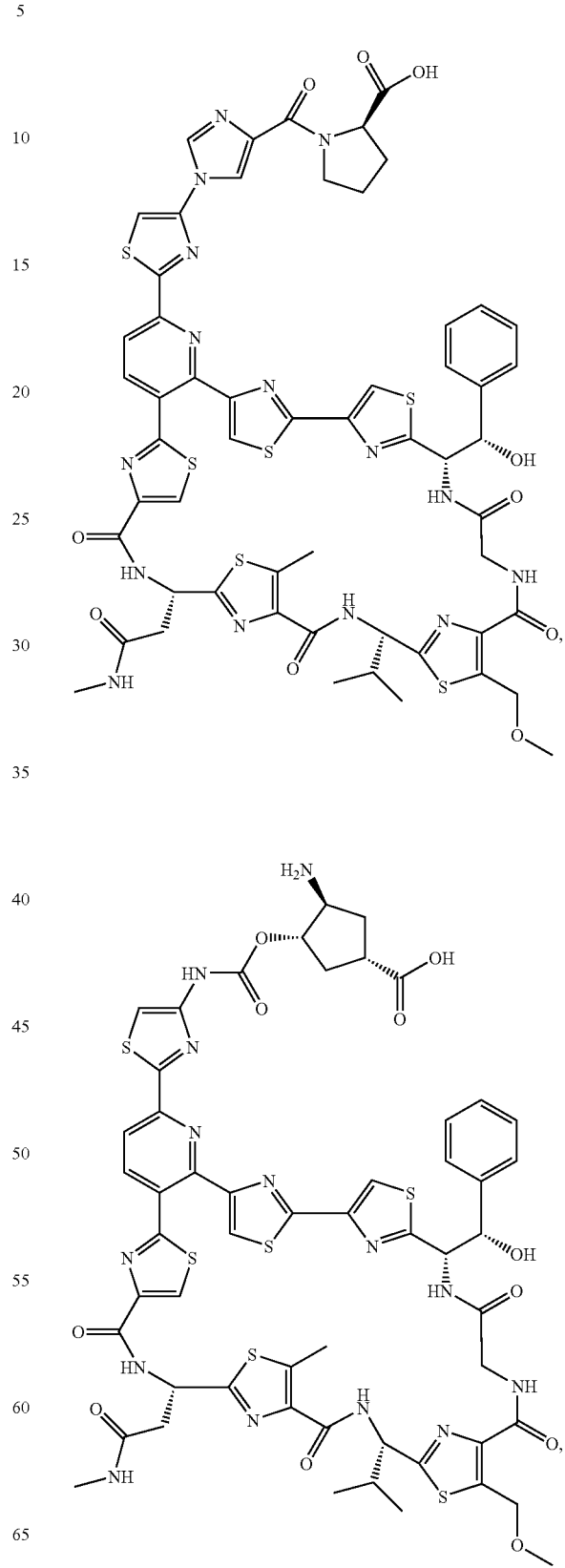

225
-continued
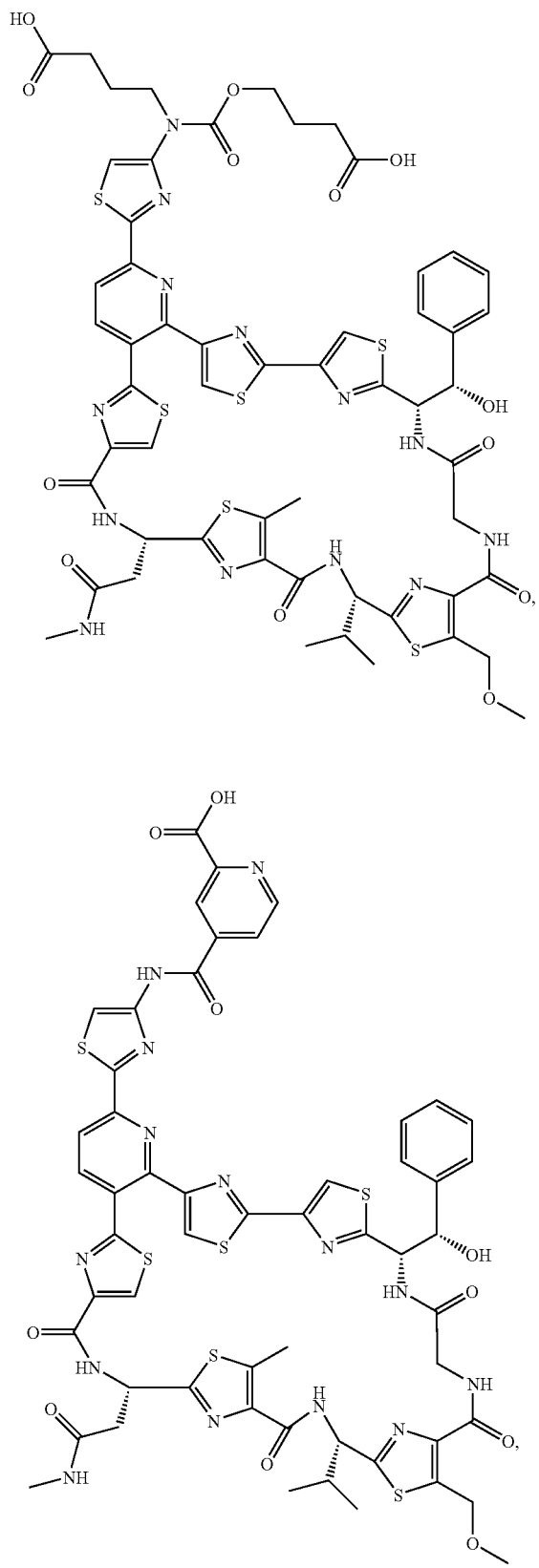
226
-continued
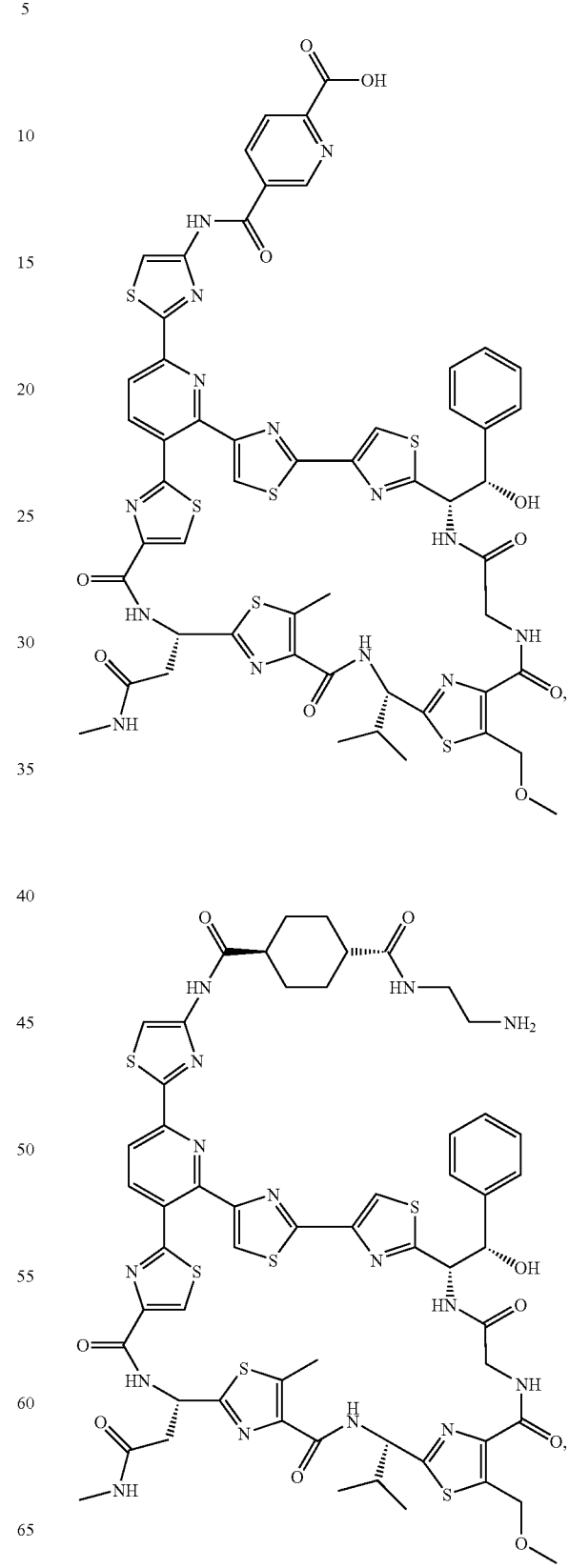

227
-continued
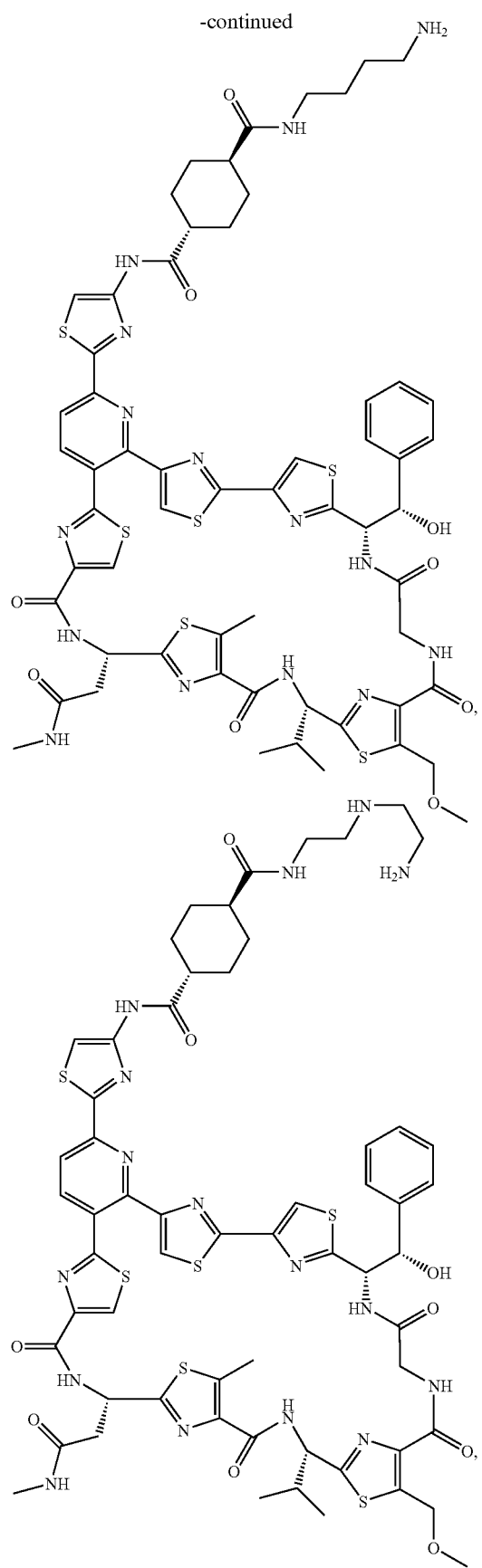
228
-continued
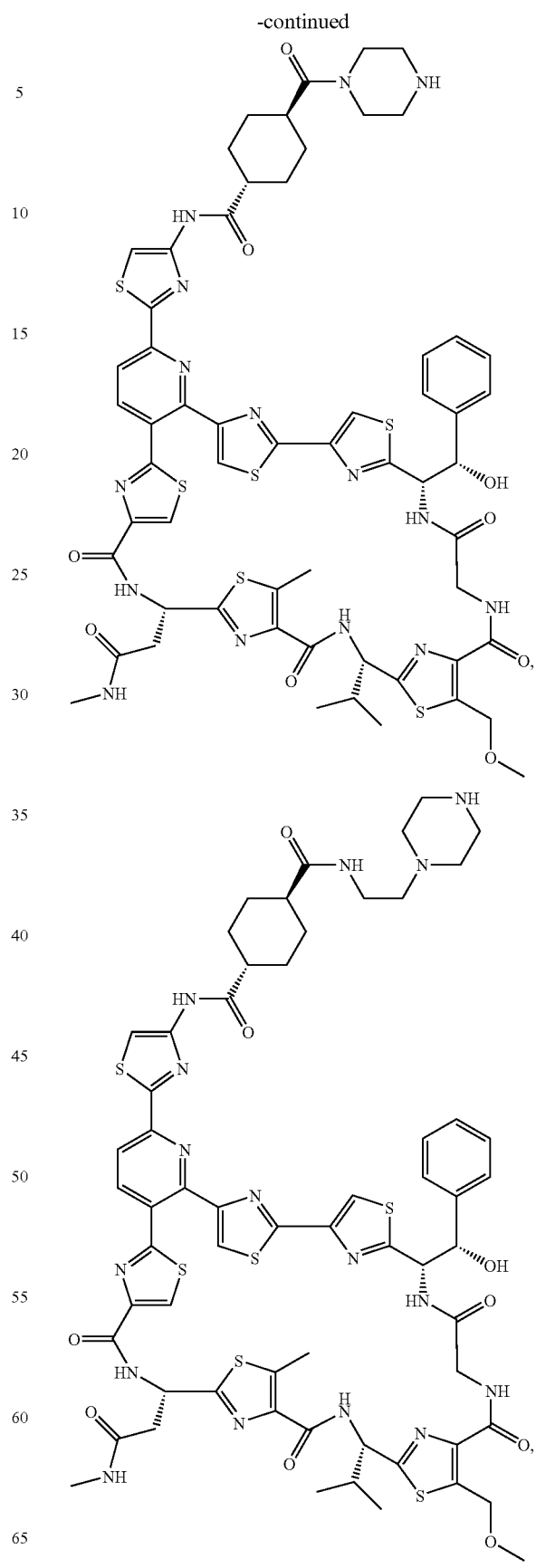

229 230
-continued -continued
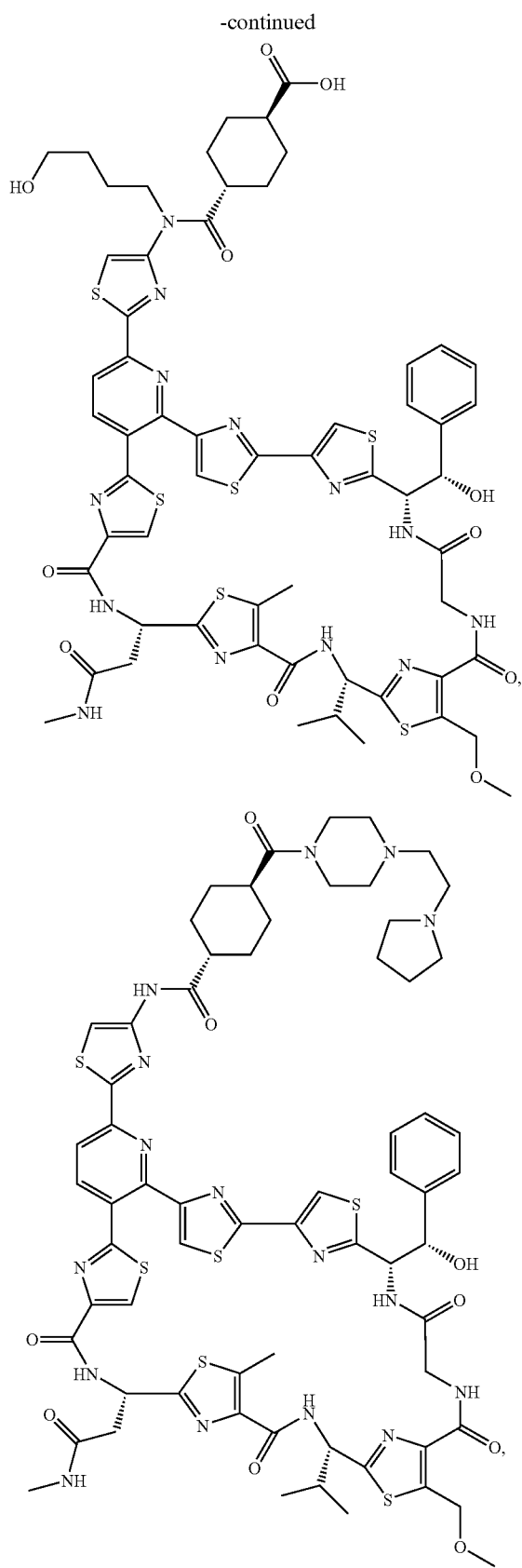
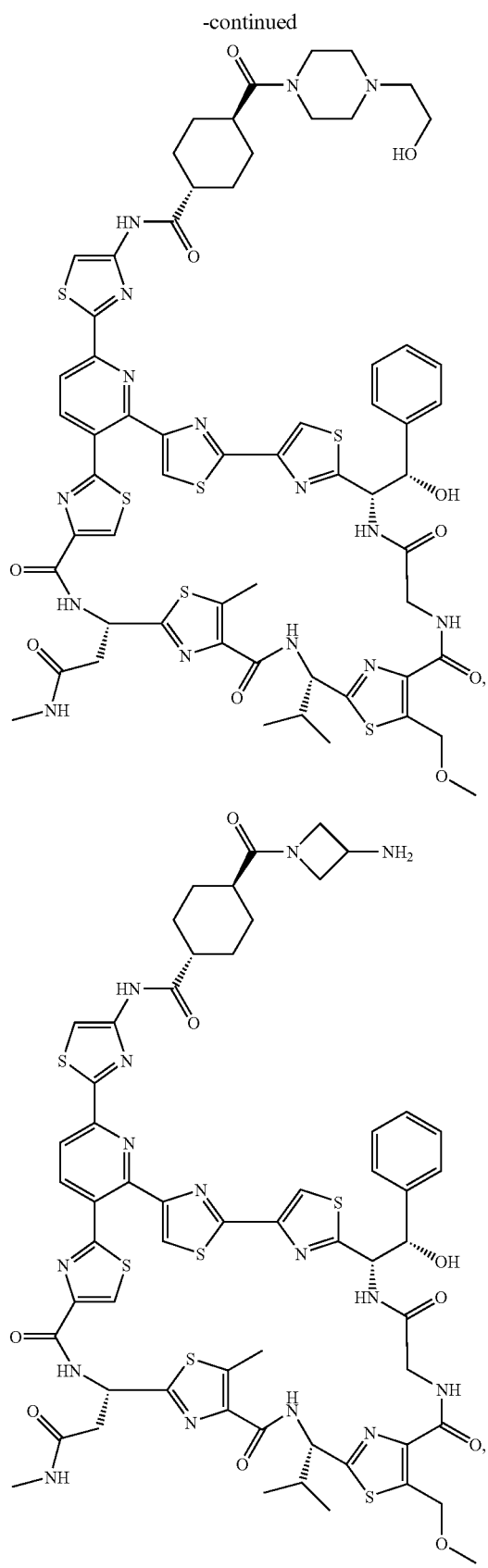

-continued

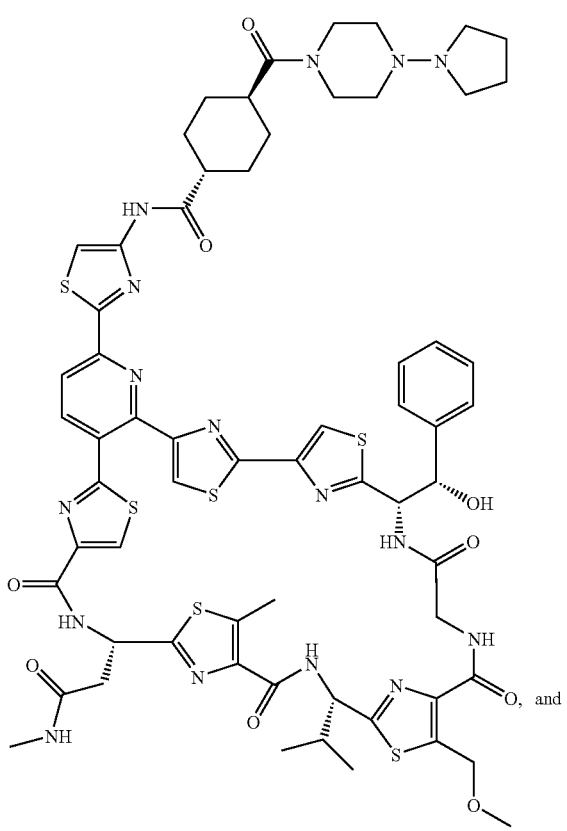

, and

-continued

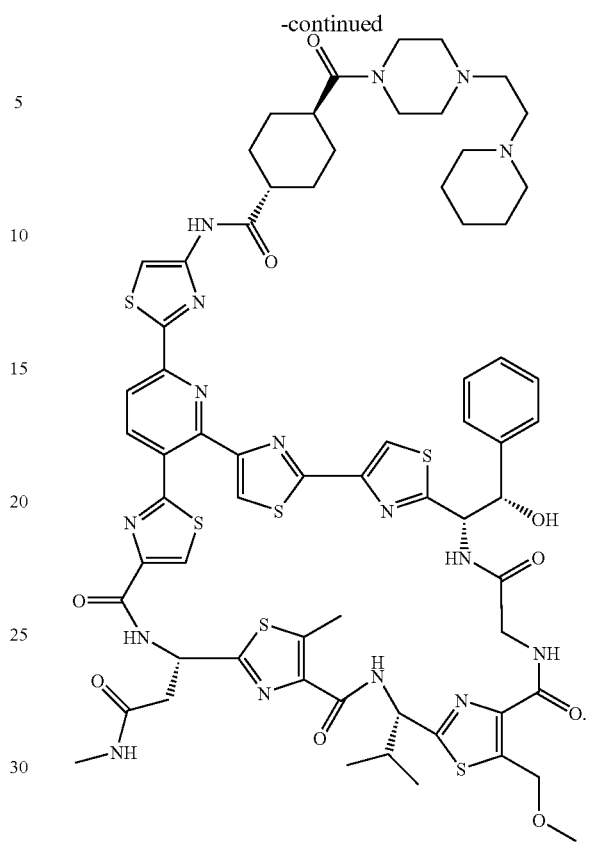

6. A method of treating a bacterial infection comprising administering to a subject in need thereof a pharmaceutically acceptable amount of a compound of claim 1 such that the bacterial infection is treated.

7. A method of inhibiting the activity of EF-Tu in a subject in need thereof, comprising administering to the subject a pharmaceutically acceptable amount of a compound of claim 1.

8. A method of treating a bacterial infection comprising administering to a subject in need thereof a pharmaceutically effective amount of a compound of claim 1 in combination with a pharmaceutically effective amount of an additional therapeutic agent, such that the bacterial infection is treated.

9. A method of treating acne in subject in need thereof comprising administering to the subject a pharmaceutically acceptable amount of a compound of claim 1.

10. A pharmaceutical composition comprising a compound of claim 1 and at least one pharmaceutically acceptable carrier or diluent.

* * * * *

UNITED STATES PATENT AND TRADEMARK OFFICE
CERTIFICATE OF CORRECTION

| | | |
|---|---|---|
| PATENT NO. | : 7,851,439 B2 | |
| APPLICATION NO. | : 11/755481 | |
| DATED | : December 14, 2010 | |
| INVENTOR(S) | : Matthew J. LaMarche et al. | |

It is certified that error appears in the above-identified patent and that said Letters Patent is hereby corrected as shown below:

Column 170

Line 44, replace "R is selected from the group consisting of $N(R^1)$ and" with --R is selected from the group consisting of $N(R^1)_2$ and--

Signed and Sealed this
Twenty-eighth Day of June, 2011

David J. Kappos
*Director of the United States Patent and Trademark Office*

UNITED STATES PATENT AND TRADEMARK OFFICE
CERTIFICATE OF CORRECTION

PATENT NO. : 7,851,439 B2
APPLICATION NO. : 11/755481
DATED : December 14, 2010
INVENTOR(S) : Matthew J. LaMarche et al.

Page 1 of 1

It is certified that error appears in the above-identified patent and that said Letters Patent is hereby corrected as shown below:

Column 170

Line 53, replace "$(R^b)]_x$-, -$[C(R^{8a})(R^b)]_x$-$C(R^a)$=$C(R^a)$-$[(C(R^a)$" with --$(R^b)]_x$-, -$[C(R^a)(R^b)]_x$-$C(R^a)$=$C(R^a)$-$[(C(R^a)$--

Column 171

Lines 19-25, replace "$R^{4b}$ is selected from the group consisting of alkyl and -$(CH_2$-$CH_2$-$0$-$)_n$- $R^9$, wherein n is an integer of 1-500, 1,000, 2,000, 3,000, 4,000, 5,000, 10,000, 20,000, 30,000, 40,000, 50,000, or 60,000 or is a mean of a plurality of integers having a value of 1-500, 1,000, 2,000, 3,000, 4,000, 5,000, 10,000, 20,000, 30,000, 40,000, 50,000, or 60,000;" with --$R^{4b}$ is alkyl;--

Signed and Sealed this
Twenty-eighth Day of February, 2012

David J. Kappos
*Director of the United States Patent and Trademark Office*